US008865186B2

(12) United States Patent
Ichtchenko et al.

(10) Patent No.: US 8,865,186 B2
(45) Date of Patent: *Oct. 21, 2014

(54) GENETICALLY ENGINEERED CLOSTRIDIAL GENES, PROTEINS ENCODED BY THE ENGINEERED GENES, AND USES THEREOF

(75) Inventors: Konstantin Ichtchenko, Brooklyn, NY (US); Philip A. Band, West Orange, NJ (US)

(73) Assignee: New York University, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/252,177

(22) Filed: Oct. 3, 2011

(65) Prior Publication Data

US 2012/0021002 A1    Jan. 26, 2012

Related U.S. Application Data

(62) Division of application No. 12/762,909, filed on Apr. 19, 2010, now Pat. No. 8,044,188, which is a division of application No. 11/284,930, filed on Nov. 22, 2005, now Pat. No. 7,785,606.

(60) Provisional application No. 60/630,175, filed on Nov. 22, 2004.

(51) Int. Cl.
| A61K 38/00 | (2006.01) |
| C12N 9/52 | (2006.01) |
| C07K 14/33 | (2006.01) |
| A61K 39/08 | (2006.01) |
| A61K 39/00 | (2006.01) |

(52) U.S. Cl.
CPC ........... *C12N 9/52* (2013.01); *A16K 2039/6037* (2013.01); *A61K 39/00* (2013.01); *C12Y 304/24069* (2013.01); *C07K 14/33* (2013.01); *A61K 39/08* (2013.01)
USPC ..................... 424/234.1; 424/239.1; 530/350

(58) Field of Classification Search
USPC ................... 435/69.1, 325, 320.1; 424/234.1
See application file for complete search history.

(56) References Cited

U.S. PATENT DOCUMENTS

| 5,750,383 A | 5/1998 | Blissard et al. |
| 5,846,929 A | 12/1998 | Johnson et al. |

(Continued)

FOREIGN PATENT DOCUMENTS

| EP | 0209281 | 1/1987 |
| WO | 9807864 | * 2/1998 |

(Continued)

OTHER PUBLICATIONS

National Institute of Allergy and Infectious Diseases, "NIAID Biodefense Research Agenda for CDC Category A Agents. Progress Report," NIH Publication # 03-5432, pp. 1-37 (2003).

(Continued)

*Primary Examiner* — Albert Navarro
*Assistant Examiner* — Ginny Portner
(74) *Attorney, Agent, or Firm* — LeClairRyan, a Professional Corporation

(57) ABSTRACT

The present invention relates to an isolated Clostridial neurotoxin propeptide having a light chain region, a heavy chain region, where the light and heavy chain regions are linked by a disulfide bond, and an intermediate region connecting the light and heavy chain regions. An isolated nucleic acid molecule encoding a Clostridial neurotoxin propeptide is also disclosed. Also disclosed is an isolated, physiologically active Clostridial neurotoxin produced by cleaving a Clostridial neurotoxin propeptide, a vaccine or antidote thereof, and methods of immunizing against or treating for toxic effects of Clostridial neurotoxins. Methods of expressing recombinant physiologically active Clostridial neurotoxins are also disclosed. Also disclosed is a chimeric protein having a heavy chain region of a Clostridial neurotoxin and a protein with therapeutic functionality. A treatment method is also disclosed.

29 Claims, 18 Drawing Sheets

(56) References Cited

U.S. PATENT DOCUMENTS

| | | | |
|---|---|---|---|
| 5,919,665 A * | 7/1999 | Williams | 435/71.1 |
| 5,939,070 A * | 8/1999 | Johnson et al. | 424/194.1 |
| 6,001,806 A | 12/1999 | Hilbert et al. | |
| 6,022,950 A | 2/2000 | Murhpy | |
| 6,037,150 A * | 3/2000 | Iatrou et al. | 435/69.7 |
| 6,051,239 A * | 4/2000 | Simpson et al. | 424/239.1 |
| 6,203,794 B1 * | 3/2001 | Dolly et al. | 424/184.1 |
| 6,261,561 B1 * | 7/2001 | Stewart et al. | 424/184.1 |
| 6,323,023 B1 | 11/2001 | Shoseyov et al. | |
| 6,461,617 B1 * | 10/2002 | Shone et al. | 424/236.1 |
| 6,787,517 B1 * | 9/2004 | Gil et al. | 514/1 |
| 6,831,059 B2 * | 12/2004 | Donovan | 514/10.3 |
| 6,852,510 B2 | 2/2005 | Bremel et al. | |
| 6,881,411 B2 * | 4/2005 | Stewart et al. | 424/184.1 |
| 6,967,088 B1 * | 11/2005 | Williams et al. | 435/69.1 |
| 7,132,259 B1 * | 11/2006 | Dolly et al. | 435/69.1 |
| 7,172,764 B2 | 2/2007 | Li et al. | |
| 7,223,577 B2 * | 5/2007 | Steward et al. | 435/183 |
| 7,227,010 B2 | 6/2007 | Smith | |
| 7,273,722 B2 * | 9/2007 | Lin et al. | 435/69.1 |
| 7,419,676 B2 | 9/2008 | Dolly et al. | |
| 7,422,877 B2 | 9/2008 | Dolly et al. | |
| 7,456,272 B2 * | 11/2008 | Lin et al. | 536/23.7 |
| 7,632,251 B2 * | 12/2009 | Lin et al. | 604/187 |
| 7,658,933 B2 * | 2/2010 | Foster et al. | 424/239.1 |
| 7,785,606 B2 * | 8/2010 | Ichtchenko et al. | 424/234.1 |
| 7,888,469 B2 * | 2/2011 | Steward et al. | 530/350 |
| 7,893,202 B1 * | 2/2011 | Steward et al. | 530/350 |
| 8,044,188 B2 * | 10/2011 | Ichtchenko et al. | 536/23.7 |
| 8,119,767 B2 * | 2/2012 | Steward et al. | 530/350 |
| 2001/0016199 A1 | 8/2001 | Johnston et al. | |
| 2002/0107199 A1 | 8/2002 | Walker | |
| 2002/0137886 A1 | 9/2002 | Lin et al. | |
| 2002/0168727 A1 * | 11/2002 | Smith et al. | 435/69.3 |
| 2002/0177545 A1 * | 11/2002 | Donovan | 514/2 |
| 2003/0027752 A1 | 2/2003 | Steward et al. | |
| 2003/0049264 A1 * | 3/2003 | Foster et al. | 424/183.1 |
| 2003/0100071 A1 | 5/2003 | Apicella et al. | |
| 2003/0143651 A1 | 7/2003 | Steward et al. | |
| 2003/0166238 A1 * | 9/2003 | Shone et al. | 435/219 |
| 2003/0215468 A1 * | 11/2003 | Williams et al. | 424/239.1 |
| 2003/0219402 A1 * | 11/2003 | Rutter | 424/85.1 |
| 2003/0229454 A1 | 12/2003 | Reinherz et al. | |
| 2004/0013687 A1 | 1/2004 | Simpson et al. | |
| 2004/0018589 A1 * | 1/2004 | Zhong | 435/69.1 |
| 2004/0052819 A1 | 3/2004 | Kingsley et al. | |
| 2004/0071736 A1 * | 4/2004 | Quinn et al. | 424/239.1 |
| 2004/0101531 A1 | 5/2004 | Curtiss, III et al. | |
| 2004/0115215 A1 | 6/2004 | Williams | |
| 2004/0115727 A1 * | 6/2004 | Steward et al. | 435/7.1 |
| 2004/0220386 A1 | 11/2004 | Steward et al. | |
| 2004/0235118 A1 * | 11/2004 | Williams | 435/69.7 |
| 2005/0060762 A1 | 3/2005 | Bleck | |
| 2005/0106182 A1 | 5/2005 | Li et al. | |
| 2005/0260230 A1 * | 11/2005 | Steward et al. | 424/239.1 |
| 2006/0024331 A1 * | 2/2006 | Fernandez-Salas et al. | 424/239.1 |
| 2006/0024794 A1 * | 2/2006 | Li et al. | 435/69.7 |
| 2006/0039929 A1 | 2/2006 | Fernandez-Salas et al. | |
| 2006/0204524 A1 | 9/2006 | Ichtchenko et al. | |
| 2007/0104737 A1 * | 5/2007 | Smith | 424/239.1 |
| 2008/0057575 A1 | 3/2008 | Fernandez-Salas et al. | |

FOREIGN PATENT DOCUMENTS

| | | | |
|---|---|---|---|
| WO | WO 98/07864 | 2/1998 | |
| WO | 01/18038 A2 | 3/2001 | |
| WO | 0114570 * | 3/2001 | C12N 15/62 |

OTHER PUBLICATIONS

Abrams, P., "The Role of Neuromodulation in the Management of Urinary Urge Incontinence," *BJU Int.* 93(7):1116 (2004).

Achem, S.R., "Treatment of Spastic Esophageal Motility Disorders," *Gastroenterol Clin. North Am.* 33(1):107-124 (2004).

Adler et al., "Botulinum Toxin Type A for Treating Voice Tremor," *Arch. Neurol.* 61(9):1416-1420 (2004).

Agarwal et al., "Structural Analysis of Botulinum Neurotoxin Type E Catalytic Domain and Its Mutant Glu212→Gln Reveals the Pivotal Role of the Glu212 Carboxylate in the Catalytic Pathway," *Biochemistry* 43(21):6637-6644 (2004).

Ahn et al., "Botulinum Toxin for Masseter Reduction in Asian Patients," *Arch. Facial Plast. Surg.* 6(3):188-191 (2004).

Aoki, K.R., "Evidence for Antinociceptive Activity of Botulinum Toxin Type A in Pain Management," *Headache* 43(Suppl 1):S9-S15 (2003).

Aquilina et al., "Reduction of a Chronic Bilateral Temporomandibular Joint Dislocation with Intermaxillary Fixation and Botulinum Toxin A," *Br J. Oral Maxillofac. Surg.* 42(3):272-273 (2004).

Bach-Rojecky & Lacković, "Antinociceptive Effect of Botulinum Toxin Type A in Rat Model of Carrageenan and Capsaicin Induced Pain," *Croat. Med. J.* 46(2):201-208 (2005).

Bade et al., "Botulinum Neurotoxin Type D Enables Cytosolic Delivery of Enzymatically Active Cargo Proteins to Neurons via Unfolded Translocation Intermediates," *J. Neurochem.* 91(6):1461-1472 (2004).

Bakheit, A.M., "Optimizing the Methods of Evaluation of the Effectiveness of Botulinum Toxin Treatment of Post-Stroke Muscle Spasticity," *J. Neurol. Neurosurg. Psychiatry* 75:665-666 (2004).

Balkrishnan et al., "Longitudinal Examination of Health Outcomes Associated with Botulinum Toxin Use in Children with Cerebral Palsy," *J. Surg. Orthop. Adv.* 13:76-80 (2004).

Bayles & Deschler, "Operative Prevention and Management of Voice-Limiting Pharyngoesophageal Spasm," *Otolaryngol Clin. North Am.* 37(3):547-558 (2004).

Bender et al., "Speech Intelligibility in Severe Adductor Spasmodic Dysphonia," *J. Speech Lang. Hear. Res.* 47(1):21-32 (2004).

Bentsianov et al., "Noncosmetic Uses of Botulinum Toxin," *Clin. Dermatol.* 22(1):82-88 (2004).

Berweck & Heinen, "Use of Botulinum Toxin in Pediatric Spasticity (Cerebral Palsy)," *Mov. Disord.* 19(Suppl 8)S162-S167 (2004).

Blersch et al., "Botulinum Toxin A and the Cutaneous Nociception in Humans: A Prospective, Double-Blind, Placebo-Controlled, Randomized Study," *J. Neurol. Sci.* 205(1):59-63 (2002).

Blumenfeld et al., "Botulinum Neurotoxin for the Treatment of Migraine and Other Primary Headache Disorders," *Dermatol. Clin.* 22(2):167-175 (2004).

Brandt & Boker, "Botulinum Toxin for the Treatment of Neck Lines and Neck Bands," *Dermatol. Clin.* 22(2):159-166 (2004).

Brisinda et al., "Botulinum Neurotoxin to Treat Chronic Anal Fissure: Results of a Randomized 'Botox vs. Dysport' Controlled Trial," *Aliment Pharmacol. Ther.*, 19(6):695-701 (2004).

Byrne et al., "Purification, Potency, and Efficacy of the Botulinum Neurotoxin Type A Binding Domain from *Pichia pastoris* as a Recombinant Vaccine Candidate," *Infect. Immun.* 66(10):4817-4822 (1998).

Caccin et al., "VAMP/Synaptobrevin Cleavage by Tetanus and Botulinum Neurotoxins is Strongly Enhanced by Acidic Liposomes," *FEBS Lett.* 542(1-3):132-136 (2003).

Capaccio et al., "Diagnosis and Therapeutic Management of Iatrogenic Parotid Sialocele," *Ann. Otol. Rhinol. Laryngol.* 113(7):562-564 (2004).

Carruthers & Carruthers, "Botox: Beyond Wrinkles," *Clin. Dermatol.* 22(1):89-93 (2004).

Carruthers & Carruthers, "Botulinum Toxin A in the Mid and Lower Face and Neck," *Dermatol. Clin.* 22(2):151-158 (2004).

Carruthers & Carruthers, "Botulinum Toxin Type A for the Treatment of Glabellar Rhytides," *Dermatol. Clin.* 22(2):137-144 (2004).

Chaddock et al., "Expression and Purification of Catalytically Active, Non-Toxic Endopeptidase Derivatives of *Clostridium botulinum* Toxin Type A," *Protein Expr. Purif.* 25(2):219-228 (2002).

Chaddock et al., "Retargeted Clostridial Endopeptidases: Inhibition of Nociceptive Neurotransmitter Release In Vitro, and Antinociceptive Activity in In Vivo Models of Pain," *Mov. Disord.* 19(Suppl 8):S42-S47 (2004).

Chao et al., "Management of Pharyngoesophageal Spasm with Botox," *Otolaryngol Clin. North Am.* 37(3):559-566 (2004).

(56) References Cited

OTHER PUBLICATIONS

Chen et al., "Altering Brow Contour with Botulinum Toxin," *Facial Plast. Surg. Clin. N. Am.* 11:457-464 (2003).
Cruz, F., "Mechanisms Involved in New Therapies for Overactive Bladder," *Urology* 63(Suppl 3A):65-73 (2004).
Cui et al., "Subcutaneous Administration of Botulinum Toxin A Reduces Formalin-Induced Pain," *Pain* 107:(1-2):125-133 (2004).
Defazio & Livrea, "Primary Blepharospasm: Diagnosis and Management," *Drugs* 64(3):237-244 (2004).
Dekleva & Dasgupta, "Nicking of Single Chain *Clostridium botulinum* Type A Neurotoxin by an Endogenous Protease," *Biochem. Biophys. Res. Commun.* 162(2):767-772 (1989).
Derman et al., "Mutations That Allow Disulfide Bond Formation in the Cytoplasm of *Escherichia coli*," *Science* 262(5140):1744-1747 (1993).
Dolly et al., "Acceptors for Botulinum Neurotoxin Reside on Motor Nerve Terminals and Mediate Its Internalization," *Nature* 307(5950):457-460 (1984).
Dong et al., "Synaptotagmins I and II Mediate Entry of Botulinum Neurotoxin B Into Cells," *J. Cell. Biol.* 162(7):1293-1303 (2003).
Eleopra et al., "Different Types of Botulinum Toxin in Humans," *Mov. Disord.* 19(Suppl 8)S53-S59 (2004).
Emonard et al., "Regulation of Matrix Metalloproteinase (MMP) Activity by the Low-Density Lipoprotein Receptor-Related Protein (LRP). A New Function for an 'Old Friend'," *Biochimie* 87(3-4):369-376 (2005).
Finn, J.C., "Botulinum Toxin Type A: Fine-Tuning Treatment of Facial Nerve Injury," *J. Drugs Dermatol.* 3(2):133-137 (2004).
Flynn, T.C., "Myobloc," *Dermatol. Clin.* 22(2):207-211 (2004).
Giannantoni et al., "Intravesical Resiniferatoxin Versus Botulinum-A Toxin Injections for Neurogenic Detrusor Overactivity: A Prospective Randomized Study," *J. Urol.* 172(1):240-243 (2004).
Glogau, R.G., "Treatment of Hyperhidrosis with Botulinum Toxin," *Dermatol. Clin.* 22(2):177-185 (2004).
Goodnough et al., "Development of a Delivery Vehicle for Intracellular Transport of Botulinum Neurotoxin Antagonists," *FEBS Lett.* 513(2-3):163-168 (2002).
Haussermann et al., "Long-Term Follow-Up of Cervical Dystonia Patients Treated with Botulinum Toxin A," *Mov. Disord.* 19(3):303-308 (2004).
Hayden et al., "Discovery and Design of Novel Inhibitors of Botulinus Neurotoxin A: Targeted 'Hinge' Peptide Libraries," *J. Appl. Toxicol.* 23(1):1-7 (2003).
Hoch et al., "Channels Formed by Botulinum, Tetanus, and Diphtheria Toxins in Planar Lipid Bilayers: Relevance to Translocation of Proteins Across Membranes," *Proc. Natl. Acad. Sci. USA* 82(6):1692-1696 (1985).
Hojilla et al., "Matrix Metalloproteinases and Their Tissue Inhibitors Direct Cell Fate During Cancer Development," *Br. J. Cancer* 89(10):1817-1821 (2003).
Hyman et al., "Botulinum Toxin (*Dysport*®) Treatment of Hip Adductor Spasticity in Multiple Sclerosis: A Prospective, Randomised, Double Blind, Placebo Controlled, Dose Ranging Study," *J. Neurol. Neurosurg. Psychiatry* 68(6):707-712 (2000).
Jankovic, J., "Botulinum Toxin in Clinical Practice," *J. Neurol. Neurosurg. Psychiatry* 75(7):951-957 (2004).
Johnson, E.A., "Clostridial Toxins as Therapeutic Agents: Benefits of Nature's Most Toxic Proteins," *Annu. Rev. Microbiol.* 53:551-575 (1999).
Jost & Aoki, "Botulinum Toxin A in Anal Fissure: Why Does It Work?" *Dis. Colon Rectum.* 47(2):257-258 (2004).
Kadkhodayan et al., "Cloning, Expression, and One-Step Purification of the Minimal Essential Domain of the Light Chain of Botulinum Neurotoxin Type A," *Protein Expr. Purif.* 19(1):125-130 (2000).
Kern et al., "Effects of Botulinum Toxin Type B on Stump Pain and Involuntary Movements of the Stump," *Am. J. Phys. Med. Rehabil.* 83(5):396-399 (2004).
Kiyatkin et al., "Induction of an Immune Response by Oral Administration of Recombinant Botulinum Toxin," *Infect. Immun.* 65(11):4586-4591 (1997).
Klein, A.W., "The Therapeutic Potential of Botulinum Toxin," *Dermatol. Surg.* 30(3):452-455 (2004).
Koriazova & Montal., "Translocation of Botulinum Neurotoxin Light Chain Protease Through the Heavy Chain Channel," *Nat. Struct. Biol.* 10(1):13-18 (2003).
Krämer et al., "Botulinum Toxin A Reduces Neurogenic Flare But Has Almost No Effect on Pain and Hyperalgesia in Human Skin," *J. Neurol.* 250(2):188-193 (2003).
Kurazono et al., "Minimal Essential Domains Specifying Toxicity of the Light Chains of Tetanus Toxin and Botulinum Neurotoxin Type A," *J. Biol. Chem.* 267(21):14721-14729 (1992).
Kyrmizakis et al., "The Use of Botulinum Toxin Type A in the Treatment of Frey and Crocodile Tears Syndromes," *J. Oral Maxillofac. Surg.* 62(7):840-844 (2004).
Lacy et al., "Crystal Structure of Botulinum Neurotoxin Type A and Implications for Toxicity," *Nat. Struct. Biol.* 5(10):898-902 (1998).
Lacy & Stevens, "Recombinant Expression and Purification of the Botulinum Neurotoxin Type A Translocation Domain," *Protein Expr. Purif.* 11(2):195-200 (1997).
Lalli et al., "Functional Characterisation of Tetanus and Botulinum Neurotoxins Binding Domains," *J. Cell Sci.* 112(Pt 16):2715-2724 (1999).
Lang, A., "History and Uses of BOTOX (Botulinum Toxin Type A)," *Lippincott's Case Manag.* 9(2):109-112 (2004).
Layeeque et al., "Botulinum Toxin Infiltration for Pain Control After Mastectomy and Expander Reconstruction," *Ann. Surg.* 240(4):608-614 (2004).
Lee et al., "A Case of Foul Genital Odor Treated with Botulinum Toxin A," *Dermatol. Surg.* 30(9):1233-1235 (2004).
Leippold et al., "Botulinum Toxin as a New Therapy Option for Voiding Disorders: Current State of the Art," *Eur. Urol.* 44(2):165-174 (2003).
Levy et al., "Botulinum Toxin A: A 9-Month Clinical and 3D In Vivo Profilometric Crow's Feet Wrinkle Formation Study," *J. Cosmet. Laser Ther.* 6(1):16-20 (2004).
Li et al., "Recombinant Forms of Tetanus Toxin Engineered for Examining and Exploiting Neuronal Trafficking Pathways," *J. Biol. Chem.* 276(33):31394-31401 (2001).
Lozsadi et al., "Botulinum Toxin A Improves Involuntary Limb Movements in Rasmussen Syndrome," *Neurology* 62(7):1233-1234 (2004).
MacKinnon et al., "Corticospinal Excitability Accompanying Ballistic Wrist Movements in Primary Dystonia," *Mov. Disord.* 19(3):273-284 (2004).
Mahowald et al., "Long Term Effects of Intra-Articular Botulinum Toxin A for Refractory Joint Pain," *Annual Meeting of the American College of Rheumatology* (Oct. 19, 2004), abstract, pp. 1-4, pp. 2and 4blank.
Mannello et al., "Matrix Metalloproteinase Inhibitors as Anticancer Therapeutics," *Curr. Cancer Drug Targets* 5:285-298 (2005).
Maskos, K., "Crystal Structures of MMPs in Complex with Physiological and Pharmacological Inhibitors," *Biochimie* 87(3-4):249-263 (2005).
Mazo et al., "Botulinic Toxin in Patients with Neurogenic Dysfunction of the Lower Urinary Tracts," *Urologia* Jul.-Aug. 2004:44-48 (2004).
Matteoli et al., "Synaptic Vesicle Endocytosis Mediates the Entry of Tetanus Neurotoxin Into Hippocampal Neurons," *Proc. Natl. Acad. Sci. USA* 93(23):13310-13315 (1996).
Montecucco, C., "How Do Tetanus and Botulinum Toxins Bind to Neuronal Membranes?" *Trends Biochem. Sci.* 11(8):314-317 (1986).
Montecucco et al., "SNARE Complexes and Neuroexocytosis: How Many, How Close?" *Trends Biochem. Sci.* 30(7):367-372 (2005).
Montecucco et al., "Structure and Function of Tetanus and Botulinum Neurotoxins," *Q. Rev. Biophys.* 28(4):423-472 (1995).
Mukherjee et al., "Endocytosis," *Physiol. Rev.* 77(3):759-803 (1997).
Namazi & Majd, "Botulinum Toxin as a Novel Addition to Anti-Arthritis Armamentarium," *Am. J. Immun.* 1(2):92-93 (2005).

(56) References Cited

OTHER PUBLICATIONS

Naumann & Jankovic, "Safety of Botulinum Toxin Type A: A Systematic Review and Meta-Analysis," *Curr. Med. Res. Opin.* 20(7):981-990 (2004).
Nishiki et al., "The High-Affinity Binding of *Clostridium botulinum* Type B Neurotoxin to Synaptotagmin II Associated with Gangliosides $G_{T1b}/G_{D1a}$," *FEBS Lett.* 378(3):253-257 (1996).
Oost et al., "Design and Synthesis of Substrate-Based Inhibitors of Botulinum Neurotoxin Type B Metalloprotease," *Biopolymers* 71(6):602-619 (2003).
Özsoy et al., "Two-Plane Injection of Botulinum Exotoxin A in Glabellar Frown Lines," *Aesth. Plast. Surg.* 28(2):114-115 (2004).
Park & Simpson, "Inhalational Poisoning by Botulinum Toxin and Inhalation Vaccination with Its Heavy-Chain Component," *Infect. Immun.* 71(3):1147-1154 (2003).
Pidcock, F.S., "The Emerging Role of Therapeutic Botulinum Toxin in the Treatment of Cerebral Palsy," *J. Pediatr.* 145(2 Suppl):S33-S35 (2004).
Pless et al., "High-Affinity, Protective Antibodies to the Binding Domain of Botulinum Neurotoxin Type A," *Infect. Immun.* 69(1):570-574 (2001).
Porta et al., "Treatment of Phonic Tics in Patients with Tourette's Syndrome Using Botulinum Toxin Type A," *Neurol. Sci.* 24(6):420-423 (2003).
Prinz et al., "The Role of the Thioredoxin and Glutaredoxin Pathways in Reducing Protein Disulfide Bonds in the *Escherichia coli* Cytoplasm," *J. Biol. Chem.* 272(25):15661-15667 (1997).
Pucinelli et al., "Botulinic Toxin for the Rehabilitation of Osteoarthritis Fixed-Flexion Knee Deformity," *Annual Meeting of the Osteoarthitis Research Society International*, pp. S143, Abstract P346 (2004).
Rajkumar & Conn, "Botulinum Toxin: A New Dimension in the Treatment of Lower Urinary Tract Dysfunction," *Urology* 64(1):2-8 (2004).
Reitz & Schurch, "Intravesical Therapy Options for Neurogenic Detrusor Overactivity," *Spinal Cord* 42(5):267-272 (2004).
Rigoni et al., "Site-Directed Mutagenesis Identifies Active-Site Residues of the Light Chain of Botulinum Neurotoxin Type A," *Biochem. Biophys. Res. Commun.* 288(5):1231-1237 (2001).
Rossetto et al., "SNARE Motif and Neurotoxins," *Nature* 372(6505):415-416 (1994).
Rummel et al., "The $H_{CC}$-Domain of Botulinum Neurotoxins A and B Exhibits a Singular Ganglioside Binding Site Displaying Serotype Specific Carbohydrate Interaction," *Mol. Microbiol.* 51(3):631-643 (2004).
Rummel et al., "Synaptotagmins I and II Act as Nerve Cell Receptors for Botulinum Neurotoxin G," *J. Biol. Chem.* 279(29):30865-30870 (2004).
Russman et al., "Cerebral Palsy: A Rational Approach to a Treatment Protocol, and the Role of Botulinum Toxin in Treatment," *Muscle Nerve* 20(Suppl 6):S181-S193 (1997).
Sadick & Matarasso, "Comparison of Botulinum Toxins A and B in the Treatment of Facial Rhytides," *Dermatol. Clin.* 22(2):221-226 (2004).
Salmanpoor & Rahmanian, "Treatment of Axillary Hyperhidrosis with Botulinum-A Toxin," *Int. J. Dermatol.* 41(7):428-430 (2002).
Sampaio et al., "Clinical Comparability of Marketed Formulations of Botulinum Toxin," *Mov. Disord.* 19(Suppl 8):S129-S136 (2004).
Schmulson & Valdovinos, "Current and Future Treatment of Chest Pain of Presumed Esophageal Origin," *Gastroenterol Clin. North Am.* 33(1):93-105 (2004).
Schurch, "The Role of Botulinum Toxin in Neurology," *Drugs of Today* 40(3):205-212 (2004).
Segelke et al., "Crystal Structure of *Clostridium botulinum* Neurotoxin Protease in a Product-Bound State: Evidence for Noncanonical Zinc Protease Activity," *Proc. Natl. Acad. Sci. USA* 101(18):6888-6893 (2004).
Shapiro et al., "Identification of a Ganglioside Recognition Domain of Tetanus Toxin Using a Novel Ganglioside Photoaffinity Ligand," *J. Biol. Chem.* 272(48):30380-30386 (1997).
Simpson, L.L., "Identification of the Major Steps in Botulinum Toxin Action," *Annu. Rev. Pharmacol. Toxicol.* 44:167-193 (2004).
Sukonpan et al., "Synthesis of Substrates and Inhibitors of Botulinum Neurotoxin Type A Metalloprotease," *J. Pept. Res.* 63(2):181-193 (2004).
Sutton et al., "Crystal Structure of a SNARE Complex Involved in Synaptic Exocytosis at 2.4 Å Resolution," *Nature* 395(6700):347-353 (1998).
Swaminathan & Eswaramoorthy, "Structural Analysis of the Catalytic and Binding Sites of *Clostridium botulinum* Neurotoxin B," *Nat. Struct. Biol.* 7(8):693-699 (2000).
Van Heyningen & Miller, "The Fixation of Tetanus Toxin by Ganglioside," *J. Gen. Microbiol.* 24:107-119 (1961).
Vartanian & Dayan, "Facial Rejuvenation Using Botulinum Toxin A: Review and Updates," *Facial Plast. Surg.* 20(1):11-19 (2004).
Wissel & Entner, "Botulinum Toxin Typ A in der Behandlung der Adduktorenspastizität (Botulinum Toxin Treatment of Hip Adductor Spasticity in Multiple Sclerosis)," *Wien. Klin. Wochesnchr.* 113[Suppl 4]:20-24 (2001).
No Author, "Botulinum Toxin (*Botox*) for Axillary Hyperhidrosis," *Med. Lett. Drugs Ther.* 46(1191):76 (2004).
Marvaud et al., "Le Botulisme: Agent, Mode D'action des Neurotoxines Botuliques, Formes D'Acquisition, Traitement et Prevention," C.R. Biologies 325:863-878 (2002) (with English abstract).
Baldwin et al., "The C-Terminus of Botulinum Neurotoxin Type A Light Chain Contributes to Solubility, Catalysis, and Stability," Protein Expression and Purification 37:187-195 (2004).
Prabakaran et al., "Botulinum Neurotoxin Types B and E: Purification, Limited Proteolysis by Endoproteinase Glu-C and Pepsin, and Comparison of their Identified Cleaved Sites Relative to the Three-Dimensional Structure of Type A Neurotoxin," Toxicon 39:1515-1531 (2001).
Shone et al., "Inactivation of *Clostridum botulinum* Type A Neurotoxin by Trypsin and Purification of Two Tryptic Fragments," European J. of Biochem. 151:75-82 (1985).
Allet et al., "A Bacterial Signal Peptide Directs Efficient Secretion of Eukaryotic Proteins in the Baculovirus Expression System," Pro. Exp. Pur. 9:61-68 (1997).
Cooke et al., "A Modified *Escherichia coli* Protein Production Strain Expressing Staphylococcal Nuclease, Capable of Auto-Hydrolysing Host Nucleic Acid," J. Biotech. 101:229-239 (2003).
Agarwal et al., Cloning, High Level Expression, Purification, and Crystallization of the Full Length *Clostridium botulinum* Neurotoxin Type E Light Chain, Pro. Exp. Pur. 34:95-102 (2004).
Gunnar von Heijne, "Signals for Protein Targeting Into and Across Membranes," Subcell. Biochem. 22:1-19 (1994).

\* cited by examiner

```
BoNT A  NNWDLFFSPSEDNFTNDLNKGEEITSDTNIEAAEENISLDLIQQYYLTFNFDNEPENISIENLSSDIIGQLELMPNIERFP
BoNT B  DNEDLFFIADKNSFSDDLSKNERIEYNTQSNYIENDFPINEL---ILDTDLISKIE-LPSENTESLTDFNV-DVPVYIKQP
BoNT C  KNTDLPFIGDISDVKTDIFLRKDINEETEVIYYPDNVSVDQV---ILSKNTSEHGQ-L--DLLYPSIDSESEILPG-FNQV
BoNT D  KNNRLPYVADKDSISQEIFENKIITDETNVQNYSDNFSLDES---ILDGQVPINPEIV--DPLLPNVNMEPLNLPG-EEIV
BoNT E  NNGELFFVASENSYNDDNINTPKEIDDTVTSNNNYENDLDQV---ILNFNSESAPG-LSDEKLNLTIQND-AYIPKYDSNG
BoNT F  NNRELFFVASESSYNENDINTPKEIDDTTNLNNNYRNNLDEV---ILDYNSETIPQ-ISNQTLNTLVQDD-SYVPRYDSNG
BoNT G  NNEDLFFIANKDSFSKDLAKAETTAYNTQNNTIENNFSIDQL---ILDNDLSSGID-LPNENTEPFTNFDDIDIPVYIKQS

BoNT A  NG--KKYELDKYTMFHYLRAQEFEHGKSRIALTNSVNEALLNPSRVYTFFSSDYVKKVNKATEAAMFLGWVEQLVYDFTDE
BoNT B  AI--KKIFTDENTISQYLYSQTFELDIRDISLTSSFDDALLFSNKVYSFFSMDYIKTANKVVEAGLFAGWVKQIVNDFVIE
BoNT C  FYDNRTQNVDYLNSYYTLESQKLSDNVEDFTFTRSIEEALDNSAKVYTYFPT-LANKVNAGVQGGLFLMWANDVVEDFTTN
BoNT D  FYDDITKYVDYLNSYYTLESQKLSNNVENITLTTSVEEALGYSNKIYTFLPS-LAEKVNKGVQAGLFLNWANEVVEDFTTN
BoNT E  TSDIEQHDVNELNVFFYLDAQKVPEGENNVNLTSSIDTALLEQPKIYTFFSSEFINNVNKPVQAALFVSWIQQVLVDFTTE
BoNT F  TSEIEEHNVVDLNVFFYLHAQKVPEGETNISLTSSIDTALSEESQVYTFFSSEFINTINKPVHAALFISWINQVIRDFTTE
BoNT G  AL--KKIFVDGDSLFEYLHAQTFPSNIENLQLTNSLNDALRNNNKVYTFFSTNLVEKANTVVGASLFVNWVKGVIDDFTSE

BoNT A  TSEVSFIDKIADITIIIPYIGPALNIGNMLYKDDFVGALIFSGAVILLEFIPEIAIPVLGTFALVSYI---ANKVLTVQTI
BoNT B  ANKSNIMDKIADISLIVPYIGLALNVGNETAKGNFENAFEIAGASILLEFIPELLIPVVGAFLLESYI---DNKNKIIKTI
BoNT C  ILRKDTLDKISDVSALIPYIGPALNISNVRRGNFTEAFAVTGVTILLEAFPEFTIPALGAFVIYSKV---QERNEIIKTI
BoNT D  IMKKDTLDKISDVSVIIPYIGPALNIGNSALRGNFKQAFATAGVAFLLEGFPEFTIPALGVFTFYSSI---QEREKIIKTI
BoNT E  ANQKSTVDKIADISIVVPYIGLALNIGNEAQKGNFKDALELLGAGILLEFEPELLIPTILVFTIKSFLGSSDNKNKVIKAI
BoNT F  ATQKSTFDKIADISLVVPYVGLALNIGNEVQKENFKEAFELLGAGILLEFVPELLIPTILVFTIKSFIGSSENKNKIIKAI
BoNT G  STQKSTIDKVSDVSIIIPYIGPALNVGNETAKENFKNAFEIGGAAILMEFIPELIVPIVGFFTLESYVG---NKGHIMTI

BoNT A  DNALSKRNEKWDEVYKYIVTNWLAKVNTQIDLIRKKMKEALENQAEATKAIINYQYNQYTEEEKNNINF--NIDDLSSKLN
BoNT B  DNALTKRNEKWSDMYGLIVAQWLSTVNTQFYTIKEGMYKALNYQAQALKFIIKYRYNIYSEKEKSNINI--DFNDINSKLN
BoNT C  DNCLEQRIKRWKDSYEWMMGTWLSRIITQFNNISYQMYDSLNYQAGAIKAKIDLEYKKYSGSDKENIKS--QVENLKNSLD
BoNT D  ENCLEQRVKRWKDSYQWMLVSNWLSRITTQFNHINYQMYDSLSYQADAIKAKIDLEYKKYSGSDKENIKS--QVENLKNSLD
BoNT E  NNALKERDEKWKEVYSFIVSNWMTKINTQFNKRKEQMYQALQNQVNAIKTIIESKYNSYTLEEKNELTNKYDIKQIENELN
BoNT F  NNSLMERETKWKEIYSWIVSNWLTRINTQFNKRKEQMYQALQNQVDAIKTVIEYKYNNYTSDERNRLESEYNINNMIREELN
BoNT G  SNALKKRDQKWTDMYGLIVSQWLSTVNTQFYTIKERMYNALNNQSQATEKIIEDQYNRYSEEDKMNINI--DFNDIDFKLN

BoNT A  ESINKAMININKFLNQCSVSYLMNSMIPYGVKRLEDFDASLKDALLKVIYDNRGT-LIGQVDRLKDKVNNTLSTDIPFQLS
BoNT B  EGINQAIDNINNFINGCSVSYLMKKMIPLAVEKLLDFDNTLKKNLNYIDENKLY-LICSAEYEKSKVNKYLKTIMPFDLS
BoNT C  VKISEAMNNINKFIRECSVTYLFKNMLPKVIDELNEFDRNTKAKLINLID-SHNIILVGEVDKLKAKVNNSFQNTIPFNIF
BoNT D  VKISEAMNNINKFIRECSVTYLFKNMLPKVIDELNKFDLRTKTELINLID-SHNIILVGEVDKLKAKVNESFENTMPFNIF
BoNT E  QKVSIAMNNIDRFLTESSISYLMKLINEVKINKLREYDENVKTYLLNYIIQHGSI-LGESQQELNSMVTDTLNNSIPFELS
BoNT F  KEVSLAMENIERFITESSIFYLMKLINEAKVSKLREYDEGVKEYLLDYISEHRSI-LGNSVQELNDLVTSTLNNSIPFELS
BoNT G  QSINLAINNIDDFINQCSISYLMNRMIFLAVKKLKDFDDNLKRDLLEYIDTNELY-LLDEVNILKSKVNRHLKDSIPFDLS

Receptor Binding Domain

BoNT A  KYVDNQRLSTETFIKNTINTSILNLRYESNHLIDLSRYASKINIGSKVNEDPIDKNQIQLFN--LESSKIEVILKNALV
BoNT B  IYTNDTILIEMFNKYNSEILNNIILNLRYKDNNLIDLSGYGAKVEVYDGVELN--DKNQFKLTSSAN--SKIRVTQNQNII
BoNT C  SYTNNSLLKDIINEYFNNINDSKILSLQNRKNTLVDTSGYNAEVSEEGDVQLNPIFPFDFKLGSSGEDRGKVIVTQNENLV
BoNT D  SYTNNSLLKDIINEYFNSINDSKILSLQNKKNALVDTSGYNAEVRVGDNVQLNTIYTNDFKLSSSGD---KIIYNLNNNIL
BoNT E  SYTDDKILISYFNKFFKRIKSSSVLNMRYKNDKYVDTSGYDSNININGDVYKYPTNKNQFGIYN--DKLSEVNISQDYII
BoNT F  SYTNDKILILYFNKLYKKIKDNSILDMRYENNKFIDISGYGSNISINGDVYIYSTNRNQFGIYSS--KPSEVNIAQNNDII
BoNT G  LYTKDTILIQVFNNYISNISSNAILSLSYRGGRLIDSSGYGATMNVGSDVIFNDIGNGQFKLNNSEN--SNITAHQSKFVV
```

Light Chain

```
BoNT A  MPFVNKQFNYKDPVN

FIG. 2B

```
BoNT A  WDIFFSPSEDNFTNDLNKGEEITSDTNIEAAEEWISLDLIQQYYLTFNFDNEPENISIENLSSDIIGQLELMPNIERFPNG-
BoNT B  EDLFFIADKNSFSDDLSKNERTEYNTQSNYIENDFPINEL---ILDTDLISKIE-LPSENTESLTDFNV-DVPVVEKQPAI-
BoNT C  TDLPFIGDISDVKTDIFLRKDTNEETEVIYYPDNVSVDQV---ILSKNTSEHGQ-L--DLTYPSIDSESEILPG-ENQVFYD
BoNT D  NRLPYVADKDSISQEIFENKIITDETNVQNYSDNFSLDES---ILDGQVPINEIV--DPTLPNVNMEPLNLPG-EEIVFYD
BoNT E  GELFFVASENSYNLDNINTPKEIDDTVTSNNNYENDLDQV---ILNFNSESAPG-LSDEKLNLTIQND-AYIPKYDSNGTSD
BoNT F  RELFFVASESSYNENDINTPKEIDDTTNLNNNYRNNLDEV---ILDYNSETIPQ-ISNQTLNTLVQDD-SIVPRYDSNGTSE
BoNT G  EDLFFIANKDSFSKDLAKAETTAYNTQNNTIENNFSIDQL---ILDNDLSSGID-LPNENTEPFTNFDDIDIPVYIKQSAL-

BoNT A  -KKYELDKYTMFHYLRAQEFEHGKSRIALTNSVNEALLNPSRVYTFFSSDIVKKVNKATEAAMFLGWVEQLVYDFTDETSEV
BoNT B  -KKIFTDENTIEQYLYSQTFPLDIRDISLTSSFDDALLFSNKVYSFFSMDYIKTANKVVEAGLFAGWVKQIVNDFVIEANKS
BoNT C  NRTQNVDYLNSYYILESQKLSDNVEDFTETRSIEEALDNSAKVYTYFPT-LANKVNAGVQGGLFLMWANDVVEDFTTNILRK
BoNT D  DITKYVDYLNSYYILESQKLSNNVENITLTTSVEEALGISNKIYTFLPS-LAEKVNKGVQAGLFLNTANEVVEDFTTNIMKK
BoNT E  IEQIDVNELNVFFYLDAQKVPEGENXNVLTSSIDTALLEQPKIYTFFSSEFINNVNKPVQAALFVSTIQQVLVDFTTEANQK
BoNT F  IEEHNVVDLNVFFYNLAQKVPEGETNISLTSSIDTRLSEESQVYTFFSSEFINTINKPVEAALFISTINQVIRDFTTEATQK
BoNT G  -KKIFVDGDSLFFILEAQTFPSNIENLQLTNSLNDALRNNNKVYTFFSTNLVEKANTVVGASLFVNKVKGVIDDFTSESTQK

BoNT A  STTDKIADITIIIPYIGPALNIGNMLYKDDFVGALIFSGAVILLEFIPEIAIPVLGTFALVSYI---ANKVLTVQTIDNALS
BoNT B  NTMDKIADISLIVPYIGLALNVGNETAKGNFENAFEIAGASILLEFIPELLIPVVGAFLLESYI---DNKNKIIKTIDNALF
BoNT C  DTLDKISDVSAIIPYIGPALNISNSVRRGNFTEAFAVTGVTILLEAFPEFTIPALGAFVIISKV---QERNELIKTIDNCLE
BoNT D  DTLDKISDVSVIIPYIGPALNIGNSALRGNFKQAFATAGVAFLLEGFPEFTIPALGVFTFYSSI---QEREKIIKTIENCLE
BoNT E  STVDKIADISIVVPYIGLALNIGNEAQKGNFKDALPLLGAGILLEFEPELLIPTILVFTIKSFLGSSDNKNKVIKAIMNALK
BoNT F  STFDKIADISLVVPYVGLALNIGNEVQKENFKEAFELLGAGILLEFVPELLIPTILVFTIKSFIGSSENKNKIIKAIMNSLM
BoNT G  STIDKVSDVSIIIPYIGPALNVGNETAKENFKNAFEIGGAAILMEFIPELIVPIVGFFTLESYVG---NKGHIIMTISNALK

BoNT A  KENEKWDEVYKYIVTNWLAKVNTQIDLIRKKMKEAIENQAEATKAIINYQYNQYTEEEKNNINF--NIDDLSSKLNESTNKA
BoNT B  KENEKWSDMYGLIVAQWLSTVNTQFYTIKEGMYKALNYQAQALKEIIKYRYNIYSEKEKSNINI--DFNDINSKLNEGINQA
BoNT C  QRIKRWKDSYEWMMGTWLSRIITQFNNISYQMYDSLNYIQAGAIKAKNDLEYKKYSGSDKENIKS--QVENLKNSLDVKISEA
BoNT D  QEVKRWKDSYQWMVSNWLSRIITQFNBINYQMYDSLSYIQADAIKAKNIDLEYKKYSGSDKENIKS--QVENLKNSLDVKISEA
BoNT E  ERDEKWKEVYSFIVSNWMTKINTQFNKRKEQMYQALQNQVNAIKTIIESKYNSYTLEEKNELTNKYDIKQIENELNQKVSIA
BoNT F  ERETKWKEIYSWIVSNWLTRINTQFNKRKEQMYQALQNQVDAIKTVIEYKYNNVTSDERNRLESEYNINNIREELNKKVSLA
BoNT G  KEDQKNTDMYGLIVSQWLSTVNTQFYTIKERMYNALNNQSQAIEKIIEDQYNRYSEEDKMNINI--DFNDIDFKLNQSINLA

BoNT A  MININKFLNQCSVSYLMNSMIPYGVKRLEDFDASLKDALLKYIYDNRGT-LIGQVDRLKDKVNNTLSTDIPFQLSKYVDNQR
BoNT B  IDMINNFINGCSVSYLMKKMIPLAVEKLLDFDNTLKNLLNYIDENKLY-LIGSAEYEKSKVNKYLKTIMPFDLSIYTNDTI
BoNT C  MNNINKFIRECSVTYLFKNMLPKVIDELNEFDRNTNAKLINLID-SENTILVGEVDRLKAKVNNSFQNTLPENIFSYTNNSL
BoNT D  MNNINKFIRECSVTYLFKNMLPKVIDELNKFDLRTKTELINLID-SHNIILVGEVDRLKAKVNESFENTMPENIFSYTNNSL
BoNT E  MNNIDRFLTESSISYLMKLINEVKINKLREYDENVKTYLLNYIIQEGSI-LGESQQELNSMVTDTINNYSIPFKLSSYTDDKI
BoNT F  MEDIERFITESSIFYLMKLINEARVSKLREYDEGVKETLLDYISEERSI-LGNSVQELNDLVTSTLNNSIPFELSSYTNDKI
BoNT G  IENIDDFINQCSISYLMNRMIPLAVKKLKDFDDNLRRDLLEYIDTNELT-LLDEVNILKSKVNRELKDSIPFDLSIYTKDTI

Receptor Binding Domain ➡

BoNT A  ILSTFTEYIKNIINTSILNLRYESNELIDLSRYASKINIGSKVNFDPIDKNQIQLFN--LESSKIEVILKNAIVYNSMYENF
BoNT B  LIEMENKYNSEILNNIILNLRYKDNNLIDLSGYGAKVEVYDGVELN--DKNQFKLTSSAN--SKIRVTQNQNIIFNSVFLDF
BoNT C  LKDIINEYFNNINDSKILSLQNRKNTLVDTSGYNALYSEEGDVQLNPIFPFDFKIGSSGEDRGKVIVTQNENIVYNSMYESF
BoNT D  LKDIINEYFNSINDSKILSLQNKKMALVDTSGYNLEVRVGDNVQLNTIYTNDFKISSSGD---KIIVLNNNILYSAIVENS
BoNT E  LISYFNKFFNNIKSSSVLNMRYKNDKYVDTSGYDSNININGDVYKYPTNKNQFGIYN--DKLSEVNIGQNDYIIPDNKYKNF
BoNT F  LILYFNKLYNNIKDNSILDMRYENNKFIDISGYGSNISINGDVYIYSTNRNQFGIYSS--KPSEVNIAQNNDIINGRYQNE
BoNT G  LIQVFNNYISNISSNAILSLSYRGGRLIDSSGYGATMNVGSDVIFNDIGNGQFKINNSEN--SNITAHQSKFVVIDSMFDNF
```

FIG. 2C

```
BoNT A  STSFWIRIPKYFNSISL---NNEYTIINCMENN-SGWKVSLNYGEIIWTLQDTQEIKQRVVFKYSQMINISDYINRWIFVTI
BoNT B  SVSFWIRIPKYKNDGIQNYIFNEYTIINCMKNN-SGWKISIRGNRIIWTLIDINGKTKSVFFEYNIREDISEYINRWFFVTI
BoNT C  SISFWIRINK-WVSNLP-----GYTIIDSVKNL-SGWSIGIISNFLVFTLKQNEDSEQSINFSYDISNNAFGY-NKWFFVTV
BoNT D  SVSFWIKISKDLTNSH----NEYTIINSIEQN-SGWKLCIRNGNIEWILQDVNRKYKSLIFDYSESLSHTGYTNKWFFVTI
BoNT E  SISFWVRIPNYDNKIVN--VNNEYTIINCMRDHNSGWKVSLNHNEIIWTLQDNAGINQKLAFNYGNANGISDYINKWIFVTI
BoNT F  SISFWVRIPKYFNKVNL---NNEYTIIDCIRNNNSGWKISLNYNKIIWTLQDTAGNNQKLVFNYTQMISISDYINKWIFVTI
BoNT G  SINFWVRTPKYNNNDIQTYLQNEYTIISCIKND-SGWKVSIKGNRIIWTLIDVNAKSKSIFFEYSIKDNISDYINKWFSITI

BoNT A  TNNRLNNSKIYINGRLIDQKPISNLGNTEASNNIMFKLDGCRDT--------BRYIFIKYFNLFDKEINEKEIKDLYDNQSN
BoNT B  TND-LNNAKIYINGKLESNTDIKDIREVIANGEIIFKLDGDIDRT--------QFIYMKYFSITNTELSQSNIEERYKIQSY
BoNT C  TNNMMGNMKIYINGKLIDTIKVKELTGINFSKTITFEINKIPDIGLITSDSDNINMWIRDFYIFAKELDGKDINILFNSLQY
BoNT D  TNNIMGYMKLIINGELKQSQKIEDLDEVKLDKTIVFGIDENIDE--------NQMLWIRDFNIFSKELSNEDINIVIEGQIL
BoNT E  TNDRLGDSKLYINGNLIDQKSIINLGNIEVSDNILFKIVNCSIT---------RYIGIRYFNIFDKELDETEIQTLYSNEPN
BoNT F  TNNRLGNSRIYINGNLIDEKSISNLGDIEVSDNILFKIVGCNDT---------RIVGIRYFKVFDTELGKTEIETLYSDEPD
BoNT G  TNDRLGNANIYINGSLKKSEKIINLDRINSSNDIDFKLINCTDT--------TKFVNIKDFNIFGRELNATEVSSLIWIQSS

BoNT A  SGILKDFWGDYLQYDKPIYMLNLYDPNKIVDVNNVGIRGYMILKGPR-GSVMTTN-IVLNSS-----LYRGTKFIIKKYIASG
BoNT B  SEYLKDFWGNPLMYNKEYYMFNAGNKNSYIKLKKDSPVG--EILT-RSKYNQNSK--VILYRD----LYIGEKFIIRRKSNS
BoNT C  TNVVKDYWGNDLRYNKEYYMYNI----DFLNR--------YMYANS-RQIVFNTRR----NNND----FNEGYKIIIKRIRGN
BoNT D  RNVIKDYWGNPLKTDIEYYIIND----NYIDR---------YIAPE-SNVLVLVR--YPDRSK----LVTGNPITIKSVSDK
BoNT E  TNILKDFWGNYLLYDKEYYLLNVLKPNNYFIDRRKDSTL----SINNIRSTILLANR--------LYSGIFVKIQRVNNS
BoNT F  PSILKDFWGNYLLYNKRYYLLNLLRTDKSITQNSN----FLNINQQR-GVYIQKPN-IFSNTR-----LYTGVEVIIRKNGST
BoNT G  TNTLKDFWGNPLRYDTQYYLFNQGMQNIYIK--------MFSKASMGET---APRTNFNNAAINYQNLYLGLRFIIKKASNS

BoNT A  N----KDNIVRNNDRVFIFV-VVKNKEYRL-----ATNASQAGV----EKILSALEIPDVGNLS------QVVVMK--------S
BoNT B  QSI--NDDIVRKEDYIYLDF-FNLNQEWRV---------YTYKIFK-KEEEKLFLAPISDSDEFYNTI---QIKEYD--------
BoNT C  T----NDTRVRGGDILYFDM-TINNKAFNLFMKNETMYADNHST----EDIYAIGLRE---------QTKDINDNIIFQIQ
BoNT D  NP---YSRILNGDNIILHM-LYNSRKYMIIRDTDIIYATQGG-----ECSQNCVYALKL---------QSNLGNYIGIGIFSI
BoNT E  ST--NDNLVRKNDQVYINFVASKTHLFPL--------YADTATTNK-EKTIKISSSGNREN------QVVVNN--------
BoNT F  DIS-NTDNFVRKNDLAYINV-VDRDVEYRL--------YADIS-IAKP-EKIIKLIRTSNSNNSLG----QIIVMD--------
BoNT G  RNINNDNIVREGDYIYLNIDNISDESYRV-------YVLVNS--K---EIQTQLFLAPINDDPTFYDVLQIKKIY--------

BoNT A  KNDQGITNKCKMNL---------QDNMGND-IGFIGFHQFNNI---------AKLVASNWYNRQI--ERSSRE---------L
BoNT B  ---EQPTYSC--QLL---FKK-DEESTDEIGLIGIHRFYESGI-VFEEYKDYFCISKWYLK----EVKRKPINLK-----L
BoNT C  PMNNTYYIAS--QIFKSNFN---GEN----ISGICSIG----------TYRFRLGGDNY-RHNYLVPTVKQGNYASLTEST
BoNT D  KNIVSKNKYC-SQIF-SSFR----EK----TMLLADI--------YKPWRFSFKNA---YT----PVAVNYETKLI-ST
BoNT E  -----SVGNNYMN----FKNNNGN----IGLLGFKA---------DTVVASTWY---YTEMRDHIN------SN
BoNT F  -----SIGNNTMN----FQNNIGGY----IGLLGFHS---------NNLVASSNY----YNNIRKNTS------SN
BoNT G  ---EKTTYNC--QILC-------EKDIKTFGLFGIGKFVKDYGYYWDTIDNIFCISQWYLRRISENINKLR---------L

BoNT A  GCSWEFIPVDDGWGERPL
BoNT B  GCNWQFIPKDEGWTE
BoNT C  STEWGFVPVSE
BoNT D  SSFWKFISRDPGWVE
BoNT E  GCFWNFISEEHGWQEK
BoNT F  GCFWSFISKEHGWQEN
BoNT G  GCNWQFIPVDEGWTE
```

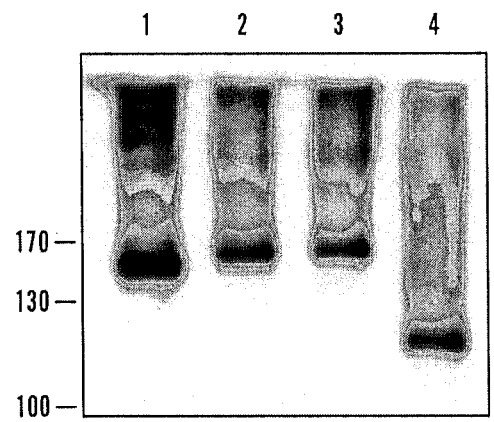
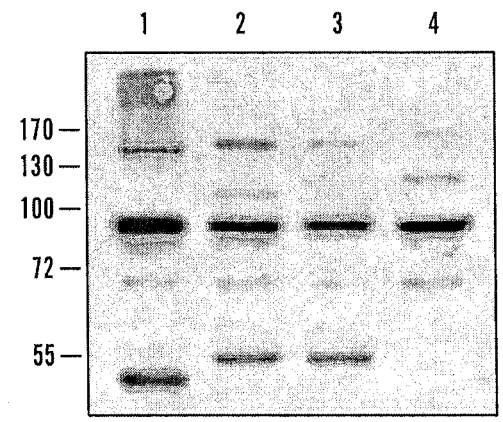
*FIG. 8A*  *FIG. 8B*
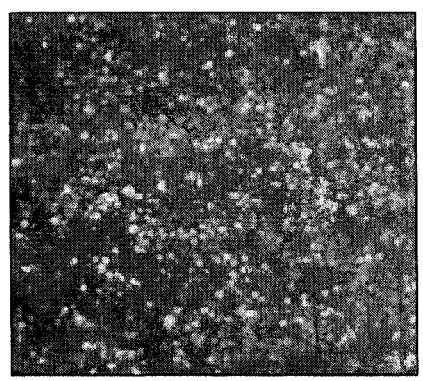
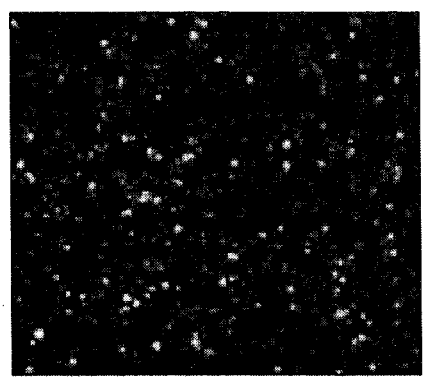
*FIG. 8C*  *FIG. 8D*

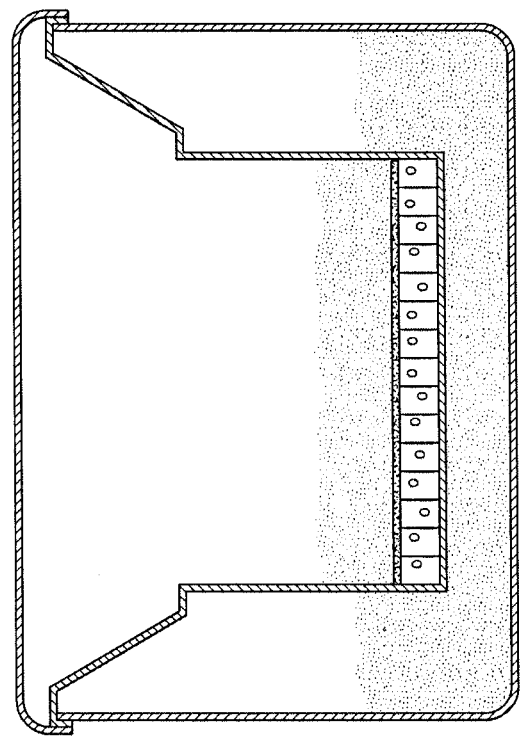
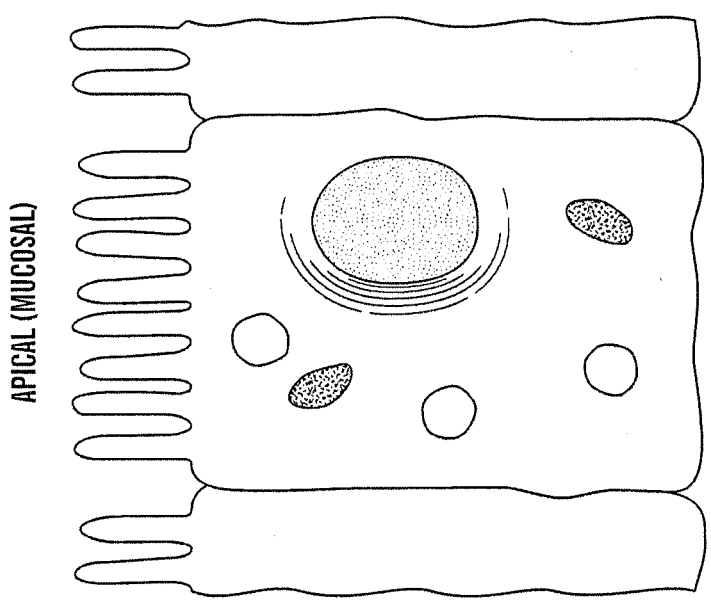
FIG. 10B TRANSWELL APPARATUS
FIG. 10A APICAL (MUCOSAL) / BASAL (SEROSAL)

FIG. 11A

```
BoNT A     MPFVNKQFNYKDPVNGVDIAYIKIPNAGQMQP

FIG. 11B

```
BoNT A    LNKGEEITSDTNIEAAEENISLDLIQQYYLTFNFDNEPENISIENLSSDIIGQLELMPNIERFPNGKKYELDKYTMFHYL
Chimera 1 LNKGEEITSDTNIEAAEENISLDLIQQYYLTFNFDNEPENISIENLSSDIIGQLELMPNIERFPNGKKYELDKYTMFHYL
Chimera 2 LNKGEEITSDTNIEAAEENISLDLIQQYYLTFNFDNEPENISIENLSSDIIGQLELMPNIERFPNGKKYELDKYTMFHYL
Chimera 3 LNKGEEITSDTNIEAAEENISLDLIQQYYLTFNFDNEPENISIENLSSDIIGQLELMPNIERFPNGKKYELDKYTMFHYL
Chimera 4 LNKGEEITSDTNIEAAEENISLDLIQQYYLTFNFDNEPENISIENLSSDIIGQLELMPNIERFPNGKKYELDKYTMFHYL
Chimera 5 LNKGEEITSDTNIEAAEENISLDLIQQYYLTFNFDNEPENISIENLSSDIIGQLELMPNIERFPNGKKYELDKYTMFHYL
Chimera 6 LNKGEEITSDTNIEAAEENISLDLIQQYYLTFNFDNEPENISIENLSSDIIGQLELMPNIERFPNGKKYELDKYTMFHYL
Chimera 7 LNKGEEITSDTNIEAAEENISLDLIQQYYLTFNFDNEPENISIENLSSDIIGQLELMPNIERFPNGKKYELDKYTMFHYL
Chimera 8 LNKGEEITSDTNIEAAEENISLDLIQQYYLTFNFDNEPENISIENLSSDIIGQLELMPNIERFPNGKKYELDKYTMFHYL
Chimera 9 LNKGEEITSDTNIEAAEENISLDLIQQYYLTFNFDNEPENISIENLSSDIIGQLELMPNIERFPNGKKYELDKYTMFHYL BoNT A    RAQEFEHGKSRIALTNSVNEALLNPSRVYTFFSSDYVKKVNKATEAAMFLGWVEQLVYDFTDETSEVSTTDKIADITIII
Chimera 1 RAQEFEHGKSRIALTNSVNEALLNPSRVYTFFSSDYVKKVNKATEAAMFLGWVEQLVYDFTDETSEVSTTDKIADITIII
Chimera 2 RAQEFEHGKSRIALTNSVNEALLNPSRVYTFFSSDYVKKVNKATEAAMFLGWVEQLVYDFTDETSEVSTTDKIADITIII
Chimera 3 RAQEFEHGKSRIALTNSVNEALLNPSRVYTFFSSDYVKKVNKATEAAMFLGWVEQLVYDFTDETSEVSTTDKIADITIII
Chimera 4 RAQEFEHGKSRIALTNSVNEALLNPSRVYTFFSSDYVKKVNKATEAAMFLGWVEQLVYDFTDETSEVSTTDKIADITIII
Chimera 5 RAQEFEHGKSRIALTNSVNEALLNPSRVYTFFSSDYVKKVNKATEAAMFLGWVEQLVYDFTDETSEVSTTDKIADITIII
Chimera 6 RAQEFEHGKSRIALTNSVNEALLNPSRVYTFFSSDYVKKVNKATEAAMFLGWVEQLVYDFTDETSEVSTTDKIADITIII
Chimera 7 RAQEFEHGKSRIALTNSVNEALLNPSRVYTFFSSDYVKKVNKATEAAMFLGWVEQLVYDFTDETSEVSTTDKIADITIII
Chimera 8 RAQEFEHGKSRIALTNSVNEALLNPSRVYTFFSSDYVKKVNKATEAAMFLGWVEQLVYDFTDETSEVSTTDKIADITIII
Chimera 9 RAQEFEHGKSRIALTNSVNEALLNPSRVYTFFSSDYVKKVNKATEAAMFLGWVEQLVYDFTDETSEVSTTDKIADITIII BoNT A    PYIGPALNIGNMLYKDDFVGALIFSGAVILLEFIPEIAIPVLGTFALVSYIANKVLTVQTIDNALSKRNEKWDEVYKYIV
Chimera 1 PYIGPALNIGNMLYKDDFVGALIFSGAVILLEFIPEIAIPVLGTFALVSYIANKVLTVQTIDNALSKRNEKWDEVYKYIV
Chimera 2 PYIGPALNIGNMLYKDDFVGALIFSGAVILLEFIPEIAIPVLGTFALVSYIANKVLTVQTIDNALSKRNEKWDEVYKYIV
Chimera 3 PYIGPALNIGNMLYKDDFVGALIFSGAVILLEFIPEIAIPVLGTFALVSYIANKVLTVQTIDNALSKRNEKWDEVYKYIV
Chimera 4 PYIGPALNIGNMLYKDDFVGALIFSGAVILLEFIPEIAIPVLGTFALVSYIANKVLTVQTIDNALSKRNEKWDEVYKYIV
Chimera 5 PYIGPALNIGNMLYKDDFVGALIFSGAVILLEFIPEIAIPVLGTFALVSYIANKVLTVQTIDNALSKRNEKWDEVYKYIV
Chimera 6 PYIGPALNIGNMLYKDDFVGALIFSGAVILLEFIPEIAIPVLGTFALVSYIANKVLTVQTIDNALSKRNEKWDEVYKYIV
Chimera 7 PYIGPALNIGNMLYKDDFVGALIFSGAVILLEFIPEIAIPVLGTFALVSYIANKVLTVQTIDNALSKRNEKWDEVYKYIV
Chimera 8 PYIGPALNIGNMLYKDDFVGALIFSGAVILLEFIPEIAIPVLGTFALVSYIANKVLTVQTIDNALSKRNEKWDEVYKYIV
Chimera 9 PYIGPALNIGNMLYKDDFVGALIFSGAVILLEFIPEIAIPVLGTFALVSYIANKVLTVQTIDNALSKRNEKWDEVYKYIV BoNT A    TNWLAKVNTQIDLIRKKMKEALENQAEATKAIINYQYNQYTEEEKNNINFNIDDLSSKLNESINKAMININKFLNQCSVS
Chimera 1 TNWLAKVNTQIDLIRKKMKEALENQAEATKAIINYQYNQYTEEEKNNINFNIDDLSSKLNESINKAMININKFLNQCSVS
Chimera 2 TNWLAKVNTQIDLIRKKMKEALENQAEATKAIINYQYNQYTEEEKNNINFNIDDLSSKLNESINKAMININKFLNQCSVS
Chimera 3 TNWLAKVNTQIDLIRKKMKEALENQAEATKAIINYQYNQYTEEEKNNINFNIDDLSSKLNESINKAMININKFLNQCSVS
Chimera 4 TNWLAKVNTQIDLIRKKMKEALENQAEATKAIINYQYNQYTEEEKNNINFNIDDLSSKLNESINKAMININKFLNQCSVS
Chimera 5 TNWLAKVNTQIDLIRKKMKEALENQAEATKAIINYQYNQYTEEEKNNINFNIDDLSSKLNESINKAMININKFLNQCSVS
Chimera 6 TNWLAKVNTQIDLIRKKMKEALENQAEATKAIINYQYNQYTEEEKNNINFNIDDLSSKLNESINKAMININKFLNQCSVS
Chimera 7 TNWLAKVNTQIDLIRKKMKEALENQAEATKAIINYQYNQYTEEEKNNINFNIDDLSSKLNESINKAMININKFLNQCSVS
Chimera 8 TNWLAKVNTQIDLIRKKMKEALENQAEATKAIINYQYNQYTEEEKNNINFNIDDLSSKLNESINKAMININKFLNQCSVS
Chimera 9 TNWLAKVNTQIDLIRKKMKEALENQAEATKAIINYQYNQYTEEEKNNINFNIDDLSSKLNESINKAMININKFLNQCSVS BoNT A    YLMNSMIPYGVKRLEDFDASLKDALLKYIYDNRGTLIGQVDRLKDKVNNTLSTDIPFQLSKYVDNQRLLSTFTEYIKNII
Chimera 1 YLMNSMIPYGVKRLEDFDASLKDALLKYIYDNRGTLIGQVDRLKDKVNNTLSTDIPFQLSKYVDNQRLLSTFTEYIKNII
Chimera 2 YLMNSMIPYGVKRLEDFDASLKDALLKYIYDNRGTLIGQVDRLKDKVNNTLSTDIPFQLSKYVDNQRLLSTFTEYIKNII
Chimera 3 YLMNSMIPYGVKRLEDFDASLKDALLKYIYDNRGTLIGQVDRLKDKVNNTLSTDIPFQLSKYVDNQRLLSTFTEYIKNII
Chimera 4 YLMNSMIPYGVKRLEDFDASLKDALLKYIYDNRGTLIGQVDRLKDKVNNTLSTDIPFQLSKYVDNQRLLSTFTEYIKNII
Chimera 5 YLMNSMIPYGVKRLEDFDASLKDALLKYIYDNRGTLIGQVDRLKDKVNNTLSTDIPFQLSKYVDNQRLLSTFTEYIKNII
Chimera 6 YLMNSMIPYGVKRLEDFDASLKDALLKYIYDNRGTLIGQVDRLKDKVNNTLSTDIPFQLSKYVDNQRLLSTFTEYIKNII
Chimera 7 YLMNSMIPYGVKRLEDFDASLKDALLKYIYDNRGTLIGQVDRLKDKVNNTLSTDIPFQLSKYVDNQRLLSTFTEYIKNII
Chimera 8 YLMNSMIPYGVKRLEDFDASLKDALLKYIYDNRGTLIGQVDRLKDKVNNTLSTDIPFQLSKYVDNQRLLSTFTEYIKNII
Chimera 9 YLMNSMIPYGVKRLEDFDASLKDALLKYIYDNRGTLIGQVDRLKDKVNNTLSTDIPFQLSKYVDNQRLLSTFTEYIKNII BoNT A    NTSILNLRYESNHLIDLSRYASKINIGSKVNFDPIDKNQIQLFNLESSKIEVILKNAIVYNSMYENFSTSFWIRIPKYFN
Chimera 1 NTSILNLRYESNHLIDLSRYASKINIGSKVNFDPIDKNQIQLFNLESSKIEVILKNAIVYNSMYENFSTSFWIRIPKYFN
Chimera 2 NTSILNLRYESNHLIDLSRYASKINIGSKVNFDPIDKNQIQLFNLESSKIEVILKNAIVYNSMYENFSTSFWIRIPKYFN
Chimera 3 NTSILNLRYESNHLIDLSRYASKINIGSKVNFDPIDKNQIQLFNLESSKIEVILKNAIVYNSMYENFSTSFWIRIPKYFN
Chimera 4 NTSILNLRYESNHLIDLSRYASKINIGSKVNFDPIDKNQIQLFNLESSKIEVILKNAIVYNSMYENFSTSFWIRIPKYFN
Chimera 5 NTSILNLRYESNHLIDLSRYASKINIGSKVNFDPIDKNQIQLFNLESSKIEVILKNAIVYNSMYENFSTSFWIRIPKYFN
Chimera 6 NTSILNLRYESNHLIDLSRYASKINIGSKVNFDPIDKNQIQLFNLESSKIEVILKNAIVYNSMYENFSTSFWIRIPKYFN
Chimera 7 NTSILNLRYESNHLIDLSRYASKINIGSKVNFDPIDKNQIQLFNLESSKIEVILKNAIVYNSMYENFSTSFWIRIPKYFN
Chimera 8 NTSILNLRYESNHLIDLSRYASKINIGSKVNFDPIDKNQIQLFNLESSKIEVILKNAIVYNSMYENFSTSFWIRIPKYFN
Chimera 9 NTSILNLRYESNHLIDLSRYASKINIGSKVNFDPIDKNQIQLFNLESSKIEVILKNAIVYNSMYENFSTSFWIRIPKYFN
```

FIG. 11C

```
BoNT A     SISLNNEYTIINCMENNSGWKVSLNYGEIIWTLQDTQEIKQRVVFKYSQMINISDYINRWIFVTITNNRLNNSKIYINGR
Chimera 1  SISLNNEYTIINCMENNSGWKVSLNYGEIIWTLQDTQEIKQRVVFKYSQMINISDYINRWIFVTITNNRLNNSKIYINGR
Chimera 2  SISLNNEYTIINCMENNSGWKVSLNYGEIIWTLQDTQEIKQRVVFKYSQMINISDYINRWIFVTITNNRLNNSKIYINGR
Chimera 3  SISLNNEYTIINCMENNSGWKVSLNYGEIIWTLQDTQEIKQRVVFKYSQMINISDYINRWIFVTITNNRLNNSKIYINGR
Chimera 4  SISLNNEYTIINCMENNSGWKVSLNYGEIIWTLQDTQEIKQRVVFKYSQMINISDYINRWIFVTITNNRLNNSKIYINGR
Chimera 5  SISLNNEYTIINCMENNSGWKVSLNYGEIIWTLQDTQEIKQRVVFKYSQMINISDYINRWIFVTITNNRLNNSKIYINGR
Chimera 6  SISLNNEYTIINCMENNSGWKVSLNYGEIIWTLQDTQEIKQRVVFKYSQMINISDYINRWIFVTITNNRLNNSKIYINGR
Chimera 7  SISLNNEYTIINCMENNSGWKVSLNYGEIIWTLQDTQEIKQRVVFKYSQMINISDYINRWIFVTITNNRLNNSKIYINGR
Chimera 8  SISLNNEYTIINCMENNSGWKVSLNYGEIIWTLQDTQEIKQRVVFKYSQMINISDYINRWIFVTITNNRLNNSKIYINGR
Chimera 9  SISLNNEYTIINCMENNSGWKVSLNYGEIIWTLQDTQEIKQRVVFKYSQMINISDYINRWIFVTITNNRLNNSKIYINGR BoNT A     LIDQKPISNLGNIHASNNIMFKLDGCRDTHRYIWIKYFNLFDKELNEKEIKDLYDNQSNSGILKDFWGDYLQYDKPYYML
Chimera 1  LIDQKPISNLGNIHASNNIMFKLDGCRDTHRYIWIKYFNLFDKELNEKEIKDLYDNQSNSGILKDFWGDYLQYDKPYYML
Chimera 2  LIDQKPISNLGNIHASNNIMFKLDGCRDTHRYIWIKYFNLFDKELNEKEIKDLYDNQSNSGILKDFWGDYLQYDKPYYML
Chimera 3  LIDQKPISNLGNIHASNNIMFKLDGCRDTHRYIWIKYFNLFDKELNEKEIKDLYDNQSNSGILKDFWGDYLQYDKPYYML
Chimera 4  LIDQKPISNLGNIHASNNIMFKLDGCRDTHRYIWIKYFNLFDKELNEKEIKDLYDNQSNSGILKDFWGDYLQYDKPYYML
Chimera 5  LIDQKPISNLGNIHASNNIMFKLDGCRDTHRYIWIKYFNLFDKELNEKEIKDLYDNQSNSGILKDFWGDYLQYDKPYYML
Chimera 6  LIDQKPISNLGNIHASNNIMFKLDGCRDTHRYIWIKYFNLFDKELNEKEIKDLYDNQSNSGILKDFWGDYLQYDKPYYML
Chimera 7  LIDQKPISNLGNIHASNNIMFKLDGCRDTHRYIWIKYFNLFDKELNEKEIKDLYDNQSNSGILKDFWGDYLQYDKPYYML
Chimera 8  LIDQKPISNLGNIHASNNIMFKLDGCRDTHRYIWIKYFNLFDKELNEKEIKDLYDNQSNSGILKDFWGDYLQYDKPYYML
Chimera 9  LIDQKPISNLGNIHASNNIMFKLDGCRDTHRYIWIKYFNLFDKELNEKEIKDLYDNQSNSGILKDFWGDYLQYDKPYYML BoNT A     NLYDPNKYIVDVNNVGIRGYMYLKGPRGSVMTTNIYLNSSLYRGTKFIIKKYASGNKDNIVRNNDRVYINVVVKNKEYRLA
Chimera 1  NLYDPNKYIVDVNNVGIRGYMYLKGPRGSVMTTNIYLNSSLYRGTKFIIKKYASGNKDNIVRNNDRVYINVVVKNKEYRLA
Chimera 2  NLYDPNKYIVDVNNVGIRGYMYLKGPRGSVMTTNIYLNSSLYRGTKFIIKKYASGNKDNIVRNNDRVYINVVVKNKEYRLA
Chimera 3  NLYDPNKYIVDVNNVGIRGYMYLKGPRGSVMTTNIYLNSSLYRGTKFIIKKYASGNKDNIVRNNDRVYINVVVKNKEYRLA
Chimera 4  NLYDPNKYIVDVNNVGIRGYMYLKGPRGSVMTTNIYLNSSLYRGTKFIIKKYASGNKDNIVRNNDRVYINVVVKNKEYRLA
Chimera 5  NLYDPNKYIVDVNNVGIRGYMYLKGPRGSVMTTNIYLNSSLYRGTKFIIKKYASGNKDNIVRNNDRVYINVVVKNKEYRLA
Chimera 6  NLYDPNKYIVDVNNVGIRGYMYLKGPRGSVMTTNIYLNSSLYRGTKFIIKKYASGNKDNIVRNNDRVYINVVVKNKEYRLA
Chimera 7  NLYDPNKYIVDVNNVGIRGYMYLKGPRGSVMTTNIYLNSSLYRGTKFIIKKYASGNKDNIVRNNDRVYINVVVKNKEYRLA
Chimera 8  NLYDPNKYIVDVNNVGIRGYMYLKGPRGSVMTTNIYLNSSLYRGTKFIIKKYASGNKDNIVRNNDRVYINVVVKNKEYRLA
Chimera 9  NLYDPNKYIVDVNNVGIRGYMYLKGPRGSVMTTNIYLNSSLYRGTKFIIKKYASGNKDNIVRNNDRVYINVVVKNKEYRLA BoNT A     TNASQAGVEKILSALEIPDVGNLSQVVVMKSKNDQGITNKCKMNLQDNNGNDIGFIGFHQFNNIAKLVASNWYNRQIERS
Chimera 1  TNASQAGVEKILSALEIPDVGNLSQVVVMKSKNDQGITNKCKMNLQDNNGNDIGFIGFHQFNNIAKLVASNWYNRQIERS
Chimera 2  TNASQAGVEKILSALEIPDVGNLSQVVVMKSKNDQGITNKCKMNLQDNNGNDIGFIGFHQFNNIAKLVASNWYNRQIERS
Chimera 3  TNASQAGVEKILSALEIPDVGNLSQVVVMKSKNDQGITNKCKMNLQDNNGNDIGFIGFHQFNNIAKLVASNWYNRQIERS
Chimera 4  TNASQAGVEKILSALEIPDVGNLSQVVVMKSKNDQGITNKCKMNLQDNNGNDIGFIGFHQFNNIAKLVASNWYNRQIERS
Chimera 5  TNASQAGVEKILSALEIPDVGNLSQVVVMKSKNDQGITNKCKMNLQDNNGNDIGFIGFHQFNNIAKLVASNWYNRQIERS
Chimera 6  TNASQAGVEKILSALEIPDVGNLSQVVVMKSKNDQGITNKCKMNLQDNNGNDIGFIGFHQFNNIAKLVASNWYNRQIERS
Chimera 7  TNASQAGVEKILSALEIPDVGNLSQVVVMKSKNDQGITNKCKMNLQDNNGNDIGFIGFHQFNNIAKLVASNWYNRQIERS
Chimera 8  TNASQAGVEKILSALEIPDVGNLSQVVVMKSKNDQGITNKCKMNLQDNNGNDIGFIGFHQFNNIAKLVASNWYNRQIERS
Chimera 9  TNASQAGVEKILSALEIPDVGNLSQVVVMKSKNDQGITNKCKMNLQDNNGNDIGFIGFHQFNNIAKLVASNWYNRQIERS BoNT A     SRTLGCSWEFIPVDDGWGERPL
Chimera 1  SRTLGCSWEFIPVDDGWGERPL
Chimera 2  SRTLGCSWEFIPVDDGWGERPL
Chimera 3  SRTLGCSWEFIPVDDGWGERPL
Chimera 4  SRTLGCSWEFIPVDDGWGERPL
Chimera 5  SRTLGCSWEFIPVDDGWGERPL
Chimera 6  SRTLGCSWEFIPVDDGWGERPL
Chimera 7  SRTLGCSWEFIPVDDGWGERPL
Chimera 8  SRTLGCSWEFIPVDDGWGERPL
Chimera 9  SRTLGCSWEFIPVDDGWGERPL
```

GENETICALLY ENGINEERED CLOSTRIDIAL GENES, PROTEINS ENCODED BY THE ENGINEERED GENES, AND USES THEREOF

This application is a division of U.S. patent application Ser. No. 12/762,909, filed Apr. 19, 2010, which is a division of U.S. patent application Ser. No. 11/284,930, filed Nov. 22, 2005, which claims the priority benefit of U.S. Provisional Patent Application Ser. No. 60/630,175, filed Nov. 22, 2004, which are hereby incorporated by reference in their entirety.

FIELD OF THE INVENTION

This invention relates to isolated Clostridial propeptides and neurotoxins, vaccines or antidotes thereof, methods of immunizing and treating subjects, isolated nucleic acid molecules encoding Clostridial propeptides and neurotoxins, methods of expression, chimeric proteins, and treatment methods.

BACKGROUND OF THE INVENTION

The Clostridial neurotoxins are a family of structurally similar proteins that target the neuronal machinery for synaptic vesicle exocytosis. Produced by anaerobic bacteria of the *Clostridium* genus, botulinum neurotoxins ("BoNT"s, seven immunologically distinct subtypes, A-G) and Tetanus neurotoxin ("TeNT") are the most poisonous substances known on a per-weight basis, with an $LD_{50}$ in the range of 0.5-2.5 ng/kg when administered by intravenous or intramuscular routes (*National Institute of Occupational Safety and Health*, "Registry of Toxic Effects of Chemical Substances (R-TECS)," Cincinnati, Ohio: National Institute of Occupational Safety and Health (1996)). BoNTs target cholinergic nerves at their neuromuscular junction, inhibiting acetylcholine release and causing peripheral neuromuscular blockade (Simpson, "Identification of the Major Steps in *Botulinum* Toxin Action," *Annu. Rev. Pharmacol. Toxicol.* 44:167-193 (2004)). BoNT serotypes A, B, and E are considered to represent the most significant threat to military and civilian populations, particularly because they can be aerosolized and delivered by inhalation (Amon et al., "*Botulinum* Toxin as a Biological Weapon: Medical and Public Health Management," *JAMA* 285:1059-1070 (2001)).

Though much work has been done to develop vaccines or antidotes which are effective against poisoning with Clostridial neurotoxins, the effectiveness of available products is limited because the available inactivated toxin preparations do not optimally mimic the native toxin. No therapeutic antidotes or vaccines have been approved for widespread use, though some preparations are available for limited use under specific circumstances. The NIAID Biodefense Research Agenda has identified the development of countermeasures against Clostridial neurotoxins as one of its most pressing goals (*National Institute of Allergy and Infectious Diseases*, "NIAID Biodefence Research Agenda for CDC category A Agents" NIH Publication #03-5308 (2002)). A prime target is understanding and preventing neurotoxin entry into target cells Immunological approaches have utilized passive protection via injection of antibodies as antitoxins, or active immunization via vaccination with toxoids, toxins chemically or genetically transformed to render them non-toxic but still immunogenic (Ramon et al., "Sur L'immunization Antitetanique et sur la Production de L'antitoxine Tetanique," *Compt. Rend. Soc. Biol.* 93:508-598 (1925)). Antibody-based anti-toxins are available in limited quantities, but no protective vaccine against Clostridial neurotoxins has been approved. A pentavalent *botulinum* toxoid (ABCDE), consisting of toxins inactivated by temperature or cross-linked with formaldehyde, is available in limited quantities, and has been shown to induce antibodies in laboratory workers and military personnel (*National Institute of Allergy and Infectious Diseases*, "NIAID Biodefence Research Agenda for CDC category A Agents. Progress Report," NIH Publication #03-5435 (2003)). An inactivated heavy chain toxoid administered by inhalation was found to protect animals against inhaled toxin doses $10^4$ times the $LD_{50}$ (Park et al., "Inhalational Poisoning by *Botulinum* Toxin and Inhalation Vaccination with Its Heavy-Chain Component," *Infect. Immun.* 71:1147-1154 (2003)). An investigational heptavalent antitoxin (A-G reactive, equine origin) against BoNT is being developed by the U.S. Department of Defense and is now being tested. Initial data demonstrate the general safety of this antitoxin, though it displays some cross-species reactogenicity in humans. Another investigational BoNT antitoxin is based on a combination of three recombinant monoclonal antibodies, which neutralize BoNT A with a high potency (Nowakowski et al., "Potent Neutralization of *Botulinum* Neurotoxin by Recombinant Oligoclonal Antibody," *Proc. Natl. Acad. Sci. USA* 99:11346-11350 (2002)). Development and testing of human monoclonal antibodies to BoNT B-G is also currently in progress and supported by NIAID (*National Institute of Allergy and Infectious Diseases*, "NIAID Biodefence Research Agenda for CDC category A Agents. Progress Report," NIH Publication #03-5435 (2003)).

Several laboratories are attempting to develop recombinant Clostridial toxin genes or fragments thereof The Department of Defense has developed a vaccine based on expression of the receptor-binding domain of the BoNT A heavy chain (*National Institute of Allergy and Infectious Diseases*, "NIAID Biodefence Research Agenda for CDC Category A Agents. Progress Report," NIH Publication #03-5435 (2003); Byrne et al., "Purification, Potency, and Efficacy of the *Botulinum* Neurotoxin Type A Binding Domain from *Pichia pastoris* as a Recombinant Vaccine Candidate," *Infect. Immun.* 66:4817-4822 (1998); and Pless et al., "High-Affinity, Protective Antibodies to the Binding Domain of *Botulinum* Neurotoxin Type A," *Infect. Immun.* 69:570-574 (2001)). A similar approach with a recombinant BoNT F fragment expressed in *Salmonella typhimurium* was found to provide partial protection of animals against the toxin (Foynes et al., "Vaccination Against Type F *Botulinum* Toxin Using Attenuated *Salmonella enterica* var Typhimurium Strains Expressing the BoNT/F $H_C$ Fragment," *Vaccine* 21:1052-1059 (2003)). A catalytically active non-toxic derivative of BoNT A expressed in *E. coli* was reported to induce toxin-neutralizing antibodies and protect animals from a BoNT challenge (Chaddock et al., "Expression and Purification of Catalytically Active, Non-Toxic Endopeptidase Derivatives of *Clostridium botulinum* Toxin Type A," *Protein Expr. Purif.* 25:219-228 (2002)). A catalytically inactive, full-length derivative of BoNT C expressed in *E. coli* was immunogenic in mice, though limitations of this system hinder expression of full-length native and active recombinant toxin (Kiyatkin et al., "Induction of an Immune Response by Oral Administration of Recombinant *Botulinum* Toxin," *Infect. Immun.* 65:4586-4591 (1997)). Rummel et al. ("Synaptotagmins I and II Act as Nerve Cell Receptors for *Botulinum* Neurotoxin G," *J. Biol. Chem.* 279:30865-30870 (2004) ("Rummel I")) and Rummel et al. ("The $H_{cc}$-domain of *Botulinum* Neurotoxins A and B Exhibit a Singular Ganglioside Binding Site Displaying Serotype-Specific Carbohydrate Interaction," *Mol. Microbiol.*

51:631-643 (2004) ("Rummel II"), report full-length BoNT A, B, and G neurotoxins expressed in an *E. coli* from plasmids encoding the respective full-length genes. Rummel I and Rummel II also report several derivatives of BoNT genes. The neurotoxins described in Rummel I and Rummel II are active only at very high concentrations. This is likely due to the fact that the neurotoxins expressed by Rummel I and Rummel II are denatured during expression, extraction, and purification from *E. coli* and achieve low physiological activity of the single chain BoNT propeptide due to improper disulfide bonding. Thus, although Rummel I and Rummel II may in fact have produced full-length recombinant BoNT peptides of serotypes A, B, and G, the properties of the neurotoxins described do not possess native structures and physiological activity.

The widely used *E. coli* expression system may be problematic for some proteins, because the *E. coli* cytosol may not provide the non-reducing environment needed for maintenance of disulfide bridges critical to the native toxin structure (Alberts et al., *Molecular Biology of the Cell*, Third Edition, Garland Publishing Inc., 112, 113, 488, 589). In addition, *E. coli* based expression systems also present practical problems associated with endotoxin removal. These limitations emphasize the importance of selecting an expression system capable of producing recombinant molecules that retain the native toxin structure and biological activity.

Data from multiple laboratories suggest that the C-terminal moiety of Clostridial toxin heavy chains ("Hc"), or the intact heavy chain ("HC") expressed or prepared by reduction/denaturation from native toxins, are functionally altered and therefore require a ~10,000-fold molar excess to delay the onset of toxin-induced paralysis (Li et al., "Recombinant Forms of Tetanus Toxin Engineered for Examining and Exploiting Neuronal Trafficking Pathways," *J. Biol. Chem.* 276:31394-31401 (2001); Lalli et al., "Functional Characterization of Tetanus and *Botulinum* Neurotoxins Binding Domains," *J. Cell Sci.* 112:2715-2724 (1999)). Some of these preparations have been completely inactive in this assay (Daniels-Holgate et al., "Productive and Non-Productive Binding of *Botulinum* Neurotoxin A to Motor Nerve Endings are Distinguished by Its Heavy Chain," *J. Neurosci. Res.* 44:263-271 (1996)). The low efficiency of HC and Hc may be due to either their increased binding affinity to non-productive sites on cells normally mediating toxin trafficking or their conformational differences from the native toxin which results in a low binding affinity for the specific binding sites at the target cells. In either case, incorrect folding, altered post-translational modification, a requirement for the N-terminal portion of the molecule (Koriazova et al., "Translocation of *Botulinum* Neurotoxin Light Chain Protease through the Heavy Chain Channel," *Nat. Struct. Biol.* 10:13-18 (2003)), or multiple other changes, may be responsible for these functionally important deficiencies. These facts suggest that the currently available preparations of BoNT or its derivatives are poor mimics of the native toxin, which may limit their therapeutic potential.

The methods currently available to produce inactivated derivatives of BoNTs as vaccines or antidotes to BoNT poisoning have met with limited success. This can be due to several factors. First, the methods used to inactivate BoNT prepared from Clostridial cultures are harsh, and may alter the toxin's native conformation in ways that may influence its immunogenicity or trafficking and absorption. Second, methods based on producing recombinant toxins have thus far only succeeded in producing either inactive toxin molecules or fragments of its protein domains. In both cases, the recombinant molecules produced are by definition significantly different from native toxin, particularly with respect to post-translational processing and disulfide bonding. Though inactivated toxins and toxin fragments have been shown to be immunogenic, the pool of polyclonal antibodies they generate will include a fraction recognizing epitopes present only on misfolded toxins.

Another area in which Clostridial neurotoxins have been extensively studied relates to their clinical use to treat dystonias, and to temporarily correct aesthetic defects in skin. These indications are specific to the neurotoxins produced by strains of *Clostridium botulinum* (BoTox), because they can be used at extremely small doses to locally paralyze specific muscles and thereby achieve therapeutic goals. All of the current products used for this indication are produced from Clostridial cultures, and there have been no reports of an active BoTox molecule produced using any type of genetic engineering technology.

A further area of interest is derived from the ability of Clostridial neurotoxins to pass undegraded through epithelial barriers via transcytosis, and specifically target nervous tissue. This has led to suggestions that Clostridial neurotoxins can be used to enable oral and inhalational carriers for therapeutic agents that cannot normally be delivered via these routes of administration, and delivery vehicles which can specifically target the peripheral and central nervous system.

The present invention is directed to overcoming these and other limitations in the art.

SUMMARY OF THE INVENTION

One aspect of the present invention relates to an isolated Clostridial neurotoxin propeptide. The propeptide has a light chain region, a heavy chain region, where the light and heavy chain regions are linked by a disulfide bond, and an intermediate region connecting the light and heavy chain regions. The intermediate region has a highly specific protease cleavage site which has three or more specific adjacent amino acid residues that are recognized by the highly specific protease in order to enable cleavage.

Another aspect of the present invention relates to an isolated nucleic acid molecule encoding the above Clostridial neurotoxin propeptide as well as expression systems and host cells containing this nucleic acid molecule.

A further aspect of the present invention relates to an isolated, physiologically active Clostridial neurotoxin produced by cleaving the above Clostridial neurotoxin propeptide. The propeptide is cleaved at the highly specific protease cleavage site. The light and heavy chain regions are linked by a disulfide bond.

Yet another aspect of the present invention relates to a vaccine or antidote including the above physiologically active, atoxic, Clostridial neurotoxin produced by cleaving the isolated Clostridial neurotoxin propeptide at the highly specific protease cleavage site. The light and heavy chain regions are linked by a disulfide bond.

Still another aspect of the present invention relates to method of immunizing a subject against toxic effects of a Clostridial neurotoxin. This method involves administering the above vaccine to the subject under conditions effective to immunize the subject against toxic effects of Clostridial neurotoxin.

Yet a further aspect of the present invention relates to a method of treating a subject for toxic effects of a Clostridial neurotoxin. This method involves administering an antidote comprising the above physiologically active, atoxic, Clostridial neurotoxin produced by cleaving the isolated Clostridial neurotoxin propeptide under conditions effective to treat the subject for toxic effects of Clostridial neurotoxin.

Still a further aspect of the present invention relates to a chimeric protein including a first protein or protein fragment having a heavy chain region of a Clostridial neurotoxin and a second protein or protein fragment linked to the first protein or protein fragment.

Another aspect of the present invention relates to a method of expressing a recombinant physiologically active Clostridial neurotoxin. This method involves providing a nucleic acid construct having a nucleic acid molecule encoding an isolated Clostridial neurotoxin propeptide. The nucleic acid construct has a heterologous promoter operably linked to the nucleic acid molecule and a 3' regulatory region operably linked to the nucleic acid molecule. The nucleic acid construct is introduced into a host cell under conditions effective to express the physiologically active Clostridial neurotoxin.

A further aspect of the present invention relates to a treatment method. This method involves contacting a patient with an isolated, physiologically active, toxic, Clostridial neurotoxin produced by cleaving the above isolated Clostridial neurotoxin propeptide.

The present invention relates to a genetic engineering platform that enables rationale design of therapeutic agents based on Clostridial toxin genes. The genetic engineering scheme is based on a two-step approach. For each Clostridial toxin serotype, gene constructs, expression systems, and purification schemes are designed that produce physiologically active, recombinant Clostridial neurotoxin. This ensures that the recombinant toxin derivatives retain structural features important for developing therapeutic candidates, or useful biologic reagents. Using the genetic constructs and expression systems developed by this paradigm, selective point mutations are then introduced to create atoxic recombinant derivatives. This two-step approach is designed to ensure that the recombinant toxin derivatives retain the immunogenicity, absorption profile, and trafficking pathways of native toxin, allowing the atoxic derivatives to have optimized therapeutic and biological properties. They also enable useful chimeric proteins to be created.

Genetically engineered forms of recombinant toxins which structurally and functionally mimic native toxins are superior to the toxoids currently in development for therapeutic purposes. They provide new approaches which can produce customized toxin derivatives in large quantities, and with mutations specifically targeted to the creation of vaccines and toxin antidotes. By focusing on solving the problems associated with producing recombinant toxins, which are physiologically active, the inactivated toxin derivatives of the present invention have distinct advantages over currently available alternatives. This is particularly true with respect to their immunogenic activity and their ability to compete with native toxin for cellular binding sites.

The methodology described herein has additional scientific and practical value because it provides a broad platform enabling facile manipulation and expression of Clostridial toxin genes. This will facilitate studies of the mechanism of Clostridial toxin action, their intracellular trafficking, and the factors responsible for their ability to transit through specific cell types without activation or toxic consequences. In addition, the BoNT constructs created can provide new tools for delivering specific reagents or drugs via oral or inhalation routes, or specifically into peripheral neurons, and enable their controlled activation at the site of intended action. Other approaches to engineer delivery tools based on chemically modified heavy chains from Clostridial neurotoxins have had limited success, possibly because the methods used to inactivate the toxin interfere with protein spatial structure (Goodnough et al., "Development of a Delivery Vehicle for Intracellular Transport of *botulinum* Neurotoxin Antagonists," *FEBS Lett.* 513:163-168 (2002), which is hereby incorporated by reference in its entirety).

BRIEF DESCRIPTION OF THE DRAWINGS

FIGS. 1A-C show comparative alignment of amino acid sequences of the seven wildtype *botulinum* neurotoxin serotypes, including *Clostridium botulinum* serotype A (SEQ ID NO: 1), *Clostridium botulinum* serotype B (SEQ ID NO: 2), *Clostridium botulinum* serotype C (SEQ ID NO: 3), *Clostridium botulinum* serotype D (SEQ ID NO: 4), *Clostridium botulinum* serotype E (SEQ ID NO: 5), *Clostridium botulinum* serotype F (SEQ ID NO: 6), and *Clostridium botulinum* serotype G (SEQ ID NO: 7). Gaps have been introduced to maximize homology. Amino acids identical in ≥50% of compared sequences are shown in black boxes Amino acids constituting the active site of the catalytic domain of metalloprotease are marked by stars. Disulfide bridge between neurotoxin cysteine residues of the light and heavy chain are shown as a long horizontal bracket. The amino acid residues constituting the minimal catalytic domain of the light chain are hatched. The first amino acid of the C-terminal part of the protein heavy chain (N872 for BoNT A), constituting receptor-binding domain are shown with the arrow Amino acids, absent in the mature dichain BoNT A molecule along with the aligned amino acids of the other BoNT serotypes are boxed. The white arrow is positioned at the first amino acid of the neurotoxins' heavy chain.

FIGS. 2A-C show comparative alignment, using the Clustal Program, of amino acid sequences of the seven *botulinum* neurotoxin serotypes, including *Clostridium botulinum* serotype A (SEQ ID NO: 8), *Clostridium botulinum* serotype B (SEQ ID NO: 9), *Clostridium botulinum* serotype C (SEQ ID NO: 10), *Clostridium botulinum* serotype D (SEQ ID NO: 11), *Clostridium botulinum* serotype E (SEQ ID NO: 12), *Clostridium botulinum* serotype F (SEQ ID NO: 13), and *Clostridium botulinum* serotype G (SEQ ID NO: 14), which have been slightly modified in accordance with the present invention. Gaps have been introduced to maximize homology. Amino acids identical in ≥50% of compared sequences are shown in black boxes Amino acids constituting the active site of the catalytic domain of metalloprotease are marked by stars. Disulfide bridge between neurotoxin cysteine residues of the light and heavy chain are shown as a long horizontal bracket. The amino acid residues constituting the minimal catalytic domain of the light chain are hatched. The first amino acid of the C-terminal part of the protein heavy chain (N876 for BoNT A), constituting receptor-binding domain are shown with the arrow Amino acids, absent in the mature dichain BoNT A molecule along with the aligned amino acids of the other BoNT serotypes are boxed. The white arrow is positioned at the first amino acid of the neurotoxins' heavy chain. Amino acid residues are modified in comparison with the wild type sequence to restrict trypsin-like proteolysis Amino acids which constitute the insertion/modification into the wild type amino acid residues and represent an enterokinase cleavage site are also shown.

FIG. 3A is a schematic representation of the native BoNT A (wt) dimer, illustrating the catalytic (~50 kDa), translocation (~50 kDa), and receptor-binding (~50 kDa) domains. FIG. 3B is a comparison of the nucleotide (SEQ ID NO: 65 (wt) and SEQ ID NO: 66 (td)) and amino acid (SEQ ID NO: 1 (wt) and SEQ ID NO: 8 (td)) sequences of the native BoNT A (wt) and its recombinant toxic derivative (td), as generated in plasmid pLitBoNTA. Sequences common to both the wt and td genes are shown as black letters on a white background, or as white boxes. White letters on a black background represent the amino acids excised from the toxin propeptide to generate the mature wt toxin. The disulfide bonds joining the LC and HC are shown as long horizontal brackets. Grey letters indicate the unique endonuclease restriction sites introduced into non-coding portions of the td DNA sequence and the Shine-Dalgarno region of the wt sequence. All other mutations introduced to modify the construct properties are also shown in grey letters. The de novo enterokinase cleavage site inserted into the td propeptide is shown by an arrow. Amino acids proximal to conceived (wt) or executed (td) mutations are numbered.

FIG. 4A shows 8% PAGE stained with Coomassie G-250. FIG. 4B shows a Western blot of the PAG shown in FIG. 4A, probed with polyclonal antibodies raised against the full-length BoNT A toxoid. Samples were treated with β-mercaptoethanol before separation. The protein molecular weight standards are shown to the far left. Lanes 1 and 2 are cleared lysate of E. coli transformed with pETcoco2 empty vector (Lane 1) or pETcocoBoNTA (Lane 2). Lane 3 is a purified preparation of native BoNT A used as positive control. Lane 4 and 5 are eluates from the Ni-NTA affinity purification of cleared E. coli lysates which have been transformed with pETcoco2 (Lane 4) or pETcocoBoNTA (Lane 5). SC: single chain propeptide. HC: Heavy Chain. LC: Light Chain.

FIG. 7A shows 8% PAGE stained with Coomassie G-250. FIG. 7B shows a Western blot of the gel in FIG. 7A, probed with polyclonal antibodies raised against full-length BoNT A toxoid. Samples were treated with (3-mercaptoethanol before the separation. Protein molecular weight standards are shown on the left. Different amounts of rEK were added to 1 μg of BoNT A td in rEK cleavage buffer and incubated at 20° C. for 8 hours. 10% of each reaction mixture was loaded per lane. The number of rEK units added per 1 g of BoNT A td were: no rEK added (Lane 1); 0.05 U of rEK (Lane 2); 0.1 U of rEK (Lane 3); 0.25 U of rEK (Lane 4); 0.5 U of rEK (Lane 5). Lane 6 is the positive control, with 0.1 μg of native BoNT A. The recombinant light chain is larger than the control because of construct design.

FIGS. 8A-D show selected features of the recombinant BoNT A derivatives illustrating their native disulfide bonding (FIGS. 8A and 8B), and the use of a signal sequence to increase secretion of the toxin derivative into the culture medium (FIGS. 8C and 8D). FIGS. 8A and 8B show PAGE of the indicated BoNT derivatives run on 10% PAGE gels, followed by Western blotting using polyclonal antibodies raised against full-length BoNT A toxoid. A protein molecular weight ladder is shown on the left. In FIG. 8A, the PAGE was run under non-reducing conditions before transfer to the nitrocellulose. In FIG. 8B, samples were treated with β-mercaptoethanol and run under reducing conditions before transfer to the nitrocellulose for Western blotting. Lane 1: Positive control, purified native BoNT A; Lane 2: BoNT A td cleaved with rEK; Lane 3: BoNT A ad cleaved with rEK; Lane 4: BoNT A gfpd cleaved with rEK. FIGS. 8C and 8D are fluorescent images of the adherent layer of Sf9 cells ($2.10^5/cm^2$) in the SF 900 II medium at 12 hours post-infection (MOI~0.1) with recombinant baculovirus expressing BoNT A gfpd containing the signal peptide for secretion (FIG. 8C), or the control recombinant baculovirus expressing GFP without added signal peptide (FIG. 8D). Emission wavelength 508 nm, magnification factor ×200, exposure time 0.1 sec.

FIGS. 10A-B illustrate a transcytosis assay for polarized cells. Human gut epithelial cells (T-84) or canine kidney cells (MDCK) will be grown subject to conditions that promote differentiation and polarization of the cell monolayer (FIG. 10A). An example of a polarized cell illustrating orientation of the apical membrane toward the top (accessible to medium in the insert) and the basal membrane oriented toward the bottom (accessible to medium in the well) (FIG. 10B). Cells will be grown on polycarbonate membranes coated with collagen in Transwell® porous bottom inserts. The inserts suspend the cell monolayer above the bottom of the well, enabling cells to feed from the top and the bottom, and to be exposed to toxin from the top and the bottom. Cultures grown in this manner differentiate into a polarized membrane with tight junctions.

FIGS. 11A-C illustrate the amino acid sequences of nine BoNT A chimeric proteins containing SNARE motif peptides substituted for alpha-helix domains in the light chain region aligned against the BoNT A ad protein (SEQ ID NO: 8). Chimera 1 (SEQ ID NO: 15) contains the full-length sequence of BoNT A ad with three SNARE motif peptides substituting light chain alpha-helix 1. Chimera 2 (SEQ ID NO: 16) contains the full-length sequence of BoNT A ad with two SNARE motif peptides substituting light chain alpha-helix 4. Chimera 3 (SEQ ID NO: 17) contains the full-length sequence of BoNT A ad with five SNARE motif peptides substituting light chain alpha-helices 1 and 4. Chimera 4 (SEQ ID NO: 18) contains the full-length sequence of BoNT A ad with three SNARE motif peptides substituting light chain alpha-helices 4 and 5. Chimera 5 (SEQ ID NO: 19) contains the full length sequence of BoNT A ad with six SNARE motif peptides substituting light chain alpha-helices 1, 4, and 5. Chimera 6 (SEQ ID NO: 20) contains the full length sequence of BoNT A ad with four SNARE motif peptides substituting light chain alpha-helices 4, 5, and 6. Chimera 7 (SEQ ID NO: 21) contains the full length sequence of BoNT A ad with five SNARE motif peptides substituting light chain alpha-helices 4, 5, 6, and 7. Chimera 8 (SEQ ID NO: 22) contains the full length sequence of BoNT A ad with seven SNARE motif peptides substituting light chain alpha-helices 1, 4, 5, and 6. Chimera 9 (SEQ ID NO: 23) contains the full length sequence of BoNT A ad with eight SNARE motif peptides substituting light chain alpha-helices 1, 4, 5, 6, and 7.

DETAILED DESCRIPTION OF THE INVENTION

Figure 3A:
FIGS. 3A-B illustrate features of the wild type BoNT A protein and gene (wt), and its toxic recombinant derivative (td).

One aspect of the present invention relates to an isolated Clostridial neurotoxin propeptide. The propeptide has a light chain region, a heavy chain region, where the light and heavy chain regions are linked by a disulfide bond, and an intermediate region connecting the light and heavy chain regions. The intermediate region has a highly specific protease cleavage site which has three or more specific adjacent amino acid residues that are recognized by the highly specific protease in order to enable cleavage.

In a preferred embodiment, the isolated Clostridial neurotoxin propeptide is from *Clostridium botulinum*. *Clostridium botulinum* has multiple serotypes (A-G). Although the Clostridial neurotoxin propeptides of the present invention may be from any of the *Clostridium botulinum* serotypes, preferable serotypes are serotype A, serotype B, and serotype E.

Figure 1A:
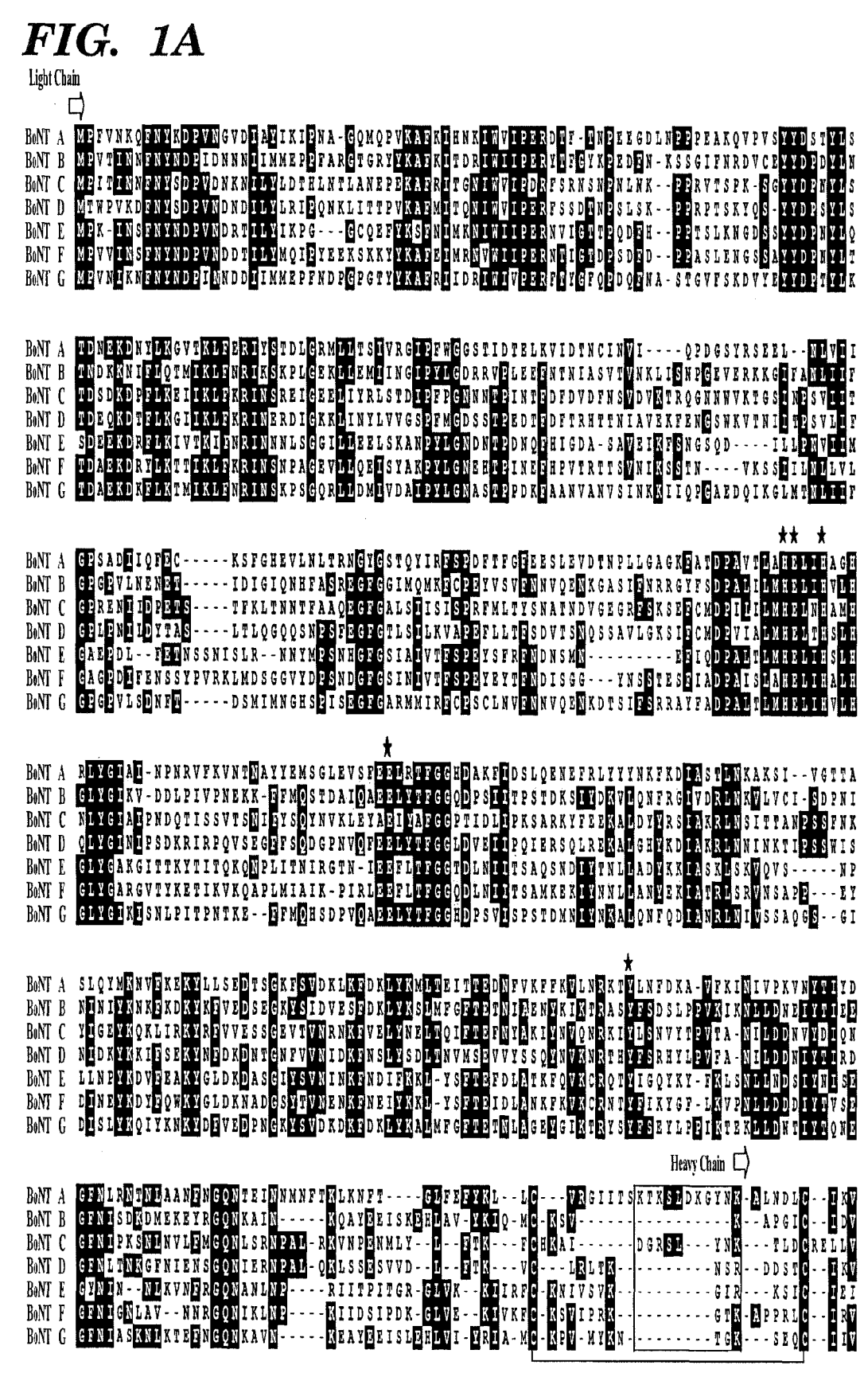
Figure 1C:
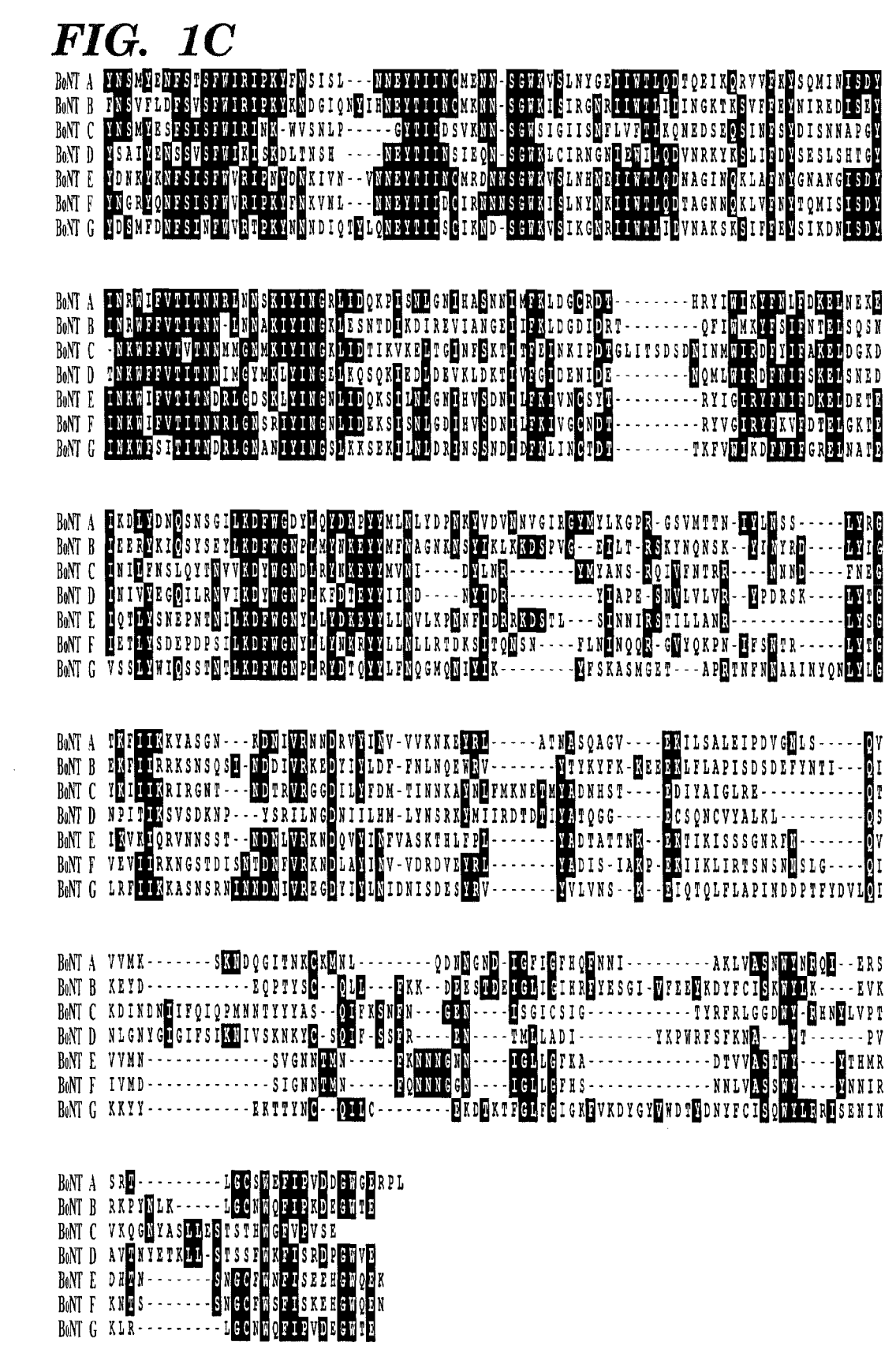

Common structural features of the wild-type *Clostridium botulinum* neurotoxin propeptides are shown in FIG. 1. These structural features are illustrated using BoNT A propeptide as an example, and are generalized among all *Clostridium botulinum* serotypes. BoNT A propeptide has two chains, a light chain ("LC") of Mr~50,000 and a heavy chain ("HC") of Mr~100,000, linked by a disulfide bond between $Cys_{429}$ and $Cys_{453}$. As illustrated in FIG. 1, all seven BoNT serotype propeptides have a light chain region and a heavy chain region linked by a disulfide bond. Two essential Cys residues, one adjacent to the C-terminus of the light chain, and a second adjacent to the N-terminus of the heavy chain are present in all seven BoNT serotypes. These two Cys residues form the single disulfide bond holding the HC and LC polypeptides together in the mature neurotoxin. This disulfide bond enables the mature neurotoxin to accomplish its native physiological activities by permitting the HC and LC to carry out their respective biological roles in concert. The disulfide bond between HC and LC polypeptides in all seven serotypes is illustrated in FIG. 1 by the solid line joining the involved Cys residues. The outlined box in FIG. 1 illustrates the intermediate region defined by amino acid residues $Lys_{438}$-$Lys_{448}$ of BoNT A. This intermediate region identifies the amino acids eliminated during maturation of wild-type BoNT A, and believed to be excised by a protease endogenous to the host microorganism. This cleavage event, described infra, generates the biologically active BoNT HC-LC dimer. The outlined amino acid residues in FIG. 1, representing amino acid residues numbered approximately in the 420 to 450 range for all seven BoNT serotypes, can be considered as a region "nonessential" to the toxins' physiological activity and, therefore, represents targets for directed mutagenesis in all seven BoNT serotypes.

All seven BoNT serotypes contain Lys or Arg residues in the intermediate region defined by the box in FIG. 1 which make the propeptides susceptible to activation by trypsin. Native BoNT A propeptide recovered from young bacterial cultures can be activated by trypsinolysis, with production of intact, S—S bound light and heavy chain. Though multiple additional trypsin-susceptible sites are present in the propeptides, they are resistant to proteolysis due to their spatial positions within the native toxin molecule (Dekleva et al., "Nicking of Single Chain *Clostridium botulinum* Type A Neurotoxin by an Endogenous Protease," *Biochem. Biophys. Res. Commun.* 162:767-772 (1989); Lacy et al., "Crystal Structure of *Botulinum* Neurotoxin Type A and Implications for Toxicity," *Nat. Struct. Biol.* 5:898-902 (1998), which are hereby incorporated by reference in their entirety). A second site in the native propeptide of several BoNT serotypes can be susceptible to trypsin cleavage when subjected to higher enzyme concentrations or incubation times (Chaddock et al., "Expression and Purification of Catalytically Active, Non-Toxic Endopeptidase Derivatives of *Clostridium botulinum* Toxin Type A," *Protein Expr. Purif.* 25:219-228 (2002), which is hereby incorporated by reference in its entirety). This trypsin-susceptible site is located in the region adjacent to the toxin receptor binding domain. This region of the HC peptide is found to be exposed to solvent in BoNT serotypes for which information is available on their 3-D crystal structure (Lacy et al., "Crystal Structure of *Botulinum* Neurotoxin Type A and Implications for Toxicity," *Nat. Struct. Biol.* 5:898-902 (1998); Swaminathan et al., "Structural Analysis of the Catalytic and Binding Sites of *Clostridium botulinum* Neurotoxin B," *Nat. Struct. Biol.* 7:693-699 (2000), which are hereby incorporated by reference in their entirety).

In a preferred embodiment, the propeptide of the present invention has an intermediate region connecting the light and heavy chain regions which has a highly specific protease cleavage site and no low-specificity protease cleavage sites. For purposes of the present invention, a highly specific protease cleavage site has three or more specific adjacent amino acid residues that are recognized by the highly specific protease in order to permit cleavage (e.g., an enterokinase cleavage site). In contrast, a low-specificity protease cleavage site has two or less adjacent amino acid residues that are recognized by a protease in order to enable cleavage (e.g., a trypsin cleavage site).

Figure 2A:
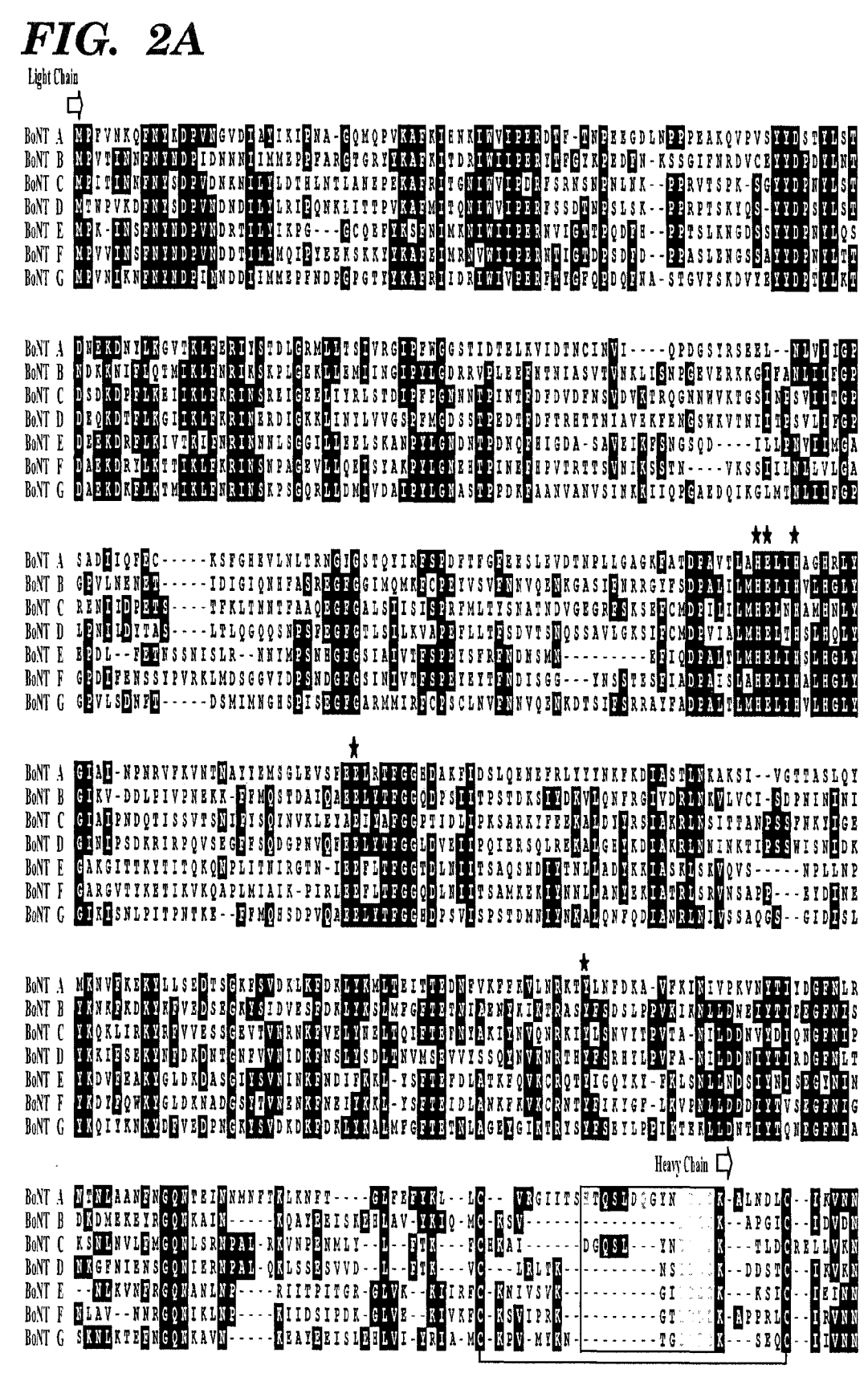

In all seven BoNT serotypes, the amino acid preceding the N-terminus of the heavy chain is a Lys or Arg residue which is susceptible to proteolysis with trypsin. This trypsin-susceptible site can be replaced with a five amino acid enterokinase cleavage site (i.e., DDDDK (SEQ ID NO: 24)) upstream of the heavy chain's N-terminus, as illustrated for the seven serotypes in FIG. 2. This modification enables standardization activation with enterokinase. In serotypes A and C, additional Lys residues within this region are mutated to either Gln or His, thereby eliminating additional trypsin-susceptible sites which might result in undesirable non-specific activation of the toxin. Trypsin-susceptible recognition sequences also occur upstream of the heavy chain's receptor-binding domain in serotypes A, E, and F. This region's susceptibility to proteolysis is consistent with its exposure to solvent in the toxin's 3-D structure, as shown by X-ray crystallography analysis. Therefore, in serotypes A, E, and F, the susceptible residues are modified to Asn (FIG. 2). Signal peptides and N-terminal affinity tags are also preferably introduced, as required, to enable secretion and recovery.

In a preferred embodiment, the isolated Clostridial neurotoxin propeptide of the present invention has light and heavy chain regions which are not truncated.

As described in greater detail infra, the isolated Clostridial neurotoxin propeptide of the present invention may include a disabling mutation in an active metalloprotease site of the propeptide. The amino acid residues constituting the minimal catalytic domain of the light chain of the propeptide are illustrated in FIG. 1 and FIG. 2 by hatching. Specific amino acid residues constituting the active site of the catalytic domain of the metalloprotease are marked by stars in FIG. 1 and FIG. 2.

The Clostridial neurotoxin propeptide of the present invention may also possess a non-native motif in the light chain region that is capable of inactivating light chain metalloprotease activity in a toxic Clostridial neurotoxin. Suitable non-native motifs capable of inactivating light chain metalloprotease activity of a toxic Clostridial neurotoxin include, without limitation, SNARE motifs, metalloprotease inhibitor motifs, such as those present in the protein family known as Tissue Inhibitors of Metalloprotease (TIMP) (Mannello et al., "Matrix Metalloproteinase Inhibitors as Anticancer Therapeutics," *Curr. Cancer Drug Targets* 5:285-298 (2005); Emonard et al., "Regulation of Matrix Metalloproteinase (MMP) Activity by the Low-Density Lipoprotein Receptor-Related Protein (LRP). A New Function for an 'Old Friend,'" *Biochimie* 87:369-376 (2005); Maskos, "Crystal Structures of MMPs in Complex with Physiological and Pharmacological Inhibitors," *Biochimie* 87:249-263 (2005), which are hereby incorporated by reference in their entirety), zinc chelating motifs based on suitably positioned sulfhydryl (preferably methionine) and acidic amino acids which become exposed upon binding of the chimeric antagonist to the active LC metalloprotease, and peptide motifs corresponding to the cleavage site on the substrate of LC metalloproteases, including transition state analogs of said cleavage site (Sukonpan et al., "Synthesis of Substrates and Inhibitors of *Botulinum* Neurotoxin Type A Metalloprotease," *J. Peptide Res.* 63:181-193 (2004); Hayden et al., "Discovery and Design of Novel Inhibitors of Botulinus Neurotoxin A: Targeted 'Hinge' Peptide Libraries," *Journal of Applied Toxicology* 23:1-7 (2003); Oost et al., "Design and Synthesis of Substrate-Based Inhibitors of *Botulinum* Neurotoxin Type B Metalloprotease," *Biopolymers (Peptide Science)* 71:602-619 (2003), which are hereby incorporated by reference in its entirety).

SNARE motif peptides have been shown to prevent cleavage of synaptic complex components in *Aplysia* neurons (Rosetto et al., "SNARE Motif and Neurotoxins," *Nature* 372: 415-416 (1994), which is hereby incorporated by reference in its entirety). SNARE motif peptides are common to the substrate binding site of known BoNT serotypes, and have been shown to inhibit the toxic LC when injected into BoNT-affected neurons (Rosetto et al., "SNARE Motif and Neurotoxins," *Nature* 372:415-416 (1994), which is hereby incorporated by reference in its entirety).

In a preferred embodiment, the Clostridial neurotoxin propeptide light chain region has one or more non-native motifs (e.g., SNARE motif peptides), which replace surface alpha-helix domains of the native propeptide. Seven surface alpha-helix domains in the light chain region of *Clostridium botulinum* serotypes are identified in FIG. 11.

A variety of Clostridial neurotoxin propeptides with light chain regions containing non-native motifs (e.g., SNARE motif peptides) in place of surface alpha-helix domains can be created. As described in greater detail below, these non-native motif bearing propeptides are generated by altering the nucleotide sequences of nucleic acids encoding the Clostridial neurotoxin propeptides.

Another aspect of the present invention relates to an isolated nucleic acid molecule encoding an isolated Clostridial neurotoxin propeptide of the present invention.

Nucleic acid molecules encoding full-length toxic Clostridial neurotoxins are well known in the art (See e.g., GenBank Accession Nos. M81186 (BoNT B); D90210 (BoNT C); S49407 (BoNT D); D90210 (BoNT E); X81714 (BoNT F); and X74162 (BoNT G)).

Nucleic acid molecules of the present invention preferably encode the amino acid sequences of FIG. 2. In particular, the nucleic acid molecules of the present invention are modified from the wild type BoNT serotype sequences to have one or more characteristics selected from the group consisting of a mutation which renders the encoded propeptide resistant to low-specificity proteolysis, one or more silent mutations that inactivate putative internal DNA regulatory elements, and one or more unique restriction sites. In particular, and as illustrated for each BoNT serotype in FIG. 2, mature neurotoxin stability and yield are optimized by site-directed mutation of residues within the intermediate region of the propeptide, thereby reducing the propeptides' susceptibility to non-specific proteolysis and poisoning of the host organism used for expression by the mature neurotoxin. Also, silent mutations are introduced into DNA regulatory elements that can affect RNA transcription or expression of the Clostridial neurotoxin propeptide in the system of choice. In addition, unique endonuclease restriction sites are introduced to enable creation of chimeric proteins.

A nucleic acid molecule of the present invention may also have a disabling mutation in a region encoding an active metalloprotease site of the propeptide, as described supra.

A nucleic acid molecule of the present invention may also have a mutation in a region encoding the light chain region, such that the nucleic acid molecule encodes, in the light chain region, a non-native motif capable of inactivating light chain metalloprotease activity in a toxic clostridial neurotoxin. Suitable non-native motifs are described supra.

A further aspect of the present invention relates to an expression system having a nucleic acid molecule encoding an isolated Clostridial neurotoxin propeptide of the present invention in a heterologous vector.

Yet another aspect of the present invention relates to a host cell having a heterologous nucleic acid molecule encoding an isolated Clostridial neurotoxin propeptide of the present invention.

Still another aspect of the present invention relates to a method of expressing a recombinant physiologically active Clostridial neurotoxin of the present invention. This method involves providing a nucleic acid construct having a nucleic acid molecule encoding an isolated Clostridial neurotoxin propeptide of the present invention. The nucleic acid construct has a heterologous promoter operably linked to the nucleic acid molecule and a 3' regulatory region operably linked to the nucleic acid molecule. The nucleic acid construct is then introduced into a host cell under conditions effective to express the physiologically active Clostridial neurotoxin.

In a preferred embodiment, the expressed neurotoxin is contacted with a highly specific protease under conditions effective to effect cleavage at the intermediate region. Preferably, the intermediate region of the Clostridial neurotoxin propeptide is not cleaved by proteases endogenous to the expression system or the host cell.

Expression of a Clostridial neurotoxin of the present invention can be carried out by introducing a nucleic acid molecule encoding a Clostridial neurotoxin propeptide into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5'→3') orientation and correct reading frame. The vector contains the necessary elements for the transcription and translation of the inserted Clostridial neurotoxin propeptide-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pFastBac series (Invitrogen), pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the Clostridial neurotoxin propeptide-encoding sequence in a cell. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the PH promoter, T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The Clostridial neurotoxin-encoding nucleic acid, a promoter molecule of choice, a suitable 3' regulatory region, and if desired, a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding a Clostridial neurotoxin is inserted into a vector in the sense (i.e., 5'→3') direction, such that the open reading frame is properly oriented for the expression of the encoded Clostridial neurotoxin propeptide under the control of a promoter of choice. Single or multiple nucleic acids may be ligated into an appropriate vector in this way, under the control of a suitable promoter, to prepare a nucleic acid construct.

Once the isolated nucleic acid molecule encoding the Clostridial neurotoxin propeptide has been inserted into an expression vector, it is ready to be incorporated into a host cell. Recombinant molecules can be introduced into cells via transformation, particularly transduction, conjugation, lipofection, protoplast fusion, mobilization, particle bombardment, or electroporation. The DNA sequences are incorporated into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like. Preferable host cells of the present invention include, but are not limited to, *Escherichia coli*, insect cells, and *Pichia pastoris* cells.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes" which encode enzymes providing for production of an identifiable compound, or other markers which indicate relevant information regarding the outcome of gene delivery, are suitable. For example, various luminescent or phosphorescent reporter genes are also appropriate, such that the presence of the heterologous gene may be ascertained visually.

In a preferred embodiment of the present invention, the expressed neurotoxin propeptide is contacted with a highly specific protease (e.g., enterokinase) under conditions effective to enable cleavage at the intermediate region of the propeptide of the present invention. Preferably, the expressed neurotoxin propeptide has one or more disulfide bridges.

Another aspect of the present invention relates to an isolated, physiologically active Clostridial neurotoxin produced by cleaving an isolated Clostridial neurotoxin propeptide of the present invention. The propeptide is cleaved at the highly specific protease cleavage site. The light and heavy chain regions are linked by a disulfide bond.

As discussed supra, Clostridial neurotoxins are synthesized as single chain propeptides which are later activated by a specific proteolysis cleavage event, generating a dimer joined by a disulfide bond. These structural features can be illustrated using BoNT A as an example, and are generally applicable to all *Clostridium botulinum* serotypes. The mature BoNT A is composed of three functional domains of Mr~50,000 (FIG. 3A), where the catalytic function responsible for toxicity is confined to the light chain (residues 1-437), the translocation activity is associated with the N-terminal half of the heavy chain (residues 448-872), and cell binding is associated with its C-terminal half (residues 873-1,295) (Johnson, "Clostridial Toxins as Therapeutic Agents: Benefits of Nature's Most Toxic Proteins," *Annu. Rev. Microbiol.* 53:551-575 (1999); Montecucco et al., "Structure and Function of Tetanus and *Botulinum* Neurotoxins," *Q. Rev. Biophys.* 28:423-472 (1995), which are hereby incorporated by reference in their entirety).

Optimized expression and recovery of recombinant neurotoxins for BoNT serotypes in a native and physiologically active state is achieved by the introduction of one or more alterations to the nucleotide sequences encoding the BoNT propeptides, as discussed supra. These mutations are designed to maximize yield of recombinant Clostridial neurotoxin, while retaining the native toxins structure and biological activity.

Isolated, full-length Clostridial neurotoxins of the present invention are physiologically active. This physiological activity includes, but is not limited to, toxin immunogenicity, trans- and intra-cellular trafficking, and cell recognition.

The mechanism of cellular binding and internalization of Clostridial toxins is still poorly understood. No specific receptor has been unambiguously identified, and the binding constants have not been characterized. The C-terminal portion of the heavy chain of all Clostridial neurotoxins binds to gangliosides (sialic acid-containing glycolipids), with a preference for gangliosides of the $G_{1b}$ series (Montecucco et al., "Structure and Function of Tetanus and *Botulinum* Neurotoxins," *Q. Rev. Biophys.* 28:423-472 (1995); Montecucco, "How Do Tetanus and *Botulinum* Toxins Bind to Neuronal Membranes?" TIBS 11:314-317 (1986); and Van Heyningen et al., "The Fixation of Tetanus Toxin by Ganglioside," *J. Gen. Microbiol.* 24:107-119 (1961), which are hereby incorporated by reference in their entirety). The sequence responsible for ganglioside binding has been identified for the structurally similar TeNT molecule, and is located within the 34 C-terminal amino acid residues of its heavy chain. BoNT A, B, C, E, and F share a high degree of homology with TeNT in this region (FIG. 1) (Shapiro et al., "Identification of a Ganglioside Recognition Domain of Tetanus Toxin Using a Novel Ganglioside Photoaffinity Ligand," *J. Biol. Chem.* 272: 30380-30386 (1997), which is hereby incorporated by reference in its entirety). Multiple types of evidence suggest the existence of at least one additional component involved in the binding of Clostridial neurotoxins to neuronal membranes (Montecucco et al., "Structure and Function of Tetanus and *Botulinum* Neurotoxins," *Q. Rev. Biophys.* 28:423-472 (1995); Montecucco, "How Do Tetanus and *Botulinum* Toxins Bind to Neuronal Membranes?" TIBS 11:314-317 (1986), which are hereby incorporated by reference in their entirety). In two reports (Nishiki et al., "The High-Affinity Binding of *Clostridium Botulinum* Type B Neurotoxin to Synaptotagmin II Associated with Gangliosides $G_{T1b}/G_{D1a}$," *FEBS Lett.* 378: 253-257 (1996); Dong et al., "Synaptotagmins I and II Mediate Entry of *Botulinum* Neurotoxin B into Cells," *J. Cell Biol.*

162:1293-1303 (2003), which are hereby incorporated by reference in their entirety), synaptotagmins were identified as possible candidates for the auxiliary BoNT B receptor, and synaptotagmins I and II were implicated as neuronal receptors for BoNT G (Rummel et al., "Synaptotagmins I and II Act as Nerve Cell Receptors for *Botulinum* Neurotoxin G," *J. Biol. Chem.* 279:30865-30870 (2004), which is hereby incorporated by reference in its entirety). However despite the structural similarity in the putative receptor-binding domain of Clostridial neurotoxins, other toxin subtypes show no affinity for synaptotagmins or synaptotagmin-related molecules. Lipid rafts (Herreros et al., "Lipid Rafts Act as Specialized Domains for Tetanus Toxin Binding and Internalization into Neurons," *Mol. Biol. Cell* 12:2947-2960 (2001), which is hereby incorporated by reference in its entirety) have been implicated as a specialized domain involved in TeNT binding and internalization into neurons, but these domains are widely distributed on multiple cell types, and therefore cannot simply explain the high specificity of the toxins for neurons.

Clostridial neurotoxins are internalized through the presynaptic membrane by an energy-dependent mechanism (Montecucco et al., "Structure and Function of Tetanus and *Botulinum* Neurotoxins," *Q. Rev. Biophys.* 28:423-472 (1995); Matteoli et al., "Synaptic Vesicle Endocytosis Mediates the Entry of Tetanus Neurotoxin into Hippocampal Neurons," *Proc. Natl. Acad. Sci. USA* 93:13310-13315 (1996); and Mukherjee et al., "Endocytosis," *Physiol. Rev.* 77:759-803 (1997), which are hereby incorporated by reference in their entirety), and rapidly appear in vesicles where they are at least partially protected from degradation (Dolly et al., "Acceptors for *Botulinum* Neurotoxin Reside on Motor Nerve Terminals and Mediate Its Internalization," *Nature* 307:457-460 (1984); Critchley et al., "Fate of Tetanus Toxin Bound to the Surface of Primary Neurons in Culture: Evidence for Rapid Internalization," *J. Cell Biol.* 100:1499-1507 (1985), which are hereby incorporated by reference in their entirety). The BoNT complex of light and heavy chains interacts with the endocytic vesicle membrane in a chaperone-like way, preventing aggregation and facilitating translocation of the light chain in a fashion similar to the protein conducting/translocating channels of smooth ER, mitochondria, and chloroplasts (Koriazova et al., "Translocation of *Botulinum* Neurotoxin Light Chain Protease through the Heavy Chain Channel," *Nat. Struct. Biol.* 10:13-18 (2003), which is hereby incorporated by reference in its entirety). Acidification of the endosome is believed to induce pore formation, which allows translocation of the light chain to the cytosol upon reduction of the interchain disulfide bond (Hoch et al., "Channels Formed by *Botulinum*, Tetanus, and Diphtheria Toxins in Planar Lipid Bilayers: Relevance to Translocation of Proteins Across Membranes," *Proc. Natl. Acad. Sci. USA* 82:1692-1696 (1985), which is hereby incorporated by reference in its entirety). Within the cytosol, the light chain displays a zinc-endopeptidase activity specific for protein components of the synaptic vesicle exocytosis apparatus. TeNT and BoNT B, D, F, and G recognize VAMP/synaptobrevin. This integral protein of the synaptic vesicle membrane is cleaved at a single peptide bond, which differs for each neurotoxin. BoNT A, C, and E recognize and cleave SNAP-25, a protein of the presynaptic membrane, at two different sites within the carboxyl terminus. BoNT C also cleaves syntaxin, another protein of the nerve plasmalemma (Montecucco et al., "Structure and Function of Tetanus and *Botulinum* Neurotoxins," *Q. Rev. Biophys.* 28:423-472 (1995); Sutton et al., "Crystal Structure of a SNARE Complex Involved in Synaptic Exocytosis at 2.4 Å Resolution," *Nature* 395:347-353 (1998), which are hereby incorporated by reference in their entirety). The cleavage of any component of the synaptic release machinery results in inhibition of acetylcholine release, ultimately leading to neuromuscular paralysis.

In one embodiment of the present invention, the isolated Clostridial neurotoxin is toxic. The toxicity of Clostridial neurotoxins is a result of a multi-step mechanism. From the circulation, BoNT targets the pre-synaptic membrane of neuromuscular junctions, where it is internalized to directly exert its toxic effect on the peripheral nervous system (Dolly et al., "Acceptors for *Botulinum* Neurotoxin Reside on Motor Nerve Terminals and Mediate Its Internalization," *Nature* 307:457-460 (1984), which is hereby incorporated by reference in its entirety). Toxicity at the neuromuscular junction involves neuron binding; internalization into endocytic vesicles, similar to those involved in synaptic vesicle recycling; activation within an acidic compartment to the proteolytically active toxin which then penetrates into the neuronal cytoplasm; and target recognition and catalytic cleavage of substrates in the neuronal machinery for synaptic vesicle exocytosis.

In an alternative embodiment of the present invention, the isolated Clostridial neurotoxin is physiologically active and atoxic. The endopeptidase activity responsible for Clostridial neurotoxin toxicity is believed to be associated with the presence of a HExxHxxH (SEQ ID NO: 25) motif in the light chain, characteristic of metalloproteases (FIG. 1). Mutagenesis of BoNT A light chain, followed by microinjection of the corresponding mRNA into presynaptic cholinergic neurons of *Aplysia californica*, allowed the minimal essential domain responsible for toxicity to be identified (Kurazono et al., "Minimal Essential Domains Specifying Toxicity of the Light Chains of Tetanus Toxin and *Botulinum* Neurotoxin Type A," *J. Biol. Chem.* 267:14721-14729 (1992), which is hereby incorporated by reference in its entirety). Site-directed mutagenesis of BoNT A light chain pinpointed the amino acid residues involved in $Zn^2$ coordination, and formation of the active metalloendoprotease core which cleaves SNAP-25 (Rigoni et al., "Site-Directed Mutagenesis Identifies Active-Site Residues of the Light Chain of *Botulinum* Neurotoxin Type A," *Biochem. Biophys. Res. Commun.* 288:1231-1237 (2001), which is hereby incorporated by reference in its entirety). The three-dimensional structures of Clostridial neurotoxins and their derivatives confirmed the mutagenesis results, and detailed the spatial organization of the protein domains. For the BoNT A holotoxin, crystal structure was obtained to a resolution of 3.3 Å (Lacy et al., "Crystal Structure of *Botulinum* Neurotoxin Type A and Implications for Toxicity," *Nat. Struct. Biol.* 5:898-902 (1998), which is hereby incorporated by reference in its entirety). The BoNT B holotoxin crystal structure was determined at 1.8 and 2.6 Å resolution (Swaminathan et al., "Structural Analysis of the Catalytic and Binding Sites of *Clostridium Botulinum* Neurotoxin B," *Nat. Struct. Biol.* 7:693-699 (2000), which is hereby incorporated by reference in its entirety). Recently, a crystal structure for BoNT E catalytic domain was determined to 2.1 Å resolution (Agarwal et al., "Structural Analysis of *Botulinum* Neurotoxin Type E Catalytic Domain and Its Mutant Glu212>Gln Reveals the Pivotal Role of the Glu212 Carboxylate in the Catalytic Pathway," *Biochemistry* 43:6637-6644 (2004), which is hereby incorporated by reference in its entirety). The later study provided multiple interesting structural details, and helps explain the complete loss of metalloendoproteolytic activity in the BoNT E LC E212>Q mutant. The availability of this detailed information on the relationship between the amino acid sequence and biological activities of Clostridial toxins enables the design of modified toxin genes with properties specifically altered for therapeutic goals.

Thus, in a preferred embodiment, the physiologically active and atoxic Clostridial neurotoxin of the present invention has a disabling mutation in an active metalloprotease site.

Figure 11A:
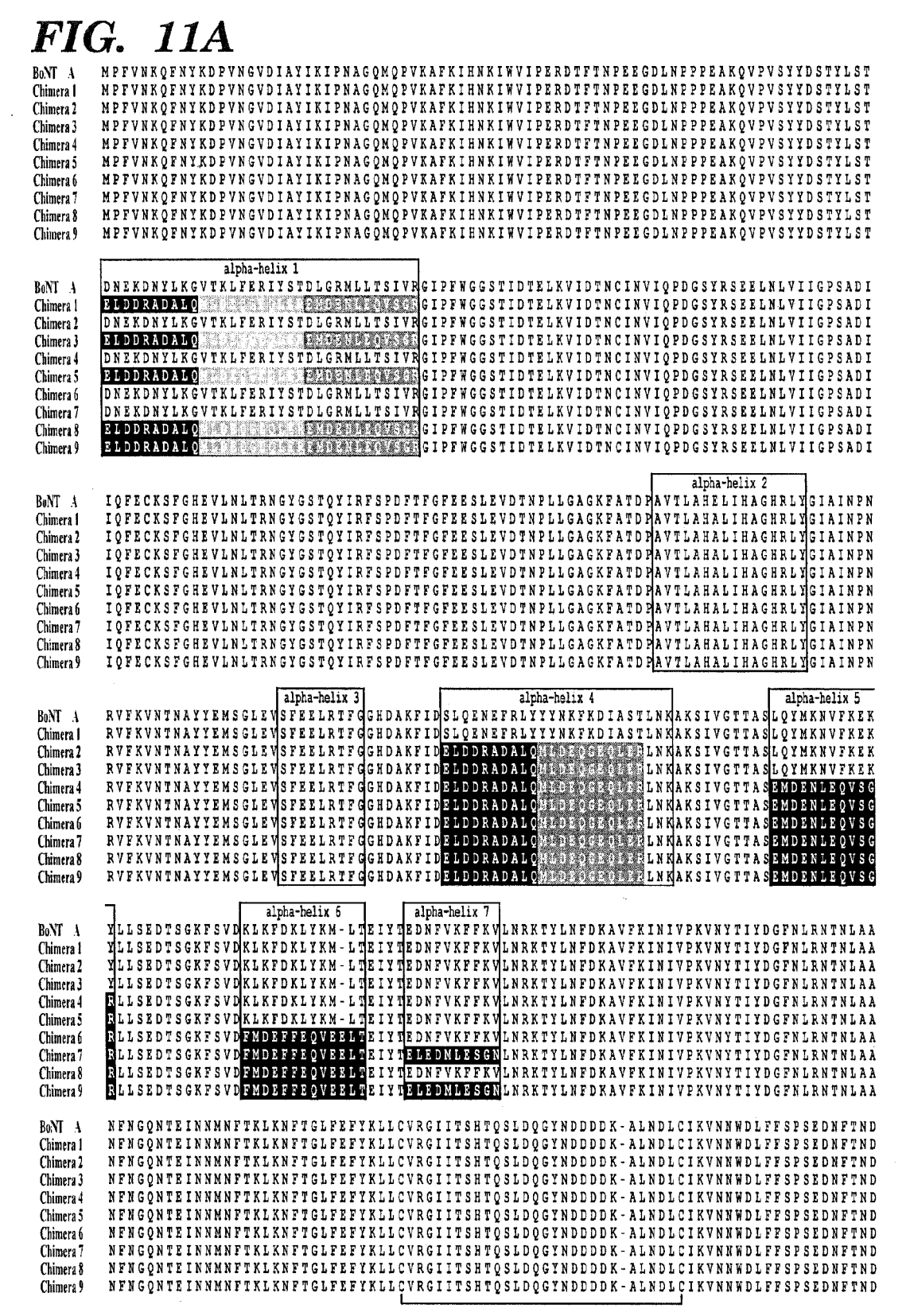

The physiologically active and atoxic Clostridial neurotoxin of the present invention may also have a non-native motif (e.g., a SNARE motif) in the light chain region that is capable of inactivating light chain metalloprotease activity in a toxic Clostridial neurotoxin. FIG. 11 illustrates the sequences of nine chimeric proteins, which are physiologically active and atoxic Clostridial neurotoxins containing at least one non-native motif in the light chain region that is capable of inactivating light chain metalloprotease activity in a toxic Clostridial neurotoxin. The non-native motifs are substituted for alpha-helix domains. When present in the physiologically active and atoxic Clostridial neurotoxin, the non-native protein motifs enable the neurotoxin to bind, inactivate, or otherwise mark the toxic light chain region of a wild type Clostridial neurotoxin for elimination from the cytosol of neurotoxin-affected neurons. As such, a physiologically active and atoxic Clostridial neurotoxin having a non-native motif in the light chain region that is capable of inactivating light chain metalloprotease activity in a toxic Clostridial neurotoxin is useful as an antidote to effectively target the cytoplasm of neurotoxin-affected neurons. Administration of such antidotes is described in greater detail below.

Yet a further aspect of the present invention relates to a vaccine or antidote having an isolated, physiologically active, atoxic, Clostridial neurotoxin produced by cleaving an isolated Clostridial neurotoxin propeptide of the present invention. The propeptide is cleaved at the highly specific protease cleavage site. The light and heavy chain regions are linked by a disulfide bond.

Developing effective vaccines and antidotes against Clostridial neurotoxins requires the preservation of structural features important to toxin trafficking and immunogenicity. From a practical perspective, this is most easily achieved by first producing recombinant molecules that retain the structural features and toxicity of native toxin, followed by selective modification to eliminate toxicity and introduce therapeutic utility. To achieve this goal, a versatile platform for the genetic manipulation of Clostridial toxin genes and for their selective modification was developed (described infra). The genetic engineering scheme can produce full-length toxic and atoxic derivatives of BoNT A, which retains important aspects of the wild toxin's native structure. This methodology can be generalized across the entire family of Clostridial neurotoxins because of their structural similarities (See FIGS. 1-2).

Thus, in a preferred embodiment, the vaccine or antidote of the present invention is a physiologically active and atoxic Clostridial neurotoxin from *Clostridium botulinum*, such as from *Clostridium botulinum* serotypes A-G. As described supra, the vaccine or antidote has the physiological activity of a wild Clostridial neurotoxin, which activity includes, but is not limited to, toxin immunogenicity, trans- and intra-cellular trafficking, and cell recognition. The Clostridial neurotoxin of the vaccine or antidote is rendered atoxic by a mutation in its active metalloprotease site, as described supra. Additional mutuations may be introduced to ensure atoxicity and introduce new biological activities, while preserving systemic trafficking and cellular targeting of the vaccine or antidote. As has also been described, the vaccine or antidote may possess non-native motifs in the light chain region that are capable of inactivating light chain metalloprotease activity in a toxic Clostridial neurotoxin.

Atoxic Clostridial neurotoxins can be tested as candidate vaccines and antidotes to BoNT poisoning. Atoxic derivatives are created using the BoNT toxic derivative constructs developed under the methods described infra. Point mutations are introduced into the toxin's active metalloprotease site to eliminate toxicity while maintaining native toxin structure, immunogenicity, trans- and intra-cellular trafficking, and cell recognition. Expression systems and purification schemes are optimized as described infra. Derivatives found to completely lack toxicity yet retain relevant biological activities of the native toxin, are evaluated for their potential as either vaccines or antidotes to BoNT poisoning. Parenteral routes of administration are tested first, followed by evaluation of oral and inhalational routes as applicable. Utility as a vaccine is determined by immunogenicity and challenge studies in mice. Utility as an antidote is first evaluated in vitro by testing the ability of atoxic derivatives to prevent neuromuscular blockade in the mouse phrenic-nerve hemidiaphragm, and to inhibit native toxin trafficking in the transcytosis assay. Effective in vitro antagonists are tested as in vivo antidotes, and may be superior to antibody-based antidotes because they more effectively mimic native toxin absorption and trafficking pathways. Antidote effectiveness in vivo is first evaluated using simultaneous dosing. Additional dosage and timing parameters relevant to using antidotes under crisis situations is further evaluated for atoxic derivatives found to be effective when administered simultaneously with toxin. Using these procedures, a series of atoxic derivatives and fusion proteins are created and their biological activities systematically catalogued. The availability of these well characterized BoNT gene constructs and toxin derivatives enables the rational design of new anti-BoNT therapeutics. Dose-response analyses and challenge studies against active neurotoxin provide data that allows the best candidate vaccines and antidotes to be selected for further development.

A further aspect of the present invention relates to method of immunizing a subject against toxic effects of a Clostridial neurotoxin. This method involves administering a vaccine of the present invention to the subject under conditions effective to immunize the subject against toxic effects of Clostridial neurotoxin.

The subject administered the vaccine may further be administered a booster of the vaccine under conditions effective to enhance immunization of the subject.

Another aspect of the present invention relates to a method of treating a subject for toxic effects of a Clostridial neurotoxin. This method involves administering an antidote comprising an isolated, physiologically active, atoxic, Clostridial neurotoxin produced by cleaving the isolated Clostridial neurotoxin propeptide of the present invention to the subject under conditions effective to treat the subject for toxic effects of Clostridial neurotoxin.

A vaccine or antidote of the present invention can be administered to a subject orally, parenterally, for example, subcutaneously, intravenously, intramuscularly, intraperitoneally, by intranasal instillation, or by application to mucous membranes, such as, that of the nose, throat, and bronchial tubes. The vaccine or antidote may be administered alone or with suitable pharmaceutical carriers, and can be in solid or liquid form such as, tablets, capsules, powders, solutions, suspensions, or emulsions.

The vaccine or antidote of the present invention may be orally administered, for example, with an inert diluent, or with an assimilable edible carrier, or may be enclosed in hard or soft shell capsules, or may be compressed into tablets, or may be incorporated directly with the food of the diet. For oral therapeutic administration, the vaccine or antidote may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The vaccine or antidote may also be administered parenterally. Solutions or suspensions can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The vaccine or antidote of the present invention may also be administered directly to the airways in the form of an aerosol. For use as aerosols, the vaccine or antidote of the present invention in solution or suspension may be packaged in a pressurized aerosol container together with suitable propellants, for example, hydrocarbon propellants like propane, butane, or isobutane with conventional adjuvants. The vaccine or antidote of the present invention also may be administered in a non-pressurized form such as in a nebulizer or atomizer.

A further aspect of the present invention relates to a chimeric protein having a first protein or protein fragment having a heavy chain region of a Clostridial neurotoxin and a second protein or protein fragment linked to the first protein or protein fragment.

In a preferred embodiment, the second protein or protein fragment has therapeutic functionality which can target specific steps in a trafficking pathway of the Clostridial neurotoxin.

BoNTs pass across epithelial surfaces without being destroyed or causing local toxicity. Passage across epithelia is believed to occur by specific binding and transcytosis. The ability of intact BoNT A to pass though pulmonary epithelia and resist proteolytic inactivation was demonstrated in rat primary alveolar epithelial cells and in immortalized human pulmonary adenocarcinoma (Calu-3) cells. The rate of transport was greater in the apical-to-basolateral direction than in the basolateral-to-apical direction, and it was blocked by serotype-specific toxin antibodies (Park et al., "Inhalational Poisoning by *Botulinum* Toxin and Inhalation Vaccination with Its Heavy-Chain Component," *Infect. Immun.* 71:1147-1154 (2003), which is hereby incorporated by reference in its entirety).

The ability of Clostridial neurotoxins to pass undegraded through epithelial barriers via transcytosis and to specifically target nervous tissue makes Clostridial neurotoxins useful in the development of oral and inhalational carriers for therapeutic agents that cannot normally be delivered via these routes of administration, and as delivery vehicles which can specifically target the peripheral and central nervous system.

Still another aspect of the present invention relates to a treatment method. This method involves contacting a patient with an isolated, physiologically active, toxic, Clostridial neurotoxin produced by cleaving an isolated Clostridial neurotoxin propeptide according to the present invention, under conditions effective to treat the patient.

By treatment, it is meant aesthetic treatment (See e.g., Carruthers et al., "*Botulinum* Toxin A in the Mid and Lower Face and Neck," *Dermatol. Clin.* 22:151-158 (2004); Lang, "History and Uses of BOTOX (*Botulinum* Toxin Type A)," *Lippincotts Case Manag.* 9:109-112 (2004); Naumann et al., "Safety of *Botulinum* Toxin Type A: A Systematic Review and Meta-Analysis," *Curr. Med. Res. Opin.* 20:981-990 (2004); Vartanian et al., "Facial Rejuvenation Using *Botulinum* Toxin A: Review and Updates," *Facial Plast. Surg.* 20:11-19 (2004), which are hereby incorporated by reference in their entirety) as well as therapeutic treatment (See e.g., Bentsianov et al., "Noncosmetic Uses of *Botulinum* Toxin," *Clin. Dermatol.* 22:82-88 (2004); Carruthers et al., "Botox: Beyond Wrinkles," *Clin. Dermatol.* 22:89-93 (2004); Jankovic, "*Botulinum* Toxin In Clinical Practice," *J. Neurol. Neurosurg. Psychiatry* 75:951-957 (2004); Klein, "The Therapeutic Potential of *Botulinum* Toxin," *Dermatol. Surg.* 30:452-455 (2004); Schurch, "The Role of *Botulinum* Toxin in Neurology," *Drugs Today (Barc)* 40:205-212 (2004), which are hereby incorporated by reference in their entirety).

Preferred treatment methods of the present invention include, but are not limited to, dermatologic, gastroenterologic, genitourinaric, and neurologic treatment.

Dermatologic treatment includes, but is not limited to, treatment for Rhtyiddess (wrinkles) (Sadick et al., "Comparison of *Botulinum* Toxins A and B in the Treatment of Facial Rhytides," *Dermatol. Clin.* 22:221-226 (2004), which is hereby incorporated by reference in its entirety), including glabellar (Carruthers et al., "*Botulinum* Toxin type A for the Treatment of Glabellar Rhytides," *Dermatol. Clin.* 22:137-144 (2004); Ozsoy et al., "Two-Plane Injection of *Botulinum* Exotoxin A in Glabellar Frown Lines," *Aesthetic Plast. Surg.* 28:114-115 (2004); which are hereby incorporated by reference in their entirety), neck lines (Brandt et al., "*Botulinum* Toxin for the Treatment of Neck Lines and Neck Bands," *Dermatol. Clin.* 22:159-166 (2004), which is hereby incorporated by reference in its entirety), crows feet (Levy et al., "*Botulinum* Toxin A: A 9-Month Clinical and 3D In Vivo Profilometric Crow's Feet Wrinkle Formation Study," *J. Cosmet. Laser Ther.* 6:16-20 (2004), which is hereby incorporated by reference in its entirety), and brow contour (Chen et al., "Altering Brow Contour with *Botulinum* Toxin," *Facial Plast. Surg. Clin. North Am.* 11:457-464 (2003), which is hereby incorporated by reference in its entirety). Other dermatologic treatment includes treatment for hypertrophic masateer muscles in Asians (Ahn et al., "*Botulinum* Toxin for Masseter Reduction in Asian Patients," *Arch. Facial Plast. Surg.* 6:188-191 (2004), which is hereby incorporated by reference in its entirety) and focal hyperhydrosis (Glogau, "Treatment of Hyperhidrosis with *Botulinum* Toxin," *Dermatol. Clin.* 22:177-185, vii (2004), which is hereby incorporated by reference in its entirety), including axillary ("*Botulinum* Toxin (Botox) for Axillary Hyperhidrosis," *Med. Lett. Drugs Ther.* 46:76 (2004), which is hereby incorporated by reference in its entirety) and genital (Lee et al., "A Case of Foul Genital Odor Treated with *Botulinum* Toxin A," *Dermatol. Surg.* 30:1233-1235 (2004), which is hereby incorporated by reference in its entirety).

Gastroentologic treatment includes, but is not limited to, treatment for esophageal motility disorders (Achem, "Treatment of Spastic Esophageal Motility Disorders," *Gastroenterol. Clin. North Am.* 33:107-124 (2004), which is hereby incorporated by reference in its entirety), pharyngeal-esophageal spasm (Bayles et al., "Operative Prevention and Management of Voice-Limiting Pharyngoesophageal Spasm," *Otolaryngol. Clin. North Am.* 37:547-558 (2004); Chao et al., "Management of Pharyngoesophageal Spasm with Botox," *Otolaryngol. Clin. North Am.* 37:559-566 (2004), which are hereby incorporated by reference in their entirety), and anal fissure (Brisinda et al., "*Botulinum* Neurotoxin to Treat Chronic Anal Fissure: Results of a Randomized 'Botox vs. Dysport' Controlled Trial," *Ailment Pharmacol. Ther.* 19:695-701 (2004); Jost et al., "*Botulinum* Toxin A in Anal Fissure: Why Does it Work?" *Dis. Colon Rectum* 47:257-258 (2004), which are hereby incorporated by reference in their entirety).

Genitourinaric treatment includes, but is not limited to, treatment for neurogenic dysfunction of the urinary tract ("Botulinic Toxin in Patients with Neurogenic Dysfunction of the Lower Urinary Tracts," *Urologia* July-August:44-48 (2004); Giannantoni et al., "Intravesical Resiniferatoxin Versus *Botulinum*-A Toxin Injections for Neurogenic Detrusor Overactivity: A Prospective Randomized Study," *J. Urol.* 172:240-243 (2004); Reitz et al., "Intravesical Therapy Options for Neurogenic Detrusor Overactivity," *Spinal Cord* 42:267-272 (2004), which are hereby incorporated by reference in their entirety), overactive bladder (Cruz, "Mechanisms Involved in New Therapies for Overactive Bladder," *Urology* 63:65-73 (2004), which is hereby incorporated by reference in its entirety), and neuromodulation of urinary urge incontinence (Abrams, "The Role of Neuromodulation in the Management of Urinary Urge Incontinence," *BJU Int.* 93:1116 (2004), which is hereby incorporated by reference in its entirety).

Neurologic treatment includes, but is not limited to, treatment for tourettes syndrome (Porta et al., "Treatment of Phonic Tics in Patients with Tourette's Syndrome Using *Botulinum* Toxin Type A," *Neurol. Sci.* 24:420-423 (2004), which is hereby incorporated by reference in its entirety) and focal muscle spasticity or dystonias (MacKinnon et al., "Corticospinal Excitability Accompanying Ballistic Wrist Movements in Primary Dystonia," *Mov. Disord.* 19:273-284 (2004), which is hereby incorporated by reference in its entirety), including, but not limited to, treatment for cervical dystonia (Haussermann et al., "Long-Term Follow-Up of Cervical Dystonia Patients Treated with *Botulinum* Toxin A," *Mov. Disord.* 19:303-308 (2004), which is hereby incorporated by reference in its entirety), primary blepharospasm (Defazio et al., "Primary Blepharospasm: Diagnosis and Management," *Drugs* 64:237-244 (2004), which is hereby incorporated by reference in its entirety), hemifacial spasm, post-stroke (Bakheit, "Optimising the Methods of Evaluation of the Effectiveness of *Botulinum* Toxin Treatment of Post-Stroke Muscle Spasticity," *J. Neurol. Neurosurg. Psychiatry* 75:665-666 (2004), which is hereby incorporated by reference in its entirety), spasmodic dysphonia (Bender et al., "Speech Intelligibility in Severe Adductor Spasmodic Dysphonia," *J. Speech Lang. Hear Res.* 47:21-32 (2004), which is hereby incorporated by reference in its entirety), facial nerve disorders (Finn, "*Botulinum* Toxin Type A: Fine-Tuning Treatment of Facial Nerve Injury," *J. Drugs Dermatol.* 3:133-137 (2004), which is hereby incorporated by reference in its entirety), and Rasmussen syndrome (Lozsadi et al., "*Botulinum* Toxin A Improves Involuntary Limb Movements in Rasmussen Syndrome," *Neurology* 62:1233-1234 (2004), which is hereby incorporated by reference in its entirety). Other neurologic treatments include treatment for amputation pain (Kern et al., "Effects of *Botulinum* Toxin Type B on Stump Pain and Involuntary Movements of the Stump," *Am. J. Phys. Med. Rehabil.* 83:396-399 (2004), which is hereby incorporated by reference in its entirety), voice tremor (Adler et al., "*Botulinum* Toxin Type A for Treating Voice Tremor," *Arch. Neurol.* 61:1416-1420 (2004), which is hereby incorporated by reference in its entirety), crocodile tear syndrome (Kyrmizakis et al., "The Use of *Botulinum* Toxin Type A in the Treatment of Frey and Crocodile Tears Syndrome," *J. Oral Maxillofac. Surg.* 62:840-844 (2004), which is hereby incorporated by reference in its entirety), marginal mandibular nerve paralysis, and pain control (Cui et al., "Subcutaneous Administration of *Botulinum* Toxin A Reduces Formalin-Induced Pain," *Pain* 107:125-133 (2004), which is hereby incorporated by reference in its entirety), including but not limited to pain after mastectomy (Layeeque et al., "*Botulinum* Toxin Infiltration for Pain Control After Mastectomy and Expander Reconstruction," *Ann. Surg.* 240:608-613 (2004), which is hereby incorporated by reference in its entirety) and chest pain of esophageal origin (Schumulson et al., "Current and Future Treatment of Chest Pain of Presumed Esophageal Origin," *Gastroenterol. Clin. North Am.* 33:93-105 (2004), which is hereby incorporated by reference in its entirety). Another neurologic treatment amenable to the methods of the present invention is headache (Blumenfeld et al., "*Botulinum* Neurotoxin for the Treatment of Migraine and Other Primary Headache Disorders," *Dermatol. Clin.* 22:167-175 (2004), which is hereby incorporated by reference in its entirety).

The methods of the present invention are also suitable for treatment of cerebral palsy (Balkrishnan et al., "Longitudinal Examination of Health Outcomes Associated with *Botulinum* Toxin Use in Children with Cerebral Palsy," *J. Surg. Orthop. Adv.* 13:76-80 (2004); Berweck et al., "Use of *Botulinum* Toxin in Pediatric Spasticity (Cerebral Palsy)," *Mov. Disord.* 19:S162-S167 (2004); Pidcock, "The Emerging Role of Therapeutic *Botulinum* Toxin in the Treatment of Cerebral Palsy," *J. Pediatr.* 145:S33-S35 (2004), which are hereby incorporated by reference in their entirety), hip adductor muscle dysfunction in multiple sclerosis (Wissel et al., "*Botulinum* Toxin Treatment of Hip Adductor Spasticity in Multiple Sclerosis," *Wien Klin Wochesnchr* 4:20-24 (2001), which is hereby incorporated by reference in its entirety), neurogenic pain and inflammation, including arthritis, iatrogenic parotid sialocele (Capaccio et al., "Diagnosis and Therapeutic Management of Iatrogenic Parotid Sialocele," *Ann. Otol. Rhinol. Laryngol.* 113:562-564 (2004), which is hereby incorporated by reference in its entirety), and chronic TMJ displacement (Aquilina et al., "Reduction of a Chronic Bilateral Temporomandibular Joint Dislocation with Intermaxillary Fixation and *Botulinum* Toxin A," *Br. J. Oral Maxillofac. Surg.* 42:272-273 (2004), which is hereby incorporated by reference in its entirety). Other conditions that can be treated by local controlled delivery of pharmaceutically active toxin include intra-articular administration for the treatment of arthritic conditions (Mahowald et al., "Long Term Effects of Intra-Articular BoNT A for Refractory Joint Pain," *Annual Meeting of the American College of Rheumatology* (2004), which is hereby incorporated by reference in its entirety), and local administration for the treatment of joint contracture (Russman et al., "Cerebral Palsy: A Rational Approach to a Treatment Protocol, and the Role of *Botulinum* Toxin in Treatment," *Muscle Nerve Suppl.* 6:S181-S193 (1997); Pucinelli et al., "Botulinic Toxin for the Rehabilitation of Osteoarthritis Fixed-Flexion Knee Deformity," *Annual Meeting of the Osteoarthitis Research Society International* (2004), which are hereby incorporated by reference in their entirety). The methods of the present invention are also suitable for the treatment of pain associated with various conditions characterized by the sensitization of nociceptors and their associated clinical syndromes, as described in Bach-Rojecky et al., "Antinociceptive Effect of *Botulinum* Toxin Type A In Rat Model of Carrageenan and Capsaicin Induced Pain," *Croat. Med. J.* 46:201-208 (2005); Aoki, "Evidence for Antinociceptive Activity of *Botulinum* Toxin Type A in Pain Management," *Headache* 43 Suppl 1:S9-15 (2003); Kramer et al., "*Botulinum* Toxin A Reduces Neurogenic Flare But Has Almost No Effect on Pain and Hyperalgesia in Human Skin," *J. Neurol.* 250:188-193 (2003); Blersch et al., "*Botulinum* Toxin A and the Cutaneous Nociception in Humans: A Prospective, Double-Blind, Placebo-Controlled, Randomized Study," *J. Neurol. Sci.* 205:59-63 (2002), which are hereby incorporated by reference in its entirety.

The methods and products of the present invention may be customized to optimize therapeutic properties (See e.g., Chaddock et al., "Retargeted Clostridial Endopeptidases Inhibition of Nociceptive Neurotransmitter Release In Vitro, and Antinociceptive Activity in In Vivo Models of Pain," *Mov. Disord.* 8:S42-S47 (2004); Finn, "*Botulinum* Toxin Type A: Fine-Tuning Treatment of Facial Nerve Injury," *J. Drugs Dermatol.* 3:133-137 (2004); Eleopra et al., "Different Types of *Botulinum* Toxin in Humans," *Mov. Disord.* 8:S53-S59 (2004); Flynn, "Myobloc," *Dermatol. Clin.* 22:207-211 (2004); and Sampaio et al., "Clinical Comparability of Marketed Formulations of *Botulinum* Toxin," *Mov. Disord.* 8:S129-S136 (2004), which are hereby incorporated by reference in their entirety).

EXAMPLES

The following examples are provided to illustrate embodiments of the present invention but are by no means intended to limit its scope.

Example 1

SDS PAGE

Samples from all intermediate purification steps, as well as pure recombinant protein, were routinely separated and visualized on 8% separating polyacrylamide gels, according to Laemmli procedure (Laemmli, "Cleavage of Structural Proteins During the Assembly of the Head of Bacteriophage T4," *Nature* 227:680-685 (1970), which is hereby incorporated by reference in its entirety). Protein bands were visualized by Bio-Safe Coomassie G-250 Stain (Bio-Rad, Cat. #161-0786).

Example 2

Western Blotting

Samples for Western blot analysis were separated on 8% SDS-polyacrylamide gels. Followed by separation, proteins were transferred to the Hybond-C nitrocellulose membrane (Amersham Biosciences, Cat. #RPN303C) in 1× Tris/Glycine buffer (Bio-Rad, Cat. #161-0734) supplemented with 20% methanol at 100 volts for 2 hours, 4° C. After the transfer, membrane was rinsed in distilled water and protein bands were visualized by staining with 0.2% Ponceau S in 1% acetic acid for 1 minute. Dye from the membrane was washed away in the Tris-buffered saline/0.1% Tween-20 buffer, pH 7.5, followed by incubation of the membrane in the blocking reagent (5% non-fat powdered milk in Tris-buffered saline/0.1% Tween-20 buffer, pH 7.5) for 16 hours at 4° C. For immunodetection, membrane was incubated with primary antibodies/immune serum at 1:7,000 dilution, in 0.5% non-fat milk in Tris-buffered saline/0.1% Tween-20 buffer, pH 7.5 at room temperature for 2 hours. Membrane was washed (6×5 min) and incubated with secondary antibody at 1:10,000 dilution at room temperature for 25 minutes. After the series of additional washing (6×5 min), immunoreactive bands were visualized using ECL (enhanced chemiluminescence) Plus Western Blotting Reagent (Amersham Biosciences, Cat. #RPN2124) according to manufacturer instructions. Hyperfilm ECL (Amersham Biosciences, Cat. #RPN1674K) was used for autoradiography with the exposure time adequate to visualize chemiluminescent bands. The proteins were identified by comparison with the positive controls and molecular weight protein standards.

Example 3

Evaluation of Recombinant Toxin Yield

The protein concentration of the purified recombinant protein fractions were determined using the BCA Protein assay reagent (Pierce, Cat. #23225) with bovine serum albumin used as standard.

Example 4

In Vitro Toxicity Assay on the Mouse Phrenic Nerve-Hemidiaphragm Preparation The toxicity of the various recombinant proteins is bioassayed on the mouse phrenic nerve-hemidiaphragm preparation (Simpson et al., "Isolation and Characterization of a Novel Human Monoclonal Antibody that Neutralizes Tetanus Toxin," *J. Pharmacol. Exp. Ther.* 254:98-103 (1990), which is hereby incorporated by reference in its entirety). Tissues are excised and suspended in physiological buffer, aerated with 95% $O_2$, 5% $CO_2$, and maintained at 35° C. The physiological solution has the following composition: 137 mM NaCl, 5 mM KCl, 1.8 mM $CaCl_2$, 1 mM $MgSO_4$, 24 mM $NaHCO_3$, 1 mM $NaH_2PO_4$, 11 mM D-glucose, and 0.01% gelatin. Phrenic nerves are stimulated continuously (1.0 Hz; 0.1-0.3 msec duration), and muscle twitch is recorded. Toxin-induced paralysis is measured as a 50% reduction in muscle twitch response to neurogenic stimulation.

Example 5

In Vitro Transcytosis Assay

Cells are grown on polycarbonate membranes with a 0.4 μm pore size in Transwell® porous bottom inserts (Corning-Costar) (FIG. 10) (Zweibaum et al., "Use of Cultured Cell Lines in Studies of Intestinal Cell Differentiation and Function," In: *Handbook of Physiology*, Section 6: "The Gastrointestinal System," Edited by Schulz et al., American Physiological Society, Bethesda, Vol. IV, 223-255; Dharmsathaphorn et al., "A Human Colonic Tumor Cell Line that Maintains Vectorial Electrolyte Transport," *Am. J. Physiol.* 246:G204-G208 (1984); and Dharmsathaphorn et al., "Established Intestinal Cell Lines as Model Systems for Electrolyte Transport Studies," *Methods Enzymol.* 192:354-389 (1990), which are hereby incorporated by reference in their entirety). The cell growth area within each insert is equivalent to 1 cm$^2$. Prior to seeding the cells, insert membranes are coated with 10 μg/cm$^2$ rat tail collagen type I. Collagen stock solution (6.7 mg/ml) are prepared in sterile 1% acetic acid and stored at 4° C. The collagen stock solution is diluted as needed in ice cold 60% ethanol, and 150 μl of the resulting solution containing 10 μg of diluted collagen is added to each well (cm$^2$).

The collagen solution is allowed to dry at room temperature overnight (ca. 18 hours). After drying, the wells are sterilized under UV light for one hour, followed by a preincubation with cell culture medium (30 minutes). The preincubation medium is removed immediately prior to addition of cells and fresh medium. Cells are plated in the Transwells® at confluent density. The volumes of medium added will be 0.5 ml to the upper chamber and 1.0 ml to the bottom chamber. Culture medium is changed every two days. The cultures maintained in 12 well plates are allowed to differentiate a minimum of 10 days before use. The integrity of cell monolayers and formation of tight junctions is visualized by monitoring the maintenance of a slightly higher medium meniscus in the inserts as compared to the bottom wells.

Formation of tight junctions is confirmed experimentally by assay of the rate of [$^3$H]-inulin diffusion from the top well into the bottom chamber or by measurement of transepithelial resistance across the monolayer. Transcytosis is assayed by replacement of medium, usually in the top well, with an appropriate volume of medium containing various concentrations of [$^{125}$I]-labeled protein of interest. Iodination is performed according to Park et al., "Inhalational Poisoning by *Botulinum* Toxin and Inhalation Vaccination with Its Heavy-Chain Component," *Infect. Immun.* 71:1147-1154 (2003), which is hereby incorporated by reference in its entirety. Transport of radiolabeled protein is monitored by sampling the entire contents of opposite wells, which is usually the bottom wells. Aliquots (0.5 ml) of the sampled medium are filtered through a Sephadex G-25 column, and 0.5 ml fractions are collected. The amount of radioactivity in the fractions is determined in a γ-counter. The amount of transcytosed protein is normalized and expressed as fmole/hr/cm$^2$. A minimum of two replicates per condition is included in each experiment, and experiments typically are reproduced at least three times.

Example 6

In Vivo Toxicity Assay in Mice

The toxicity of proteins of interest are bioassayed in mice. Proteins are diluted in phosphate buffered saline, including 1 mg/ml bovine serum albumin, and injected intraperitoneally (i.p.) into animals. The proteins are administered in a 100 μl aliquot of solution at concentrations of 1-100 ng per animal (average weight ~25 g). Any animals that survive exposure to the toxic derivatives are monitored for a total of 2 weeks to detect any non-specific toxicity.

Example 7

The BoNT Substrate-Cleavage Assay

Engineered proteins are assayed for endoprotease activity using either mouse brain synaptosomes and recombinant SNAP-25 for BoNT A and BoNT E as the source of the substrate. Native or reduced proteins are incubated with 10 to 50 μg of synaptosomal membranes in reaction buffer containing 50 mM HEPES, pH 7.1, 20 μM ZnCl$_2$, and 1% N-octyl-β-D-glucopyranoside. Reduced protein are prepared by incubation with DTT (20 mM; 1 hr; room temperature) in phosphate buffered saline. The cleavage reaction is initiated by addition of engineered protein (200 nM final concentration) to substrate, and the reaction is allowed to proceed for 3 hours at 37° C. Endoprotease activity is assayed using Western blot analysis and anti-C-terminal SNAP-25 antibodies (StressGen) for immunodetection of substrate. For visualization of SNAP-25, samples are separated on 16.5% Tris-tricine gels. After separation, proteins are transferred to nitrocellulose membranes (Micron Separations) in Tris-glycine transfer buffer at 50 volts for 1 hr. Blotted membranes are rinsed in distilled water and stained for 1 min with 0.2% Ponceau S in 1% acetic acid. Following a brief rinse with distilled water, molecular weight markers and transferred proteins are visualized. Membranes are destained in phosphate buffered saline-Tween (pH 7.5; 0.1% Tween 20), then blocked with 5% non-fat powdered milk in phosphate buffered saline-Tween for 1 hr at room temperature. Subsequently, membranes are incubated in 0.5% milk with a 1:5,000 dilution of anti-SNAP-25 polyclonal antibody. Secondary antibody is used at 1:20,000 dilution. Membranes are washed again (5×) and visualized using enhanced chemiluminescence (SuperSignal®West Pico, Pierce) according to manufacturer's instructions. Membranes are exposed to film (Hyperfilm ECL, Amersham Biosciences) for times adequate to visualize chemiluminescent bands. Peptides are identified by comparison with known standards. The BoNT B substrate-cleavage assay is performed according to the published protocol (Caccin et al., "VAMP/Synaptobrevin Cleavage by Tetanus and *Botulinum* Neurotoxins is Strongly Enhanced by Acidic Liposomes," *FEBS Lett.* 542:132-136 (2003), which is hereby incorporated by reference in its entirety).

Example 8

Cloning Procedures

Preparation of the DNA Template for PCR

Outlined in detail infra are the procedures used to engineer BoNT A derivatives. A similar strategy for engineering all BoNT derivatives can be carried out.

25 μg of the pure *Clostridium botulinum* type A (Hall strain) genomic DNA was isolated from bacterial pellet separated from the 100 ml of the culture according to Sambrook et al., *Molecular Cloning: A Laboratory Manual*, Second Edition, Plainview, N.Y.: Cold Spring Harbor Laboratory Press (1989), which is hereby incorporated by reference in its entirety. DNA was precipitated and dissolved in 1×TE, pH 8.0, at concentration ~0.8 mg/ml.

Genomic DNA, isolated from the mixture of the anaerobic bacteria from the soil, was prepared according to the following protocol: 1000 g of the soil taken from Central Park, New York, were triturated in 2 liters of Dulbecco's phosphate-buffered saline (DPBS) (Invitrogen, Cat. #14190-144). Crude extract was filtered through Kimwipes EX-L wipes (Kimberly-Clark, Neenah, Wis.) and concentrated on a stirred ultrafiltration cell (Millipore (Billerica, Mass.), Cat. #5123) with Ultracel 100-KDa cutoff membrane (Millipore, Cat. #14432) to a final volume of 5 ml. Four liters of cooked meat medium (Difco (Franklin Lakes, N.J.), Cat. #226720), prepared according to manufacturer's protocol were inoculated with 5 ml of concentrated soil extract. After 168-hour incubation at 37° C. without agitation or aeration, a mixture of anaerobic bacteria was separated from the supernatant by centrifugation on Sorwall GS3 rotor (7000 rpm, 25 min., 4° C.) and processed for the isolation of the total genomic DNA on Qiagen (Valencia, Calif.) Genomic tips (Cat. #10262), with additional components also purchased from Qiagen (Cat. #19060, Cat. #19133, Cat. #19101), according to manufacturer's protocol (Qiagen Genomic DNA Handbook). From the cells recovered from 4 liters of the media on ten Qiagen Genomic tips, 6 mg of the genomic DNA were isolated. DNA was precipitated and dissolved in 1×TE, pH 8.0 at concentration ~1 mg/ml.

Example 9

PCR Amplification of BoNT DNA

25 μg of the mixed genomic DNA or 5 μg of the pure *Clostridium botulinum* type A genomic DNA were used per one 100-μl PCR reaction setting. Reaction conditions were designed according to manufacturer's protocols supplied with Platinum®Pfx polymerase (Invitrogen, Cat. #11708-021). All oligonucleotides and linkers were designed according to the sequence of *botulinum* Neurotoxin type A cDNA obtained from Genebank (Accession #: M30196). Annealing temperatures were deduced from the structure of each set of the oligonucleotides used for the PCR.

Example 10

Engineering of Non-Expression Vector pLitBoNTA, Carrying Coding Part of BoNT A td Plasmid encoding *botulinum* Neurotoxin A light chain (pLitBoNTALC) was obtained by the following protocol: The annealed phosphorylated linkers

```
                                      (SEQ ID NO: 26)
CBA1:  5'-pCTAGCATGCCATTTGTTAATAAACAATTTAATTATAAG
and
                                      (SEQ ID NO: 27)
CBA2:  5'-pGATCCTTATAATTAAATTGTTTATTAACAAATGGCATG
``` were subcloned into vector pcDNA3.1/Zeo(+) (Invitrogen, Cat. #V86020), pre-digested with the restriction endonucleases NheI and BamHI and dephosphorylated, resulting in plasmid pcDBoNTALC1. The 620 b.p. PCR product, obtained on genomic DNA as a template with the oligonucleotides

```
CBA03:
                                      (SEQ ID NO: 28)
5'-TATCTGCAGGGATCCTGTAAATGGTGTTGATATTGCTT

ATATAAAATTCC and

CBA04:
                                      (SEQ ID NO: 29)
5'-TATGAATTCACCGGTCCGCGGGATCTGTAGCAAATTT

GCCTGCACC
``` was digested with the restriction endonucleases BamHI and EcoRI and subcloned into pre-digested plasmid pcDBoNTALC1, resulting in plasmid pcDBoNTALC2. The 630 b.p. PCR product, obtained on genomic DNA as a template with the oligonucleotides

```
CBA05:
                                      (SEQ ID NO: 30)
5'-TATACCGCGGTAACATTAGCACATGAACTTATACA

TGCTGGACATAGATTATATG
and

CBA06:
                                      (SEQ ID NO: 31)
5'-CATAGAATTCAAACAATCCAGTAAAATTTTTTAGTTT

AGTAAAATTCATATTATTAATTTCTGTATTTTGACC,
``` was digested with the restriction endonucleases SacII and EcoRI and subcloned into pre-digested plasmid pcDBoNTLC2, resulting in plasmid pcDBoNTLC3. The annealed phosphorylated linkers

```
CBA8:
                                      (SEQ ID NO: 32)
5'-pAAT TCTATAAGTTGCTATGTGTAAGAGGGATAAT

ACTAGTCACACTCAATCT
and

CBA9:
                                      (SEQ ID NO: 33)
5'-pCTAGAGATTGAGTGTGACTAGTTATTATCCCTCTTA

CACATAGCAACTTATAG
``` were subcloned into vector pcDBoNTLC3, pre-digested with the restriction endonucleases EcoR and XbaI and dephosphorylated, resulting in plasmid pcDBoNTALC. The annealed phosphorylated linkers

```
CBA10:
                                      (SEQ ID NO: 34)
5'-pCGCGTTAGCCATAAATCTGGTTATAAGCGCGC

GAGGTGTTAAGTG
and

CBA11:
                                      (SEQ ID NO: 35)
5'-pCTAGCACTTAACACCTCGCGCGCTTATAACCAGA

TTTATGGCTAA
``` were subcloned into vector pLitmus38i (New England Biolabs, Cat. #N3538S), pre-digested with the restriction endonucleases MluI and NheI and dephosphorylated, resulting in plasmid pLit38iMod. The 1230 b.p. DNA fragment, isolated from the plasmid pcDBoNALC after its digest with restriction endonucleases NheI and ApaI was subcloned into pre-digested and dephosphorylated vector pLit38iMod, resulting in plasmid pLitBoNTALC.

Plasmid encoding *botulinum* Neurotoxin A heavy chain (pLitBoNTAHC) was obtained by the following protocol: The 1450 b.p. PCR product obtained on the genomic DNA as a template with the oligonucleotides

```
CBA12:
                                       (SEQ ID NO: 36)
5'-AATCTGCAGCCACAGCTGTGGGGTACCTTAATTGGTCA

AGTAGATAGATTAAAAGATAAAGTTAATAATACACTTAGTACAGA

TATACC
and

CBA13:
                                       (SEQ ID NO: 37)
5'-ATTAGGGCCCTTAATTAAGCGGCCGCCTCGAGC

TATTACAGTGGCCTTTCTCCCCATCCATCATCTACAGGAATAAATTC
``` was digested with restriction endonucleases ApaI and PstI and subcloned into pre-digested and dephosphorylated vector pLitmus38i, resulting in plasmid pLitBoNTAHC1. Two PCR products, 490 b.p., obtained on the genomic DNA as a template with the oligonucleotides

```
CBA14:
                                       (SEQ ID NO: 38)
5'-ATACTGCAGTCTAGACCAAGGATACAATGACGATG

ATGATAAGGCA TTAAATGATTTATGTATCAAAGTTAATAATTGGG
and

CBA15:
                                       (SEQ ID NO: 39)
5'-GCCTAAAAACATAGCCGCTTCGGTCGCTTTATTAACTT

TCTTTACATAGTCTGAAG
``` and 720 b.p., obtained on genomic DNA as a template with the oligonucleotides

```
CBA16:
                                       (SEQ ID NO: 40)
5'-TAATAAAGCGACCGAAGCGGCTATGTTTTTAGGCT

GGGTAGAACAATTAG
and

CBA17:
                                       (SEQ ID NO: 41)
5'-TATAGGGCCCCCTAGGGGTACCTCTATTATCATATATAT

ACTTTAATAATGCATCTTTAAGAC
``` were mixed with the molar ratio 1:1 and re-PCRed with oligonucleotides CBA14 and CBA17, resulting in 1170 b.p. PCR product, which was digested with restriction endonucleases PstI and KpnI and subcloned into pre-digested and dephosphorylated vector pLitBoNTAHC1, leading to plasmid pLitBoNTAHC.

Plasmid pLitBoNTA, encoding the entire sequence of BoNT A was obtained by ligating a 2615 b.p. DNA fragment from the vector pLitBoNTAHC, digested with restriction endonucleases XbaI and ApaI into pre-digested and dephosphorylated vector pLitBoNTALC. The size of pLitBoNTA is 6712 b.p. with 3900 b.p. of BoNT A coding sequence.

Example 11

Engineering Plasmid pETcBoNTA for the BoNT A td Expression in *E. coli* pETCBoNTA was obtained by subcloning DNA fragment obtained after the digest of pLitBoNTA vector with NheI and NotI into pre-digested and dephosphorylated expression vector pETcoco2 (Novagen (San Diego, Calif.), Cat. #71148-3) and resulted in 16,194 b.p. BoNT A td expression vector pETCBoNTA.

Example 12

Engineering Donor Plasmid pFBSecBoNTA for the Expression of BoNT A td in Insect Cells pFBSecBoNTA was obtained by the following protocol: 112 b.p. PCR product, synthesized on plasmid pBac-3 (Novagen, Cat. #70088-3) with oligonucleotides

```
CBA 22:
                                       (SEQ ID NO: 42)
5'-TAAGCGCGCAGAATTCTCTAGAAT GCCCATGTTAAGCGCTATTG
and CBA23:
                                       (SEQ ID NO: 43)
5'-TAAGCTAGCGTGATGGTGGTGATGATGGACCATGGCC
``` and digested with restriction endonucleases BssHII and NheI was subcloned into pre-digested and dephosphorylated vector pLitBoNTA, resulting in plasmid pLitSecBoNTA. DNA fragment, isolated from pLitSecBoNTA digested with BssHII and NotI was subcloned into pre-digested and dephosphorylated vector pFastBac™1 (Invitrogen, Cat. #10360-014), resulting in 8764 b.p. plasmid pFBSecBoNTA.

Example 13

Engineering the BoNT A Coding Sequence to Enable Expression of Toxin Derivatives The DNA template was obtained as either pure genomic DNA isolated from *Clostridium botulinum* type A cultures, or as mixed genomic DNA isolated from anaerobic bacteria of soil. BoNT A DNA was amplified by PCR using the high fidelity Platinum Pfx polymerase (Invitrogen, Carlsbad, Calif.). The full-length coding sequence of BoNT A toxic derivative (td) was obtained after consecutive subcloning of five PCR fragments and two phosphorylated linkers into the modified vector pLitmus38i (New England Biolabs, Beverly, Mass.), resulting in plasmid pLitBoNTA. This strategy was used to minimize infidelity during the PCR reaction and to enable the introduction of targeted mutations and endonuclease restriction sites for subsequent engineering of expressed toxin products.

Figure 3B:
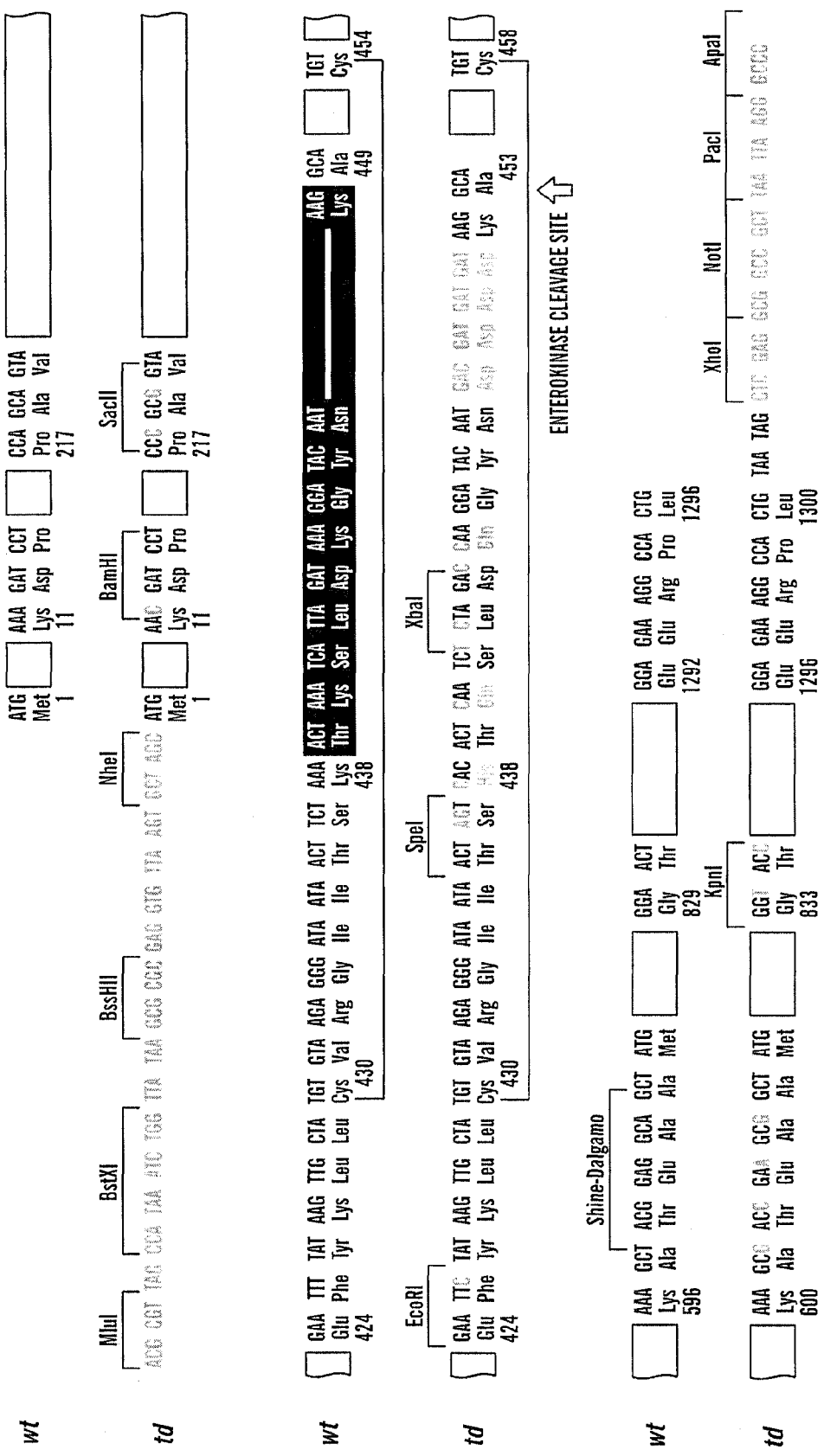

The details of the final construct (td) in comparison with native BoNT A (wt) are shown in FIG. 3, illustrating new restriction sites, eliminated alternative translation sites, and amino acids inserted or substituted. The construct encoding full-length BoNT A td was obtained by ligation of the DNA inserts from the plasmid encoding the toxin heavy chain ("HC") into the plasmid encoding the toxin light chain ("LC"). Plasmid encoding the LC of BoNT A td was generated by consecutive ligation of two PCR products and two phosphorylated linkers into vector pLitmus38i. It contains multiple unique restriction sites upstream from the 5'-end of the LC sequence, the unique endonuclease restriction site NheI upstream from the first methionine codon, and endonuclease restriction sites for BamHI and EcoRI introduced by silent mutations flanking the minimal catalytic domain (Kadkhodayan et al., "Cloning, Expression, and One-Step Purification of the Minimal Essential Domain of the Light Chain of *Botulinum* Neurotoxin Type A," *Protein Expr. Purif.* 19:125-130 (2000), which is hereby incorporated by reference in its entirety) of the protein at the codons for $Lys_{11}$ and $Phe_{425}$. Two additional mutations encoding substitutions $Lys_{438}$>His and $Lys_{440}$>Gln were introduced to minimize non-specific proteolysis of the BoNT A td propeptide during expression. A unique restriction site for XbaI was introduced by silent mutation at the codon. Plasmid, encoding the HC of BoNT A td, was generated by consecutive ligation of two PCR products into the pLitmus38i vector. First, the PCR product encoding the receptor-binding domain of BoNT A was subcloned into the vector pLitmus38i. Second, the PCR product encoding the toxin's translocation domain, obtained by re-PCR of two smaller PCR products was subcloned into plasmid encoding the toxin's receptor binding domain. The final plasmid contains a unique XbaI site at the 5'-end of the coding sequence introduced by silent mutation of the codon $Asp_{443}$, mutation of $Lys_{444}$>Gln to minimize non-specific proteolysis of the BoNT A td propeptide, insertion of codons for four aspartic acid residues between $Asn_{447}$ and $Lys_{448}$ to create an enterokinase cleavage site, four silent mutations at $Ala_{597}$, $Thr_{598}$, $Glu_{599}$, and $Ala_{600}$ to inactivate the putative internal DNA regulatory element, a unique KpnI site introduced at the codon for $Gly_{829}$ by silent mutagenesis, and multiple unique restriction sites at the 3'-end of the construct after the stop codon. DNA encoding the $Ala_{597}$-$Ala_{699}$ sequence was mutated, because it contains an internal Shine-Dalgarno sequence upstream from internal methionine codon which can result in co-translational contamination of recombinant protein expressed in *E. coli* (Lacy et al., "Recombinant Expression and Purification of the *Botulinum* Neurotoxin Type A Translocation Domain," *Protein Expr. Purif.* 11:195-200 (1997), which is hereby incorporated by reference in its entirety), the initial choice for an expression system to test.

A second full-length BoNT A gene derivative was designed to render the BoNT A atoxic (ad, atoxic derivative). Using site-directed mutagenesis with two synthetic oligonucleotides, a single point mutation, $E_{224}$>A, was introduced into plasmid pLitBoNTA to inactivate the proteolytic activity responsible for BoNT A neurotoxicity resulting in plasmid pLitBoNTAME224A (Kurazono et al., "Minimal Essential Domains Specifying Toxicity of the Light Chains of Tetanus Toxin and *Botulinum* Neurotoxin Type A," *J. Biol. Chem.* 267:14721-14729 (1992); Lacy et al., "Crystal Structure of *Botulinum* Neurotoxin Type A and Implications for Toxicity," *Nat. Struct. Biol.* 5:898-902 (1998); Agarwal et al., "Structural Analysis of *Botulinum* Neurotoxin Type E Catalytic Domain and Its Mutant Glu212>Gln Reveals the Pivotal Role of the Glu212 Carboxylate in the Catalytic Pathway," *Biochemistry* 43:6637-6644 (2004), which are hereby incorporated by reference in their entirety). Atoxic derivatives produced in this way will better preserve the structural moieties responsible for toxin immunogenicity, trafficking, and cell recognition sites.

A third full-length BoNT A derivative was designed to test the utility of the genetic engineering methodology to produce fusion proteins, using GFP as an example. The sequence encoding the minimal catalytic domain of the BoNT A LC (Kadkhodayan et al., "Cloning, Expression, and One-Step Purification of the Minimal Essential Domain of the Light Chain of *Botulinum* Neurotoxin Type A," *Protein Expr. Purif.* 19:125-130 (2000), which is hereby incorporated by reference in its entirety) was excised from plasmid pLitBoNTA and replaced with a GFP-coding sequence to create plasmid pLitGFPBoNTAHC encoding a GFP derivative of BoNT A (gfpd). The GFP-encoding sequence was obtained by PCR with two synthetic oligonucleotides on the plasmid pEGFP-N3 (Clontech, Palo Alto, Calif.). The fusion protein was specifically designed to preserve structural features responsible for cell binding and intracellular trafficking.

All intermediate DNA constructs as well as plasmids pLitBoNTA, pLitBoNTAME224A, and pLitGFPBoNTAHC were checked by multiple restriction digests. pLitBoNTA and pLitBoNTAME224A were sequenced with twelve BoNT A-specific synthetic oligonucleotides, while pLitGFPBoN-TAHC was sequenced with ten BoNT A-specific synthetic oligonucleotides and two GFP-specific oligonucleotides as primers, resulting in a set of overlapping sequences which covered all coding parts of all of the above plasmids. All sequences were demonstrated to be free of unexpected mutations.

Example 14

Expression of the Recombinant BoNT A Derivatives in *E. coli*

Expression plasmids were transfected into *E. coli* Rosetta-gami B (DE3) competent cells (Novagen, Cat. #71136-3) by the heat-shock method according to manufacturer protocol. Bacterial cultures were grown in LB media containing 50 mg/l carbenicillin, 15 mg/l kanamycin, 12.5 mg/l tetracycline and 34 mg/l chloramphenicol. Various conditions, affecting the plasmid copy number per cell without and with addition of L-arabinose (0.01% final concentration) to the bacterial medium were tested. All bacterial cultures used for protein expression were grown at 37° C. until reaching OD@600 nm ~0.3-0.4. Prior to the induction of the expression, bacterial cultures were split to test influence of the temperature on the yield and quality of the expressed product. Upon induction (OD@600 nm ~0.5-0.7), cultures were grown at 37° C., 25° C., and 12° C. Final IPTG concentration in the growth medium used for induction was 0.5 mM. For the time-course study, samples of the culture at 1, 3, 6, 9, and 12 hours after induction were collected and analyzed. Under the optimal conditions the *E. coli* cultures were incubated overnight in the presence of L-arabinose at 37° C. until reaching OD ~0.4@600 nm. The temperature of the bacterial suspensions was then lowered to 12° C. over one hour, and IPTG was added to a final concentration of 0.5 mM. After induction, culture growth was allowed to continue in a shaker incubator at 12° C. for six more hours. The bacterial pellet was then harvested by centrifugation on Sorwall GS3 rotor (7000 rpm, 25 min., 4° C.) and processed for recombinant protein isolation. Cells kept on ice were resuspended in BugBuster lysis reagent (Novagen, Cat. #70584-4) with the volume ratio cell paste:BugBuster solubilization reagent 1:5. The nucleic acid degradation reagent benzonaze was used instead of the mixture sonication (Novagen, Cat. #70746-3), 1000 U/ml final concentration, recombinant lysozyme (Novagen, Cat. #71110-4), 50 U/ml final concentration, and a cocktail of protease inhibitors "Complete" (Roche (Switzerland), Cat. #1697498), 1 tablet/50 ml final concentration were added simultaneously to the paste in the process of resuspension. Approximately 30 minutes after resuspension, the non-viscous lysate was cleared by centrifugation on Sorwall SS34 rotor (17000 rpm, 25 min, 4° C.) and processed for the further protein purification.

An *E. coli* expression system was the first tested for a number of reasons. First, other laboratories have reported expression of recombinant partial length BoNT A domains in this system (Rigoni et al., "Site-Directed Mutagenesis Identifies Active-Site Residues of the Light Chain of *Botulinum* Neurotoxin Type A," *Biochem. Biophys. Res. Commun.* 288:1231-1237 (2001); Chaddock et al., "Expression and Purification of Catalytically Active, Non-Toxic Endopeptidase Derivatives of *Clostridium Botulinum* Toxin Type A," *Protein Expr. Purif.* 25:219-228 (2002); Lalli et al., "Functional Characterization of Tetanus and *Botulinum* Neurotoxins Binding Domains," *J. Cell Sci.* 112:2715-2724 (1999); Kadkhodayan et al., "Cloning, Expression, and One-Step Purification of the Minimal Essential Domain of the Light Chain of *Botulinum* Neurotoxin Type A," *Protein Expr. Purif.* 19:125-130 (2000); Lacy et al., "Recombinant Expression and Purification of the *Botulinum* Neurotoxin Type A Translocation Domain," *Protein Expr. Purif.* 11:195-200 (1997), which are hereby incorporated by reference in their entirety). A second reason for selecting an *E. coli* expression system is that many recombinant proteins can be expressed in *E. coli* with good yield and stability. A third reason is that non-canonical *E. coli* codons in the BoNT A sequence can be overcome by utilizing a bacterial strain carrying a plasmid encoding tRNA for the rare codons. A fourth reason is that toxicity of the full-length BoNT A to the host can be minimized by using an expression plasmid that allows regulation of the transition from low to medium plasmid copy numbers. Fifth, proper disulfide bridge formation in the recombinant proteins can be optimized by utilizing an *E. coli* strain with trxB$^-$ gor$^-$ mutations. Sixth, degradation of recombinant proteins in the host can be minimized by utilizing an *E. coli* Rosetta-gami strain with lon$^-$ ompT$^-$ mutations, in which two major proteolytic enzymes are inactivated.

Expression plasmids were obtained by single-step subcloning of the coding portion of BoNT A derivatives—td, ad, and gfpd into the expression vector pETcoco2 (Novagen, San Diego, Calif.). The resulting constructs contain DNA, encoding sequence MHHHHHHGAS . . . (SEQ ID NO: 44) and flanked with NheI unique restriction site in front of the first native methionine codon. The pETcoco system combines the advantages of T7 promoter-driven protein expression with the ability to control plasmid copy number. The pETcoco vectors are normally maintained at one copy per cell. In the single-copy state, pETcoco clones are extremely stable, which is especially important for target genes that are toxic to the host. Copy number can be amplified to 20-50 copies per cell by the addition of L-arabinose to the culture medium. The pETcoco vectors in λDE3 lysogenic hosts can be induced to increase expression of the target gene by as much as 2,500-fold over background when IPTG is added to the culture media. A 6-His tag was added to each recombinant protein to enable affinity purification. The affinity tag was added to the N-terminus, because prior studies found that addition of an affinity tag to the C-terminus results in loss of the toxin's physiological activity (Shapiro et al., "Identification of a Ganglioside Recognition Domain of Tetanus Toxin Using a Novel Ganglioside Photoaffinity Ligand," *J. Biol. Chem.* 272:30380-30386 (1997), which is hereby incorporated by reference in its entirety), while adding a hexahistidine tag to the N-terminus allowed expression and purification of the light chain domain with retained enzymatic activity (Kadkhodayan et al., "Cloning, Expression, and One-Step Purification of the Minimal Essential Domain of the Light Chain of *Botulinum* Neurotoxin Type A," *Protein Expr. Purif.* 19:125-130 (2000), which is hereby incorporated by reference in its entirety).

All expression constructs were transformed into *E. coli* Rosetta-gami B (DE3) competent cells (Novagen) and were grown in LB media containing ampicillin, kanamycin, tetracycline, and chloramphenicol. Ampicillin was added to select for colonies carrying pETcoco derived bla marker, kanamycin and tetracyclin were added to select for thioredoxin (trxB) and glutathione reductase (gor) mutations, thus improving the chances for proper disulfide bond formation in the *E. coli* cytoplasm (Derman et al., "Mutations that Allow Disulfide Bond Formation in the Cytoplasm of *Escherichia Coli*," *Science* 262:1744-1747 (1993); Prinz et al., "The Role of the Thioredoxin and Glutaredoxin Pathways in Reducing Protein Disulfide Bonds in the *Escherichia Coli* Cytoplasm," *J. Biol. Chem.* 272:15661-15667 (1997), which are hereby incorporated by reference in their entirety). Chloramphenicol was added to the medium to select for colonies containing helper plasmids that provide tRNAs for rare codons, thereby increasing the expression of proteins such as BoNT A encoded by DNA with codons non-canonical for *E. coli*.

Multiple conditions were tested to optimize expression of the BoNT A full length derivatives. Cultures were grown with and without L-arabinose in the media, and different IPTG concentrations were evaluated for induction. Incubation temperatures and time were also optimized for BoNT derivative expression. Under optimal conditions, the *E. coli* cultures were incubated overnight in the presence of L-arabinose at 37° C. until reaching OD ~0.4 at 600 nm. The temperature of the bacterial suspensions was then lowered to 12° C. over one hour, and IPTG was added to a final concentration 0.5 mM. After induction, culture growth was allowed to continue in a shaker incubator at 12° C. for six more hours. The bacterial pellet was then harvested by centrifugation, lysed with Bug-Buster lysis reagent (Novagen) in the presence of nucleic acid degradation reagent benzonaze (Novagen), lysozyme, and a cocktail of protease inhibitors. The lysate was cleared by centrifugation and purified by incubation with a Ni-NTA affinity resin. The supernatant and eluate from the Ni-NTA agarose were run on 8% SDS PAGE gels, and analyzed by Western blotting with polyclonal antibodies raised against the full-length BoNT A inactivated toxioid. Rosetta-gami B (DE3) *E. coli* transformed with the empty vector was used as the negative control. Native BoNT A in SDS-PAGE loading buffer was used as the positive control.

Figure 4A:
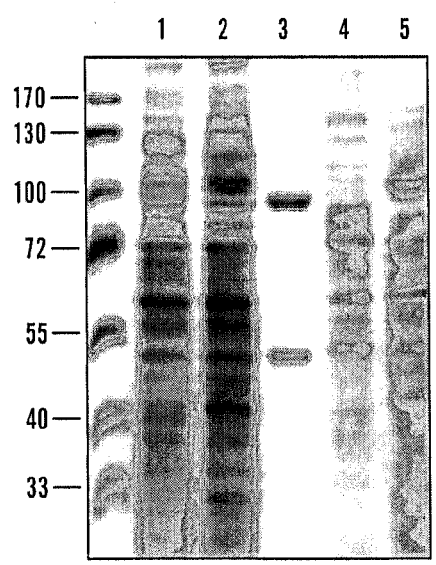
FIGS. 4A-B show expression and purification of the toxic derivative of BoNT A (td) in E. coli.
Figure 4B:
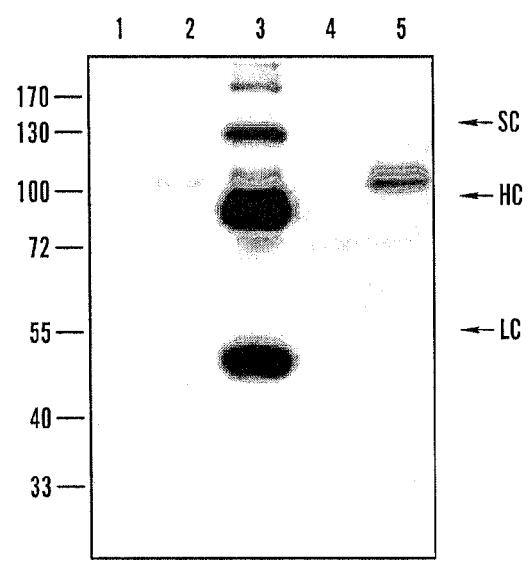

FIG. 4 illustrates the results of *E. coli* expression and purification protocols for BoNT A td. The expressed protein was soluble and could be purified using the chelate affinity tag. However, the molecular weight of the recombinant BoNT A td full length propeptide expressed was significantly lower than that of the native full-length BoNT A propeptide. Extensive proteolysis was observed with all purification and expression protocols tested in *E. coli*, even when the toxin derivatives were expressed by the cells in the single-copy plasmid state. This instability may be related to the systems available in *E. coli* for post-translational processing of proteins, with improper folding and disulfide bonding making the recombinant toxins susceptible to degradation. Similar results were obtained when attempting to express the atoxic (ad) and GFP-(gfpd) derivatives of BoNT A in *E. coli*. The problems encountered with *E. coli* based expression systems with respect to native protein folding and extensive proteolysis of the recombinant product, may be resolved by modification and optimization of the *E. coli* expression system.

Example 15

Expression of BoNT A Derivatives in Baculovirus-Based System

Bac-to-Bac® baculovirus expression system (Invitrogen, Cat. #10359-016) was used for the generation of the recombinant baculoviruses. A protocol for the insect cell culture was taken from the manual supplied with the kit. Recombinant donor plasmids were transformed into Max Efficiency DH10Bac™ competent cells (Invitrogen, Cat. #10361-012). Colonies containing recombinant bacmid were identified by disruption of the lacZa gene and selected by the absence of developing blue color, while growing on the plate with the chromogenic substrate Bluo-gal (Invitrogen, Cat. #15519-028). High molecular weight DNA was isolated from the selected colonies on DNA plasmid purification system (Qiagen, Cat. #12245). Transposition of the DNA of interest into baculovirus genome was confirmed by PCR on high molecular weight DNA with oligonucleotides CBA14 and CBA17, resulting in amplification of 1170 b.p. DNA band in samples where transposition took place. Bacmids were used to transfect serum-free medium adapted Sf9 insect cells (Invitrogen, Cat. #11496-015) to produce baculoviruses. Transfection was performed by the following protocol: $9 \times 10^5$ cells were seeded per one 35-mm well in 2 ml of unsupplemented Grace's insect cell culture medium (Invitrogen, Cat. #11595-030). Cells from a 3 to 4 day-old suspension culture in mid-log phase with a viability of >97% were used for experiment. Cells were attached to the plastic at 27° C. for at least one hour in advance and transfected with the lipophylic complexes, formed after mixing bacmid with Cellfectin® transfection reagent (Invitrogen, Cat. #10362-010), according to the protocol supplied by the manufacturer. 72 hours after transfection, the supernatant containing recombinant baculoviruses was harvested and separated from the cells by low-speed centrifugation (Sorwall GS 3 Rotor, 2000 rpm, 20 min, 4° C.). The supernatant represents the primary baculoviral stock. Amplification of this baculoviral stock and viral plaque assay was performed according to the protocol supplied by the manufacturer. Experiments related to identification of the optimal MOI and time-course studies of recombinant protein expression were also performed according to the manufacturer recommendations.

For the purpose of protein expression, Sf9 cells were grown as a shaken culture in a SF900 II serum-free medium (Invitrogen, Cat. #10902-088) at 27° C. in humidified atmosphere. At the density of the cell culture ~$1.2 \times 10^6$/ml, baculovirus stock in the same medium was added to suspension at MOI ~0.1. Incubation continues for another ~50 hours, after which medium was separated from the cells by centrifugation (Sorwall GS 3 Rotor, 2000 rpm, 20 min, 4° C.) and further processed for the protein purification by the procedure outlined below. Sf9 cells are very sensitive to growth conditions. They require a constant temperature of 27±1° C., good aeration of shaking cultures, and a sterile environment. If ambient temperatures rise above 27° C., refrigeration is required in the incubator used. An incubator sufficiently large to produce sufficient quantities of BoNT derivatives for biological testing is recommended.

To avoid poisoning of the insect cell host, the BoNT A td construct was modified by adding a signal peptide to provide for secretion of the recombinant proteins to the medium. Targeting the recombinant toxins for secretion also resulted in proper disulfide bond formation between the toxin's light and heavy chains. Improvements to this expression system were tested as described infra.

To increase the total yield of the recombinant protein, donor recombinant baculovirus plasmids and bacmids were generated with an expression cassette that allows expression of the recombinant protein to be driven by two separate and independent promoters simultaneously, p10 and PH (donor plasmid pFastBac™ Dual, Invitrogen, Cat. #10712-024).

To stabilize and increase the titer of the recombinant baculoviral stock, an approach outlined in BaculoDirect® Expression System protocol (Invitrogen (Carlsbad, Calif.), Cat. #12562-021) was used that allows negative selection to remove non-recombinant baculovirus that tend to appear in amplified stocks over the time. To improve purification of the toxins, the affinity of the recombinantly expressed proteins for Ni-NTA resin was increased by generating additional BoNT constructs with longer N-terminal His tags.

The advantages of a baculovirus expression system include proper disulfide bridge formation which has been demonstrated for numerous recombinant proteins in this system; protein purification, which is facilitated when serum-free culture medium is utilized and the expressed proteins contain a short secretory signal and affinity tag; physiological activity similar to native progenitors can be retained in the expressed products; and the absence of endotoxins endogenous to *E. coli*, which facilitates biological testing and therapeutic use of the expressed proteins (Allen et al., "Recombinant Human Nerve Growth Factor for Clinical Trials: Protein Expression, Purification, Stability and Characterisation of Binding to Infusion Pumps," *J. Biochem. Biophys. Methods.* 47:239-255 (2001); Curtis et al., "Insect Cell Production of a Secreted form of Human Alpha(1)-Proteinase Inhibitor as a Bifunctional Protein which Inhibits Neutrophil Elastase and has Growth Factor-Like Activities," *J. Biotechnol.* 93:35-44 (2002), which are hereby incorporated by reference in their entirety). The disadvantages of this system are its cost, time-consuming procedures, and generally the yield of proteins is not as high as in *E. coli*. Furthermore, because the regulated exocytosis machinery is well preserved across eukaryotic species from yeast to mammals, expression of BoNT A in this system can potentially lead to the host poisoning and cellular death. Nonetheless, since Clostridial neurotoxins are known to pass through epithelial cells by transcytosis without any toxic affects (Simpson, "Identification of the Major Steps in Botulinum Toxin Action," *Annu. Rev. Pharmacol. Toxicol.* 44:167-193 (2004); Park et al., "Inhalational Poisoning by Botulinum Toxin and Inhalation Vaccination with Its Heavy-Chain Component," *Infect. Immun.* 71:1147-1154 (2003), which are hereby incorporated by reference in their entirety), and the toxin constructs described herein are designed to remain in the single-chain propeptide form until processed to dichain mature form by enterokinase, this system is worth further testing.

Figure 5:
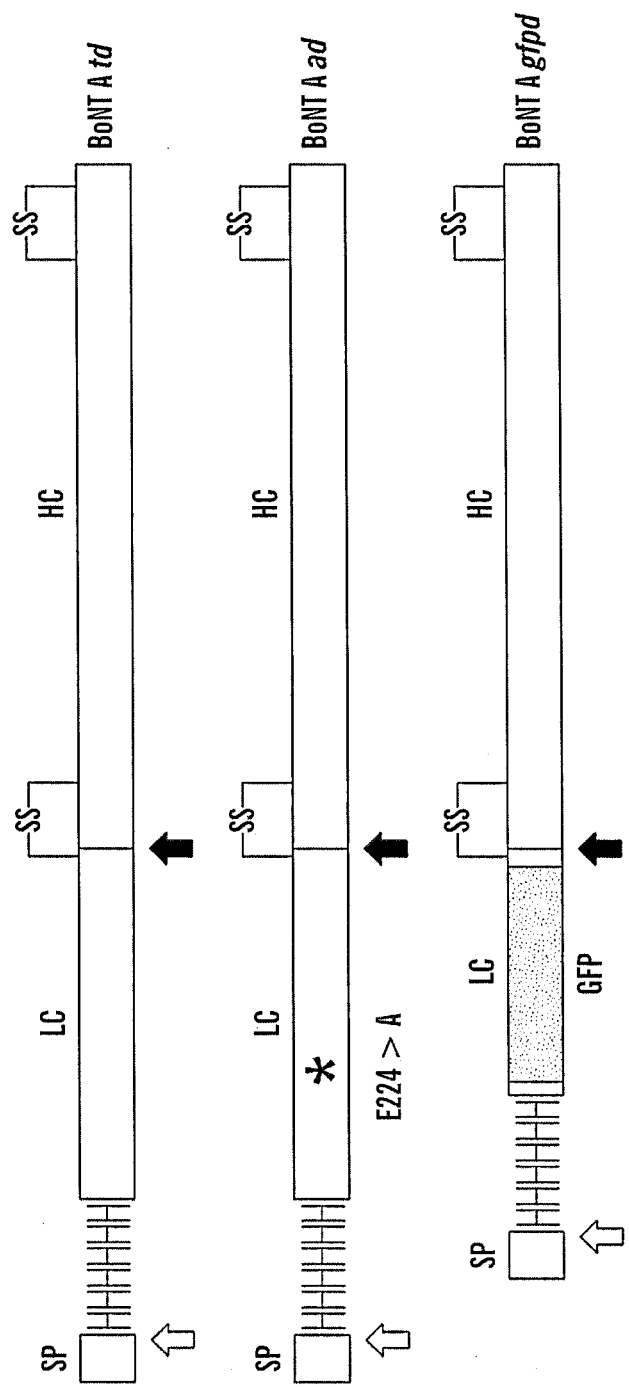
FIG. 5 is a schematic representation of the three recombinant BoNT A derivatives expressed in a baculovirus system. BoNT A td: toxic derivative of BoNT A. BoNT A ad: atoxic derivative of BoNT A. BoNT A gfpd: green fluorescent protein (GFP) derivative of BoNT A. Further modifications introduced into the td sequence depicted in FIG. 3 include the introduction of a signal sequence and a hexahistidine tag (e.g., SEQ ID NO: 45) in front of the first native methionine for affinity purification. The difference between td and ad is a single amino acid substitution, E224>A, in the active center of toxin's catalytic domain. To create BoNT A gfpd, amino acids $Tyr_{10}$-$Leu_{416}$ of the native toxin's minimal catalytic domain were substituted with GFP. White and black arrows represent secretase and enterokinase cleavage sites, respectively.

Plasmid constructs for expression of BoNT A derivatives in this system were subcloned into the donor vector pFastBac™1 (Invitrogen). To facilitate secretion of the recombinant proteins into the media and to allow purification of the recombinant proteins on Ni-NTA agarose, a DNA sequence coding the gp64 signal peptide and a hexahistidine affinity tag MPMLSAIVLYVLLAAAAHSAFAAMVHHH-HHHSAS . . . (SEQ ID NO: 45), flanked with unique NheI restriction site in front of the first native methionine codon, was introduced by cloning of PCR product into all constructs. FIG. 5 provides a schematic representation of the BoNT A derivatives targeted for expression in the baculovirus system. The signal peptide shown in the illustrated recombinant proteins is removed by secretase processing during intracellular trafficking (von Heijne, "Signals for Protein Targeting Into and Across Membranes," *Subcell. Biochem.* 22:1-19 (1994), which is hereby incorporated by reference in its entirety). Expression of the genes in the vector pFastBac™1 is controlled by the *Autographa californica* multiple nuclear polyhedrosis virus (AcMNPV) polyhedrin (PH) promoter. Recombinant donor plasmids were transformed into DH10Bac® *E. coli* competent cells. Once the pFastBac™ based expression plasmid is in cellular cytoplasm, transposition occurs between the arms of mini-Tn7 element flanking the expression cassette in pFastBac™ based vector and the mini-attTn7 target site on the baculovirus shuttle vector (bacmid), already present in the cells. This event generates a recombinant bacmid. Transposition requires additional proteins supplied by helper plasmids also present in competent cells. Selection of the recombinant bacmid clones was performed visually (by size and color). The molecular nature of the isolated DNAs was confirmed by PCR with the specific oligonucleotide primers.

Recombinant bacmids and negative control bacmids (obtained as a result of transposition with empty donor plasmids) were transfected into Sf9 insect cells with the lipophilic reagent Cellfectin (Invitrogen). After 96 hours the recombinant baculoviral stock was harvested and used for infection of freshly seeded Sf9 cells.

Secondary baculoviral stock was used for multiple purposes, which include, testing the expression of recombinant proteins, amplifying recombinant baculoviruses and generating tertiary stock for future use, calculating the titer of recombinant baculoviruses, identifying the optimal ratio for multiplicity of infection (MOI), and establishing the optimal time course for protein expression. Baculovirus titer was calculated for each newly amplified baculoviral stock. For all BoNT A constructs tested, the optimal MOI was found to be ~0.1 pfu per cell and the optimal time for the protein harvest was found to be ~50 hours after infection. When recombinant proteins were allowed to accumulate in the media for 72 hours or longer, a significant portion of the recombinant protein was degraded due to virus-induced cellular lysis.

Figure 6:
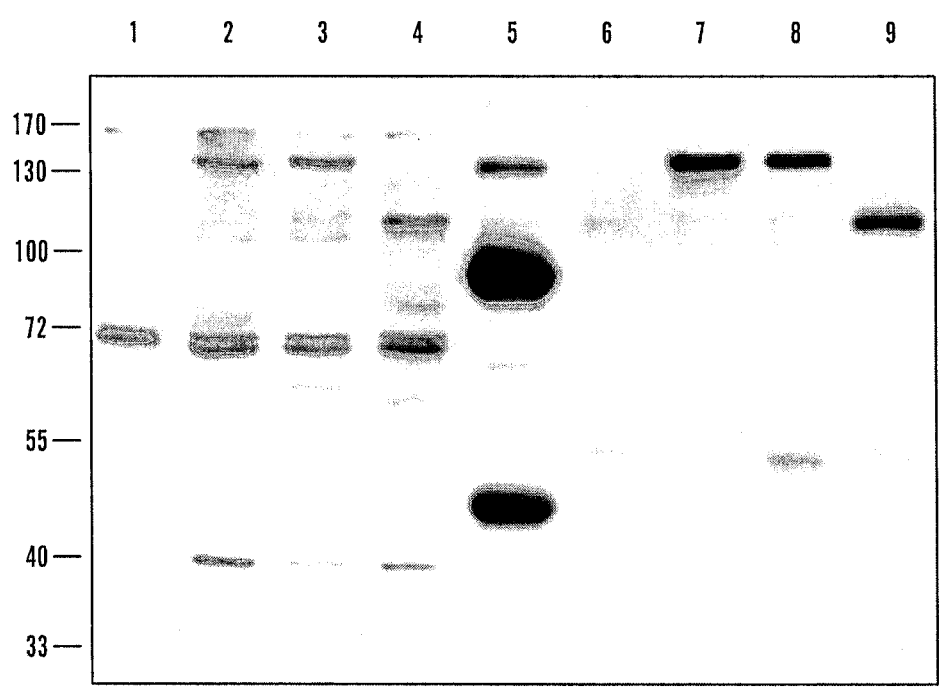
FIG. 6 shows expression of BoNT A derivatives in a baculovirus system by Western blot, probed with polyclonal antibodies raised against full-length BoNT A toxoid. Samples were treated with β-mercaptoethanol before separation. Protein molecular weight standards are shown on the left. Lane 1, 2, 3, and 4: conditioned media from Sf9 cells infected with empty bacmid (Lane 1), or recombinant bacmids derived from pFBSBoNTA (Lane 2), pFBSBoNTAME224A (Lane 3) or pFBSGFPBoNTAHC (Lane 4). Lane 5 is native BoNT A as a positive control. Lanes 6, 7, 8, and 9: eluate after Ni-NTA affinity purification of conditioned media from Sf9 cells transfected with empty bacmid (Lane 6), or recombinant bacmids derived from pFBSBoNTA (Lane 7), pFBSBoNTAME224A (Lane 8), or pFBSGFPBONTAHC (Lane 9).

FIG. 6 illustrates the protein expression results for the toxic (td), atoxic (ad), and GFP-linked (gfpd) full-length propeptide derivatives of BoNT A (cultures harvested at 50 hrs). All recombinant proteins were soluble and secreted into the media, could be purified by binding to the affinity resin, and have the expected mobility on SDS PAGE comparable to the mobility of single chain wt BoNT A. The recombinant BoNT A derivatives expressed using these conditions were free of degradation products recognized by the polyclonal antibody.

Example 16

Enterokinase Processing and LC-HC Disulfide Bridges

Figure 7A:
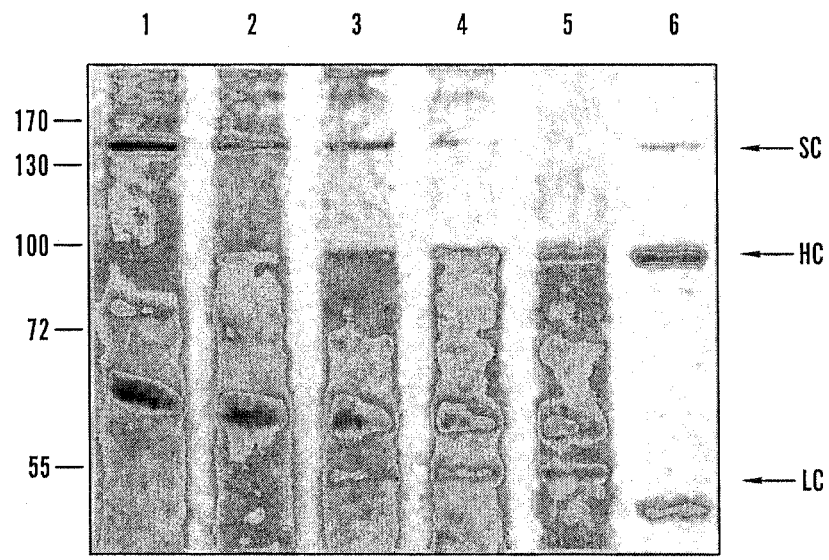
FIGS. 7A-B illustrate the concentration of recombinant enterokinase (rEK) required to effect complete cleavage of BoNT A toxic derivative (td) propeptide.
Figure 7B:
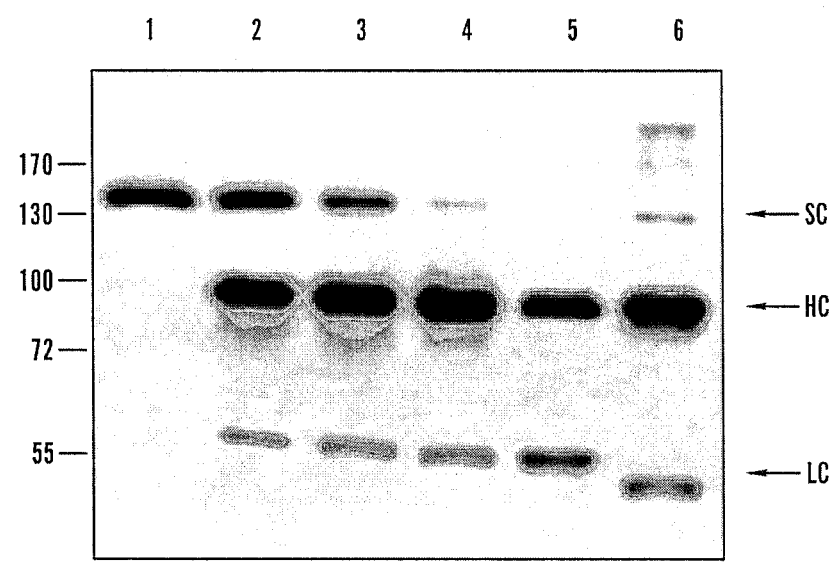

FIG. 7 illustrates a dosage-titration curve for cleavage of the propeptide constructs with recombinant enterokinase (rEK), using the td derivative as an example. For the processing of the single-chain (SC) protein, different amounts have been applied to the BoNT A td. Using 0.5 U of the enzyme at 20° C. for 8 hours was found to completely digest 1 µg of the sc BoNT A td.

To evaluate whether the disulfide bridges between the light and heavy chains of the recombinant proteins were properly formed, the recombinant propeptide derivatives were compared on reducing and non-reducing gels after digestion with excess rEK. Western blots were probed with polyclonal antibodies raised against native full-length BoNT A toxoid. The results of this experiment, shown in FIGS. 8A and 8B, demonstrate that all of the recombinant propeptides were processed into a two-subunit form by rEK, and that the subunits could be readily separated after reduction of the disulfide bridges, as expected.

Expression of a GFP-linked derivative of BoNT A is demonstrated by the green fluorescence of Sf9 cells 12 hours after infection with the recombinant baculovirus expressing BoNT A gfpd (FIGS. 8C and 8D). The significant difference in the background of FIG. 8C (recombinant baculovirus expressing BoNT A gfpd with secretion signal) versus FIG. 8D (recombinant baculovirus expressing GFP control), is believed to result from the secretion of the fluorescent recombinant protein into the media.

Example 17

Purification of the Recombinant BoNT A Derivatives

Methods to purify reasonable quantities of the full-length BoNT A derivatives were developed using BoNT A td as an example. Though the recombinant protein was found to bind to Ni-NTA resin (FIG. 5), the affinity was not sufficient to establish a one step purification scheme. The protein bound to the Ni-NTA resin in 5 mM imidazole, but was eluted from the affinity column by 40 mM imidazole. At this concentration of imidazole, there are other proteins present in the eluate, and therefore additional steps are needed to separate recombinant protein from contaminants.

Similar results were observed with the minimal essential domain of BoNT A expressed and purified in *E. coli* (Kadkhodayan et al., "Cloning, Expression, and One-Step Purification of the Minimal Essential Domain of the Light Chain of *Botulinum* Neurotoxin Type A," *Protein Expr. Purif.* 19:125-130 (2000), which is hereby incorporated by reference in its entirety). The stable minimal essential domain of the LC expressed with two 6-His tags on the N- and C-termini of the protein was eluted from the Ni-NTA column by 90 mM imidazole, still a relatively low concentration of affinity eluant. Poor accessibility of the affinity tags may explain these difficulties. Interestingly, there were two fractions of the same protein from the affinity column, with the second fraction eluted in 250 mM imidazole. While 90 mM imidazole fraction was enzymatically active, as was shown in SNAP-25 peptide cleavage assay, the higher concentration imidazole eluate was not. Denaturation of the protein may explain its absence of activity and high affinity for the chelate matrix.

Figure 9:
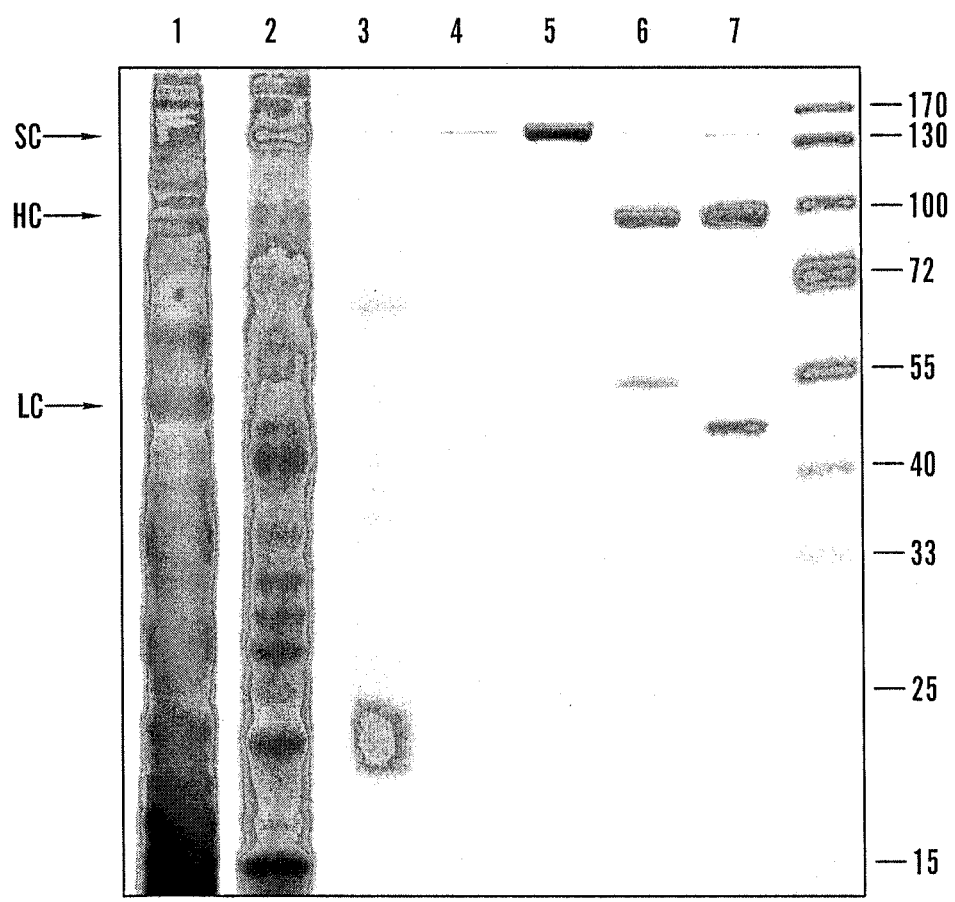
FIG. 9 is a BoNT A td purification table of 8% PAGE stained with Coomassie G-250. Samples were separated in the presence of β-mercaptoethanol. Lane 1: concentrated and dialyzed Sf9 medium, loaded on DEAE Sepharose; Lane 2: 100 mM NaCl eluate from DEAE Sepharose; Lane 3: 200 mM NaCl eluate from MonoS column; Lane 4: 60 mM imidazole eluate from Ni-NTA agarose; Lane 5: material, eluted from the FPLC gel-filtration column; Lane 6: material, eluted from the FPLC gel-filtration column and digested with rEK; Lane 7: positive control, purified native BoNT A. Protein molecular weight ladder is shown on the right.

A multi-step protocol was developed for purifying BoNT A td to homogeneity. Sf9 cells (viable cells count before infection ~1.2·10$^6$/ml) grown at 27° C. in SF900II serum-free media in humidified atmosphere at 125 rpm in shaking culture were harvested and separated from the medium. At ~50 hours after infection with recombinant baculovirus (MOI~0.1), the medium was collected, precipitated with ammonium sulfate or concentrated, dialyzed, and subjected to sequential DEAE-sepharose chromatography, MonoS chromatography, Ni-NTA affinity chromatography, and FPLC-based gel filtration chromatography. FIG. 9 illustrates the results of protein purification. The yield of the pure recombinant protein was 0.35 mg from one liter of serum-free medium. The pure protein eluted from the final gel-filtration column was competent for further processing with rEK. After the rEK cleavage, chloride ions containing buffer need to be substituted with phosphate or HEPES-based buffer to avoid instability of the recombinant toxin derivatives.

Approximately 2 ml of supernatant or cleared lysate was concentrated on Amicon Ultra-4 centrifugal filter device (Millipore, Cat. #UFC803024) to ~1 ml. The concentration procedure was done in parallel with multiple rounds of buffer substitution aimed at removing substances which could contribute to Ni$^{2+}$-stripping from the affinity resin. Final buffer composition was equal to the Ni-NTA Equilibration Buffer (infra). 20 µl of Ni-NTA suspension equilibrated in the Ni-NTA Equilibration Buffer (1:1 v/v) was added to the sample, followed by the sample incubation on the rotating platform for 1 hour. After incubation, affinity matrix was separated from the supernatant by centrifugation (3000 g, 1 min), and washed three times with Ni-NTA Equilibration Buffer, followed by centrifugation. The washing buffer was aspirated and the resin was resuspended in ~200 µl of SDS-PAGE loading buffer. The liquid was used for the further analysis by SDS PAGE and Western blotting.

TABLE 1

BoNT A td Purification
Composition of the buffers used:

DEAE Sepharose Equilibration Buffer: 20 mM $NaH_2PO_4$,
1 mM EDTA, pH 8.0
DEAE Sepharose Wash Buffer: 50 mM NaCl, 20 mM $NaH_2PO_4$, pH 8.0
DEAE Sepharose Elution Buffer:
500 mM NaCl, 20 mM $NaH_2PO_4$, pH 8.0
Mono S Equilibration Buffer: 20 mM $NaH_2PO_4$, pH 6.8
Mono S Wash Buffer: 25 mM NaCl, 20 mM $NaH_2PO_4$, pH 6.8
Mono S Elution Buffer: 300 mM NaCl, 20 mM $NaH_2PO_4$, pH 6.8
Ni-NTA Equilibration Buffer: 5 mM imidazole,
50 mM $NaH_2PO_4$, 300 mM NaCl, pH 8.0
Ni-NTA Wash Buffer I:
Same as above but made up with 10 mM imidazole
Ni-NTA Wash Buffer II:
Same as above but made up with 20 mM imidazole
Ni-NTA Elution Buffer:
Same as above but made up with 60 mM imidazole
HiLoad 16/60 Superdex 200PG Equilibration Buffer:
50 mM NaCl, 20 mM Tris-HCl, pH 7.5

All concentration, dialysis, and chromatography steps were performed at 4° C. 300 ml of the conditioned insect medium was either concentrated on the stirred ultrafiltration cell (Millipore, Cat. #5123) with Ultracel 100-KDa cutoff membrane (Millipore, Cat. #14432) to the final volume 5 ml, or the total protein from the medium was precipitated by addition of ammonium sulfate (60 g/100 ml) with slow stirring. Pellet was separated from the supernatant by centrifugation (5000 g, 20 min, 4° C.) and dissolved in 5 ml of DEAE-Sepharose Equilibration Buffer. Recombinant protein recovered from the first procedure was less denatured, and this procedure is preferable for future work. Scale-up production of the BoNT derivatives for biological testing could be accomplished with Tangential Flow Concentration System (Pellicon 2, Millipore, Cat. #XX42PLK60) which would enable large volumes of the media to be processed. During membrane concentration or ammonium sulfate precipitation, an insoluble precipitate forms from the pluronic surfactant included in the SF900 II media (to prevent cellular aggregation and to reduce shearing forces, thereby improving the stability of the Sf9 insect cells). The insoluble pluronic pellet was removed by centrifugation of the concentrate/ammonium sulfate precipitate (5000 g, 20 min, 4° C.), and recombinant toxin in the pellet was recovered by extracting twice with DEAE-Sepharose Equilibration Buffer, followed by centrifugation.

Recovered combined supernatant was dialyzed against 100× volumes of DEAE-Sepharose Equilibration Buffer for 16 hours, separated from the residual pellet by centrifugation, and loaded on a column (1.5×10 cm) packed with DEAE-Sepharose Fast Flow (Amersham Biosciences, Cat. #17-0709-01) pre-equilibrated in the same buffer at a buffer flow rate of 0.5 ml/min. The column was washed with ~15 volumes of DEAE Sepharose Wash Buffer and then a linear gradient of 100 ml DEAE Sepharose Wash Buffer: 100 ml DEAE Sepharose Elution Buffer was applied. 4-ml fractions were collected and their content was analyzed by PAGE and Western blotting. Fractions containing recombinant protein were combined and dialyzed against 100× volumes of the Mono S Equilibration Buffer for 16 hours. Resulting combined dialyzate was cleared by centrifugation and loaded at 1 ml/min on MonoS 5/50 GL FPLC column (Amersham Biosciences, Cat. #17-5168-01), pre-equilibrated in the same buffer. Column was washed with 100 ml of Mono S Wash Buffer and the linear gradient of 100 ml Mono S Wash Buffer: 100 ml Mono S Elution Buffer was applied. 2-ml fractions were collected and their content was analyzed by PAGE and Western blotting.

The fractions containing recombinant protein were combined, concentrated on the stirred ultrafiltration cell with Ultracel 100-KDa cutoff membrane to the final volume of 20 ml with sequential buffer change to Ni-NTA Equilibration Buffer. Combined fractions were loaded on a 1×4 cm column with Ni-NTA affinity resin (Novagen, Cat. #70666) pre-equilibrated in the same buffer at a buffer flow rate of 1 ml/min. The column was sequentially washed with 100 ml of Ni-NTA Wash Buffer I, followed by 100 ml of Ni-NTA Wash Buffer II, and protein was eluted from the column by 50 ml of Ni-NTA Elution Buffer. All fractions were analyzed by PAGE and Western blotting. Elution fractions enriched in recombinant protein were concentrated sequentially on the stirred ultrafiltration cell with Ultracel 100-KDa cutoff membrane followed by Amicon Ultra-4 centrifugal filter device (Millipore, Cat. #UFC803024) to a final volume of 1 ml and loaded on the FPLC HiLoad 16/60 Superdex 200PG gel filtration column (Amersham Biosciences, Cat. #17-1069-01), equilibrated with HiLoad 16/60 Superdex 200PG Equilibration Buffer. The buffer flow rate was 1 ml/min and 1-ml fractions from the column were collected and analyzed by PAGE and Western blotting.

The multi-step protocol developed for BoNT A td purification provided a yield ~0.35 mg of pure protein per liter of serum-free medium. It is believed that this procedure can be optimized to provide yields in the range of 0.7-0.9 mg/l. Several reasons may explain the relatively low yield in the purification of BoNT A td: 1) Significant amounts of the recombinant toxin may be lost due to non-specific adsorption to the brand-new separation media; 2) The delays which occurred between purification steps may have resulted in degradation of recombinant toxins. These delays were impossible to avoid during the initial purification attempts, because it was necessary to analyze the recombinant products before proceeding to the next purification step. The following modifications, aimed at simplifying and improving the current purification scheme, were tested.

Example 18

Biological Testing of the Recombinant BoNT A Derivatives

Two types of experiments were performed to assess whether the recombinant toxins retained the biological activities of native toxin. These were performed using the BoNT A td derivative, which was produced in sufficient quantities for biological testing. In the first test, recombinant BoNT A td was administered to mice by the intravenous route (~1 ng per mouse) and the time-to-death was monitored. Death was observed approximately 12 minutes after injection. Prior symptoms of muscular weakness or paralysis were not obvious. In the second test, recombinant BoNT A td was added to mouse phrenic nerve-hemidiaphragm preparations, and its ability to inhibit acetylcholine release evoked by stimulation of the nerve trunk (0.2 Hz) was evaluated by monitoring muscle twitch. At a concentration of $~1\times10^{-11}$ M, recombinant BoNT A td produced neuromuscular blockade in 167±17 min (n=4). To insure that the blockade could be attributed to a *botulinum* toxin-type action, a final experiment was done, in which the polypeptide was pre-incubated (room temperature, 60 min) with rabbit antiserum raised against the carboxy terminal half of the native BoNT A heavy chain (i.e. receptor-binding domain). In these experiments (n=3), there was no neuromuscular blockade, even when the tissues were monitored for ca. 400 minutes. The pharmaceutical preparation marketed by Allergan Inc., as "BoTox" produces neuromuscular blockade in 100 minutes at a concentration of approximately $1 \times 10^{-11}$ M (60 Units per ml). The BoNT A, B, and G recombinant products produced by Rummel (supra) require 60 to 1000 times more BoNT to effect neuromuscular blockade in a similar timeframe.

Example 19

Preparation and Modification of the BoNT Gene Constructs

DNA and protein sequences for Clostridial toxins are accessed from the Gene bank. Constructs encoding full-length toxins are available from a number of laboratories. These known sequences and constructs provide an efficient starting point for the planned genetic manipulations.

The first type of mutation introduced is designed to improve toxin stability by site-directed mutations of low specificity protease-sensitive residues within the light-heavy chain junction region, thereby reducing susceptibility to non-specific activation and poisoning of the host organism. The second type of mutation will be introduced to create a highly specific enterokinase cleavage site between the light and heavy chains, thereby enabling external control of the cleavage event leading to toxin maturation. The third type of mutation to be introduced is designed to silently inactivate DNA elements affecting RNA transcription and protein expression in the system of choice. The fourth type of modification is designed to introduce unique restriction sites that enable easy manipulation of the toxin gene, its protein products, and chimeric proteins which may be created as required.

The modified BoNT A constructs used to produce the BoNT A toxic derivative (td) described infra demonstrates the feasibility of these methods. The objective is to determine how to best adapt the methods developed for BoNT A to producing other Clostridial neurotoxins, and in the process optimize the methodology and create a library of toxin derivatives with customized biological properties. Molecular cloning techniques are generally known in the art, and other full-length neurotoxins have successfully been cloned (Ichtchenko et al., "Alpha-Latrotoxin Action Probed with Recombinant Toxin: Receptors Recruit Alpha-Latrotoxin but do not Transduce an Exocytotic Signal," *EMBO J.* 17:6188-6199 (1998), which is hereby incorporated by reference in its entirety).

Example 20

Creation and Expression of Recombinant BoNT Molecules Minimally Modified to Eliminate Toxicity To create atoxic derivatives ("ad") that most closely resemble the native toxin with respect to their structure and physiologic activity, a single amino acid point mutation is introduced into the active site of the toxin's metalloprotease catalytic domain. Though most toxin features in this molecule remain the same as in the native toxin, it is devoid of toxicity, because it is unable to cleave its substrate in the synaptic exocytosis machinery. The atoxic derivatives thus created are superior to other BoNT preparations being developed as vaccines, because of their structural similarity to native toxin, and their ability to generate an immune response at diverse sites along the native toxin's absorption and trafficking route. Because these derivatives are likely to compete with native toxin for the same binding sites and trafficking pathways, they may also be superior to antibody preparations as antidotes to BoNT poisoning.

The cloning and expression strategies developed can be duplicated as closely as possible in applying the methods to BoNT B and E, thereby minimizing the possibility of creating significant molecular alterations in the atoxic derivatives which might decrease their therapeutic potential. The validity of this assumption is demonstrated supra with the BoNT A atoxic derivative (ad), which has been shown to be essentially identical to native BoNT A with respect to expression level, antibody recognition, disulfide bonding, cleavage with enterokinase, and binding to Ni-NTA affinity resin.

An outline of the steps necessary to produce atoxic derivatives of BoNT B and E is as follows. Constructs encoding the atoxic derivatives (ad) of BoNT B and E are obtained by site-directed mutagenesis of BoNT B and BoNT E td constructs, using procedures established for BoNT A ad, as detailed supra. Expression constructs for BoNT B ad and BoNT E ad in the different expression systems to be tested are prepared using a protocol similar to that established for BoNT A ad, as detailed supra. The expression system, purification protocol, and rEK-cleavage protocol for BoNT B and E ad replicate the optimized procedure developed for BoNT A td and ad, as outlined supra. The expression and purification system chosen to produce the atoxic derivatives is based on the quality and yield produced by the expression systems tested.

The atoxic derivatives are tested in a substrate cleavage assay using SNAP 25 or VAMP as substrates. Though no residual proteolytic activity in the single-amino acid mutated atoxic derivatives is expected, if the rate of substrate hydrolysis for any particular atoxic derivative is significantly higher than zero, a second amino acid residue, corresponding to $His_{227}$ in BoNT A, is mutated at the toxin's active site before proceeding for its further biological and functional characterization.

Prophetic Example 21

Preparation of DNA Starting Material for BoNT Serotypes B and E

DNA template for all BoNT serotypes for PCR amplification can be obtained from either pure *Clostridium* cultures (serotype-specific) or soil-derived anaerobic cultures from which mixed genomic DNA as a starting material may be prepared. High fidelity Platinum®Pfx polymerase is used for all PCR reactions to minimize amplification errors. BoNT B and E serotypes are described in subsequent examples.

Prophetic Example 22

Constructs for BoNT B and E

A set of oligonucleotides similar to those used for obtaining the full-length coding sequence of BoNT A td may be designed for BoNT B and E, using sequences available from Gene bank (accession number M81186 for BoNT B and X62683 for BoNT E). Sequences are carefully evaluated for unwanted DNA regulatory elements and other features that could affect protein expression in *E. coli*, baculovirus, and *Pichia pastoris* expression systems, and such elements eliminated by silent site-directed mutagenesis. Additional mutations targeted to remove low-specificity proteolysis sites in the toxin's LC-HC junction are introduced, and to introduce an enterokinase cleavage site in the LC-HC junction region. Based on the toxin sequence alignments and domain structure illustrated in FIGS. 1-3, gene regions which can be modified without affecting the recombinant toxin's biological properties are identified, and Nhe I, XbaI, KpnI, and XhoI restriction sites are introduced, similar to the design scheme executed for BoNT A td. If such mutations are impossible to make through silent mutagenesis, restriction sites are introduced via neutral amino acid insertion into structurally flexible portions of the protein sequence. Any redundant restriction sites created are eliminated by silent site-directed mutagenesis. BoNT DNA sequences that can cause premature termination of gene transcription in the expression systems or interfere with the protein expression are also modified. Expression in *Pichia pastoris* (Henikoff et al., "Sequences Responsible for Transcription Termination on a Gene Segment in *Saccharomyces Cerevisiae*," *Mol. Cell Biol.* 4:1515-1520 (1984); Irniger et al., "Different Classes of Polyadenylation Sites in the Yeast *Saccharomyces Cerevisiae*," *Mol. Cell Biol.* 11:3060-3069 (1991); Scorer et al., "The Intracellular Production and Secretion of HIV-1 Envelope Protein in the Methylotrophic Yeast *Pichia Pastoris*," *Gene* 136:111-119 (1993), which are hereby incorporated by reference in their entirety) requires the elimination of such sequences by designing a set of PCR oligonucleotide primers which can suppress premature termination of transcription from AT-rich templates. These procedures produce constructs containing modified coding sequences for BoNT B and BoNT E td, which are used in subsequent expression studies.

Endonuclease restriction digests are used to check all intermediate DNA products. The final full-length DNA is sequenced to prove absence of unwanted mutations.

Molecular biocomputing software, supplied by the DNAstar is used to analyze and compare DNA and protein sequences. This will also optimize the creation of synthetic oligonucleotides and optimal reaction conditions for all reactions of PCR amplification.

Prophetic Example 23

Expression, Purification, and Biochemical Analysis of Toxic Derivatives

Expression and purification of full-length, functionally active toxins has proven difficult in laboratories using alternative construct designs and expression systems. The ideal construct and expression system preferably do not segregate Clostridial toxins, because they contain coding sequences non-typical for the host; are not poisoned by entry of active toxin into the cytosol where it may disrupt the apparatus for regulated exocytosis, which is similar in most eukaryotes; and allow normal post-translational modification of the expressed toxins, particularly formation of disulfide bridges.

Two expression systems were tested for each toxin serotype A: baculovirus and *E. coli*. Because the baculovirus expression system was found to be most effective for expressing full-length BoNT A td, this was used as a starting point and benchmark for all the toxins. Though much concentration was centered on the baculovirus expression system, alternatives were evaluated, taking scale-up and cost into consideration, and work can be performed to optimize expression of all serotypes in these systems, as well as in other expression systems such as *Pichia pastoris*.

Work that was performed to optimize expression and purification are described supra. The effect of these modifications on nativity of the toxin was evaluated in each case.

Prophetic Example 24

*E. coli* Expression System

Attempts to produce full-length BoNT A in *E. coli* resulted in a major C-terminally truncated propeptide which was significantly smaller than expected for the BoNT A propeptide (FIG. 4). In the future, the C-terminal composition of this product will be analyzed by microsequencing, identifying putative proteolytic cleavage sites specific to the *E. coli* system, and redesigning the pETcoco expression construct with amino acid substitutions designed to suppress this effect. It is possible the proteolysis site is similar to that recognized by trypsin, which has been demonstrated to cleave within the C-terminal BoNT A receptor-binding domain when applied in excessive amounts (Chaddock et al., "Expression and Purification of Catalytically Active, Non-Toxic Endopeptidase Derivatives of *Clostridium Botulinum* Toxin Type A," *Protein Expr. Purif.* 25:219-228 (2002), which is hereby incorporated by reference in its entirety). Expression of re-designed construct will use the advanced Rosetta-gami B (DE3) *E. coli* strain, as described infra.

Prophetic Example 25

Targeting Secretion to the Periplasm

Targeting recombinant proteins for secretion to the *E. coli* periplasm can improve stability and post-translational disulfide bond formation. The coding portion of the BoNT A td sequence will be subcloned into pET39b(+) vector (Novagen, Cat. #70090-3) which contains the signal required for export and periplasmic folding of target proteins. This system is designed for cloning and expression of peptide sequences fused with the 208 amino acids DsbA•Tag™. DsbA is a periplasmic enzyme that catalyzes the formation and isomerization of disulfide bonds (Rietsch et al., "An In vivo Pathway for Disulfide Bond Isomerization in *Escherichia coli*," *Proc. Natl. Acad. Sci. USA* 93:13048-13053 (1996); Sone et al., "Differential In vivo Roles Played by DsbA and DsbC in the Formation of Protein Disulfide Bonds," *J. Biol. Chem.* 272: 10349-10352 (1997); Missiakas et al., "The *Escherichia coli* DsbC (xprA) Gene Encodes a Periplasmic Protein Involved in Disulfide Bond Formation," *EMBO J.* 13:2013-2020 (1994); Zapun et al., "Structural and Functional Characterization of DsbC, a Protein Involved in Disulfide Bond Formation in *Escherichia coli*," *Biochemistry* 34:5075-5089 (1995); Raina et al., "Making and Breaking Disulfide Bonds," *Annu. Rev. Microbiol.* 51:179-202 (1997), which are hereby incorporated by reference in their entirety). It is possible that the degradation of BoNT A described infra occurs as a result of *E. coli* incompetence to properly form disulfide bridges for proteins which accumulate in the cytoplasm. The DsbA vector may enhance solubility and proper folding of recombinant BoNTs in the non-reducing periplasmic environment (Collins-Racie et al., "Production of Recombinant Bovine Enterokinase Catalytic Subunit in *Escherichia coli* Using the Novel Secretory Fusion Partner DsbA," *Biotechnology* 13:982-987 (1995), which is hereby incorporated by reference in its entirety). Though the yield of recombinant proteins targeted to the periplasm is usually low, periplasmic expression in E. coli is worth continued consideration.

Prophetic Example 26

Pichia pastoris Expression System

Multi-copy Pichia pastoris expression kit (Invitrogen, Cat. #K1750-01) is used to obtain recombinant proteins. Recombinant plasmid on the backbone of the vector pPIC9K, carrying gene of interest and targeted for incorporation into Pichia genome is digested by restriction endonuclease SalI for linearization and transformed in the Pichia strains GS115 and KM71 by spheroplasting method with zymolyase, according to the supplied manufacturer's protocol. Primary and secondary rounds of the transformants selection on the histidine-deficient medium and in the presence of Geneticin is performed according to the same protocol. Protein expression is induced by the addition of methanol (0.5% final concentration) into the culture medium. Disrupted cells and medium are analyzed by SDS-PAGE and Western blotting.

Though the baculovirus expression system was found to provide satisfactory level of protein expression of BoNT A, recombinant protein expression in Pichia pastoris (methylotrophic yeast capable of metabolizing methanol as its sole carbon source) was evaluated because of the multiple reports describing successful expression in this system, including fragments of botulinum neurotoxin type A (Byrne et al., "Purification, Potency, and Efficacy of the botulinum Neurotoxin Type A Binding Domain from Pichia pastoris as a Recombinant Vaccine Candidate," Infect. Immun. 66:4817-4822 (1998), which is hereby incorporated by reference in its entirety). This system has the advantages of low cost, post-translational modification of the recombinant proteins typical for eukaryotes, and low amounts of naturally secreted products, which facilitate purification of the recombinant proteins. The Pichia expression system also can provide better yields than the baculovirus system. Disadvantages of the Pichia system include cumbersome procedures of cloning into the Pichia genome and selection of multiple-copy recombinants, the possibility of extensive glycosylation of some recombinant proteins, and the possibility of premature termination of RNA transcripts synthesized from AT-rich templates, a known characteristic of the Clostridial toxin genes. These unwanted internal DNA features in BoNT genes were eliminated at the cloning stage. The system was the first to be tested with BoNT A td to establish benchmarks for comparison to other expression systems.

Prophetic Example 27

Engineering of the Expression Constructs Targeted for Secretion

The coding part of the modified N-terminally 6-His tagged BoNT A td was subcloned into vector pPIC9K, which provides the alpha-factor secretion signal from S. cerevisiae in the expression plasmid. This should result in secretion of the expressed protein into the medium. The construct was linearized by restriction endonuclease Sal I and transfected by spheroplasting method into KM71 and GS115 strains of Pichia pastoris. Primary selection of the transformants was performed by testing ability of the cells to grow on histidine-deficient media, trait deficient in the wild-type cells. Second round of selection was performed in the presence of antibiotic Geneticin which allowed the identification of clones with multiple inserts of the gene of interest by the correlation between the number of the copies of the gene of interest and increased concentration of Geneticin in the growth medium. The ability of identified clones to express protein of interest will be tested by growing cells in the methanol-containing medium.

Prophetic Example 28

Lengthening of the His Affinity Tag

The length of the histidine affinity tag at the N-termini of the BoNT A td were increased, and two more constructs—8-His and 12-His tagged were tested for their ability to confer higher affinity for Ni-NTA agarose in the recombinant BoNT products. This approach has been used successfully for other recombinant proteins which showed a similar decreased affinity for Ni-NTA affinity purification media (Ichtchenko et al., "Alpha-Latrotoxin Action Probed with Recombinant Toxin: Receptors Recruit Alpha-Latrotoxin but do not Transduce an Exocytotic Signal," EMBO J. 17:6188-6199 (1998); Rudenko et al., "Structure of the LDL Receptor Extracellular Domain at Endosomal pH," Science 298:2353-2358 (2002), which are hereby incorporated by reference in their entirety). If improved purification of recombinant BoNT A td can be achieved, at least two steps of ion-exchange chromatography can be omitted from the current purification scheme.

Example 29

Engineering the Non-Expression Plasmid pLitBoNTAME224A Containing the Full-Length Sequence of BoNT A ad The plasmid encoding full-length BoNT A ad cDNA with protease-inactivating mutation E224>A was created by the site-directed mutagenesis of the plasmid pLitBoNTA with phosphorylated oligonucleotides

```
CBA18:
                                    (SEQ ID NO: 46)
5'-pCCCGCGGTGACATTAGCACATGCACTTATACATGCTGG
and CBA19:
                                    (SEQ ID NO: 47)
5'-pCATGTGCTAATGTCACCGCGGGATCTGTAGCAAATTTG
``` using GeneTailor™ Site-Directed Mutagenesis System (Invitrogen, Cat. #12397-014) and Platinum® Pfx DNA Polymerase (Invitrogen, Cat. #11708-021), according to the protocol supplied by the manufacturer. The size of pLitBoNTAME224A is 6712 b.p. with 3900 b.p. coding sequence.

Example 30

Engineering of the Non-Expression Plasmid pLitGFPBoNTAHC, Containing Full-Length Sequence of BoNT A gfpd The plasmid pLitGFPBoNTAHC, encoding chimeric protein where minimal essential catalytic domain of the BoNT A light chain was substituted with the GFP was created by the following protocol: 742 b.p. PCR product, obtained on plasmid pEGFP-N3 (Clontech, Cat. #632313) with oligonucleotides

CBA20:

(SEQ ID NO: 48)
5'-ATTAAGGATCCTGTGAGCAAGGGCGAGGAGCTGTTCACCG and

CBA21:

(SEQ ID NO: 49)
5'-TATGAATTCAAACAATCCAGTAAAATTTTCTTGTACAGCTCGTCCATGCC and digested with restriction endocucleases BamHI and EcoRI and subcloned into pre-digested and dephosphorylated vector pLitBoNTALC, resulting in plasmid pLitGFPLC. 2615 b.p. DNA fragment from the vector pLitBoNTAHC, digested with restriction endonucleases XbaI and ApaI was subcloned into pre-digested and dephosphorylated vector pLitGFPLC, resulting in plasmid pLitGFPBoNTAHC. The size of pLitGFPBoNTAHC is 6216 b.p. with 3404 b.p. of coding sequence.

Example 31

Engineering of the Expression Plasmids pETCBoNTAME224A and pETCGFPBoNTAHC for the Expression of BoNT A ad and BoNT A gfpd in *E. coli*

The plasmids were obtained by subcloning DNA fragments isolated from pLitmus-based vectors digested with NheI and NotI into pre-digested and dephosphorylated expression vector pETcoco2 (Novagen, Cat. #71148-3) and resulted in 16,194 b.p. BoNT A E224>A mutant expression vector pETCBoNTAME224A and 15,699 b.p. BoNT A chimeric vector pETCGFPBoNTAHC, where minimal essential catalytic domain of the BoNT A light chain was substituted with the GFP.

Example 32

Engineering of the Donor Plasmids pFBSecBoNTAME224A and pFBSecGFPBoNTAHC for the Expression of BoNT A ad and BoNT A gfpd in Baculovirus Expression System The plasmids were obtained by the following protocol: 112 b.p. PCR product synthesized on plasmid pBac-3 (Novagen, Cat. #70088-3) with oligonucleotides

CBA 22:

(SEQ ID NO: 50)
5'-TAAGCGCGCAGAATTCTCTAGAATGCCCATGTTAAGCGCTATTG and

CBA23:

(SEQ ID NO: 51)
5'-TAAGCTAGCGTGATGGTGGTGATGATGGACCATGGCC and digested with restriction endonucleases BssHII and NheI was subcloned into pre-digested and dephosphorylated pLitmus-based vectors, resulting in plasmids pLitSecBoNTAME224A and pLitSecGFPBoNTAHC. DNA fragments from these vectors, obtained as a result of the digest with BssHII and NotI, were subcloned into pre-digested and dephosphorylated vector pFastBac™1 (Invitrogen, Cat. #10360-014), resulting in 8764 b.p. pFBSecBoNTAME224A and 8568 b.p. pFBSecGFPBoNTAHC donor plasmids.

Example 33

Chimera Proteins that Target the Cytosol of Neurotoxin-Affected Neurons

A genetic engineering platform designed to produce BoNT antidotes that can effectively target the cytoplasm of BoNT-affected neurons has been developed. Antidotes designed pursuant to this platform have the potential to be effectively administered to a subject for extended time periods after exposure to toxic Clostridial neurotoxin, and would improve the practical logistics of administering antidote to large populations in an emergency setting. Using genetic constructs of the isolated BoNT A light chain, protein motifs are introduced to bind, inactivate, or otherwise mark toxic wild-type Clostridial neurotoxin (e.g., *Clostridium botulinum*) light chain for elimination from the cytosol of neurotoxin-affected neurons. Chimeric light chains with optimized antidote activity can subsequently be recombined with derivitized constructs of the Clostridial neurotoxin heavy chain to produce full-length Clostridial neurotoxin chimeras that can deliver antidote activity to the cytosol of Clostridial neurotoxin-affected neurons. Expression systems can be developed and tested (as described above) to ensure that the structural features and post-translational modifications responsible for native Clostridial neurotoxin trafficking are preserved. Produced Clostridial neurotoxin antidotes of this sort can effectively target neurotoxin-affected neurons when administered by oral or inhalational routes and can be used to rescue patients already experiencing symptoms of Clostridial neurotoxin intoxication (e.g., patients on an artificial respirator).

Using the plasmid encoding atoxic BoNT A light chain, a first library of BoNT A ad light chain chimeras containing SNARE motif peptides substituting light chain alpha-helix regions has been designed and created. The SNARE motif is recognized by all seven BoNT serotypes, and prior work has demonstrated physiological exocytosis (Rossetto et al., "SNARE Motif and Neurotoxins," *Nature* 372:415-416 (1994), which is hereby incorporated by reference in its entirety). The chimeras are constructed to retain the interface responsible for BoNT light chain dimerization (Segelke et al., "Crystal Structure of *Closridium Botulinum* Neurotoxin Protease in a Product-Bound State: Evidence for Noncanonical Zinc Protease Activity," *Proc. Natl. Acad. Sci. USA* 101:6888-6893 (2004), which is hereby incorporated by reference in its entirety), allowing them to preferentially bind to wild-type light chains and potentially inactivate or otherwise destabilize the toxic neurotoxin. Engineering of non-expression plasmids containing the full-length sequence of BoNT A (atoxic derivative, ad) with non-native SNARE motif peptides (illustrated in FIG. 11) to produce the light chain chimeric libraries is described in the following paragraphs.

Light Chain of BoNT A

The plasmid encoding mutated light chain of BoNT A cDNA with metalloprotease-inactivating mutation E224>A (pLitBoNTALCME224A) was created by the site-directed mutagenesis of the plasmid pLitBoNTALC with phosphorylated oligonucleotides (SEQ ID NO: 46)
CBA18: 5'-pCCCGCGGTGACATTAGCACATGCACTTATACATGCTGG and (SEQ ID NO: 47)
CBA19: 5'-pCATGTGCTAATGTCACCGCGGGATCTGTAGCAAATTTG using GeneTailor™ Site-Directed Mutagenesis System (Invitrogen, Cat. #12397-014) and Platinum® Pfx DNA Polymerase (Invitrogen, Cat. #11708-021), according to the protocol supplied by the manufacturer. The resulting plasmid pLitBoNTALCME224A is 4042 b.p. with a 1230 b.p. coding sequence.

Chimera 1

The non-expression plasmid pLitBoNTACH1, containing the full-length sequence of BoNT A ad with three SNARE motif peptides substituting BoNT A light chain alpha-helix 1, was created by site-directed mutagenesis of the plasmid pLitBoNTAME224A with phosphorylated oligonucleotides CBCH1:
(SEQ ID NO: 52)
5'-pGAGTTGTTCGCCTTGCTCATCCAACATCTGCAACGCGTCAGCTCGG TCATCCAACTCTGTACTTAAATATGTTGAATCATAATATGAAACTGG
and CBCH2:
(SEQ ID NO: 53)
5'-pGAGCGCGAAATGGATGAAAACCTAGAGCAGGTGAGCGGCCGAGGAA

TACCATTTTGGGGTGGAAGTACAATAGATACAG using Exsite™ PCR-Based Site-Directed Mutagenesis Kit (Stratagene, Cat. #200502) with modification. The ExSite™ DNA polymerase blend included in the kit was substituted with a blend consisting of 75% of TaKaRa LA Taq DNA polymerase (Takara, Cat. # RR002A) and 25% of Platinum® Pfx polymerase (Invitrogen, Cat. #11708-021). The mutagenesis reaction and selection of the mutant plasmid were performed according to the protocol, included in the original Exsite™ PCR-Based Site-Directed Mutagenesis Kit. For selection purposes, two de novo endonuclease restriction sites—MluI and XhoI—were introduced into the plasmid.

Chimera 2

The non-expression plasmid pLitBoNTACH2, containing the full-length sequence of BoNT A ad with two SNARE motif peptides substituting BoNT A light chain alpha-helix 4, was created by site-directed mutagenesis of the plasmid pLitBoNTAME224A with phosphorylated oligonucleotides CBCH3:
(SEQ ID NO: 54)
5'-pCGCGTCTGCCCTATCGTCTAGTTCATCTATAAACTTTGCATCATGT CCCCC
and CBCH4:
(SEQ ID NO: 55)
5'-pTTACAAATGCTAGACGAACAGGGAGAGCAGCTCGAGAGGCTTAATA

A AGCTAAATCAATAGTAGGTACTACTGC using Exsite™ PCR-Based Site-Directed Mutagenesis Kit with the modifications, described above.

Chimera 3

The non-expression plasmid pLitBoNTACH3, containing the full-length sequence of BoNT A ad with five SNARE motifs peptides substituting BoNT A light chain alpha-helices 1 and 4, was created by site-directed mutagenesis of the plasmid pLitBoNTACH1 with phosphorylated oligonucleotides CBCH3:
(SEQ ID NO: 54)
5'-pCGCGTCTGCCCTATCGTCTAGTTCATCTATAAACTTTGCATCATGT CC CCC
and CBCH4:
(SEQ ID NO: 55)
5'-pTTACAAATGCTAGACGAACAGGGAGAGCAGCTCGAGAGGC TTAAT

AAAGCTAAATCAATAGTAGGTACTACTGC using Exsite™ PCR-Based Site-Directed Mutagenesis Kit with the modifications described above.

Chimera 4

The non-expression plasmid pLitBoNTACH4, containing the full-length sequence of BoNT A ad with three SNARE motif peptides substituting light chain alpha-helices 4 and 5, was created by site-directed mutagenesis of the plasmid pLitBoNTACH2 with phosphorylated oligonucleotides CBCH5:
(SEQ ID NO: 56)
5'-pGCTTACTTGTTCCAAATTCTCGTCCATCTCTGAAGCAGTAGTACCT AC TATTGATTTAGC
and CBCH6:
(SEQ ID NO: 57)
5'-pGGCCGTCTCCTATCTGAAGATACATCTGG using Exsite™ PCR-Based Site-Directed Mutagenesis Kit with the modifications described above. For the selection purposes, de novo endonuclease restriction site Eco52I was introduced into the plasmid.

Chimera 5

The non-expression plasmid pLitBoNTACH5, containing the full-length sequence of BoNT A ad with six SNARE motif peptides substituting BoNT A light chain alpha-helices 1, 4, and 5, was created by site-directed mutagenesis of the plasmid pLitBoNTACH2 with phosphorylated oligonucleotides CBCH5:
(SEQ ID NO: 56)
5'-pGCTTACTTGTTCCAAATTCTCGTCCATCTCTGAAGCAGTAGTACCT AC TATTGATTTAGC
and CBCH6:
(SEQ ID NO: 57)
5'-pGGCCGTCTCCTATCTGAAGATACATCTGG using Exsite™ PCR-Based Site-Directed Mutagenesis Kit with the modifications described above. For the selection purposes, de novo endonuclease restriction site Eco52I was introduced into the plasmid.

Chimera 6

The non-expression plasmid pLitBoNTACH6, containing the full-length sequence of BoNT A ad with four SNARE motif peptides substituting BoNT A light chain alpha-helices 4, 5, and 6, was created by site-directed mutagenesis of the plasmid pLitBoNTACH4 with phosphorylated oligonucleotides

CBCH7:

(SEQ ID NO: 58)
5'-pAATTCATCCATGAAATCTACCGAAAATTTTCC
and

CBCH8:

(SEQ ID NO: 59)
5'-pCTTTGAACAGGTGGAGGAATTAACAGAGATTTACACAGAGG using Exsite™ PCR-Based Site-Directed Mutagenesis Kit with the modifications described above. For the selection purposes, de novo endonuclease restriction site EcoRI was introduced into the plasmid.

Chimera 7

The non-expression plasmid pLitBoNTACH7, containing the full-length sequence of BoNT A ad with five SNARE motif peptides substituting BoNT A light chain alpha-helices 4, 5, 6, and 7, was created by site-directed mutagenesis of the plasmid pLitBoNTACH6 with phosphorylated oligonucleotides

CBCH9:

(SEQ ID NO: 60)
5'-pTCGAGCTCTGTGTAAATCTCTGTTAATTCC
and

CBCH10:

(SEQ ID NO: 61)
5'-pGGACATGCTGGAGAGTGGGAATCTTAACAGAAAAACATATTTGAAT

TTTG using Exsite™ PCR-Based Site-Directed Mutagenesis Kit with the modifications described above. For the selection purposes, de novo endonuclease restriction site XhoI was introduced into the plasmid.

Chimera 8

The non-expression plasmid pLitBoNTACH8, containing the full-length sequence of BoNT A ad with seven SNARE motif peptides substituting BoNT A light chain alpha-helices 1, 4, 5, and 6, was created by site-directed mutagenesis of the plasmid pLitBoNTACH5 with phosphorylated oligonucleotides

CBCH7:

(SEQ ID NO: 58)
5'-pAATTCATCCATGAAATCTACCGAAAATTTTCC
and

CBCH8:

(SEQ ID NO: 59)
5'-pCTTTGAACAGGTGGAGGAATTAACAGAGATTTACACAGAGG using Exsite™ PCR-Based Site-Directed Mutagenesis Kit with the modifications described above. For the selection purposes, de novo endonuclease restriction site EcoRI was introduced into the plasmid.

Chimera 9

The non-expression plasmid pLitBoNTACH9, containing the full-length sequence of BoNT A ad with eight SNARE motif peptides substituting BoNT A light chain alpha-helices 1, 4, 5, 6, and 7, was created by site-directed mutagenesis of the plasmid pLitBoNTACH8 with phosphorylated oligonucleotides

CBCH9:

(SEQ ID NO: 60)
5'-pTCGAGCTCTGTGTAAATCTCTGTTAATTCC
and

CBCH10:

(SEQ ID NO: 61)
5'-pGGACATGCTGGAGAGTGGGAATCTTAACAGAAAAACATATTTGAAT

TTTG using Exsite™ PCR-Based Site-Directed Mutagenesis Kit with the modifications described above. For the selection purposes, de novo endonuclease restriction site XhoI was introduced into the plasmid.

Green Fluorescence Protein

The non-expression plasmid pLitEGFP, containing the full-length sequence of GFP for the fusions with BoNT A light chain, BoNT A light chain ad, and BoNT A light chain ad chimeric derivatives, was created by subcloning ~750 b.p. product obtained by PCR on plasmid pEGFP-N3 (Clontech, Cat. #6080-1) with oligonucleotides EGFPs:

(SEQ ID NO: 62)
5'-TATTACGCGTGCGCGCTATGAATTCTATAAGTTGCTAATGGTGAGCA

AGGGCGAGGAGCTGTTCACCGGG and

EGFPa:

(SEQ ID NO: 63)
5'-ATTAGGGCCCCTATTACTTGTACAGCTCGTCCATGCCGAGAGTGATC

CC and digested with restriction endonucleases MluI and ApaI into vector pLitmus38i (NEB, Cat. #N3538S) pre-digested with MluI and ApaI and dephosphorylated. The size of the resulting pLitEGFP was 3479 b.p.

Light Chain of BoNT A td Fused with EGFP

The non-expression vector pLitBoNTALCEGFP carrying light chain of BoNT A td, fused with EGFP, was created by subcloning the 1296 b.p. DNA fragment obtained from the digest of the plasmid pLitBoNTALC with restriction endonucleases BssHII and EcoRI into vector pLitEGFP pre-digested with BssHII and EcoRI and dephosphorylated. The size of the resulting plasmid was ~4800 b.p.

Light Chain of BoNT A ad Fused with EGFP

The non-expression vector pLitBoNTAME224ALCEGFP carrying the sequence of the light chain of BoNT A ad, fused with EGFP, was created by subcloning the 1296 b.p. DNA fragment obtained from the digest of the plasmid pLitBoNTAME224A with restriction endonucleases BssHII and EcoRI into vector pLitEGFP pre-digested with BssHII and EcoRI and dephosphorylated. The size of the resulting plasmid was ~4800 b.p.

Light Chain of Chimera 1 Fused with EGFP

The non-expression vector pLitBoNTACH1EGFP, carrying the sequence of the BoNT A ad light chain with three SNARE motif peptides substituting BoNT A light chain alpha-helix 1, fused with EGFP, was created by subcloning the 1296 b.p. DNA fragment obtained from the digest of the plasmid pLitBoNTACH1, with restriction endonucleases BssHII and EcoRI into vector pLitEGFP pre-digested with BssHII and EcoRI and dephosphorylated. The size of the resulting plasmid was ~4800 b.p.

Light Chain of Chimera 2 Fused with EGFP

The non-expression vector pLitBoNTACH2EGFP, carrying the sequence of the BoNT A ad light chain with two SNARE motif peptides substituting BoNT A light chain alpha-helix 4, fused with EGFP, was created by subcloning the 1296 b.p. DNA fragment obtained from the digest of the plasmid pLitBoNTACH2 with restriction endonucleases BssHII and EcoRI into vector pLitEGFP pre-digested with BssHII and EcoRI and dephosphorylated. The size of the resulting plasmid was ~4800 b.p.

Light Chain of Chimera 3 Fused with EGFP

The non-expression vector pLitBoNTACH3EGFP, carrying the sequence of the BoNT A ad light chain with five SNARE motif peptides substituting BoNT A light chain alpha-helices 1 and 4, fused with EGFP, was created by subcloning the 1296 b.p. DNA fragment obtained from the digest of the plasmid pLitBoNTACH3 with restriction endonucleases BssHII and EcoRI into vector pLitEGFP pre-digested with BssHII and EcoRI and dephosphorylated. The size of the resulting plasmid was ~4800 b.p.

Light Chain of Chimera 4 Fused with EGFP

The non-expression vector pLitBoNTACH4EGFP, carrying the sequence of the BoNT A ad light chain with three SNARE motif peptides substituting BoNT A light chain alpha-helices 4 and 5, fused with EGFP, was created by subcloning the 1296 b.p. DNA fragment obtained from the digest of the plasmid pLitBoNTACH4 with restriction endonucleases BssHII and EcoRI into vector pLitEGFP pre-digested with BssHII and EcoRI and dephosphorylated. The size of the resulting plasmid was ~4800 b.p.

Light Chain of Chimera 5 Fused with EGFP

The non-expression vector pLitBoNTACH5EGFP, carrying the sequence of the BoNT A ad light chain with six SNARE motif peptides substituting BoNT A light chain alpha-helices 1, 4, and 5, fused with EGFP, was created by subcloning the 1296 b.p. DNA fragment, obtained from the digest of the plasmid pLitBoNTACH5 with restriction endonucleases BssHII and EcoRI into vector pLitEGFP pre-digested with BssHII and EcoRI and dephosphorylated. The size of the resulting plasmid was ~4800 b.p.

Light Chain of Chimer 6 Fused with EGFP

The non-expression vector pLitBoNTACH6EGFP, carrying the sequence of the BoNT A ad light chain with four SNARE motif peptides substituting BoNT A light chain alpha-helices 4, 5, and 6, fused with EGFP, was created by subcloning 1296 b.p. DNA fragment, obtained from the incomplete digest with EcoRI of the 2019 b.p. DNA fragment, obtained from the plasmid pLitBoNTACH6, digested with restriction endonucleases BssHII and AlwNI, into vector pLitEGFP pre-digested with BssHII and EcoRI and dephosphorylated. The size of the resulting plasmid was ~4800 b.p.

Light Chain of Chimera 7 Fused with EGFP

The non-expression vector pLitBoNTACH7EGFP, carrying the sequence of the BoNT A ad light chain with five SNARE motif peptides substituting BoNT A light chain alpha-helices 4, 5, 6, and 7, fused with EGFP, was created by subcloning the 1296 b.p. DNA fragment, obtained from the incomplete digest with EcoRI of the 2019 b.p. DNA fragment, obtained from the plasmid pLitBoNTACH7 digested with restriction endonucleases BssHII and AlwNI into vector pLitEGFP pre-digested with BssHII and EcoRI and dephosphorylated. The size of the resulting plasmid was ~4800 b.p.

Light Chain of Chimera 8 Fused with EGFP

The non-expression vector pLitBoNTACH8EGFP, carrying the sequence of the BoNT A ad light chain with seven SNARE motif peptides substituting BoNT A light chain alpha-helices 1, 4, 5, and 6, fused with EGFP, was created by subcloning the 1296 b.p. DNA fragment obtained from the incomplete digest with EcoRI of the 1754 b.p. DNA fragment obtained from the plasmid pLitBoNTACH8 digested with restriction endonucleases BssHII and HincII into vector pLitEGFP pre-digested with restriction endonucleases BssHII and EcoRI and dephosphorylated. The size of the resulting plasmid was ~4800 b.p.

Light Chain of Chimera 9 Fused with EGFP

The non-expression vector pLitBoNTACH9EGFP, carrying the sequence of the BoNT A ad light chain with eight SNARE motif peptides substituting BoNT A light chain alpha-helices 1, 4, 5, 6, and 7, fused with EGFP, was created by subcloning the 1296 b.p. DNA fragment obtained from the incomplete digest with EcoRI of the 1754 b.p. DNA fragment obtained from the plasmid pLitBoNTACH9 digested with restriction endonucleases BssHII and HincII, into vector pLitEGFP pre-digested with restriction endonucleases BssHII and EcoRI and dephosphorylated. The size of the resulting plasmid was ~4800 b.p.

Sindbis Expression Vector—EGFP

The Sindbis expression vector pSinEGFP, carrying the EGFP sequence was created by subcloning the ~750 b.p. DNA fragment obtained from the plasmid pLitEGFP sequentially digested with restriction endonuclease EcoRI filled-in with Klenow fragment, and digested with restriction endonuclease ApaI into vector pSinRep5 (Invitrogen, Cat. #K750-1) pre-digested with restriction endonucleases StuI and ApaI and dephosphorylated. The size of the resulting plasmid was ~10,250 b.p.

Sindbis Expression Vector—BoNT A td Light Chain Fused with EGFP

The Sindbis expression vector pSinBoNTALCEGFP, carrying the sequence of BoNT A td light, chain fused with EGFP, was created by subcloning the ~2,050 b.p. DNA fragment obtained from the plasmid pLitBoNTALCEGFP, digested with restriction endonucleases NheI and ApaI into vector pSinRep5 pre-digested with restriction endonucleases XbaI and ApaI and dephosphorylated. The size of the resulting plasmid was ~11,550 b.p.

Sindbis Expression Vector—BoNT A ad Light Chain Fused with EGFP

The Sindbis expression vector pSinBoNTAME224ALCEGFP, carrying the sequence of BoNT A ad light, chain fused with EGFP was created by subcloning the ~2,050 b.p. DNA fragment obtained from the plasmid pLitBoNTAME224ALCEGFP digested with restriction endonucleases NheI and ApaI into vector pSinRep5 pre-digested with restriction endonucleases XbaI and ApaI and dephosphorylated. The size of the resulting plasmid was ~11,550 b.p.

Sindbis Expression Vector—Light Chain of Chimera 1 Fused with EGFP

The Sindbis expression vector pSinBoNTACH1EGFP, carrying the sequence of BoNT A ad light chain with three SNARE motif peptides substituting BoNT A light chain alpha-helix 1, fused with EGFP, was created by subcloning the ~2,050 b.p. DNA fragment obtained from the plasmid pLitBoNTACH1EGFP digested with restriction endonucleases NheI and ApaI into vector pSinRep5 pre-digested with restriction endonucleases XbaI and ApaI and dephosphorylated. The size of the resulting plasmid was ~11,550 b.p.

Sindbis Expression Vector—Light Chain of Chimera 2 Fused with EGFP

The Sindbis expression vector pSinBoNTACH2EGFP, carrying the sequence of BoNT A ad light chain with two SNARE motif peptides substituting BoNT A light chain alpha-helix 4, fused with EGFP, was created by subcloning the ~2,050 b.p. DNA fragment obtained from the plasmid pLitBoNTACH2EGFP, digested with restriction endonucleases NheI and ApaI into vector pSinRep5 (Invitrogen, Cat.

K750-1) pre-digested with restriction endonucleases XbaI and ApaI and dephosphorylated. The size of the resulting plasmid was ~11,550 b.p.

Sindbis Expression Vector—Light Chain of Chimera 3 Fused with EGFP

The Sindbis expression vector pSinBoNTACH3EGFP, carrying the sequence of BoNT A ad light chain with five SNARE motif peptides substituting BoNT A light chain alpha-helices 1 and 4, fused with EGFP, was created by subcloning the ~2,050 b.p. DNA fragment obtained from the plasmid pLitBoNTACH3EGFP digested with restriction endonucleases NheI and ApaI into vector pSinRep5 pre-digested with restriction endonucleases XbaI and ApaI and dephosphorylated. The size of the resulting plasmid was ~11,550 b.p.

Sindbis Expression Vector—Light Chain of Chimera 4 Fused with EGFP

The Sindbis expression vector pSinBoNTACH4EGFP, carrying the sequence of BoNT A ad light chain with three SNARE motif peptides substituting BoNT A light chain alpha-helices 4 and 5, fused with EGFP, was created by subcloning the ~2,050 b.p. DNA fragment obtained from the plasmid pLitBoNTACH4EGFP digested with restriction endonucleases NheI and ApaI into vector pSinRep5 pre-digested with restriction endonucleases XbaI and ApaI and dephosphorylated. The size of the resulting plasmid was ~11,550 b.p.

Sindbis Expression Vector—Light Chain of Chimera 5 Fused with EGFP

The Sindbis expression vector pSinBoNTACH5EGFP, carrying the sequence of BoNT A ad light chain with six SNARE motif peptides substituting BoNT A light chain alpha-helices 1, 4, and 5, fused with EGFP, was created by subcloning the ~2,050 b.p. DNA fragment obtained from the plasmid pLitBoNTACH5EGFP digested with restriction endonucleases NheI and ApaI into vector pSinRep5 pre-digested with restriction endonucleases XbaI and ApaI and dephosphorylated. The size of the resulting plasmid was ~11,550 b.p.

Sindbis Expression Vector—Light Chain of Chimera 6 Fused with EGFP

The Sindbis expression vector pSinBoNTACH6EGFP, carrying the sequence of BoNT A ad light chain with four SNARE motif peptides substituting BoNT A light chain alpha-helices 4, 5, and 6, fused with EGFP, was created by subcloning ~2,050 b.p. DNA fragment obtained from the plasmid pLitBoNTACH6EGFP digested with restriction endonucleases NheI and ApaI into vector pSinRep5 pre-digested with restriction endonucleases XbaI and ApaI and dephosphorylated. The size of the resulting plasmid was ~11,550 b.p.

Sindbis Expression Vector—Light Chain of Chimera 7 Fused with EGFP

The Sindbis expression vector pSinBoNTACH7EGFP, carrying the sequence of BoNT A ad light chain with five SNARE motif peptides substituting BoNT A light chain alpha-helices 4, 5, 6, and 7, fused with EGFP, was created by subcloning the ~2,050 b.p. DNA fragment obtained from the plasmid pLitBoNTACH7EGFP digested with restriction endonucleases NheI and ApaI into vector pSinRep5 pre-digested with restriction endonucleases XbaI and ApaI and dephosphorylated. The size of the resulting plasmid was ~11,550 b.p.

Sindbis Expression Vector—Light Chain of Chimera 8 Fused with EGFP

The Sindbis expression vector pSinBoNTACH8EGFP, carrying the sequence of BoNT A ad light chain with seven SNARE motif peptides substituting BoNT A light chain alpha-helices 1, 4, 5, and 6, fused with EGFP, was created by subcloning the ~2,050 b.p. DNA fragment obtained from the plasmid pLitBoNTACH8EGFP digested with restriction endonucleases NheI and ApaI into vector pSinRep5 pre-digested with restriction endonucleases XbaI and ApaI and dephosphorylated. The size of the resulting plasmid was ~11,550 b.p.

Sindbis Expression Vector—Light Chain of Chimera 9 Fused with EGFP

The Sindbis expression vector pSinBoNTACH9EGFP, carrying the sequence of BoNT A ad light chain with eight SNARE motif peptides substituting BoNT A light chain alpha-helices 1, 4, 5, 6, and 7, fused with EGFP, was created by subcloning the ~2,050 b.p. DNA fragment obtained from the plasmid pLitBoNTACH9EGFP digested with restriction endonucleases NheI and ApaI into vector pSinRep5 pre-digested with restriction endonucleases XbaI and ApaI and dephosphorylated. The size of the resulting plasmid was ~11,550 b.p.

The Sindbis expression vectors were prepared for RNA synthesis. The plasmids pSinEGFP, pSinBoNTALCEGFP, pSinBoNTAME224ALCEGFP, pSinBoNTACH1EGFP, pSinBoNTACH2EGFP, pSinBoNTACH3EGFP, pSinBoNTACH4EGFP, pSinBoNTACH5EGFP, pSinBoNTACH6EGFP, pSinBoNTACH7EGFP, pSinBoNTACH8EGFP, and pSinBoNTACH9EGFP were linearized by the digest with restriction endonuclease NotI. The linearized plasmids were used for the RNA synthesis according to the protocol supplied with Sindbis expression system kit (Invitrogen, Cat. #K750-1).

DSGXXS Motif Library

To further mark the antagonist wild-type BoNT A light chain complex for elimination, a second library of light chain chimeras will be produced. This library will incorporate the DSGXXS (SEQ ID NO: 64) motif into the chimeras produced in the first library. The motif DSGXXS is present in a variety of cytosolic proteins and has been shown to target them for degradation via the proteosome pathway upon its phosphorylation (Cardozo et al., "The SCF Ubiquitin Ligase: Insights Into a Molecular Machine," *Nat. Rev. Mol. Cell Biol.* 5:739-751 (2004); Busino et al., "Degradation of Cdc25A by Beta-TrCP During S Phase and In Response to DNA Damage," *Nature* 426:87-91 (2003), which are hereby incorporated by reference in their entirety). The motif will be positioned to cause minimal interference with the 3D structure of the ancestral protein (i.e., wild-type BoNT A light chain).

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. An isolated, physiologically active Clostridial neurotoxin comprising:
   a light chain terminating at its C-terminus with a lysine residue of a highly specific protease cleavage site comprising three or more specific adjacent amino acid residues that are recognized by a highly specific protease to enable cleavage and
   a heavy chain, wherein the light chain and the heavy chain are linked by a disulfide bond.

2. The isolated Clostridial neurotoxin according to claim 1, wherein the neurotoxin is from *Clostridium botulinum*.

3. The isolated Clostridial neurotoxin according to claim 2, wherein the *Clostridium botulinum* has a serotype selected from the group consisting of *Clostridium botulinum* serotype A, *Clostridium botulinum* serotype B, *Clostridium botulinum* serotype C, *Clostridium botulinum* serotype D, *Clostridium*

*botulinum* serotype E, *Clostridium botulinum* serotype F, and *Clostridium botulinum* serotype G.

4. The isolated Clostridial neurotoxin according to claim 1, wherein said physiological activity is selected from the group consisting of toxin immunogenicity, trans- and intra-cellular trafficking, and cell recognition.

5. The isolated Clostridial neurotoxin according to claim 1, wherein the neurotoxin is toxic.

6. The isolated Clostridial neurotoxin according to claim 1, wherein the neurotoxin is atoxic.

7. The isolated Clostridial neurotoxin according to claim 6, wherein the neurotoxin has a disabling mutation in an active metalloprotease site.

8. The isolated Clostridial neurotoxin according to claim 6, wherein the light chain comprises a non-native motif capable of inactivating light chain metalloprotease activity in a toxic Clostridial neurotoxin.

9. The isolated Clostridial neurotoxin according to claim 1, wherein the neurotoxin further comprises:
a signal peptide coupled to the light chain, wherein the signal peptide is suitable to permit secretion of the neurotoxin from a eukaryotic cell to a medium and
an affinity tag located between the signal peptide and the light chain.

10. The isolated Clostridial neurotoxin according to claim 9, wherein the affinity tag is a hexahistidine affinity tag.

11. The isolated Clostridial neurotoxin according to claim 10, wherein the affinity tag comprises SEQ ID NO: 45.

12. The isolated Clostridial neurotoxin according to claim 1, wherein the heavy chain comprises a modification at a Lys amino acid residue adjacent to a receptor binding domain.

13. The isolated Clostridial neurotoxin according to claim 12, wherein the modification is a Lys to Asn substitution.

14. The isolated Clostridial neurotoxin according to claim 1, wherein the highly specific protease cleavage site is an enterokinase cleavage site of SEQ ID NO:24.

15. A vaccine or antidote comprising the isolated Clostridial neurotoxin according to claim 6.

16. The vaccine or antidote according to claim 15, wherein the neurotoxin is from *Clostridium botulinum*.

17. The vaccine or antidote according to claim 16, wherein the *Clostridium botulinum* has a serotype selected from the group consisting of *Clostridium botulinum* serotype A, *Clostridium botulinum* serotype B, *Clostridium botulinum* serotype C, *Clostridium botulinum* serotype D, *Clostridium botulinum* serotype E, *Clostridium botulinum* serotype F, and *Clostridium botulinum* serotype G.

18. The vaccine or antidote according to claim 15, wherein the neurotoxin has a disabling mutation in an active metalloprotease site.

19. The vaccine or antidote according to claim 15, wherein said physiological activity is selected from the group consisting of toxin immunogenicity, trans- and intra-cellular trafficking, and cell recognition.

20. A method of immunizing a subject against toxic effects of a Clostridial neurotoxin, said method comprising:
administering the vaccine according to claim 15 to the subject under conditions effective to immunize the subject against toxic effects of Clostridial neurotoxin.

21. The method according to claim 20, wherein the neurotoxin is from *Clostridium botulinum*.

22. The method according to claim 21, wherein the *Clostridium botulinum* has a serotype selected from the group consisting of *Clostridium botulinum* serotype A, *Clostridium botulinum* serotype B, *Clostridium botulinum* serotype C, *Clostridium botulinum* serotype D, *Clostridium botulinum* serotype E, *Clostridium botulinum* serotype F, and *Clostridium botulinum* serotype G.

23. The method according to claim 20, wherein the neurotoxin has a disabling mutation in an active metalloprotease site.

24. The method according to claim 20 further comprising:
administering a booster of the vaccine to the subject under conditions effective to enhance immunization of the subject.

25. A method of treating a subject for toxic effects of a Clostridial neurotoxin, said method comprising:
administering the antidote according to claim 15 to the subject under conditions effective to treat the subject for toxic effects of Clostridial neurotoxin.

26. The method according to claim 25, wherein the neurotoxin is from *Clostridium botulinum*.

27. The method according to claim 26, wherein the *Clostridium botulinum* has a serotype selected from the group consisting of *Clostridium botulinum* serotype A, *Clostridium botulinum* serotype B, *Clostridium botulinum* serotype C, *Clostridium botulinum* serotype D, *Clostridium botulinum* serotype E, *Clostridium botulinum* serotype F, and *Clostridium botulinum* serotype G.

28. The method according to claim 25, wherein the neurotoxin has a disabling mutation in an active metalloprotease site.

29. A treatment method comprising:
contacting a patient with an isolated Clostridial neurotoxin according to claim 5 under conditions effective to treat the patient.

* * * * *

SEQUENCE LISTING

<160> NUMBER OF SEQ ID NOS: 66

<210> SEQ ID NO 1

<211> LENGTH: 1296
<212> TYPE: PRT
<213> ORGANISM: Clostridium botulinum (serotype A)

<400> SEQUENCE: 1

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Thr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn

```
385                 390                 395                 400
    Phe Asn Gly Gln Asn Thr Glu Ile Asn Asn Met Asn Phe Thr Lys Leu
                    405                 410                 415
    Lys Asn Phe Thr Gly Leu Phe Glu Phe Tyr Lys Leu Leu Cys Val Arg
                    420                 425                 430
    Gly Ile Ile Thr Ser Lys Thr Ser Leu Asp Lys Gly Tyr Asn Lys
                    435                 440                 445
    Ala Leu Asn Asp Leu Cys Ile Lys Val Asn Asn Trp Asp Leu Phe Phe
    450                 455                 460
    Ser Pro Ser Glu Asp Asn Phe Thr Asn Asp Leu Asn Lys Gly Glu Glu
    465                 470                 475                 480
    Ile Thr Ser Asp Thr Asn Ile Glu Ala Ala Glu Asn Ile Ser Leu
                    485                 490                 495
    Asp Leu Ile Gln Gln Tyr Tyr Leu Thr Phe Asn Phe Asn Glu Pro
                    500                 505                 510
    Glu Asn Ile Ser Ile Glu Asn Leu Ser Ser Asp Ile Ile Gly Gln Leu
                    515                 520                 525
    Glu Leu Met Pro Asn Ile Glu Arg Phe Pro Asn Gly Lys Lys Tyr Glu
        530                 535                 540
    Leu Asp Lys Tyr Thr Met Phe His Tyr Leu Arg Ala Gln Glu Phe Glu
    545                 550                 555                 560
    His Gly Lys Ser Arg Ile Ala Leu Thr Asn Ser Val Asn Glu Ala Leu
                    565                 570                 575
    Leu Asn Pro Ser Arg Val Tyr Thr Phe Phe Ser Ser Asp Tyr Val Lys
                    580                 585                 590
    Lys Val Asn Lys Ala Thr Glu Ala Ala Met Phe Leu Gly Trp Val Glu
                    595                 600                 605
    Gln Leu Val Tyr Asp Phe Thr Asp Glu Thr Ser Glu Val Ser Thr Thr
        610                 615                 620
    Asp Lys Ile Ala Asp Ile Thr Ile Ile Pro Tyr Ile Gly Pro Ala
    625                 630                 635                 640
    Leu Asn Ile Gly Asn Met Leu Tyr Lys Asp Asp Phe Val Gly Ala Leu
                    645                 650                 655
    Ile Phe Ser Gly Ala Val Ile Leu Leu Glu Phe Ile Pro Glu Ile Ala
                    660                 665                 670
    Ile Pro Val Leu Gly Thr Phe Ala Leu Val Ser Tyr Ile Ala Asn Lys
                    675                 680                 685
    Val Leu Thr Val Gln Thr Ile Asp Asn Ala Leu Ser Lys Arg Asn Glu
    690                 695                 700
    Lys Trp Asp Glu Val Tyr Lys Tyr Ile Val Thr Asn Trp Leu Ala Lys
    705                 710                 715                 720
    Val Asn Thr Gln Ile Asp Leu Ile Arg Lys Lys Met Lys Glu Ala Leu
                    725                 730                 735
    Glu Asn Gln Ala Glu Ala Thr Lys Ala Ile Ile Asn Tyr Gln Tyr Asn
                    740                 745                 750
    Gln Tyr Thr Glu Glu Glu Lys Asn Asn Ile Asn Phe Asn Ile Asp Asp
                    755                 760                 765
    Leu Ser Ser Lys Leu Asn Glu Ser Ile Asn Lys Ala Met Ile Asn Ile
                    770                 775                 780
    Asn Lys Phe Leu Asn Gln Cys Ser Val Ser Tyr Leu Met Asn Ser Met
    785                 790                 795                 800
    Ile Pro Tyr Gly Val Lys Arg Leu Glu Asp Phe Asp Ala Ser Leu Lys
                    805                 810                 815
```

```
Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
            850                 855                 860

Thr Phe Thr Glu Tyr Ile Lys Asn Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
            930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg
            1010                1015                1020

Leu Asn Asn Ser Lys Ile Tyr Ile Asn Gly Arg Leu Ile Asp Gln
            1025                1030                1035

Lys Pro Ile Ser Asn Leu Gly Asn Ile His Ala Ser Asn Asn Ile
            1040                1045                1050

Met Phe Lys Leu Asp Gly Cys Arg Asp Thr His Arg Tyr Ile Trp
            1055                1060                1065

Ile Lys Tyr Phe Asn Leu Phe Asp Lys Glu Leu Asn Glu Lys Glu
            1070                1075                1080

Ile Lys Asp Leu Tyr Asp Asn Gln Ser Asn Ser Gly Ile Leu Lys
            1085                1090                1095

Asp Phe Trp Gly Asp Tyr Leu Gln Tyr Asp Lys Pro Tyr Tyr Met
            1100                1105                1110

Leu Asn Leu Tyr Asp Pro Asn Lys Tyr Val Asp Val Asn Asn Val
            1115                1120                1125

Gly Ile Arg Gly Tyr Met Tyr Leu Lys Gly Pro Arg Gly Ser Val
            1130                1135                1140

Met Thr Thr Asn Ile Tyr Leu Asn Ser Ser Leu Tyr Arg Gly Thr
            1145                1150                1155

Lys Phe Ile Ile Lys Lys Tyr Ala Ser Gly Asn Lys Asp Asn Ile
            1160                1165                1170

Val Arg Asn Asn Asp Arg Val Tyr Ile Asn Val Val Val Lys Asn
            1175                1180                1185

Lys Glu Tyr Arg Leu Ala Thr Asn Ala Ser Gln Ala Gly Val Glu
            1190                1195                1200

Lys Ile Leu Ser Ala Leu Glu Ile Pro Asp Val Gly Asn Leu Ser
            1205                1210                1215
```

-continued

```
Gln Val Val Met Lys Ser Lys Asn Asp Gln Gly Ile Thr Asn
    1220            1225            1230

Lys Cys Lys Met Asn Leu Gln Asp Asn Asn Gly Asn Asp Ile Gly
    1235            1240            1245

Phe Ile Gly Phe His Gln Phe Asn Asn Ile Ala Lys Leu Val Ala
    1250            1255            1260

Ser Asn Trp Tyr Asn Arg Gln Ile Glu Arg Ser Ser Arg Thr Leu
    1265            1270            1275

Gly Cys Ser Trp Glu Phe Ile Pro Val Asp Asp Gly Trp Gly Glu
    1280            1285            1290

Arg Pro Leu
    1295

<210> SEQ ID NO 2
<211> LENGTH: 1291
<212> TYPE: PRT
<213> ORGANISM: Clostridium botulinum (serotype B)

<400> SEQUENCE: 2

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
            115                 120                 125

Phe Asn Thr Asn Ile Ala Ser Val Thr Val Asn Lys Leu Ile Ser Asn
        130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
        210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
            275                 280                 285
```

-continued

```
Tyr Asp Lys Val Leu Gln Asn Phe Arg Gly Ile Val Asp Arg Leu Asn
            290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
                325                 330                 335
Lys Tyr Ser Ile Asp Val Glu Ser Phe Asp Lys Leu Tyr Lys Ser Leu
            340                 345                 350
Met Phe Gly Phe Thr Glu Thr Asn Ile Ala Glu Asn Tyr Lys Ile Lys
                355                 360                 365
Thr Arg Ala Ser Tyr Phe Ser Asp Ser Leu Pro Pro Val Lys Ile Lys
370                 375                 380
Asn Leu Leu Asp Asn Glu Ile Tyr Thr Ile Glu Glu Gly Phe Asn Ile
385                 390                 395                 400
Ser Asp Lys Asp Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
            420                 425                 430
Lys Ile Gln Met Cys Lys Ser Val Lys Ala Pro Gly Ile Cys Ile Asp
                435                 440                 445
Val Asp Asn Glu Asp Leu Phe Phe Ile Ala Asp Lys Asn Ser Phe Ser
450                 455                 460
Asp Asp Leu Ser Lys Asn Glu Arg Ile Glu Tyr Asn Thr Gln Ser Asn
465                 470                 475                 480
Tyr Ile Glu Asn Asp Phe Pro Ile Asn Glu Leu Ile Leu Asp Thr Asp
                485                 490                 495
Leu Ile Ser Lys Ile Glu Leu Pro Ser Glu Asn Thr Glu Ser Leu Thr
            500                 505                 510
Asp Phe Asn Val Asp Val Pro Val Tyr Glu Lys Gln Pro Ala Ile Lys
                515                 520                 525
Lys Ile Phe Thr Asp Glu Asn Thr Ile Phe Gln Tyr Leu Tyr Ser Gln
            530                 535                 540
Thr Phe Pro Leu Asp Ile Arg Asp Ile Ser Leu Thr Ser Ser Phe Asp
545                 550                 555                 560
Asp Ala Leu Leu Phe Ser Asn Lys Val Tyr Ser Phe Phe Ser Met Asp
                565                 570                 575
Tyr Ile Lys Thr Ala Asn Lys Val Val Glu Ala Gly Leu Phe Ala Gly
            580                 585                 590
Trp Val Lys Gln Ile Val Asn Asp Phe Val Ile Glu Ala Asn Lys Ser
                595                 600                 605
Asn Thr Met Asp Lys Ile Ala Asp Ile Ser Leu Ile Val Pro Tyr Ile
            610                 615                 620
Gly Leu Ala Leu Asn Val Gly Asn Glu Thr Ala Lys Gly Asn Phe Glu
625                 630                 635                 640
Asn Ala Phe Glu Ile Ala Gly Ala Ser Ile Leu Leu Glu Phe Ile Pro
                645                 650                 655
Glu Leu Leu Ile Pro Val Val Gly Ala Phe Leu Leu Glu Ser Tyr Ile
            660                 665                 670
Asp Asn Lys Asn Lys Ile Ile Lys Thr Ile Asp Asn Ala Leu Thr Lys
                675                 680                 685
Arg Asn Glu Lys Trp Ser Asp Met Tyr Gly Leu Ile Val Ala Gln Trp
            690                 695                 700
```

```
Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Lys Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
        995                 1000                1005

Asn Asn Leu Asn Asn Ala Lys Ile Tyr Ile Asn Gly Lys Leu Glu
    1010                1015                1020

Ser Asn Thr Asp Ile Lys Asp Ile Arg Glu Val Ile Ala Asn Gly
    1025                1030                1035

Glu Ile Ile Phe Lys Leu Asp Gly Asp Ile Asp Arg Thr Gln Phe
    1040                1045                1050

Ile Trp Met Lys Tyr Phe Ser Ile Phe Asn Thr Glu Leu Ser Gln
    1055                1060                1065

Ser Asn Ile Glu Glu Arg Tyr Lys Ile Gln Ser Tyr Ser Glu Tyr
    1070                1075                1080

Leu Lys Asp Phe Trp Gly Asn Pro Leu Met Tyr Asn Lys Glu Tyr
    1085                1090                1095

Tyr Met Phe Asn Ala Gly Asn Lys Asn Ser Tyr Ile Lys Leu Lys
    1100                1105                1110

Lys Asp Ser Pro Val Gly Glu Ile Leu Thr Arg Ser Lys Tyr Asn
```

-continued

```
            1115                1120                 1125

Gln Asn Ser Lys Tyr Ile Asn Tyr Arg Asp Leu Tyr Ile Gly Glu
        1130                1135                1140

Lys Phe Ile Ile Arg Arg Lys Ser Asn Ser Gln Ser Ile Asn Asp
    1145                1150                1155

Asp Ile Val Arg Lys Glu Asp Tyr Ile Tyr Leu Asp Phe Phe Asn
1160                1165                1170

Leu Asn Gln Glu Trp Arg Val Tyr Thr Tyr Lys Tyr Phe Lys Lys
    1175                1180                1185

Glu Glu Glu Lys Leu Phe Leu Ala Pro Ile Ser Asp Ser Asp Glu
        1190                1195                1200

Phe Tyr Asn Thr Ile Gln Ile Lys Glu Tyr Asp Glu Gln Pro Thr
    1205                1210                1215

Tyr Ser Cys Gln Leu Leu Phe Lys Lys Asp Glu Glu Ser Thr Asp
1220                1225                1230

Glu Ile Gly Leu Ile Gly Ile His Arg Phe Tyr Glu Ser Gly Ile
        1235                1240                1245

Val Phe Glu Glu Tyr Lys Asp Tyr Phe Cys Ile Ser Lys Trp Tyr
1250                1255                1260

Leu Lys Glu Val Lys Arg Lys Pro Tyr Asn Leu Lys Leu Gly Cys
    1265                1270                1275

Asn Trp Gln Phe Ile Pro Lys Asp Glu Gly Trp Thr Glu
    1280                1285                1290

<210> SEQ ID NO 3
<211> LENGTH: 1291
<212> TYPE: PRT
<213> ORGANISM: Clostridium botulinum (serotype C)

<400> SEQUENCE: 3

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190
```

-continued

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
        260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
        290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
        340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
        370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
        420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
        500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
        580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp

-continued

```
            610                 615                 620
Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                    645                 650                 655

Thr Ile Leu Leu Glu Ala Phe Pro Glu Phe Thr Ile Pro Ala Leu Gly
                660                 665                 670

Ala Phe Val Ile Tyr Ser Lys Val Gln Glu Arg Asn Glu Ile Ile Lys
                675                 680                 685

Thr Ile Asp Asn Cys Leu Glu Gln Arg Ile Lys Arg Trp Lys Asp Ser
690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
                740                 745                 750

Asp Lys Glu Asn Ile Lys Ser Gln Val Glu Asn Leu Lys Asn Ser Leu
            755                 760                 765

Asp Val Lys Ile Ser Glu Ala Met Asn Asn Ile Asn Lys Phe Ile Arg
770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
                820                 825                 830

Lys Ala Lys Val Asn Asn Ser Phe Gln Asn Thr Ile Pro Phe Asn Ile
            835                 840                 845

Phe Ser Tyr Thr Asn Asn Ser Leu Leu Lys Asp Ile Ile Asn Glu Tyr
850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
                900                 905                 910

Ser Ser Gly Glu Asp Arg Gly Lys Val Ile Val Thr Gln Asn Glu Asn
            915                 920                 925

Ile Val Tyr Asn Ser Met Tyr Glu Ser Phe Ser Ile Ser Phe Trp Ile
930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ser Asn Phe
                965                 970                 975

Leu Val Phe Thr Leu Lys Gln Asn Glu Asp Ser Glu Gln Ser Ile Asn
                980                 985                 990

Phe Ser Tyr Asp Ile Ser Asn Asn Ala Pro Gly Tyr Asn Lys Trp Phe
                995                 1000                1005

Phe Val Thr Val Thr Asn Asn Met Met Gly Asn Met Lys Ile Tyr
        1010                1015                1020

Ile Asn Gly Lys Leu Ile Asp Thr Ile Lys Val Lys Glu Leu Thr
        1025                1030                1035
```

```
Gly Ile Asn Phe Ser Lys Thr Ile Thr Phe Glu Ile Asn Lys Ile
            1040                1045                1050

Pro Asp Thr Gly Leu Ile Thr Ser Asp Ser Asp Asn Ile Asn Met
        1055                1060                1065

Trp Ile Arg Asp Phe Tyr Ile Phe Ala Lys Glu Leu Asp Gly Lys
    1070                1075                1080

Asp Ile Asn Ile Leu Phe Asn Ser Leu Gln Tyr Thr Asn Val Val
1085                1090                1095

Lys Asp Tyr Trp Gly Asn Asp Leu Arg Tyr Asn Lys Glu Tyr Tyr
1100                1105                1110

Met Val Asn Ile Asp Tyr Leu Asn Arg Tyr Met Tyr Ala Asn Ser
    1115                1120                1125

Arg Gln Ile Val Phe Asn Thr Arg Arg Asn Asn Asn Asp Phe Asn
        1130                1135                1140

Glu Gly Tyr Lys Ile Ile Ile Lys Arg Ile Arg Gly Asn Thr Asn
    1145                1150                1155

Asp Thr Arg Val Arg Gly Gly Asp Ile Leu Tyr Phe Asp Met Thr
        1160                1165                1170

Ile Asn Asn Lys Ala Tyr Asn Leu Phe Met Lys Asn Glu Thr Met
    1175                1180                1185

Tyr Ala Asp Asn His Ser Thr Glu Asp Ile Tyr Ala Ile Gly Leu
    1190                1195                1200

Arg Glu Gln Thr Lys Asp Ile Asn Asp Asn Ile Ile Phe Gln Ile
    1205                1210                1215

Gln Pro Met Asn Asn Thr Tyr Tyr Tyr Ala Ser Gln Ile Phe Lys
    1220                1225                1230

Ser Asn Phe Asn Gly Glu Asn Ile Ser Gly Ile Cys Ser Ile Gly
    1235                1240                1245

Thr Tyr Arg Phe Arg Leu Gly Gly Asp Trp Tyr Arg His Asn Tyr
    1250                1255                1260

Leu Val Pro Thr Val Lys Gln Gly Asn Tyr Ala Ser Leu Leu Glu
    1265                1270                1275

Ser Thr Ser Thr His Trp Gly Phe Val Pro Val Ser Glu
    1280                1285                1290

<210> SEQ ID NO 4
<211> LENGTH: 1276
<212> TYPE: PRT
<213> ORGANISM: Clostridium botulinum (serotype D)

<400> SEQUENCE: 4

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
                20                  25                  30

Pro Val Lys Ala Phe Met Ile Thr Gln Asn Ile Trp Val Ile Pro Glu
            35                  40                  45

Arg Phe Ser Ser Asp Thr Asn Pro Ser Leu Ser Lys Pro Pro Arg Pro
        50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
```

-continued

```
                100                 105                 110
Gly Ser Pro Phe Met Gly Asp Ser Ser Thr Pro Glu Asp Thr Phe Asp
            115                 120                 125

Phe Thr Arg His Thr Thr Asn Ile Ala Val Glu Lys Phe Glu Asn Gly
130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
            165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
            195                 200                 205

Gln Ser Ser Ala Val Leu Gly Lys Ser Ile Phe Cys Met Asp Pro Val
            210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
            245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
            275                 280                 285

Leu Arg Glu Lys Ala Leu Gly His Tyr Lys Asp Ile Ala Lys Arg Leu
290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
            325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
            355                 360                 365

Val Lys Asn Arg Thr His Tyr Phe Ser Arg His Tyr Leu Pro Val Phe
370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
            405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
            435                 440                 445

Thr Cys Ile Lys Val Lys Asn Asn Arg Leu Pro Tyr Val Ala Asp Lys
            450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Asn Phe Ser Leu Asp Glu Ser Ile
            485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
            515                 520                 525
```

```
Phe Tyr Asp Asp Ile Thr Lys Tyr Val Asp Tyr Leu Asn Ser Tyr Tyr
    530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
                580                 585                 590

Leu Phe Leu Asn Trp Ala Asn Glu Val Val Glu Asp Phe Thr Thr Asn
        595                 600                 605

Ile Met Lys Lys Asp Thr Leu Asp Lys Ile Ser Asp Val Ser Val Ile
610                 615                 620

Ile Pro Tyr Ile Gly Pro Ala Leu Asn Ile Gly Asn Ser Ala Leu Arg
625                 630                 635                 640

Gly Asn Phe Lys Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
                660                 665                 670

Tyr Ser Ser Ile Gln Glu Arg Glu Lys Ile Ile Lys Thr Ile Glu Asn
            675                 680                 685

Cys Leu Glu Gln Arg Val Lys Arg Trp Lys Asp Ser Tyr Gln Trp Met
690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
                740                 745                 750

Ile Lys Ser Gln Val Glu Asn Leu Lys Asn Ser Leu Asp Val Lys Ile
        755                 760                 765

Ser Glu Ala Met Asn Asn Ile Asn Lys Phe Ile Arg Glu Cys Ser Val
770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Met Pro Phe Asn Ile Phe Ser Tyr Thr
        835                 840                 845

Asn Asn Ser Leu Leu Lys Asp Ile Ile Asn Glu Tyr Phe Asn Ser Ile
850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
                900                 905                 910

Lys Ile Ile Val Asn Leu Asn Asn Asn Ile Leu Tyr Ser Ala Ile Tyr
            915                 920                 925

Glu Asn Ser Ser Val Ser Phe Trp Ile Lys Ile Ser Lys Asp Leu Thr
930                 935                 940
```

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
            965                 970                 975

Asp Val Asn Arg Lys Tyr Lys Ser Leu Ile Phe Asp Tyr Ser Glu Ser
        980                 985                 990

Leu Ser His Thr Gly Tyr Thr Asn Lys Trp Phe Phe Val Thr Ile Thr
            995                 1000                1005

Asn Asn Ile Met Gly Tyr Met Lys Leu Tyr Ile Asn Gly Glu Leu
1010                1015                1020

Lys Gln Ser Gln Lys Ile Glu Asp Leu Asp Glu Val Lys Leu Asp
1025                1030                1035

Lys Thr Ile Val Phe Gly Ile Asp Glu Asn Ile Asp Glu Asn Gln
1040                1045                1050

Met Leu Trp Ile Arg Asp Phe Asn Ile Phe Ser Lys Glu Leu Ser
1055                1060                1065

Asn Glu Asp Ile Asn Ile Val Tyr Glu Gly Gln Ile Leu Arg Asn
1070                1075                1080

Val Ile Lys Asp Tyr Trp Gly Asn Pro Leu Lys Phe Asp Thr Glu
1085                1090                1095

Tyr Tyr Ile Ile Asn Asp Asn Tyr Ile Asp Arg Tyr Ile Ala Pro
1100                1105                1110

Glu Ser Asn Val Leu Val Leu Val Arg Tyr Pro Asp Arg Ser Lys
1115                1120                1125

Leu Tyr Thr Gly Asn Pro Ile Thr Ile Lys Ser Val Ser Asp Lys
1130                1135                1140

Asn Pro Tyr Ser Arg Ile Leu Asn Gly Asp Asn Ile Ile Leu His
1145                1150                1155

Met Leu Tyr Asn Ser Arg Lys Tyr Met Ile Ile Arg Asp Thr Asp
1160                1165                1170

Thr Ile Tyr Ala Thr Gln Gly Gly Glu Cys Ser Gln Asn Cys Val
1175                1180                1185

Tyr Ala Leu Lys Leu Gln Ser Asn Leu Gly Asn Tyr Gly Ile Gly
1190                1195                1200

Ile Phe Ser Ile Lys Asn Ile Val Ser Lys Asn Lys Tyr Cys Ser
1205                1210                1215

Gln Ile Phe Ser Ser Phe Arg Glu Asn Thr Met Leu Leu Ala Asp
1220                1225                1230

Ile Tyr Lys Pro Trp Arg Phe Ser Phe Lys Asn Ala Tyr Thr Pro
1235                1240                1245

Val Ala Val Thr Asn Tyr Glu Thr Lys Leu Leu Ser Thr Ser Ser
1250                1255                1260

Phe Trp Lys Phe Ile Ser Arg Asp Pro Gly Trp Val Glu
1265                1270                1275

<210> SEQ ID NO 5
<211> LENGTH: 1251
<212> TYPE: PRT
<213> ORGANISM: Clostridium botulinum (serotype E)

<400> SEQUENCE: 5

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

```
Phe Asn Ile Met Lys Asn Ile Trp Ile Ile Pro Glu Arg Asn Val Ile
         35                  40                  45

Gly Thr Thr Pro Gln Asp Phe His Pro Pro Thr Ser Leu Lys Asn Gly
 50                  55                  60

Asp Ser Ser Tyr Tyr Asp Pro Asn Tyr Leu Gln Ser Asp Glu Glu Lys
 65                  70                  75                  80

Asp Arg Phe Leu Lys Ile Val Thr Lys Ile Phe Asn Arg Ile Asn Asn
                 85                  90                  95

Asn Leu Ser Gly Gly Ile Leu Leu Glu Glu Leu Ser Lys Ala Asn Pro
                100                 105                 110

Tyr Leu Gly Asn Asp Asn Thr Pro Asp Asn Gln Phe His Ile Gly Asp
                115                 120                 125

Ala Ser Ala Val Glu Ile Lys Phe Ser Asn Gly Ser Gln Asp Ile Leu
130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
                180                 185                 190

Arg Phe Asn Asp Asn Ser Met Asn Glu Phe Ile Gln Asp Pro Ala Leu
                195                 200                 205

Thr Leu Met His Glu Leu Ile His Ser Leu His Gly Leu Tyr Gly Ala
                210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
                275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
                355                 360                 365

Tyr Asn Ile Ser Glu Gly Tyr Asn Ile Asn Asn Leu Lys Val Asn Phe
                370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
                420                 425                 430

Glu Leu Phe Phe Val Ala Ser Glu Asn Ser Tyr Asn Asp Asp Asn Ile
                435                 440                 445
```

```
Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
                500                 505                 510

Asp Val Asn Glu Leu Asn Val Phe Phe Tyr Leu Asp Ala Gln Lys Val
                515                 520                 525

Pro Glu Gly Glu Asn Asn Val Asn Leu Thr Ser Ser Ile Asp Thr Ala
530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
                580                 585                 590

Val Asp Lys Ile Ala Asp Ile Ser Ile Val Pro Tyr Ile Gly Leu
                595                 600                 605

Ala Leu Asn Ile Gly Asn Glu Ala Gln Lys Gly Asn Phe Lys Asp Ala
610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
                660                 665                 670

Glu Arg Asp Glu Lys Trp Lys Glu Val Tyr Ser Phe Ile Val Ser Asn
                675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
                740                 745                 750

Ile Ala Met Asn Asn Ile Asp Arg Phe Leu Thr Glu Ser Ser Ile Ser
                755                 760                 765

Tyr Leu Met Lys Leu Ile Asn Glu Val Lys Ile Asn Lys Leu Arg Glu
770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
                820                 825                 830

Asp Lys Ile Leu Ile Ser Tyr Phe Asn Lys Phe Phe Lys Arg Ile Lys
                835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
```

```
                    865                 870                 875                 880
            Tyr Pro Thr Asn Lys Asn Gln Phe Gly Ile Tyr Asn Asp Lys Leu Ser
                            885                 890                 895
            Glu Val Asn Ile Ser Gln Asn Asp Tyr Ile Ile Tyr Asp Asn Lys Tyr
                            900                 905                 910
            Lys Asn Phe Ser Ile Ser Phe Trp Val Arg Ile Pro Asn Tyr Asp Asn
                            915                 920                 925
            Lys Ile Val Asn Val Asn Asn Glu Tyr Thr Ile Ile Asn Cys Met Arg
                930                 935                 940
            Asp Asn Asn Ser Gly Trp Lys Val Ser Leu Asn His Asn Glu Ile Ile
            945                 950                 955                 960
            Trp Thr Leu Gln Asp Asn Ala Gly Ile Asn Gln Lys Leu Ala Phe Asn
                            965                 970                 975
            Tyr Gly Asn Ala Asn Gly Ile Ser Asp Tyr Ile Asn Lys Trp Ile Phe
                            980                 985                 990
            Val Thr Ile Thr Asn Asp Arg Leu  Gly Asp Ser Lys Leu  Tyr Ile Asn
                            995                 1000                1005
            Gly Asn  Leu Ile Asp Gln Lys  Ser Ile Leu Asn Leu  Gly Asn Ile
                1010                1015                1020
            His Val  Ser Asp Asn Ile Leu  Phe Lys Ile Val Asn  Cys Ser Tyr
                1025                1030                1035
            Thr Arg  Tyr Ile Gly Ile Arg  Tyr Phe Asn Ile Phe  Asp Lys Glu
                1040                1045                1050
            Leu Asp  Glu Thr Glu Ile Gln  Thr Leu Tyr Ser Asn  Glu Pro Asn
                1055                1060                1065
            Thr Asn  Ile Leu Lys Asp Phe  Trp Gly Asn Tyr Leu  Leu Tyr Asp
                1070                1075                1080
            Lys Glu  Tyr Tyr Leu Leu Asn  Val Leu Lys Pro Asn  Asn Phe Ile
                1085                1090                1095
            Asp Arg  Arg Lys Asp Ser Thr  Leu Ser Ile Asn Asn  Ile Arg Ser
                1100                1105                1110
            Thr Ile  Leu Leu Ala Asn Arg  Leu Tyr Ser Gly Ile  Lys Val Lys
                1115                1120                1125
            Ile Gln  Arg Val Asn Asn Ser  Ser Thr Asn Asp Asn  Leu Val Arg
                1130                1135                1140
            Lys Asn  Asp Gln Val Tyr Ile  Asn Phe Val Ala Ser  Lys Thr His
                1145                1150                1155
            Leu Phe  Pro Leu Tyr Ala Asp  Thr Ala Thr Asn Lys  Glu Lys
                1160                1165                1170
            Thr Ile  Lys Ile Ser Ser Ser  Gly Asn Arg Phe Asn  Gln Val Val
                1175                1180                1185
            Val Met  Asn Ser Val Gly Asn  Asn Thr Met Asn Phe  Lys Asn Asn
                1190                1195                1200
            Asn Gly  Asn Asn Ile Gly Leu  Leu Gly Phe Lys Ala  Asp Thr Val
                1205                1210                1215
            Val Ala  Ser Thr Trp Tyr Tyr  Thr His Met Arg Asp  His Thr Asn
                1220                1225                1230
            Ser Asn  Gly Cys Phe Trp Asn  Phe Ile Ser Glu Glu  His Gly Trp
                1235                1240                1245
            Gln Glu  Lys
                1250

<210> SEQ ID NO 6
```

<211> LENGTH: 1277
<212> TYPE: PRT
<213> ORGANISM: Clostridium botulinum (serotype F)

<400> SEQUENCE: 6

```
Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Ile Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
```

```
            385                 390                 395                 400
Asn Arg Gly Gln Asn Ile Lys Leu Asn Pro Lys Ile Ile Asp Ser Ile
                405                 410                 415
Pro Asp Lys Gly Leu Val Glu Lys Ile Val Lys Phe Cys Lys Ser Val
                420                 425                 430
Ile Pro Arg Lys Gly Thr Lys Ala Pro Pro Arg Leu Cys Ile Arg Val
                435                 440                 445
Asn Asn Arg Glu Leu Phe Phe Val Ala Ser Glu Ser Ser Tyr Asn Glu
450                 455                 460
Asn Asp Ile Asn Thr Pro Lys Glu Ile Asp Asp Thr Thr Asn Leu Asn
465                 470                 475                 480
Asn Asn Tyr Arg Asn Asn Leu Asp Glu Val Ile Leu Asp Tyr Asn Ser
                485                 490                 495
Glu Thr Ile Pro Gln Ile Ser Asn Gln Thr Leu Asn Thr Leu Val Gln
                500                 505                 510
Asp Asp Ser Tyr Val Pro Arg Tyr Asp Ser Asn Gly Thr Ser Glu Ile
                515                 520                 525
Glu Glu His Asn Val Val Asp Leu Asn Val Phe Phe Tyr Leu His Ala
                530                 535                 540
Gln Lys Val Pro Glu Gly Glu Thr Asn Ile Ser Leu Thr Ser Ser Ile
545                 550                 555                 560
Asp Thr Ala Leu Ser Glu Glu Ser Gln Val Tyr Thr Phe Phe Ser Ser
                565                 570                 575
Glu Phe Ile Asn Thr Ile Asn Lys Pro Val His Ala Ala Leu Phe Ile
                580                 585                 590
Ser Trp Ile Asn Gln Val Ile Arg Asp Phe Thr Thr Glu Ala Thr Gln
                595                 600                 605
Lys Ser Thr Phe Asp Lys Ile Ala Asp Ile Ser Leu Val Val Pro Tyr
                610                 615                 620
Val Gly Leu Ala Leu Asn Ile Gly Asn Glu Val Gln Lys Glu Asn Phe
625                 630                 635                 640
Lys Glu Ala Phe Glu Leu Leu Gly Ala Gly Ile Leu Leu Glu Phe Val
                645                 650                 655
Pro Glu Leu Leu Ile Pro Thr Ile Leu Val Phe Thr Ile Lys Ser Phe
                660                 665                 670
Ile Gly Ser Ser Glu Asn Lys Asn Lys Ile Ile Lys Ala Ile Asn Asn
                675                 680                 685
Ser Leu Met Glu Arg Glu Thr Lys Trp Lys Glu Ile Tyr Ser Trp Ile
                690                 695                 700
Val Ser Asn Trp Leu Thr Arg Ile Asn Thr Gln Phe Asn Lys Arg Lys
705                 710                 715                 720
Glu Gln Met Tyr Gln Ala Leu Gln Asn Gln Val Asp Ala Ile Lys Thr
                725                 730                 735
Val Ile Glu Tyr Lys Tyr Asn Asn Tyr Thr Ser Asp Glu Arg Asn Arg
                740                 745                 750
Leu Glu Ser Glu Tyr Asn Ile Asn Asn Ile Arg Glu Glu Leu Asn Lys
                755                 760                 765
Lys Val Ser Leu Ala Met Glu Asn Ile Glu Arg Phe Ile Thr Glu Ser
                770                 775                 780
Ser Ile Phe Tyr Leu Met Lys Leu Ile Asn Glu Ala Lys Val Ser Lys
785                 790                 795                 800
Leu Arg Glu Tyr Asp Glu Gly Val Lys Glu Tyr Leu Leu Asp Tyr Ile
                805                 810                 815
```

```
Ser Glu His Arg Ser Ile Leu Gly Asn Ser Val Gln Glu Leu Asn Asp
            820                 825                 830

Leu Val Thr Ser Thr Leu Asn Ser Ile Pro Phe Glu Leu Ser Ser
            835                 840                 845

Tyr Thr Asn Asp Lys Ile Leu Ile Leu Tyr Phe Asn Lys Leu Tyr Lys
850                 855                 860

Lys Ile Lys Asp Asn Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asp
                885                 890                 895

Val Tyr Ile Tyr Ser Thr Asn Arg Asn Gln Phe Gly Ile Tyr Ser Ser
            900                 905                 910

Lys Pro Ser Glu Val Asn Ile Ala Gln Asn Asn Asp Ile Ile Tyr Asn
            915                 920                 925

Gly Arg Tyr Gln Asn Phe Ser Ile Ser Phe Trp Val Arg Ile Pro Lys
            930                 935                 940

Tyr Phe Asn Lys Val Asn Leu Asn Asn Glu Tyr Thr Ile Ile Asp Cys
945                 950                 955                 960

Ile Arg Asn Asn Asn Ser Gly Trp Lys Ile Ser Leu Asn Tyr Asn Lys
                965                 970                 975

Ile Ile Trp Thr Leu Gln Asp Thr Ala Gly Asn Asn Gln Lys Leu Val
                980                 985                 990

Phe Asn Tyr Thr Gln Met Ile Ser Ile Ser Asp Tyr Ile Asn Lys Trp
            995                 1000                1005

Ile Phe Val Thr Ile Thr Asn Asn Arg Leu Gly Asn Ser Arg Ile
    1010                1015                1020

Tyr Ile Asn Gly Asn Leu Ile Asp Glu Lys Ser Ile Ser Asn Leu
    1025                1030                1035

Gly Asp Ile His Val Ser Asp Asn Ile Leu Phe Lys Ile Val Gly
    1040                1045                1050

Cys Asn Asp Thr Arg Tyr Val Gly Ile Arg Tyr Phe Lys Val Phe
    1055                1060                1065

Asp Thr Glu Leu Gly Lys Thr Glu Ile Glu Thr Leu Tyr Ser Asp
    1070                1075                1080

Glu Pro Asp Pro Ser Ile Leu Lys Asp Phe Trp Gly Asn Tyr Leu
    1085                1090                1095

Leu Tyr Asn Lys Arg Tyr Tyr Leu Leu Asn Leu Leu Arg Thr Asp
    1100                1105                1110

Lys Ser Ile Thr Gln Asn Ser Asn Phe Leu Asn Ile Asn Gln Gln
    1115                1120                1125

Arg Gly Val Tyr Gln Lys Pro Asn Ile Phe Ser Asn Thr Arg Leu
    1130                1135                1140

Tyr Thr Gly Val Glu Val Ile Ile Arg Lys Asn Gly Ser Thr Asp
    1145                1150                1155

Ile Ser Asn Thr Asp Asn Phe Val Arg Lys Asn Asp Leu Ala Tyr
    1160                1165                1170

Ile Asn Val Val Asp Arg Asp Val Glu Tyr Arg Leu Tyr Ala Asp
    1175                1180                1185

Ile Ser Ile Ala Lys Pro Glu Lys Ile Ile Lys Leu Ile Arg Thr
    1190                1195                1200

Ser Asn Ser Asn Asn Ser Leu Gly Gln Ile Ile Val Met Asp Ser
    1205                1210                1215
```

Ile Gly Asn Asn Thr Met Asn Phe Gln Asn Asn Asn Gly Gly Asn
1220                1225                1230

Ile Gly Leu Leu Gly Phe His Ser Asn Asn Leu Val Ala Ser Ser
1235                1240                1245

Trp Tyr Tyr Asn Asn Ile Arg Lys Asn Thr Ser Ser Asn Gly Cys
1250                1255                1260

Phe Trp Ser Phe Ile Ser Lys Glu His Gly Trp Gln Glu Asn
1265                1270                1275

<210> SEQ ID NO 7
<211> LENGTH: 1297
<212> TYPE: PRT
<213> ORGANISM: Clostridium botulinum (serotype G)

<400> SEQUENCE: 7

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
                20                  25                  30

Tyr Tyr Lys Ala Phe Arg Ile Ile Asp Arg Ile Trp Ile Val Pro Glu
            35                  40                  45

Arg Phe Thr Tyr Gly Phe Gln Pro Asp Gln Phe Asn Ala Ser Thr Gly
        50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

```
Gln Ile Tyr Lys Asn Lys Tyr Asp Phe Val Glu Pro Asn Gly Lys
                325                 330                 335

Tyr Ser Val Asp Lys Asp Lys Phe Asp Lys Leu Tyr Lys Ala Leu Met
                340                 345                 350

Phe Gly Phe Thr Glu Thr Asn Leu Ala Gly Glu Tyr Gly Ile Lys Thr
            355                 360                 365

Arg Tyr Ser Tyr Phe Ser Glu Tyr Leu Pro Pro Ile Lys Thr Glu Lys
            370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
                420                 425                 430

Ile Ala Met Cys Lys Pro Val Met Tyr Lys Asn Thr Gly Lys Ser Glu
                435                 440                 445

Gln Cys Ile Ile Val Asn Asn Glu Asp Leu Phe Phe Ile Ala Asn Lys
                450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
                500                 505                 510

Glu Pro Phe Thr Asn Phe Asp Asp Ile Asp Ile Pro Val Tyr Ile Lys
                515                 520                 525

Gln Ser Ala Leu Lys Lys Ile Phe Val Asp Gly Asp Ser Leu Phe Glu
                530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
                580                 585                 590

Ser Leu Phe Val Asn Trp Val Lys Gly Val Ile Asp Asp Phe Thr Ser
                595                 600                 605

Glu Ser Thr Gln Lys Ser Thr Ile Asp Lys Val Ser Asp Val Ser Ile
                610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
                660                 665                 670

Leu Glu Ser Tyr Val Gly Asn Lys Gly His Ile Ile Met Thr Ile Ser
                675                 680                 685

Asn Ala Leu Lys Lys Arg Asp Gln Lys Trp Thr Asp Met Tyr Gly Leu
                690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735
```

-continued

Lys Ile Ile Glu Asp Gln Tyr Asn Arg Tyr Ser Glu Glu Asp Lys Met
              740                 745                 750

Asn Ile Asn Ile Asp Phe Asn Asp Ile Asp Phe Lys Leu Asn Gln Ser
              755                 760                 765

Ile Asn Leu Ala Ile Asn Asn Ile Asp Asp Phe Ile Asn Gln Cys Ser
        770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                  805                 810                 815

Thr Asn Glu Leu Tyr Leu Leu Asp Glu Val Asn Ile Leu Lys Ser Lys
              820                 825                 830

Val Asn Arg His Leu Lys Asp Ser Ile Pro Phe Asp Leu Ser Leu Tyr
              835                 840                 845

Thr Lys Asp Thr Ile Leu Ile Gln Val Phe Asn Asn Tyr Ile Ser Asn
              850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                  885                 890                 895

Ile Phe Asn Asp Ile Gly Asn Gly Gln Phe Lys Leu Asn Asn Ser Glu
              900                 905                 910

Asn Ser Asn Ile Thr Ala His Gln Ser Lys Phe Val Val Tyr Asp Ser
              915                 920                 925

Met Phe Asp Asn Phe Ser Ile Asn Phe Trp Val Arg Thr Pro Lys Tyr
        930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                  965                 970                 975

Arg Ile Ile Trp Thr Leu Ile Asp Val Asn Ala Lys Ser Lys Ser Ile
              980                 985                 990

Phe Phe Glu Tyr Ser Ile Lys Asp Asn Ile Ser Asp Tyr Ile Asn Lys
              995                 1000                1005

Trp Phe Ser Ile Thr Ile Thr Asn Asp Arg Leu Gly Asn Ala Asn
        1010                1015                1020

Ile Tyr Ile Asn Gly Ser Leu Lys Lys Ser Glu Lys Ile Leu Asn
        1025                1030                1035

Leu Asp Arg Ile Asn Ser Ser Asn Asp Ile Asp Phe Lys Leu Ile
        1040                1045                1050

Asn Cys Thr Asp Thr Thr Lys Phe Val Trp Ile Lys Asp Phe Asn
        1055                1060                1065

Ile Phe Gly Arg Glu Leu Asn Ala Thr Glu Val Ser Ser Leu Tyr
        1070                1075                1080

Trp Ile Gln Ser Ser Thr Asn Thr Leu Lys Asp Phe Trp Gly Asn
        1085                1090                1095

Pro Leu Arg Tyr Asp Thr Gln Tyr Tyr Leu Phe Asn Gln Gly Met
        1100                1105                1110

Gln Asn Ile Tyr Ile Lys Tyr Phe Ser Lys Ala Ser Met Gly Glu
        1115                1120                1125

Thr Ala Pro Arg Thr Asn Phe Asn Asn Ala Ala Ile Asn Tyr Gln
        1130                1135                1140

Asn Leu Tyr Leu Leu Arg Phe Ile Ile Lys Lys Ala Ser Asn Ser

```
            1145                1150                1155

Arg Asn  Ile Asn Asn Asp  Asn Ile Val Arg Glu  Gly Asp Tyr Ile
    1160                1165                1170

Tyr Leu  Asn Ile Asp Asn  Ile Ser Asp Glu Ser  Tyr Arg Val Tyr
    1175                1180                1185

Val Leu  Val Asn Ser Lys  Glu Ile Gln Thr Gln  Leu Phe Leu Ala
    1190                1195                1200

Pro Ile  Asn Asp Asp Pro  Thr Phe Tyr Asp Val  Leu Gln Ile Gly
    1205                1210                1215

Lys Lys  Tyr Tyr Glu Lys  Thr Thr Tyr Asn Cys  Gln Ile Leu Cys
    1220                1225                1230

Glu Lys  Asp Thr Lys Thr  Phe Gly Leu Phe Gly  Ile Gly Lys Phe
    1235                1240                1245

Val Lys  Asp Tyr Gly Tyr  Val Trp Asp Thr Tyr  Asp Asn Tyr Phe
    1250                1255                1260

Cys Ile  Ser Gln Trp Tyr  Leu Arg Arg Ile Ser  Glu Asn Ile Asn
    1265                1270                1275

Lys Leu  Arg Leu Gly Cys  Asn Trp Gln Phe Ile  Pro Val Asp Glu
    1280                1285                1290

Gly Trp  Thr Glu
    1295

<210> SEQ ID NO 8
<211> LENGTH: 1300
<212> TYPE: PRT
<213> ORGANISM: Artificial
<220> FEATURE:
<223> OTHER INFORMATION: Atoxic derivative of Clostridium botulinum
      serotype A neurotoxin

<400> SEQUENCE: 8

Met Pro Phe Val Asn  Lys Gln Phe Asn Tyr  Lys Asp Pro Val Asn Gly
1                 5                   10                  15

Val Asp Ile Ala Tyr  Ile Lys Ile Pro Asn  Ala Gly Gln Met Gln Pro
                 20                  25                  30

Val Lys Ala Phe Lys  Ile His Asn Lys Ile  Trp Val Ile Pro Glu Arg
             35                  40                  45

Asp Thr Phe Thr Asn  Pro Glu Glu Gly Asp  Leu Asn Pro Pro Pro Glu
         50                  55                  60

Ala Lys Gln Val Pro  Val Ser Tyr Tyr Asp  Ser Thr Tyr Leu Ser Thr
65                   70                  75                  80

Asp Asn Glu Lys Asp  Asn Tyr Leu Lys Gly  Val Thr Lys Leu Phe Glu
                 85                  90                  95

Arg Ile Tyr Ser Thr  Asp Leu Gly Arg Met  Leu Leu Thr Ser Ile Val
            100                 105                 110

Arg Gly Ile Pro Phe  Trp Gly Gly Ser Thr  Ile Asp Thr Glu Leu Lys
        115                 120                 125

Val Ile Asp Thr Asn  Cys Ile Asn Val Ile  Gln Pro Asp Gly Ser Tyr
    130                 135                 140

Arg Ser Glu Glu Leu  Asn Leu Val Ile Ile  Gly Pro Ser Ala Asp Ile
145                 150                 155                 160

Ile Gln Phe Glu Cys  Lys Ser Phe Gly His  Glu Val Leu Asn Leu Thr
                165                 170                 175

Arg Asn Gly Tyr Gly  Ser Thr Gln Tyr Ile  Arg Phe Ser Pro Asp Phe
            180                 185                 190
```

```
Thr Phe Gly Phe Glu Glu Ser Leu Glu Val Asp Thr Asn Pro Leu Leu
        195                 200                 205
Gly Ala Gly Lys Phe Ala Thr Asp Pro Ala Val Thr Leu Ala His Glu
210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
            260                 265                 270
Phe Ile Asp Ser Leu Gln Glu Asn Glu Phe Arg Leu Tyr Tyr Tyr Asn
        275                 280                 285
Lys Phe Lys Asp Ile Ala Ser Thr Leu Asn Lys Ala Lys Ser Ile Val
    290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Thr Thr Glu Asp
            340                 345                 350
Asn Phe Val Lys Phe Phe Lys Val Leu Asn Arg Lys Thr Tyr Leu Asn
        355                 360                 365
Phe Asp Lys Ala Val Phe Lys Ile Asn Ile Val Pro Lys Val Asn Tyr
    370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser His Thr Gln Ser Leu Asp Gln Gly Tyr Asn Asp
        435                 440                 445
Asp Asp Asp Lys Ala Leu Asn Asp Leu Cys Ile Lys Val Asn Asn Trp
    450                 455                 460
Asp Leu Phe Phe Ser Pro Ser Glu Asp Asn Phe Thr Asn Asp Leu Asn
465                 470                 475                 480
Lys Gly Glu Glu Ile Thr Ser Asp Thr Asn Ile Glu Ala Ala Glu Glu
                485                 490                 495
Asn Ile Ser Leu Asp Leu Ile Gln Gln Tyr Tyr Leu Thr Phe Asn Phe
            500                 505                 510
Asp Asn Glu Pro Glu Asn Ile Ser Ile Glu Asn Leu Ser Ser Asp Ile
        515                 520                 525
Ile Gly Gln Leu Glu Leu Met Pro Asn Ile Glu Arg Phe Pro Asn Gly
    530                 535                 540
Lys Lys Tyr Glu Leu Asp Lys Tyr Thr Met Phe His Tyr Leu Arg Ala
545                 550                 555                 560
Gln Glu Phe Glu His Gly Lys Ser Arg Ile Ala Leu Thr Asn Ser Val
                565                 570                 575
Asn Glu Ala Leu Leu Asn Pro Ser Arg Val Tyr Thr Phe Phe Ser Ser
            580                 585                 590
Asp Tyr Val Lys Lys Val Asn Lys Ala Thr Glu Ala Ala Met Phe Leu
        595                 600                 605
Gly Trp Val Glu Gln Leu Val Tyr Asp Phe Thr Asp Glu Thr Ser Glu
```

```
                610             615             620
Val Ser Thr Thr Asp Lys Ile Ala Asp Ile Thr Ile Ile Ile Pro Tyr
625             630             635             640

Ile Gly Pro Ala Leu Asn Ile Gly Asn Met Leu Tyr Lys Asp Asp Phe
                645             650             655

Val Gly Ala Leu Ile Phe Ser Gly Ala Val Ile Leu Leu Glu Phe Ile
                660             665             670

Pro Glu Ile Ala Ile Pro Val Leu Gly Thr Phe Ala Leu Val Ser Tyr
                675             680             685

Ile Ala Asn Lys Val Leu Thr Val Gln Thr Ile Asp Asn Ala Leu Ser
690             695             700

Lys Arg Asn Glu Lys Trp Asp Glu Val Tyr Lys Tyr Ile Val Thr Asn
705             710             715             720

Trp Leu Ala Lys Val Asn Thr Gln Ile Asp Leu Ile Arg Lys Lys Met
                725             730             735

Lys Glu Ala Leu Glu Asn Gln Ala Glu Ala Thr Lys Ala Ile Ile Asn
                740             745             750

Tyr Gln Tyr Asn Gln Tyr Thr Glu Glu Lys Asn Asn Ile Asn Phe
                755             760             765

Asn Ile Asp Asp Leu Ser Ser Lys Leu Asn Glu Ser Ile Asn Lys Ala
770             775             780

Met Ile Asn Ile Asn Lys Phe Leu Asn Gln Cys Ser Val Ser Tyr Leu
785             790             795             800

Met Asn Ser Met Ile Pro Tyr Gly Val Lys Arg Leu Glu Asp Phe Asp
                805             810             815

Ala Ser Leu Lys Asp Ala Leu Leu Lys Tyr Ile Tyr Asp Asn Arg Gly
                820             825             830

Thr Leu Ile Gly Gln Val Asp Arg Leu Lys Asp Lys Val Asn Asn Thr
                835             840             845

Leu Ser Thr Asp Ile Pro Phe Gln Leu Ser Lys Tyr Val Asp Asn Gln
                850             855             860

Arg Leu Leu Ser Thr Phe Thr Glu Tyr Ile Asn Asn Ile Ile Asn Thr
865             870             875             880

Ser Ile Leu Asn Leu Arg Tyr Glu Ser Asn His Leu Ile Asp Leu Ser
                885             890             895

Arg Tyr Ala Ser Lys Ile Asn Ile Gly Ser Lys Val Asn Phe Asp Pro
                900             905             910

Ile Asp Lys Asn Gln Ile Gln Leu Phe Asn Leu Glu Ser Ser Lys Ile
                915             920             925

Glu Val Ile Leu Lys Asn Ala Ile Val Tyr Asn Ser Met Tyr Glu Asn
930             935             940

Phe Ser Thr Ser Phe Trp Ile Arg Ile Pro Lys Tyr Phe Asn Ser Ile
945             950             955             960

Ser Leu Asn Asn Glu Tyr Thr Ile Ile Asn Cys Met Glu Asn Asn Ser
                965             970             975

Gly Trp Lys Val Ser Leu Asn Tyr Gly Glu Ile Ile Trp Thr Leu Gln
                980             985             990

Asp Thr Gln Glu Ile Lys Gln Arg Val Val Phe Lys Tyr Ser Gln Met
                995             1000            1005

Ile Asn Ile Ser Asp Tyr Ile Asn Arg Trp Ile Phe Val Thr Ile
    1010            1015            1020

Thr Asn Asn Arg Leu Asn Asn Ser Lys Ile Tyr Ile Asn Gly Arg
    1025            1030            1035
```

```
Leu Ile Asp Gln Lys Pro Ile Ser Asn Leu Gly Asn Ile His Ala
    1040                1045                1050

Ser Asn Asn Ile Met Phe Lys Leu Asp Gly Cys Arg Asp Thr His
    1055                1060                1065

Arg Tyr Ile Trp Ile Lys Tyr Phe Asn Leu Phe Asp Lys Glu Leu
    1070                1075                1080

Asn Glu Lys Glu Ile Lys Asp Leu Tyr Asp Asn Gln Ser Asn Ser
    1085                1090                1095

Gly Ile Leu Lys Asp Phe Trp Gly Asp Tyr Leu Gln Tyr Asp Lys
    1100                1105                1110

Pro Tyr Tyr Met Leu Asn Leu Tyr Asp Pro Asn Lys Tyr Val Asp
    1115                1120                1125

Val Asn Asn Val Gly Ile Arg Gly Tyr Met Tyr Leu Lys Gly Pro
    1130                1135                1140

Arg Gly Ser Val Met Thr Thr Asn Ile Tyr Leu Asn Ser Ser Leu
    1145                1150                1155

Tyr Arg Gly Thr Lys Phe Ile Ile Lys Lys Tyr Ala Ser Gly Asn
    1160                1165                1170

Lys Asp Asn Ile Val Arg Asn Asn Asp Arg Val Tyr Ile Asn Val
    1175                1180                1185

Val Val Lys Asn Lys Glu Tyr Arg Leu Ala Thr Asn Ala Ser Gln
    1190                1195                1200

Ala Gly Val Glu Lys Ile Leu Ser Ala Leu Glu Ile Pro Asp Val
    1205                1210                1215

Gly Asn Leu Ser Gln Val Val Val Met Lys Ser Lys Asn Asp Gln
    1220                1225                1230

Gly Ile Thr Asn Lys Cys Lys Met Asn Leu Gln Asp Asn Asn Gly
    1235                1240                1245

Asn Asp Ile Gly Phe Ile Gly Phe His Gln Phe Asn Asn Ile Ala
    1250                1255                1260

Lys Leu Val Ala Ser Asn Trp Tyr Asn Arg Gln Ile Glu Arg Ser
    1265                1270                1275

Ser Arg Thr Leu Gly Cys Ser Trp Glu Phe Ile Pro Val Asp Asp
    1280                1285                1290

Gly Trp Gly Glu Arg Pro Leu
    1295                1300

<210> SEQ ID NO 9
<211> LENGTH: 1295
<212> TYPE: PRT
<213> ORGANISM: Artificial
<220> FEATURE:
<223> OTHER INFORMATION: Atoxic derivative of Clostridium botulinum
      serotype B neurotoxin

<400> SEQUENCE: 9

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
```

-continued

```
                65                  70                  75                  80
        Thr Asn Asp Lys Lys Asn Ile Phe Leu Gln Thr Met Ile Lys Leu Phe
                            85                  90                  95
        Asn Arg Ile Lys Ser Lys Pro Leu Gly Glu Lys Leu Leu Glu Met Ile
                        100                 105                 110
        Ile Asn Gly Ile Pro Tyr Leu Gly Asp Arg Arg Val Pro Leu Glu Glu
                        115                 120                 125
        Phe Asn Thr Asn Ile Ala Ser Val Thr Val Asn Lys Leu Ile Ser Asn
                        130                 135                 140
        Pro Gly Glu Val Glu Arg Lys Lys Gly Ile Phe Ala Asn Leu Ile Ile
        145                 150                 155                 160
        Phe Gly Pro Gly Pro Val Leu Asn Glu Asn Glu Thr Ile Asp Ile Gly
                        165                 170                 175
        Ile Gln Asn His Phe Ala Ser Arg Glu Gly Phe Gly Ile Met Gln
                        180                 185                 190
        Met Lys Phe Cys Pro Glu Tyr Val Ser Val Phe Asn Asn Val Gln Glu
                        195                 200                 205
        Asn Lys Gly Ala Ser Ile Phe Asn Arg Arg Gly Tyr Phe Ser Asp Pro
                        210                 215                 220
        Ala Leu Ile Leu Met His Glu Leu Ile His Val Leu His Gly Leu Tyr
        225                 230                 235                 240
        Gly Ile Lys Val Asp Asp Leu Pro Ile Val Pro Asn Glu Lys Lys Phe
                        245                 250                 255
        Phe Met Gln Ser Thr Asp Ala Ile Gln Ala Glu Glu Leu Tyr Thr Phe
                        260                 265                 270
        Gly Gly Gln Asp Pro Ser Ile Ile Thr Pro Ser Thr Asp Lys Ser Ile
                        275                 280                 285
        Tyr Asp Lys Val Leu Gln Asn Phe Arg Gly Ile Val Asp Arg Leu Asn
                        290                 295                 300
        Lys Val Leu Val Cys Ile Ser Asp Pro Asn Ile Asn Ile Asn Ile Tyr
        305                 310                 315                 320
        Lys Asn Lys Phe Lys Asp Lys Tyr Lys Phe Val Glu Asp Ser Glu Gly
                        325                 330                 335
        Lys Tyr Ser Ile Asp Val Glu Ser Phe Asp Lys Leu Tyr Lys Ser Leu
                        340                 345                 350
        Met Phe Gly Phe Thr Glu Thr Asn Ile Ala Glu Asn Tyr Lys Ile Lys
                        355                 360                 365
        Thr Arg Ala Ser Tyr Phe Ser Asp Ser Leu Pro Pro Val Lys Ile Lys
                        370                 375                 380
        Asn Leu Leu Asp Asn Glu Ile Tyr Thr Ile Glu Glu Gly Phe Asn Ile
        385                 390                 395                 400
        Ser Asp Lys Asp Met Glu Lys Glu Tyr Arg Gly Gln Asn Lys Ala Ile
                        405                 410                 415
        Asn Lys Gln Ala Tyr Glu Glu Ile Ser Lys Glu His Leu Ala Val Tyr
                        420                 425                 430
        Lys Ile Gln Met Cys Lys Ser Val Asp Asp Asp Lys Ala Pro Gly
                        435                 440                 445
        Ile Cys Ile Asp Val Asp Asn Glu Asp Leu Phe Ile Ala Asp Lys
                        450                 455                 460
        Asn Ser Phe Ser Asp Asp Leu Ser Lys Asn Glu Arg Ile Glu Tyr Asn
        465                 470                 475                 480
        Thr Gln Ser Asn Tyr Ile Glu Asn Asp Phe Pro Ile Asn Glu Leu Ile
                        485                 490                 495
```

-continued

```
Leu Asp Thr Asp Leu Ile Ser Lys Ile Glu Leu Pro Ser Glu Asn Thr
            500                 505                 510

Glu Ser Leu Thr Asp Phe Asn Val Asp Val Pro Val Tyr Glu Lys Gln
            515                 520                 525

Pro Ala Ile Lys Lys Ile Phe Thr Asp Glu Asn Thr Ile Phe Gln Tyr
            530                 535                 540

Leu Tyr Ser Gln Thr Phe Pro Leu Asp Ile Arg Asp Ile Ser Leu Thr
545                 550                 555                 560

Ser Ser Phe Asp Asp Ala Leu Leu Phe Ser Asn Lys Val Tyr Ser Phe
            565                 570                 575

Phe Ser Met Asp Tyr Ile Lys Thr Ala Asn Lys Val Val Glu Ala Gly
            580                 585                 590

Leu Phe Ala Gly Trp Val Lys Gln Ile Val Asn Asp Phe Val Ile Glu
            595                 600                 605

Ala Asn Lys Ser Asn Thr Met Asp Lys Ile Ala Asp Ile Ser Leu Ile
            610                 615                 620

Val Pro Tyr Ile Gly Leu Ala Leu Asn Val Gly Asn Glu Thr Ala Lys
625                 630                 635                 640

Gly Asn Phe Glu Asn Ala Phe Glu Ile Ala Gly Ala Ser Ile Leu Leu
            645                 650                 655

Glu Phe Ile Pro Glu Leu Leu Ile Pro Val Val Gly Ala Phe Leu Leu
            660                 665                 670

Glu Ser Tyr Ile Asp Asn Lys Asn Lys Ile Ile Lys Thr Ile Asp Asn
            675                 680                 685

Ala Leu Thr Lys Arg Asn Glu Lys Trp Ser Asp Met Tyr Gly Leu Ile
            690                 695                 700

Val Ala Gln Trp Leu Ser Thr Val Asn Thr Gln Phe Tyr Thr Ile Lys
705                 710                 715                 720

Glu Gly Met Tyr Lys Ala Leu Asn Tyr Gln Ala Gln Ala Leu Lys Glu
            725                 730                 735

Ile Ile Lys Tyr Arg Tyr Asn Ile Tyr Ser Glu Lys Glu Lys Ser Asn
            740                 745                 750

Ile Asn Ile Asp Phe Asn Asp Ile Asn Ser Lys Leu Asn Glu Gly Ile
            755                 760                 765

Asn Gln Ala Ile Asp Asn Ile Asn Asn Phe Ile Asn Gly Cys Ser Val
            770                 775                 780

Ser Tyr Leu Met Lys Lys Met Ile Pro Leu Ala Val Glu Lys Leu Leu
785                 790                 795                 800

Asp Phe Asp Asn Thr Leu Lys Lys Asn Leu Leu Asn Tyr Ile Asp Glu
            805                 810                 815

Asn Lys Leu Tyr Leu Ile Gly Ser Ala Glu Tyr Glu Lys Ser Lys Val
            820                 825                 830

Asn Lys Tyr Leu Lys Thr Ile Met Pro Phe Asp Leu Ser Ile Tyr Thr
            835                 840                 845

Asn Asp Thr Ile Leu Ile Glu Met Phe Asn Lys Tyr Asn Ser Glu Ile
            850                 855                 860

Leu Asn Asn Ile Ile Leu Asn Leu Arg Tyr Lys Asp Asn Asn Leu Ile
865                 870                 875                 880

Asp Leu Ser Gly Tyr Gly Ala Lys Val Glu Val Tyr Asp Gly Val Glu
            885                 890                 895

Leu Asn Asp Lys Asn Gln Phe Lys Leu Thr Ser Ser Ala Asn Ser Lys
            900                 905                 910
```

```
Ile Arg Val Thr Gln Asn Gln Asn Ile Ile Phe Asn Ser Val Phe Leu
        915                 920                 925

Asp Phe Ser Val Ser Phe Trp Ile Arg Ile Pro Lys Tyr Lys Asn Asp
930                 935                 940

Gly Ile Gln Asn Tyr Ile His Asn Glu Tyr Thr Ile Ile Asn Cys Met
945                 950                 955                 960

Lys Asn Asn Ser Gly Trp Lys Ile Ser Ile Arg Gly Asn Arg Ile Ile
            965                 970                 975

Trp Thr Leu Ile Asp Ile Asn Gly Lys Thr Lys Ser Val Phe Phe Glu
            980                 985                 990

Tyr Asn Ile Arg Glu Asp Ile Ser Glu Tyr Ile Asn Arg Trp Phe Phe
        995                 1000                1005

Val Thr Ile Thr Asn Asn Leu Asn Asn Ala Lys Ile Tyr Ile Asn
    1010                1015                1020

Gly Lys Leu Glu Ser Asn Thr Asp Ile Lys Asp Ile Arg Glu Val
    1025                1030                1035

Ile Ala Asn Gly Glu Ile Ile Phe Lys Leu Asp Gly Asp Ile Asp
    1040                1045                1050

Arg Thr Gln Phe Ile Trp Met Lys Tyr Phe Ser Ile Phe Asn Thr
    1055                1060                1065

Glu Leu Ser Gln Ser Asn Ile Glu Glu Arg Tyr Lys Ile Gln Ser
    1070                1075                1080

Tyr Ser Glu Tyr Leu Lys Asp Phe Trp Gly Asn Pro Leu Met Tyr
    1085                1090                1095

Asn Lys Glu Tyr Tyr Met Phe Asn Ala Gly Asn Lys Asn Ser Tyr
    1100                1105                1110

Ile Lys Leu Lys Lys Asp Ser Pro Val Gly Glu Ile Leu Thr Arg
    1115                1120                1125

Ser Lys Tyr Asn Gln Asn Ser Lys Tyr Ile Asn Tyr Arg Asp Leu
    1130                1135                1140

Tyr Ile Gly Glu Lys Phe Ile Ile Arg Arg Lys Ser Asn Ser Gln
    1145                1150                1155

Ser Ile Asn Asp Asp Ile Val Arg Lys Glu Asp Tyr Ile Tyr Leu
    1160                1165                1170

Asp Phe Phe Asn Leu Asn Gln Glu Trp Arg Val Tyr Thr Tyr Lys
    1175                1180                1185

Tyr Phe Lys Lys Glu Glu Glu Lys Leu Phe Leu Ala Pro Ile Ser
    1190                1195                1200

Asp Ser Asp Glu Phe Tyr Asn Thr Ile Gln Ile Lys Glu Tyr Asp
    1205                1210                1215

Glu Gln Pro Thr Tyr Ser Cys Gln Leu Leu Phe Lys Lys Asp Glu
    1220                1225                1230

Glu Ser Thr Asp Glu Ile Gly Leu Ile Gly Ile His Arg Phe Tyr
    1235                1240                1245

Glu Ser Gly Ile Val Phe Glu Glu Tyr Lys Asp Tyr Phe Cys Ile
    1250                1255                1260

Ser Lys Trp Tyr Leu Lys Glu Val Lys Arg Lys Pro Tyr Asn Leu
    1265                1270                1275

Lys Leu Gly Cys Asn Trp Gln Phe Ile Pro Lys Asp Glu Gly Trp
    1280                1285                1290

Thr Glu
    1295
```

```
<210> SEQ ID NO 10
<211> LENGTH: 1295
<212> TYPE: PRT
<213> ORGANISM: Artificial
<220> FEATURE:
<223> OTHER INFORMATION: Atoxic derivative of Clostridium botulinum
      serotype C neurotoxin

<400> SEQUENCE: 10

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365
```

```
Val Gln Asn Arg Lys Ile Tyr Leu Ser Asn Val Tyr Thr Pro Val Thr
    370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
                405                 410                 415
Arg Asn Pro Ala Leu Arg Lys Val Asn Pro Glu Asn Met Leu Tyr Leu
                420                 425                 430
Phe Thr Lys Phe Cys His Lys Ala Ile Asp Gly Gln Ser Leu Tyr Asn
            435                 440                 445
Asp Asp Asp Lys Thr Leu Asp Cys Arg Glu Leu Leu Val Lys Asn
450                 455                 460
Thr Asp Leu Pro Phe Ile Gly Asp Ile Ser Asp Val Lys Thr Asp Ile
465                 470                 475                 480
Phe Leu Arg Lys Asp Ile Asn Glu Glu Thr Glu Val Ile Tyr Tyr Pro
                485                 490                 495
Asp Asn Val Ser Val Asp Gln Val Ile Leu Ser Lys Asn Thr Ser Glu
                500                 505                 510
His Gly Gln Leu Asp Leu Leu Tyr Pro Ser Ile Asp Ser Glu Ser Glu
            515                 520                 525
Ile Leu Pro Gly Glu Asn Gln Val Phe Tyr Asp Asn Arg Thr Gln Asn
530                 535                 540
Val Asp Tyr Leu Asn Ser Tyr Tyr Tyr Leu Glu Ser Gln Lys Leu Ser
545                 550                 555                 560
Asp Asn Val Glu Asp Phe Thr Phe Thr Arg Ser Ile Glu Glu Ala Leu
                565                 570                 575
Asp Asn Ser Ala Lys Val Tyr Thr Tyr Phe Pro Thr Leu Ala Asn Lys
                580                 585                 590
Val Asn Ala Gly Val Gln Gly Gly Leu Phe Leu Met Trp Ala Asn Asp
            595                 600                 605
Val Val Glu Asp Phe Thr Thr Asn Ile Leu Arg Lys Asp Thr Leu Asp
            610                 615                 620
Lys Ile Ser Asp Val Ser Ala Ile Ile Pro Tyr Ile Gly Pro Ala Leu
625                 630                 635                 640
Asn Ile Ser Asn Ser Val Arg Arg Gly Asn Phe Thr Glu Ala Phe Ala
                645                 650                 655
Val Thr Gly Val Thr Ile Leu Leu Glu Ala Phe Pro Glu Phe Thr Ile
            660                 665                 670
Pro Ala Leu Gly Ala Phe Val Ile Tyr Ser Lys Val Gln Glu Arg Asn
            675                 680                 685
Glu Ile Ile Lys Thr Ile Asp Asn Cys Leu Glu Gln Arg Ile Lys Arg
        690                 695                 700
Trp Lys Asp Ser Tyr Glu Trp Met Met Gly Thr Trp Leu Ser Arg Ile
705                 710                 715                 720
Ile Thr Gln Phe Asn Asn Ile Ser Tyr Gln Met Tyr Asp Ser Leu Asn
                725                 730                 735
Tyr Gln Ala Gly Ala Ile Lys Ala Lys Ile Asp Leu Glu Tyr Lys Lys
                740                 745                 750
Tyr Ser Gly Ser Asp Lys Glu Asn Ile Lys Ser Gln Val Glu Asn Leu
            755                 760                 765
Lys Asn Ser Leu Asp Val Lys Ile Ser Glu Ala Met Asn Asn Ile Asn
770                 775                 780
Lys Phe Ile Arg Glu Cys Ser Val Thr Tyr Leu Phe Lys Asn Met Leu
```

-continued

```
            785                 790                 795                 800
Pro Lys Val Ile Asp Glu Leu Asn Glu Phe Asp Arg Asn Thr Lys Ala
                805                 810                 815
Lys Leu Ile Asn Leu Ile Asp Ser His Asn Ile Ile Leu Val Gly Glu
                820                 825                 830
Val Asp Lys Leu Lys Ala Lys Val Asn Asn Ser Phe Gln Asn Thr Ile
                835                 840                 845
Pro Phe Asn Ile Phe Ser Tyr Thr Asn Asn Ser Leu Leu Lys Asp Ile
        850                 855                 860
Ile Asn Glu Tyr Phe Asn Asn Ile Asn Asp Ser Lys Ile Leu Ser Leu
865                 870                 875                 880
Gln Asn Arg Lys Asn Thr Leu Val Asp Thr Ser Gly Tyr Asn Ala Glu
                885                 890                 895
Val Ser Glu Glu Gly Asp Val Gln Leu Asn Pro Ile Phe Pro Phe Asp
            900                 905                 910
Phe Lys Leu Gly Ser Ser Gly Glu Asp Arg Gly Lys Val Ile Val Thr
            915                 920                 925
Gln Asn Glu Asn Ile Val Tyr Asn Ser Met Tyr Glu Ser Phe Ser Ile
        930                 935                 940
Ser Phe Trp Ile Arg Ile Asn Lys Trp Val Ser Asn Leu Pro Gly Tyr
945                 950                 955                 960
Thr Ile Ile Asp Ser Val Lys Asn Asn Ser Gly Trp Ser Ile Gly Ile
                965                 970                 975
Ile Ser Asn Phe Leu Val Phe Thr Leu Lys Gln Asn Glu Asp Ser Glu
            980                 985                 990
Gln Ser Ile Asn Phe Ser Tyr Asp Ile Ser Asn Asn Ala Pro Gly Tyr
        995                 1000                1005
Asn Lys Trp Phe Phe Val Thr Val Thr Asn Asn Met Met Gly Asn
        1010                1015                1020
Met Lys Ile Tyr Ile Asn Gly Lys Leu Ile Asp Thr Ile Lys Val
        1025                1030                1035
Lys Glu Leu Thr Gly Ile Asn Phe Ser Lys Thr Ile Thr Phe Glu
        1040                1045                1050
Ile Asn Lys Ile Pro Asp Thr Gly Leu Ile Thr Ser Asp Ser Asp
        1055                1060                1065
Asn Ile Asn Met Trp Ile Arg Asp Phe Tyr Ile Phe Ala Lys Glu
        1070                1075                1080
Leu Asp Gly Lys Asp Ile Asn Ile Leu Phe Asn Ser Leu Gln Tyr
        1085                1090                1095
Thr Asn Val Val Lys Asp Tyr Trp Gly Asn Asp Leu Arg Tyr Asn
        1100                1105                1110
Lys Glu Tyr Tyr Met Val Asn Ile Asp Tyr Leu Asn Arg Tyr Met
        1115                1120                1125
Tyr Ala Asn Ser Arg Gln Ile Val Phe Asn Thr Arg Arg Asn Asn
        1130                1135                1140
Asn Asp Phe Asn Glu Gly Tyr Lys Ile Ile Ile Lys Arg Ile Arg
        1145                1150                1155
Gly Asn Thr Asn Asp Thr Arg Val Arg Gly Gly Asp Ile Leu Tyr
        1160                1165                1170
Phe Asp Met Thr Ile Asn Asn Lys Ala Tyr Asn Leu Phe Met Lys
        1175                1180                1185
Asn Glu Thr Met Tyr Ala Asp Asn His Ser Thr Glu Asp Ile Tyr
        1190                1195                1200
```

```
Ala Ile Gly Leu Arg Glu Gln Thr Lys Asp Ile Asn Asp Asn Ile
    1205                1210                1215

Ile Phe Gln Ile Gln Pro Met Asn Asn Thr Tyr Tyr Tyr Ala Ser
    1220                1225                1230

Gln Ile Phe Lys Ser Asn Phe Asn Gly Glu Asn Ile Ser Gly Ile
    1235                1240                1245

Cys Ser Ile Gly Thr Tyr Arg Phe Arg Leu Gly Gly Asp Trp Tyr
    1250                1255                1260

Arg His Asn Tyr Leu Val Pro Thr Val Lys Gln Gly Asn Tyr Ala
    1265                1270                1275

Ser Leu Leu Glu Ser Thr Ser Thr His Trp Gly Phe Val Pro Val
    1280                1285                1290

Ser Glu
    1295

<210> SEQ ID NO 11
<211> LENGTH: 1280
<212> TYPE: PRT
<213> ORGANISM: Artificial
<220> FEATURE:
<223> OTHER INFORMATION: Atoxic derivative of Clostridium botulinum
      serotype D neurotoxin

<400> SEQUENCE: 11

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
                20                  25                  30

Pro Val Lys Ala Phe Met Ile Thr Gln Asn Ile Trp Val Ile Pro Glu
            35                  40                  45

Arg Phe Ser Ser Asp Thr Asn Pro Ser Leu Ser Lys Pro Pro Arg Pro
        50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
```

```
                    245                 250                 255
Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
            275                 280                 285

Leu Arg Glu Lys Ala Leu Gly His Tyr Lys Asp Ile Ala Lys Arg Leu
290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
            355                 360                 365

Val Lys Asn Arg Thr His Tyr Phe Ser Arg His Tyr Leu Pro Val Phe
370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Asp Asp Asp Asp
            435                 440                 445

Lys Asp Asp Ser Thr Cys Ile Lys Val Lys Asn Asn Arg Leu Pro Tyr
450                 455                 460

Val Ala Asp Lys Asp Ser Ile Ser Gln Glu Ile Phe Glu Asn Lys Ile
465                 470                 475                 480

Ile Thr Asp Glu Thr Asn Val Gln Asn Tyr Ser Asp Asn Phe Ser Leu
                485                 490                 495

Asp Glu Ser Ile Leu Asp Gly Gln Val Pro Ile Asn Pro Glu Ile Val
            500                 505                 510

Asp Pro Leu Leu Pro Asn Val Asn Met Glu Pro Leu Asn Leu Pro Gly
            515                 520                 525

Glu Glu Ile Val Phe Tyr Asp Asp Ile Thr Lys Tyr Val Asp Tyr Leu
            530                 535                 540

Asn Ser Tyr Tyr Tyr Leu Glu Ser Gln Lys Leu Ser Asn Asn Val Glu
545                 550                 555                 560

Asn Ile Thr Leu Thr Thr Ser Val Glu Glu Ala Leu Gly Tyr Ser Asn
                565                 570                 575

Lys Ile Tyr Thr Phe Leu Pro Ser Leu Ala Glu Lys Val Asn Lys Gly
            580                 585                 590

Val Gln Ala Gly Leu Phe Leu Asn Trp Ala Asn Glu Val Val Glu Asp
            595                 600                 605

Phe Thr Thr Asn Ile Met Lys Lys Asp Thr Leu Asp Lys Ile Ser Asp
610                 615                 620

Val Ser Val Ile Ile Pro Tyr Ile Gly Pro Ala Leu Asn Ile Gly Asn
625                 630                 635                 640

Ser Ala Leu Arg Gly Asn Phe Lys Gln Ala Phe Ala Thr Ala Gly Val
                645                 650                 655

Ala Phe Leu Leu Glu Gly Phe Pro Glu Phe Thr Ile Pro Ala Leu Gly
            660                 665                 670
```

```
Val Phe Thr Phe Tyr Ser Ser Ile Gln Glu Arg Glu Lys Ile Ile Lys
            675                 680                 685

Thr Ile Glu Asn Cys Leu Glu Gln Arg Val Lys Arg Trp Lys Asp Ser
690                 695                 700

Tyr Gln Trp Met Val Ser Asn Trp Leu Ser Arg Ile Thr Thr Gln Phe
705                 710                 715                 720

Asn His Ile Asn Tyr Gln Met Tyr Asp Ser Leu Ser Tyr Gln Ala Asp
                725                 730                 735

Ala Ile Lys Ala Lys Ile Asp Leu Glu Tyr Lys Lys Tyr Ser Gly Ser
                740                 745                 750

Asp Lys Glu Asn Ile Lys Ser Gln Val Glu Asn Leu Lys Asn Ser Leu
                755                 760                 765

Asp Val Lys Ile Ser Glu Ala Met Asn Asn Ile Asn Lys Phe Ile Arg
770                 775                 780

Glu Cys Ser Val Thr Tyr Leu Phe Lys Asn Met Leu Pro Lys Val Ile
785                 790                 795                 800

Asp Glu Leu Asn Lys Phe Asp Leu Arg Thr Lys Thr Glu Leu Ile Asn
                805                 810                 815

Leu Ile Asp Ser His Asn Ile Ile Leu Val Gly Glu Val Asp Arg Leu
                820                 825                 830

Lys Ala Lys Val Asn Glu Ser Phe Glu Asn Thr Met Pro Phe Asn Ile
                835                 840                 845

Phe Ser Tyr Thr Asn Asn Ser Leu Leu Lys Asp Ile Ile Asn Glu Tyr
                850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Val Gly
                885                 890                 895

Asp Asn Val Gln Leu Asn Thr Ile Tyr Thr Asn Asp Phe Lys Leu Ser
                900                 905                 910

Ser Ser Gly Asp Lys Ile Ile Val Asn Leu Asn Asn Asn Ile Leu Tyr
                915                 920                 925

Ser Ala Ile Tyr Glu Asn Ser Ser Val Ser Phe Trp Ile Lys Ile Ser
                930                 935                 940

Lys Asp Leu Thr Asn Ser His Asn Glu Tyr Thr Ile Ile Asn Ser Ile
945                 950                 955                 960

Glu Gln Asn Ser Gly Trp Lys Leu Cys Ile Arg Asn Gly Asn Ile Glu
                965                 970                 975

Trp Ile Leu Gln Asp Val Asn Arg Lys Tyr Lys Ser Leu Ile Phe Asp
                980                 985                 990

Tyr Ser Glu Ser Leu Ser His Thr Gly Tyr Thr Asn Lys Trp Phe Phe
                995                 1000                1005

Val Thr Ile Thr Asn Asn Ile Met Gly Tyr Met Lys Leu Tyr Ile
            1010                1015                1020

Asn Gly Glu Leu Lys Gln Ser Gln Lys Ile Glu Asp Leu Asp Glu
            1025                1030                1035

Val Lys Leu Asp Lys Thr Ile Val Phe Gly Ile Asp Glu Asn Ile
            1040                1045                1050

Asp Glu Asn Gln Met Leu Trp Ile Arg Asp Phe Asn Ile Phe Ser
            1055                1060                1065

Lys Glu Leu Ser Asn Glu Asp Ile Asn Ile Val Tyr Glu Gly Gln
            1070                1075                1080
```

```
Ile Leu Arg Asn Val Ile Lys Asp Tyr Trp Gly Asn Pro Leu Lys
    1085                1090                1095

Phe Asp Thr Glu Tyr Tyr Ile Ile Asn Asp Asn Tyr Ile Asp Arg
1100                1105                1110

Tyr Ile Ala Pro Glu Ser Asn Val Leu Val Leu Val Arg Tyr Pro
    1115                1120                1125

Asp Arg Ser Lys Leu Tyr Thr Gly Asn Pro Ile Thr Ile Lys Ser
    1130                1135                1140

Val Ser Asp Lys Asn Pro Tyr Ser Arg Ile Leu Asn Gly Asp Asn
    1145                1150                1155

Ile Ile Leu His Met Leu Tyr Asn Ser Arg Lys Tyr Met Ile Ile
    1160                1165                1170

Arg Asp Thr Asp Thr Ile Tyr Ala Thr Gln Gly Gly Glu Cys Ser
    1175                1180                1185

Gln Asn Cys Val Tyr Ala Leu Lys Leu Gln Ser Asn Leu Gly Asn
    1190                1195                1200

Tyr Gly Ile Gly Ile Phe Ser Ile Lys Asn Ile Val Ser Lys Asn
    1205                1210                1215

Lys Tyr Cys Ser Gln Ile Phe Ser Ser Phe Arg Glu Asn Thr Met
    1220                1225                1230

Leu Leu Ala Asp Ile Tyr Lys Pro Trp Arg Phe Ser Phe Lys Asn
    1235                1240                1245

Ala Tyr Thr Pro Val Ala Val Thr Asn Tyr Glu Thr Lys Leu Leu
    1250                1255                1260

Ser Thr Ser Ser Phe Trp Lys Phe Ile Ser Arg Asp Pro Gly Trp
    1265                1270                1275

Val Glu
    1280

<210> SEQ ID NO 12
<211> LENGTH: 1255
<212> TYPE: PRT
<213> ORGANISM: Artificial
<220> FEATURE:
<223> OTHER INFORMATION: Atoxic derivative of Clostridium botulinum
      serotype E neurotoxin

<400> SEQUENCE: 12

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140
```

```
Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
            165                 170                 175

Gly Phe Gly Ser Ile Ala Ile Val Thr Phe Ser Pro Glu Tyr Ser Phe
        180                 185                 190

Arg Phe Asn Asp Asn Ser Met Asn Glu Phe Ile Gln Asp Pro Ala Leu
    195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Asp Asp Asp Lys Lys Ser Ile Cys Ile Glu
            420                 425                 430

Ile Asn Asn Gly Glu Leu Phe Phe Val Ala Ser Glu Asn Ser Tyr Asn
435                 440                 445

Asp Asp Asn Ile Asn Thr Pro Lys Glu Ile Asp Asp Thr Val Thr Ser
450                 455                 460

Asn Asn Asn Tyr Glu Asn Asp Leu Asp Gln Val Ile Leu Asn Phe Asn
465                 470                 475                 480

Ser Glu Ser Ala Pro Gly Leu Ser Asp Glu Lys Leu Asn Leu Thr Ile
            485                 490                 495

Gln Asn Asp Ala Tyr Ile Pro Lys Tyr Asp Ser Asn Gly Thr Ser Asp
        500                 505                 510

Ile Glu Gln His Asp Val Asn Glu Leu Asn Val Phe Phe Tyr Leu Asp
    515                 520                 525

Ala Gln Lys Val Pro Glu Gly Glu Asn Asn Val Asn Leu Thr Ser Ser
    530                 535                 540

Ile Asp Thr Ala Leu Leu Glu Gln Pro Lys Ile Tyr Thr Phe Phe Ser
545                 550                 555                 560
```

```
Ser Glu Phe Ile Asn Asn Val Asn Lys Pro Val Gln Ala Ala Leu Phe
                565                 570                 575

Val Ser Trp Ile Gln Gln Val Leu Val Asp Phe Thr Thr Glu Ala Asn
            580                 585                 590

Gln Lys Ser Thr Val Asp Lys Ile Ala Asp Ile Ser Ile Val Val Pro
        595                 600                 605

Tyr Ile Gly Leu Ala Leu Asn Ile Gly Asn Glu Ala Gln Lys Gly Asn
    610                 615                 620

Phe Lys Asp Ala Leu Glu Leu Leu Gly Ala Gly Ile Leu Leu Glu Phe
625                 630                 635                 640

Glu Pro Glu Leu Leu Ile Pro Thr Ile Leu Val Phe Thr Ile Lys Ser
                645                 650                 655

Phe Leu Gly Ser Ser Asp Asn Lys Asn Lys Val Ile Lys Ala Ile Asn
            660                 665                 670

Asn Ala Leu Lys Glu Arg Asp Glu Lys Trp Lys Glu Val Tyr Ser Phe
        675                 680                 685

Ile Val Ser Asn Trp Met Thr Lys Ile Asn Thr Gln Phe Asn Lys Arg
    690                 695                 700

Lys Glu Gln Met Tyr Gln Ala Leu Gln Asn Gln Val Asn Ala Ile Lys
705                 710                 715                 720

Thr Ile Ile Glu Ser Lys Tyr Asn Ser Tyr Thr Leu Glu Glu Lys Asn
                725                 730                 735

Glu Leu Thr Asn Lys Tyr Asp Ile Lys Gln Ile Glu Asn Glu Leu Asn
            740                 745                 750

Gln Lys Val Ser Ile Ala Met Asn Asn Ile Asp Arg Phe Leu Thr Glu
        755                 760                 765

Ser Ser Ile Ser Tyr Leu Met Lys Leu Ile Asn Glu Val Lys Ile Asn
    770                 775                 780

Lys Leu Arg Glu Tyr Asp Glu Asn Val Lys Thr Tyr Leu Leu Asn Tyr
785                 790                 795                 800

Ile Ile Gln His Gly Ser Ile Leu Gly Glu Ser Gln Gln Glu Leu Asn
                805                 810                 815

Ser Met Val Thr Asp Thr Leu Asn Asn Ser Ile Pro Phe Lys Leu Ser
            820                 825                 830

Ser Tyr Thr Asp Asp Lys Ile Leu Ile Ser Tyr Phe Asn Lys Phe Phe
        835                 840                 845

Asn Asn Ile Lys Ser Ser Ser Val Leu Asn Met Arg Tyr Lys Asn Asp
    850                 855                 860

Lys Tyr Val Asp Thr Ser Gly Tyr Asp Ser Asn Ile Asn Ile Asn Gly
865                 870                 875                 880

Asp Val Tyr Lys Tyr Pro Thr Asn Lys Asn Gln Phe Gly Ile Tyr Asn
                885                 890                 895

Asp Lys Leu Ser Glu Val Asn Ile Ser Gln Asn Asp Tyr Ile Ile Tyr
            900                 905                 910

Asp Asn Lys Tyr Lys Asn Phe Ser Ile Ser Phe Trp Val Arg Ile Pro
        915                 920                 925

Asn Tyr Asp Asn Lys Ile Val Asn Val Asn Asn Glu Tyr Thr Ile Ile
    930                 935                 940

Asn Cys Met Arg Asp Asn Asn Ser Gly Trp Lys Val Ser Leu Asn His
945                 950                 955                 960

Asn Glu Ile Ile Trp Thr Leu Gln Asp Asn Ala Gly Ile Asn Gln Lys
                965                 970                 975

Leu Ala Phe Asn Tyr Gly Asn Ala Asn Gly Ile Ser Asp Tyr Ile Asn
```

```
                    980             985              990
Lys Trp Ile Phe Val Thr Ile Thr  Asn Asp Arg Leu Gly  Asp Ser Lys
        995              1000             1005

Leu Tyr Ile Asn Gly Asn Leu  Ile Asp Gln Lys Ser  Ile Leu Asn
        1010             1015             1020

Leu Gly Asn Ile His Val Ser  Asp Asn Ile Leu Phe  Lys Ile Val
        1025             1030             1035

Asn Cys Ser Tyr Thr Arg Tyr  Ile Gly Ile Arg Tyr  Phe Asn Ile
        1040             1045             1050

Phe Asp Lys Glu Leu Asp Glu  Thr Glu Ile Gln Thr  Leu Tyr Ser
        1055             1060             1065

Asn Glu Pro Asn Thr Asn Ile  Leu Lys Asp Phe Trp  Gly Asn Tyr
        1070             1075             1080

Leu Leu Tyr Asp Lys Glu Tyr  Tyr Leu Leu Asn Val  Leu Lys Pro
        1085             1090             1095

Asn Asn Phe Ile Asp Arg Arg  Lys Asp Ser Thr Leu  Ser Ile Asn
        1100             1105             1110

Asn Ile Arg Ser Thr Ile Leu  Leu Ala Asn Arg Leu  Tyr Ser Gly
        1115             1120             1125

Ile Lys Val Lys Ile Gln Arg  Val Asn Asn Ser Ser  Thr Asn Asp
        1130             1135             1140

Asn Leu Val Arg Lys Asn Asp  Gln Val Tyr Ile Asn  Phe Val Ala
        1145             1150             1155

Ser Lys Thr His Leu Phe Pro  Leu Tyr Ala Asp Thr  Ala Thr Thr
        1160             1165             1170

Asn Lys Glu Lys Thr Ile Lys  Ile Ser Ser Ser Gly  Asn Arg Phe
        1175             1180             1185

Asn Gln Val Val Val Met Asn  Ser Val Gly Asn Asn  Thr Met Asn
        1190             1195             1200

Phe Lys Asn Asn Asn Gly Asn  Asn Ile Gly Leu Leu  Gly Phe Lys
        1205             1210             1215

Ala Asp Thr Val Val Ala Ser  Thr Trp Tyr Tyr Thr  His Met Arg
        1220             1225             1230

Asp His Thr Asn Ser Asn Gly  Cys Phe Trp Asn Phe  Ile Ser Glu
        1235             1240             1245

Glu His Gly Trp Gln Glu Lys
        1250             1255

<210> SEQ ID NO 13
<211> LENGTH: 1281
<212> TYPE: PRT
<213> ORGANISM: Artificial
<220> FEATURE:
<223> OTHER INFORMATION: Atoxic derivative of Clostridium botulinum
      serotype F neurotoxin

<400> SEQUENCE: 13

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60
```

-continued

```
Leu Glu Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Thr Ile Lys Leu Phe Lys
                 85                  90                  95

Arg Ile Asn Ser Asn Pro Ala Gly Glu Val Leu Leu Gln Glu Ile Ser
                100                 105                 110

Tyr Ala Lys Pro Tyr Leu Gly Asn Glu His Thr Pro Ile Asn Glu Phe
                115                 120                 125

His Pro Val Thr Arg Thr Ser Val Asn Ile Lys Ser Ser Thr Asn
            130                 135                 140

Val Lys Ser Ser Ile Ile Leu Asn Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
                180                 185                 190

Val Thr Phe Ser Pro Glu Tyr Glu Tyr Thr Phe Asn Asp Ile Ser Gly
                195                 200                 205

Gly Tyr Asn Ser Ser Thr Glu Ser Phe Ile Ala Asp Pro Ala Ile Ser
                210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Ile Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
                275                 280                 285

Asn Leu Leu Ala Asn Tyr Glu Lys Ile Ala Thr Arg Leu Ser Arg Val
                290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
                340                 345                 350

Glu Ile Asp Leu Ala Asn Lys Phe Lys Val Lys Cys Arg Asn Thr Tyr
                355                 360                 365

Phe Ile Lys Tyr Gly Phe Leu Lys Val Pro Asn Leu Leu Asp Asp Asp
                370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Val
                420                 425                 430

Ile Pro Arg Lys Gly Thr Asp Asp Asp Lys Ala Pro Pro Arg Leu
                435                 440                 445

Cys Ile Arg Val Asn Asn Arg Glu Leu Phe Phe Val Ala Ser Glu Ser
450                 455                 460

Ser Tyr Asn Glu Asn Asp Ile Asn Thr Pro Lys Glu Ile Asp Asp Thr
465                 470                 475                 480

Thr Asn Leu Asn Asn Asn Tyr Arg Asn Asn Leu Asp Glu Val Ile Leu
```

-continued

```
                485                 490                 495

Asp Tyr Asn Ser Glu Thr Ile Pro Gln Ile Ser Asn Gln Thr Leu Asn
            500                 505                 510

Thr Leu Val Gln Asp Asp Ser Tyr Val Pro Arg Tyr Asp Ser Asn Gly
            515                 520                 525

Thr Ser Glu Ile Glu Glu His Asn Val Val Asp Leu Asn Val Phe Phe
            530                 535                 540

Tyr Leu His Ala Gln Lys Val Pro Glu Gly Glu Thr Asn Ile Ser Leu
545                 550                 555                 560

Thr Ser Ser Ile Asp Thr Ala Leu Ser Glu Glu Ser Gln Val Tyr Thr
            565                 570                 575

Phe Phe Ser Ser Glu Phe Ile Asn Thr Ile Asn Lys Pro Val His Ala
            580                 585                 590

Ala Leu Phe Ile Ser Trp Ile Asn Gln Val Ile Arg Asp Phe Thr Thr
            595                 600                 605

Glu Ala Thr Gln Lys Ser Thr Phe Asp Lys Ile Ala Asp Ile Ser Leu
            610                 615                 620

Val Val Pro Tyr Val Gly Leu Ala Leu Asn Ile Gly Asn Glu Val Gln
625                 630                 635                 640

Lys Glu Asn Phe Lys Glu Ala Phe Glu Leu Leu Gly Ala Gly Ile Leu
            645                 650                 655

Leu Glu Phe Val Pro Glu Leu Leu Ile Pro Thr Ile Leu Val Phe Thr
            660                 665                 670

Ile Lys Ser Phe Ile Gly Ser Ser Glu Asn Lys Asn Lys Ile Ile Lys
            675                 680                 685

Ala Ile Asn Asn Ser Leu Met Glu Arg Glu Thr Lys Trp Lys Glu Ile
            690                 695                 700

Tyr Ser Trp Ile Val Ser Asn Trp Leu Thr Arg Ile Asn Thr Gln Phe
705                 710                 715                 720

Asn Lys Arg Lys Glu Gln Met Tyr Gln Ala Leu Gln Asn Gln Val Asp
            725                 730                 735

Ala Ile Lys Thr Val Ile Glu Tyr Lys Tyr Asn Asn Tyr Thr Ser Asp
            740                 745                 750

Glu Arg Asn Arg Leu Glu Ser Glu Tyr Asn Ile Asn Asn Ile Arg Glu
            755                 760                 765

Glu Leu Asn Lys Lys Val Ser Leu Ala Met Glu Asn Ile Glu Arg Phe
            770                 775                 780

Ile Thr Glu Ser Ser Ile Phe Tyr Leu Met Lys Leu Ile Asn Glu Ala
785                 790                 795                 800

Lys Val Ser Lys Leu Arg Glu Tyr Asp Glu Gly Val Lys Glu Tyr Leu
            805                 810                 815

Leu Asp Tyr Ile Ser Glu His Arg Ser Ile Leu Gly Asn Ser Val Gln
            820                 825                 830

Glu Leu Asn Asp Leu Val Thr Ser Thr Leu Asn Asn Ser Ile Pro Phe
            835                 840                 845

Glu Leu Ser Ser Tyr Thr Asn Asp Lys Ile Leu Ile Leu Tyr Phe Asn
            850                 855                 860

Lys Leu Tyr Asn Asn Ile Lys Asp Asn Ser Ile Leu Asp Met Arg Tyr
865                 870                 875                 880

Glu Asn Asn Lys Phe Ile Asp Ile Ser Gly Tyr Gly Ser Asn Ile Ser
            885                 890                 895

Ile Asn Gly Asp Val Tyr Ile Tyr Ser Thr Asn Arg Asn Gln Phe Gly
            900                 905                 910
```

Ile Tyr Ser Ser Lys Pro Ser Glu Val Asn Ile Ala Gln Asn Asn Asp
            915                 920                 925

Ile Ile Tyr Asn Gly Arg Tyr Gln Asn Phe Ser Ile Ser Phe Trp Val
930                 935                 940

Arg Ile Pro Lys Tyr Phe Asn Lys Val Asn Leu Asn Asn Glu Tyr Thr
945                 950                 955                 960

Ile Ile Asp Cys Ile Arg Asn Asn Ser Gly Trp Lys Ile Ser Leu
            965                 970                 975

Asn Tyr Asn Lys Ile Ile Trp Thr Leu Gln Asp Thr Ala Gly Asn Asn
            980                 985                 990

Gln Lys Leu Val Phe Asn Tyr Thr Gln Met Ile Ser Ile Ser Asp Tyr
            995                 1000                1005

Ile Asn Lys Trp Ile Phe Val Thr Ile Thr Asn Asn Arg Leu Gly
    1010                1015                1020

Asn Ser Arg Ile Tyr Ile Asn Gly Asn Leu Ile Asp Glu Lys Ser
    1025                1030                1035

Ile Ser Asn Leu Gly Asp Ile His Val Ser Asp Asn Ile Leu Phe
    1040                1045                1050

Lys Ile Val Gly Cys Asn Asp Thr Arg Tyr Val Gly Ile Arg Tyr
    1055                1060                1065

Phe Lys Val Phe Asp Thr Glu Leu Gly Lys Thr Glu Ile Glu Thr
    1070                1075                1080

Leu Tyr Ser Asp Glu Pro Asp Pro Ser Ile Leu Lys Asp Phe Trp
    1085                1090                1095

Gly Asn Tyr Leu Leu Tyr Asn Lys Arg Tyr Tyr Leu Leu Asn Leu
    1100                1105                1110

Leu Arg Thr Asp Lys Ser Ile Thr Gln Asn Ser Asn Phe Leu Asn
    1115                1120                1125

Ile Asn Gln Gln Arg Gly Val Tyr Gln Lys Pro Asn Ile Phe Ser
    1130                1135                1140

Asn Thr Arg Leu Tyr Thr Gly Val Glu Val Ile Ile Arg Lys Asn
    1145                1150                1155

Gly Ser Thr Asp Ile Ser Asn Thr Asp Asn Phe Val Arg Lys Asn
    1160                1165                1170

Asp Leu Ala Tyr Ile Asn Val Val Asp Arg Asp Val Glu Tyr Arg
    1175                1180                1185

Leu Tyr Ala Asp Ile Ser Ala Lys Pro Glu Lys Ile Ile Lys
    1190                1195                1200

Leu Ile Arg Thr Ser Asn Ser Asn Asn Ser Leu Gly Gln Ile Ile
    1205                1210                1215

Val Met Asp Ser Ile Gly Asn Asn Thr Met Asn Phe Gln Asn Asn
    1220                1225                1230

Asn Gly Gly Asn Ile Gly Leu Leu Gly Phe His Ser Asn Asn Leu
    1235                1240                1245

Val Ala Ser Ser Trp Tyr Tyr Asn Asn Ile Arg Lys Asn Thr Ser
    1250                1255                1260

Ser Asn Gly Cys Phe Trp Ser Phe Ile Ser Lys Glu His Gly Trp
    1265                1270                1275

Gln Glu Asn
    1280

<210> SEQ ID NO 14
<211> LENGTH: 1301

```
<212> TYPE: PRT
<213> ORGANISM: Artificial
<220> FEATURE:
<223> OTHER INFORMATION: Atoxic derivative of Clostridium botulinum
      serotype G neurotoxin

<400> SEQUENCE: 14
```

| | | | | | | | | | | | | | | | |
|---|---|---|---|---|---|---|---|---|---|---|---|---|---|---|---|
| Met | Pro | Val | Asn | Ile | Lys | Asn | Phe | Asn | Tyr | Asn | Asp | Pro | Ile | Asn | Asn |
| 1 | | | | 5 | | | | | 10 | | | | | 15 | |
| Asp | Asp | Ile | Ile | Met | Met | Glu | Pro | Phe | Asn | Asp | Pro | Gly | Pro | Gly | Thr |
| | | | 20 | | | | | 25 | | | | | 30 | | |
| Tyr | Tyr | Lys | Ala | Phe | Arg | Ile | Ile | Asp | Arg | Ile | Trp | Ile | Val | Pro | Glu |
| | | | 35 | | | | | 40 | | | | | 45 | | |
| Arg | Phe | Thr | Tyr | Gly | Phe | Gln | Pro | Asp | Gln | Phe | Asn | Ala | Ser | Thr | Gly |
| | | 50 | | | | | 55 | | | | | 60 | | | |
| Val | Phe | Ser | Lys | Asp | Val | Tyr | Glu | Tyr | Tyr | Asp | Pro | Thr | Tyr | Leu | Lys |
| 65 | | | | | 70 | | | | | 75 | | | | | 80 |
| Thr | Asp | Ala | Glu | Lys | Asp | Lys | Phe | Leu | Lys | Thr | Met | Ile | Lys | Leu | Phe |
| | | | | 85 | | | | | 90 | | | | | 95 | |
| Asn | Arg | Ile | Asn | Ser | Lys | Pro | Ser | Gly | Gln | Arg | Leu | Leu | Asp | Met | Ile |
| | | | 100 | | | | | 105 | | | | | 110 | | |
| Val | Asp | Ala | Ile | Pro | Tyr | Leu | Gly | Asn | Ala | Ser | Thr | Pro | Pro | Asp | Lys |
| | | | 115 | | | | | 120 | | | | | 125 | | |
| Phe | Ala | Ala | Asn | Val | Ala | Asn | Val | Ser | Ile | Asn | Lys | Lys | Ile | Ile | Gln |
| | | 130 | | | | | 135 | | | | | 140 | | | |
| Pro | Gly | Ala | Glu | Asp | Gln | Ile | Lys | Gly | Leu | Met | Thr | Asn | Leu | Ile | Ile |
| 145 | | | | | 150 | | | | | 155 | | | | | 160 |
| Phe | Gly | Pro | Gly | Pro | Val | Leu | Ser | Asp | Asn | Phe | Thr | Asp | Ser | Met | Ile |
| | | | | 165 | | | | | 170 | | | | | 175 | |
| Met | Asn | Gly | His | Ser | Pro | Ile | Ser | Glu | Gly | Phe | Gly | Ala | Arg | Met | Met |
| | | | 180 | | | | | 185 | | | | | 190 | | |
| Ile | Arg | Phe | Cys | Pro | Ser | Cys | Leu | Asn | Val | Phe | Asn | Asn | Val | Gln | Glu |
| | | | 195 | | | | | 200 | | | | | 205 | | |
| Asn | Lys | Asp | Thr | Ser | Ile | Phe | Ser | Arg | Arg | Ala | Tyr | Phe | Ala | Asp | Pro |
| | | 210 | | | | | 215 | | | | | 220 | | | |
| Ala | Leu | Thr | Leu | Met | His | Glu | Leu | Ile | His | Val | Leu | His | Gly | Leu | Tyr |
| 225 | | | | | 230 | | | | | 235 | | | | | 240 |
| Gly | Ile | Lys | Ile | Ser | Asn | Leu | Pro | Ile | Thr | Pro | Asn | Thr | Lys | Glu | Phe |
| | | | | 245 | | | | | 250 | | | | | 255 | |
| Phe | Met | Gln | His | Ser | Asp | Pro | Val | Gln | Ala | Glu | Glu | Leu | Tyr | Thr | Phe |
| | | | 260 | | | | | 265 | | | | | 270 | | |
| Gly | Gly | His | Asp | Pro | Ser | Val | Ile | Ser | Pro | Ser | Thr | Asp | Met | Asn | Ile |
| | | | 275 | | | | | 280 | | | | | 285 | | |
| Tyr | Asn | Lys | Ala | Leu | Gln | Asn | Phe | Gln | Asp | Ile | Ala | Asn | Arg | Leu | Asn |
| | | | | 290 | | | | | 295 | | | | | 300 | |
| Ile | Val | Ser | Ser | Ala | Gln | Gly | Ser | Gly | Ile | Asp | Ile | Ser | Leu | Tyr | Lys |
| 305 | | | | | 310 | | | | | 315 | | | | | 320 |
| Gln | Ile | Tyr | Lys | Asn | Lys | Tyr | Asp | Phe | Val | Glu | Asp | Pro | Asn | Gly | Lys |
| | | | | 325 | | | | | 330 | | | | | 335 | |
| Tyr | Ser | Val | Asp | Lys | Asp | Lys | Phe | Asp | Lys | Leu | Tyr | Lys | Ala | Leu | Met |
| | | | 340 | | | | | 345 | | | | | 350 | | |
| Phe | Gly | Phe | Thr | Glu | Thr | Asn | Leu | Ala | Gly | Glu | Tyr | Gly | Ile | Lys | Thr |
| | | | | 355 | | | | | 360 | | | | | 365 | |
| Arg | Tyr | Ser | Tyr | Phe | Ser | Glu | Tyr | Leu | Pro | Pro | Ile | Lys | Thr | Glu | Lys |
| | | 370 | | | | | 375 | | | | | 380 | | | |

```
Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
            405                 410                 415

Lys Glu Ala Tyr Glu Glu Ile Ser Leu Glu His Leu Val Ile Tyr Arg
                420                 425                 430

Ile Ala Met Cys Lys Pro Val Met Tyr Lys Asn Thr Gly Asp Asp Asp
            435                 440                 445

Asp Lys Ser Glu Gln Cys Ile Ile Val Asn Asn Glu Asp Leu Phe Phe
        450                 455                 460

Ile Ala Asn Lys Asp Ser Phe Ser Lys Asp Leu Ala Lys Ala Glu Thr
465                 470                 475                 480

Ile Ala Tyr Asn Thr Gln Asn Asn Thr Ile Glu Asn Asn Phe Ser Ile
                485                 490                 495

Asp Gln Leu Ile Leu Asp Asn Asp Leu Ser Ser Gly Ile Asp Leu Pro
            500                 505                 510

Asn Glu Asn Thr Glu Pro Phe Thr Asn Phe Asp Asp Ile Asp Ile Pro
        515                 520                 525

Val Tyr Ile Lys Gln Ser Ala Leu Lys Lys Ile Phe Val Asp Gly Asp
            530                 535                 540

Ser Leu Phe Glu Tyr Leu His Ala Gln Thr Phe Pro Ser Asn Ile Glu
545                 550                 555                 560

Asn Leu Gln Leu Thr Asn Ser Leu Asn Asp Ala Leu Arg Asn Asn Asn
                565                 570                 575

Lys Val Tyr Thr Phe Phe Ser Thr Asn Leu Val Glu Lys Ala Asn Thr
            580                 585                 590

Val Val Gly Ala Ser Leu Phe Val Asn Trp Val Lys Gly Val Ile Asp
        595                 600                 605

Asp Phe Thr Ser Glu Ser Thr Gln Lys Ser Thr Ile Asp Lys Val Ser
    610                 615                 620

Asp Val Ser Ile Ile Ile Pro Tyr Ile Gly Pro Ala Leu Asn Val Gly
625                 630                 635                 640

Asn Glu Thr Ala Lys Glu Asn Phe Lys Asn Ala Phe Glu Ile Gly Gly
                645                 650                 655

Ala Ala Ile Leu Met Glu Phe Ile Pro Glu Leu Ile Val Pro Ile Val
            660                 665                 670

Gly Phe Phe Thr Leu Glu Ser Tyr Val Gly Asn Lys Gly His Ile Ile
        675                 680                 685

Met Thr Ile Ser Asn Ala Leu Lys Lys Arg Asp Gln Lys Trp Thr Asp
    690                 695                 700

Met Tyr Gly Leu Ile Val Ser Gln Trp Leu Ser Thr Val Asn Thr Gln
705                 710                 715                 720

Phe Tyr Thr Ile Lys Glu Arg Met Tyr Asn Ala Leu Asn Asn Gln Ser
                725                 730                 735

Gln Ala Ile Glu Lys Ile Ile Glu Asp Gln Tyr Asn Arg Tyr Ser Glu
            740                 745                 750

Glu Asp Lys Met Asn Ile Asn Ile Asp Phe Asn Asp Ile Asp Phe Lys
        755                 760                 765

Leu Asn Gln Ser Ile Asn Leu Ala Ile Asn Asn Ile Asp Asp Phe Ile
    770                 775                 780

Asn Gln Cys Ser Ile Ser Tyr Leu Met Asn Arg Met Ile Pro Leu Ala
785                 790                 795                 800
```

Val Lys Lys Leu Lys Asp Phe Asp Asp Asn Leu Lys Arg Asp Leu Leu
                805                 810                 815

Glu Tyr Ile Asp Thr Asn Glu Leu Tyr Leu Leu Asp Glu Val Asn Ile
            820                 825                 830

Leu Lys Ser Lys Val Asn Arg His Leu Lys Asp Ser Ile Pro Phe Asp
        835                 840                 845

Leu Ser Leu Tyr Thr Lys Asp Thr Ile Leu Ile Gln Val Phe Asn Asn
    850                 855                 860

Tyr Ile Ser Asn Ile Ser Ser Asn Ala Ile Leu Ser Leu Ser Tyr Arg
865                 870                 875                 880

Gly Gly Arg Leu Ile Asp Ser Ser Gly Tyr Gly Ala Thr Met Asn Val
                885                 890                 895

Gly Ser Asp Val Ile Phe Asn Asp Ile Gly Asn Gly Gln Phe Lys Leu
            900                 905                 910

Asn Asn Ser Glu Asn Ser Asn Ile Thr Ala His Gln Ser Lys Phe Val
        915                 920                 925

Val Tyr Asp Ser Met Phe Asp Asn Phe Ser Ile Asn Phe Trp Val Arg
    930                 935                 940

Thr Pro Lys Tyr Asn Asn Asn Asp Ile Gln Thr Tyr Leu Gln Asn Glu
945                 950                 955                 960

Tyr Thr Ile Ile Ser Cys Ile Lys Asn Asp Ser Gly Trp Lys Val Ser
                965                 970                 975

Ile Lys Gly Asn Arg Ile Ile Trp Thr Leu Ile Asp Val Asn Ala Lys
            980                 985                 990

Ser Lys Ser Ile Phe Phe Glu Tyr Ser Ile Lys Asp Asn Ile Ser Asp
        995                 1000                1005

Tyr Ile Asn Lys Trp Phe Ser Ile Thr Ile Thr Asn Asp Arg Leu
    1010                1015                1020

Gly Asn Ala Asn Ile Tyr Ile Asn Gly Ser Leu Lys Lys Ser Glu
    1025                1030                1035

Lys Ile Leu Asn Leu Asp Arg Ile Asn Ser Ser Asn Asp Ile Asp
    1040                1045                1050

Phe Lys Leu Ile Asn Cys Thr Asp Thr Thr Lys Phe Val Trp Ile
    1055                1060                1065

Lys Asp Phe Asn Ile Phe Gly Arg Glu Leu Asn Ala Thr Glu Val
    1070                1075                1080

Ser Ser Leu Tyr Trp Ile Gln Ser Ser Thr Asn Thr Leu Lys Asp
    1085                1090                1095

Phe Trp Gly Asn Pro Leu Arg Tyr Asp Thr Gln Tyr Tyr Leu Phe
    1100                1105                1110

Asn Gln Gly Met Gln Asn Ile Tyr Ile Lys Tyr Phe Ser Lys Ala
    1115                1120                1125

Ser Met Gly Glu Thr Ala Pro Arg Thr Asn Phe Asn Asn Ala Ala
    1130                1135                1140

Ile Asn Tyr Gln Asn Leu Tyr Leu Gly Leu Arg Phe Ile Ile Lys
    1145                1150                1155

Lys Ala Ser Asn Ser Arg Asn Ile Asn Asn Asp Asn Ile Val Arg
    1160                1165                1170

Glu Gly Asp Tyr Ile Tyr Leu Asn Ile Asp Asn Ile Ser Asp Glu
    1175                1180                1185

Ser Tyr Arg Val Tyr Val Leu Val Asn Ser Lys Glu Ile Gln Thr
    1190                1195                1200

Gln Leu Phe Leu Ala Pro Ile Asn Asp Asp Pro Thr Phe Tyr Asp

```
              1205                1210                1215
Val Leu Gln Ile Lys Lys Tyr Tyr Glu Lys Thr Thr Tyr Asn Cys
    1220                1225                1230

Gln Ile Leu Cys Glu Lys Asp Thr Lys Thr Phe Gly Leu Phe Gly
    1235                1240                1245

Ile Gly Lys Phe Val Lys Asp Tyr Gly Tyr Val Trp Asp Thr Tyr
    1250                1255                1260

Asp Asn Tyr Phe Cys Ile Ser Gln Trp Tyr Leu Arg Arg Ile Ser
    1265                1270                1275

Glu Asn Ile Asn Lys Leu Arg Leu Gly Cys Asn Trp Gln Phe Ile
    1280                1285                1290

Pro Val Asp Glu Gly Trp Thr Glu
    1295                1300

<210> SEQ ID NO 15
<211> LENGTH: 1300
<212> TYPE: PRT
<213> ORGANISM: Artificial
<220> FEATURE:
<223> OTHER INFORMATION: Clostridium botulinum serotype A neurotoxin,
      chimera 1

<400> SEQUENCE: 15

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Glu Leu Asp Asp Arg Ala Asp Ala Leu Gln Met Leu Asp Glu Gln Gly
                85                  90                  95

Glu Gln Leu Glu Arg Glu Met Asp Glu Asn Leu Glu Gln Val Ser Gly
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Ala
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255
```

```
Glu Val Ser Phe Glu Leu Arg Thr Phe Gly His Asp Ala Lys
            260             265             270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser His Thr Gln Ser Leu Asp Gln Gly Tyr Asn Asp
        435                 440                 445

Asp Asp Asp Lys Ala Leu Asn Asp Leu Cys Ile Lys Val Asn Asn Trp
450                 455                 460

Asp Leu Phe Phe Ser Pro Ser Glu Asp Asn Phe Thr Asn Asp Leu Asn
465                 470                 475                 480

Lys Gly Glu Glu Ile Thr Ser Asp Thr Asn Ile Glu Ala Ala Glu Glu
                485                 490                 495

Asn Ile Ser Leu Asp Leu Ile Gln Gln Tyr Tyr Leu Thr Phe Asn Phe
            500                 505                 510

Asp Asn Glu Pro Glu Asn Ile Ser Ile Glu Asn Leu Ser Ser Asp Ile
        515                 520                 525

Ile Gly Gln Leu Glu Leu Met Pro Asn Ile Glu Arg Phe Pro Asn Gly
    530                 535                 540

Lys Lys Tyr Glu Leu Asp Lys Tyr Thr Met Phe His Tyr Leu Arg Ala
545                 550                 555                 560

Gln Glu Phe Glu His Gly Lys Ser Arg Ile Ala Leu Thr Asn Ser Val
                565                 570                 575

Asn Glu Ala Leu Leu Asn Pro Ser Arg Val Tyr Thr Phe Phe Ser Ser
            580                 585                 590

Asp Tyr Val Lys Lys Val Asn Lys Ala Thr Glu Ala Ala Met Phe Leu
        595                 600                 605

Gly Trp Val Glu Gln Leu Val Tyr Asp Phe Thr Asp Glu Thr Ser Glu
    610                 615                 620

Val Ser Thr Thr Asp Lys Ile Ala Asp Ile Thr Ile Ile Pro Tyr
625                 630                 635                 640

Ile Gly Pro Ala Leu Asn Ile Gly Asn Met Leu Tyr Lys Asp Asp Phe
                645                 650                 655

Val Gly Ala Leu Ile Phe Ser Gly Ala Val Ile Leu Leu Glu Phe Ile
            660                 665                 670

Pro Glu Ile Ala Ile Pro Val Leu Gly Thr Phe Ala Leu Val Ser Tyr
```

```
            675                 680                 685
Ile Ala Asn Lys Val Leu Thr Val Gln Thr Ile Asp Asn Ala Leu Ser
    690                 695                 700
Lys Arg Asn Glu Lys Trp Asp Glu Val Tyr Lys Tyr Ile Val Thr Asn
705                 710                 715                 720
Trp Leu Ala Lys Val Asn Thr Gln Ile Asp Leu Ile Arg Lys Lys Met
            725                 730                 735
Lys Glu Ala Leu Glu Asn Gln Ala Glu Ala Thr Lys Ala Ile Ile Asn
            740                 745                 750
Tyr Gln Tyr Asn Gln Tyr Thr Glu Glu Lys Asn Asn Ile Asn Phe
            755                 760                 765
Asn Ile Asp Asp Leu Ser Ser Lys Leu Asn Glu Ser Ile Asn Lys Ala
            770                 775                 780
Met Ile Asn Ile Asn Lys Phe Leu Asn Gln Cys Ser Val Ser Tyr Leu
785                 790                 795                 800
Met Asn Ser Met Ile Pro Tyr Gly Val Lys Arg Leu Glu Asp Phe Asp
                805                 810                 815
Ala Ser Leu Lys Asp Ala Leu Leu Lys Tyr Ile Tyr Asp Asn Arg Gly
            820                 825                 830
Thr Leu Ile Gly Gln Val Asp Arg Leu Lys Asp Lys Val Asn Asn Thr
            835                 840                 845
Leu Ser Thr Asp Ile Pro Phe Gln Leu Ser Lys Tyr Val Asp Asn Gln
            850                 855                 860
Arg Leu Leu Ser Thr Phe Thr Glu Tyr Ile Lys Asn Ile Ile Asn Thr
865                 870                 875                 880
Ser Ile Leu Asn Leu Arg Tyr Glu Ser Asn His Leu Ile Asp Leu Ser
                885                 890                 895
Arg Tyr Ala Ser Lys Ile Asn Ile Gly Ser Lys Val Asn Phe Asp Pro
            900                 905                 910
Ile Asp Lys Asn Gln Ile Gln Leu Phe Asn Leu Glu Ser Ser Lys Ile
            915                 920                 925
Glu Val Ile Leu Lys Asn Ala Ile Val Tyr Asn Ser Met Tyr Glu Asn
            930                 935                 940
Phe Ser Thr Ser Phe Trp Ile Arg Ile Pro Lys Tyr Phe Asn Ser Ile
945                 950                 955                 960
Ser Leu Asn Asn Glu Tyr Thr Ile Ile Asn Cys Met Glu Asn Asn Ser
                965                 970                 975
Gly Trp Lys Val Ser Leu Asn Tyr Gly Glu Ile Ile Trp Thr Leu Gln
            980                 985                 990
Asp Thr Gln Glu Ile Lys Gln Arg Val Val Phe Lys Tyr Ser Gln Met
            995                 1000                1005
Ile Asn Ile Ser Asp Tyr Ile Asn Arg Trp Ile Phe Val Thr Ile
    1010                1015                1020
Thr Asn Asn Arg Leu Asn Asn Ser Lys Ile Tyr Ile Asn Gly Arg
    1025                1030                1035
Leu Ile Asp Gln Lys Pro Ile Ser Asn Leu Gly Asn Ile His Ala
    1040                1045                1050
Ser Asn Asn Ile Met Phe Lys Leu Asp Gly Cys Arg Asp Thr His
    1055                1060                1065
Arg Tyr Ile Trp Ile Lys Tyr Phe Asn Leu Phe Asp Lys Glu Leu
    1070                1075                1080
Asn Glu Lys Glu Ile Lys Asp Leu Tyr Asp Asn Gln Ser Asn Ser
    1085                1090                1095
```

```
Gly Ile Leu Lys Asp Phe Trp Gly Asp Tyr Leu Gln Tyr Asp Lys
            1100                1105                1110

Pro Tyr Tyr Met Leu Asn Leu Tyr Asp Pro Asn Lys Tyr Val Asp
    1115                1120                1125

Val Asn Asn Val Gly Ile Arg Gly Tyr Met Tyr Leu Lys Gly Pro
    1130                1135                1140

Arg Gly Ser Val Met Thr Thr Asn Ile Tyr Leu Asn Ser Ser Leu
    1145                1150                1155

Tyr Arg Gly Thr Lys Phe Ile Ile Lys Lys Tyr Ala Ser Gly Asn
    1160                1165                1170

Lys Asp Asn Ile Val Arg Asn Asn Asp Arg Val Tyr Ile Asn Val
    1175                1180                1185

Val Val Lys Asn Lys Glu Tyr Arg Leu Ala Thr Asn Ala Ser Gln
    1190                1195                1200

Ala Gly Val Glu Lys Ile Leu Ser Ala Leu Glu Ile Pro Asp Val
    1205                1210                1215

Gly Asn Leu Ser Gln Val Val Val Met Lys Ser Lys Asn Asp Gln
    1220                1225                1230

Gly Ile Thr Asn Lys Cys Lys Met Asn Leu Gln Asp Asn Asn Gly
    1235                1240                1245

Asn Asp Ile Gly Phe Ile Gly Phe His Gln Phe Asn Asn Ile Ala
    1250                1255                1260

Lys Leu Val Ala Ser Asn Trp Tyr Asn Arg Gln Ile Glu Arg Ser
    1265                1270                1275

Ser Arg Thr Leu Gly Cys Ser Trp Glu Phe Ile Pro Val Asp Asp
    1280                1285                1290

Gly Trp Gly Glu Arg Pro Leu
    1295                1300

<210> SEQ ID NO 16
<211> LENGTH: 1300
<212> TYPE: PRT
<213> ORGANISM: Artificial
<220> FEATURE:
<223> OTHER INFORMATION: Clostridium botulinum serotype A neurotoxin,
      chimera 2

<400> SEQUENCE: 16

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
```

```
            130                 135                 140
Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Ala
        210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Glu Leu Asp Asp Arg Ala Asp Ala Leu Gln Met Leu Asp
            275                 280                 285

Glu Gln Gly Glu Gln Leu Glu Arg Leu Asn Lys Ala Lys Ser Ile Val
        290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser His Thr Gln Ser Leu Asp Gln Gly Tyr Asn Asp
            435                 440                 445

Asp Asp Asp Lys Ala Leu Asn Asp Leu Cys Ile Lys Val Asn Asn Trp
        450                 455                 460

Asp Leu Phe Phe Ser Pro Ser Glu Asp Asn Phe Thr Asn Asp Leu Asn
465                 470                 475                 480

Lys Gly Glu Glu Ile Thr Ser Asp Thr Asn Ile Glu Ala Ala Glu Glu
                485                 490                 495

Asn Ile Ser Leu Asp Leu Ile Gln Gln Tyr Tyr Leu Thr Phe Asn Phe
                500                 505                 510

Asp Asn Glu Pro Glu Asn Ile Ser Ile Glu Asn Leu Ser Ser Asp Ile
            515                 520                 525

Ile Gly Gln Leu Glu Leu Met Pro Asn Ile Glu Arg Phe Pro Asn Gly
        530                 535                 540

Lys Lys Tyr Glu Leu Asp Lys Tyr Thr Met Phe His Tyr Leu Arg Ala
545                 550                 555                 560
```

```
Gln Glu Phe Glu His Gly Lys Ser Arg Ile Ala Leu Thr Asn Ser Val
                565                 570                 575

Asn Glu Ala Leu Leu Asn Pro Ser Arg Val Tyr Thr Phe Phe Ser Ser
            580                 585                 590

Asp Tyr Val Lys Lys Val Asn Lys Ala Thr Glu Ala Ala Met Phe Leu
        595                 600                 605

Gly Trp Val Glu Gln Leu Val Tyr Asp Phe Thr Asp Glu Thr Ser Glu
    610                 615                 620

Val Ser Thr Thr Asp Lys Ile Ala Asp Ile Thr Ile Ile Ile Pro Tyr
625                 630                 635                 640

Ile Gly Pro Ala Leu Asn Ile Gly Asn Met Leu Tyr Lys Asp Asp Phe
                645                 650                 655

Val Gly Ala Leu Ile Phe Ser Gly Ala Val Ile Leu Leu Glu Phe Ile
            660                 665                 670

Pro Glu Ile Ala Ile Pro Val Leu Gly Thr Phe Ala Leu Val Ser Tyr
        675                 680                 685

Ile Ala Asn Lys Val Leu Thr Val Gln Thr Ile Asp Asn Ala Leu Ser
    690                 695                 700

Lys Arg Asn Glu Lys Trp Asp Glu Val Tyr Lys Tyr Ile Val Thr Asn
705                 710                 715                 720

Trp Leu Ala Lys Val Asn Thr Gln Ile Asp Leu Ile Arg Lys Lys Met
                725                 730                 735

Lys Glu Ala Leu Glu Asn Gln Ala Glu Ala Thr Lys Ala Ile Ile Asn
            740                 745                 750

Tyr Gln Tyr Asn Gln Tyr Thr Glu Glu Lys Asn Asn Ile Asn Phe
        755                 760                 765

Asn Ile Asp Asp Leu Ser Ser Lys Leu Asn Glu Ser Ile Asn Lys Ala
    770                 775                 780

Met Ile Asn Ile Asn Lys Phe Leu Asn Gln Cys Ser Val Ser Tyr Leu
785                 790                 795                 800

Met Asn Ser Met Ile Pro Tyr Gly Val Lys Arg Leu Glu Asp Phe Asp
                805                 810                 815

Ala Ser Leu Lys Asp Ala Leu Leu Lys Tyr Ile Tyr Asp Asn Arg Gly
            820                 825                 830

Thr Leu Ile Gly Gln Val Asp Arg Leu Lys Asp Lys Val Asn Asn Thr
        835                 840                 845

Leu Ser Thr Asp Ile Pro Phe Gln Leu Ser Lys Tyr Val Asp Asn Gln
    850                 855                 860

Arg Leu Leu Ser Thr Phe Thr Glu Tyr Ile Lys Asn Ile Ile Asn Thr
865                 870                 875                 880

Ser Ile Leu Asn Leu Arg Tyr Glu Ser Asn His Leu Ile Asp Leu Ser
                885                 890                 895

Arg Tyr Ala Ser Lys Ile Asn Ile Gly Ser Lys Val Asn Phe Asp Pro
            900                 905                 910

Ile Asp Lys Asn Gln Ile Gln Leu Phe Asn Leu Glu Ser Ser Lys Ile
        915                 920                 925

Glu Val Ile Leu Lys Asn Ala Ile Val Tyr Asn Ser Met Tyr Glu Asn
    930                 935                 940

Phe Ser Thr Ser Phe Trp Ile Arg Ile Pro Lys Tyr Phe Asn Ser Ile
945                 950                 955                 960

Ser Leu Asn Asn Glu Tyr Thr Ile Ile Asn Cys Met Glu Asn Asn Ser
                965                 970                 975
```

```
Gly Trp Lys Val Ser Leu Asn Tyr Gly Ile Ile Trp Thr Leu Gln
            980                 985                 990

Asp Thr Gln Glu Ile Lys Gln Arg Val Val Phe Lys Tyr Ser Gln Met
        995                1000                1005

Ile Asn Ile Ser Asp Tyr Ile Asn Arg Trp Ile Phe Val Thr Ile
   1010                1015                1020

Thr Asn Asn Arg Leu Asn Asn Ser Lys Ile Tyr Ile Asn Gly Arg
   1025                1030                1035

Leu Ile Asp Gln Lys Pro Ile Ser Asn Leu Gly Asn Ile His Ala
   1040                1045                1050

Ser Asn Asn Ile Met Phe Lys Leu Asp Gly Cys Arg Asp Thr His
   1055                1060                1065

Arg Tyr Ile Trp Ile Lys Tyr Phe Asn Leu Phe Asp Lys Glu Leu
   1070                1075                1080

Asn Glu Lys Glu Ile Lys Asp Leu Tyr Asp Asn Gln Ser Asn Ser
   1085                1090                1095

Gly Ile Leu Lys Asp Phe Trp Gly Asp Tyr Leu Gln Tyr Asp Lys
   1100                1105                1110

Pro Tyr Tyr Met Leu Asn Leu Tyr Asp Pro Asn Lys Tyr Val Asp
   1115                1120                1125

Val Asn Asn Val Gly Ile Arg Gly Tyr Met Tyr Leu Lys Gly Pro
   1130                1135                1140

Arg Gly Ser Val Met Thr Thr Asn Ile Tyr Leu Asn Ser Ser Leu
   1145                1150                1155

Tyr Arg Gly Thr Lys Phe Ile Ile Lys Lys Tyr Ala Ser Gly Asn
   1160                1165                1170

Lys Asp Asn Ile Val Arg Asn Asn Asp Arg Val Tyr Ile Asn Val
   1175                1180                1185

Val Val Lys Asn Lys Glu Tyr Arg Leu Ala Thr Asn Ala Ser Gln
   1190                1195                1200

Ala Gly Val Glu Lys Ile Leu Ser Ala Leu Glu Ile Pro Asp Val
   1205                1210                1215

Gly Asn Leu Ser Gln Val Val Val Met Lys Ser Lys Asn Asp Gln
   1220                1225                1230

Gly Ile Thr Asn Lys Cys Lys Met Asn Leu Gln Asp Asn Asn Gly
   1235                1240                1245

Asn Asp Ile Gly Phe Ile Gly Phe His Gln Phe Asn Asn Ile Ala
   1250                1255                1260

Lys Leu Val Ala Ser Asn Trp Tyr Asn Arg Gln Ile Glu Arg Ser
   1265                1270                1275

Ser Arg Thr Leu Gly Cys Ser Trp Glu Phe Ile Pro Val Asp Asp
   1280                1285                1290

Gly Trp Gly Glu Arg Pro Leu
   1295                1300

<210> SEQ ID NO 17
<211> LENGTH: 1300
<212> TYPE: PRT
<213> ORGANISM: Artificial
<220> FEATURE:
<223> OTHER INFORMATION: Clostridium botulinum serotype A neurotoxin,
      chimera 3

<400> SEQUENCE: 17

Met Pro Phe Val Asn Lys Gln Phe Asn Tyr Lys Asp Pro Val Asn Gly
 1               5                   10                  15
```

-continued

```
Val Asp Ile Ala Tyr Ile Lys Ile Pro Asn Ala Gly Gln Met Gln Pro
         20                  25                  30

Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
         50                  55                  60

Ala Lys Gln Val Pro Val Ser Tyr Tyr Asp Ser Thr Tyr Leu Ser Thr
65                   70                  75                  80

Glu Leu Asp Asp Arg Ala Asp Ala Leu Gln Met Leu Asp Glu Gln Gly
                 85                  90                  95

Glu Gln Leu Glu Arg Glu Met Asp Glu Asn Leu Glu Gln Val Ser Gly
            100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Ala
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Glu Leu Asp Asp Arg Ala Asp Ala Leu Gln Met Leu Asp
        275                 280                 285

Glu Gln Gly Glu Gln Leu Glu Arg Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430
```

-continued

```
Gly Ile Ile Thr Ser His Thr Gln Ser Leu Asp Gln Gly Tyr Asn Asp
            435                 440                 445

Asp Asp Asp Lys Ala Leu Asn Asp Leu Cys Ile Lys Val Asn Asn Trp
450                 455                 460

Asp Leu Phe Phe Ser Pro Ser Glu Asp Asn Phe Thr Asn Asp Leu Asn
465                 470                 475                 480

Lys Gly Glu Glu Ile Thr Ser Asp Thr Asn Ile Glu Ala Ala Glu Glu
                485                 490                 495

Asn Ile Ser Leu Asp Leu Ile Gln Gln Tyr Tyr Leu Thr Phe Asn Phe
            500                 505                 510

Asp Asn Glu Pro Glu Asn Ile Ser Ile Glu Asn Leu Ser Ser Asp Ile
            515                 520                 525

Ile Gly Gln Leu Glu Leu Met Pro Asn Ile Glu Arg Phe Pro Asn Gly
530                 535                 540

Lys Lys Tyr Glu Leu Asp Lys Tyr Thr Met Phe His Tyr Leu Arg Ala
545                 550                 555                 560

Gln Glu Phe Glu His Gly Lys Ser Arg Ile Ala Leu Thr Asn Ser Val
                565                 570                 575

Asn Glu Ala Leu Leu Asn Pro Ser Arg Val Tyr Thr Phe Phe Ser Ser
            580                 585                 590

Asp Tyr Val Lys Lys Val Asn Lys Ala Thr Glu Ala Ala Met Phe Leu
595                 600                 605

Gly Trp Val Glu Gln Leu Val Tyr Asp Phe Thr Asp Glu Thr Ser Glu
610                 615                 620

Val Ser Thr Thr Asp Lys Ile Ala Asp Ile Thr Ile Ile Ile Pro Tyr
625                 630                 635                 640

Ile Gly Pro Ala Leu Asn Ile Gly Asn Met Leu Tyr Lys Asp Asp Phe
                645                 650                 655

Val Gly Ala Leu Ile Phe Ser Gly Ala Val Ile Leu Leu Glu Phe Ile
            660                 665                 670

Pro Glu Ile Ala Ile Pro Val Leu Gly Thr Phe Ala Leu Val Ser Tyr
            675                 680                 685

Ile Ala Asn Lys Val Leu Thr Val Gln Thr Ile Asp Asn Ala Leu Ser
690                 695                 700

Lys Arg Asn Glu Lys Trp Asp Glu Val Tyr Lys Tyr Ile Val Thr Asn
705                 710                 715                 720

Trp Leu Ala Lys Val Asn Thr Gln Ile Asp Leu Ile Arg Lys Lys Met
                725                 730                 735

Lys Glu Ala Leu Glu Asn Gln Ala Glu Ala Thr Lys Ala Ile Ile Asn
            740                 745                 750

Tyr Gln Tyr Asn Gln Tyr Thr Glu Glu Glu Lys Asn Asn Ile Asn Phe
            755                 760                 765

Asn Ile Asp Asp Leu Ser Ser Lys Leu Asn Glu Ser Ile Asn Lys Ala
770                 775                 780

Met Ile Asn Ile Asn Lys Phe Leu Asn Gln Cys Ser Val Ser Tyr Leu
785                 790                 795                 800

Met Asn Ser Met Ile Pro Tyr Gly Val Lys Arg Leu Glu Asp Phe Asp
                805                 810                 815

Ala Ser Leu Lys Asp Ala Leu Leu Lys Tyr Ile Tyr Asp Asn Arg Gly
            820                 825                 830

Thr Leu Ile Gly Gln Val Asp Arg Leu Lys Asp Lys Val Asn Asn Thr
835                 840                 845

Leu Ser Thr Asp Ile Pro Phe Gln Leu Ser Lys Tyr Val Asp Asn Gln
```

```
                850                 855                 860
Arg Leu Leu Ser Thr Phe Thr Glu Tyr Ile Lys Asn Ile Ile Asn Thr
865                 870                 875                 880

Ser Ile Leu Asn Leu Arg Tyr Glu Ser Asn His Leu Ile Asp Leu Ser
                885                 890                 895

Arg Tyr Ala Ser Lys Ile Asn Ile Gly Ser Lys Val Asn Phe Asp Pro
                900                 905                 910

Ile Asp Lys Asn Gln Ile Gln Leu Phe Asn Leu Glu Ser Ser Lys Ile
                915                 920                 925

Glu Val Ile Leu Lys Asn Ala Ile Val Tyr Asn Ser Met Tyr Glu Asn
                930                 935                 940

Phe Ser Thr Ser Phe Trp Ile Arg Ile Pro Lys Tyr Phe Asn Ser Ile
945                 950                 955                 960

Ser Leu Asn Asn Glu Tyr Thr Ile Ile Asn Cys Met Glu Asn Asn Ser
                965                 970                 975

Gly Trp Lys Val Ser Leu Asn Tyr Gly Glu Ile Ile Trp Thr Leu Gln
                980                 985                 990

Asp Thr Gln Glu Ile Lys Gln Arg Val Val Phe Lys Tyr Ser Gln Met
                995                 1000                1005

Ile Asn Ile Ser Asp Tyr Ile Asn Arg Trp Ile Phe Val Thr Ile
                1010                1015                1020

Thr Asn Asn Arg Leu Asn Asn Ser Lys Ile Tyr Ile Asn Gly Arg
                1025                1030                1035

Leu Ile Asp Gln Lys Pro Ile Ser Asn Leu Gly Asn Ile His Ala
                1040                1045                1050

Ser Asn Asn Ile Met Phe Lys Leu Asp Gly Cys Arg Asp Thr His
                1055                1060                1065

Arg Tyr Ile Trp Ile Lys Tyr Phe Asn Leu Phe Asp Lys Glu Leu
                1070                1075                1080

Asn Glu Lys Glu Ile Lys Asp Leu Tyr Asp Asn Gln Ser Asn Ser
                1085                1090                1095

Gly Ile Leu Lys Asp Phe Trp Gly Asp Tyr Leu Gln Tyr Asp Lys
                1100                1105                1110

Pro Tyr Tyr Met Leu Asn Leu Tyr Asp Pro Asn Lys Tyr Val Asp
                1115                1120                1125

Val Asn Asn Val Gly Ile Arg Gly Tyr Met Tyr Leu Lys Gly Pro
                1130                1135                1140

Arg Gly Ser Val Met Thr Thr Asn Ile Tyr Leu Asn Ser Ser Leu
                1145                1150                1155

Tyr Arg Gly Thr Lys Phe Ile Ile Lys Lys Tyr Ala Ser Gly Asn
                1160                1165                1170

Lys Asp Asn Ile Val Arg Asn Asn Asp Arg Val Tyr Ile Asn Val
                1175                1180                1185

Val Val Lys Asn Lys Glu Tyr Arg Leu Ala Thr Asn Ala Ser Gln
                1190                1195                1200

Ala Gly Val Glu Lys Ile Leu Ser Ala Leu Glu Ile Pro Asp Val
                1205                1210                1215

Gly Asn Leu Ser Gln Val Val Val Met Lys Ser Lys Asn Asp Gln
                1220                1225                1230

Gly Ile Thr Asn Lys Cys Lys Met Asn Leu Gln Asp Asn Asn Gly
                1235                1240                1245

Asn Asp Ile Gly Phe Ile Gly Phe His Gln Phe Asn Asn Ile Ala
                1250                1255                1260
```

```
Lys Leu Val Ala Ser Asn Trp Tyr Asn Arg Gln Ile Glu Arg Ser
    1265                1270                1275

Ser Arg Thr Leu Gly Cys Ser Trp Glu Phe Ile Pro Val Asp Asp
    1280                1285                1290

Gly Trp Gly Glu Arg Pro Leu
    1295                1300

<210> SEQ ID NO 18
<211> LENGTH: 1300
<212> TYPE: PRT
<213> ORGANISM: Artificial
<220> FEATURE:
<223> OTHER INFORMATION: Clostridium botulinum serotype A, chimera 4

<400> SEQUENCE: 18

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Ala
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Glu Leu Asp Asp Arg Ala Asp Ala Leu Gln Met Leu Asp
        275                 280                 285

Glu Gln Gly Glu Gln Leu Glu Arg Leu Asn Lys Ala Lys Ser Ile Val
    290                 295                 300

Gly Thr Thr Ala Ser Glu Met Asp Glu Asn Leu Glu Gln Val Ser Gly
305                 310                 315                 320
```

```
Arg Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser His Thr Gln Ser Leu Asp Gln Gly Tyr Asn Asp
                435                 440                 445

Asp Asp Asp Lys Ala Leu Asn Asp Leu Cys Ile Lys Val Asn Asn Trp
            450                 455                 460

Asp Leu Phe Phe Ser Pro Ser Glu Asp Asn Phe Thr Asn Asp Leu Asn
465                 470                 475                 480

Lys Gly Glu Glu Ile Thr Ser Asp Thr Asn Ile Glu Ala Ala Glu Glu
                485                 490                 495

Asn Ile Ser Leu Asp Leu Ile Gln Gln Tyr Tyr Leu Thr Phe Asn Phe
                500                 505                 510

Asp Asn Glu Pro Glu Asn Ile Ser Ile Glu Asn Leu Ser Ser Asp Ile
            515                 520                 525

Ile Gly Gln Leu Glu Leu Met Pro Asn Ile Glu Arg Phe Pro Asn Gly
            530                 535                 540

Lys Lys Tyr Glu Leu Asp Lys Tyr Thr Met Phe His Tyr Leu Arg Ala
545                 550                 555                 560

Gln Glu Phe Glu His Gly Lys Ser Arg Ile Ala Leu Thr Asn Ser Val
                565                 570                 575

Asn Glu Ala Leu Leu Asn Pro Ser Arg Val Tyr Thr Phe Phe Ser Ser
                580                 585                 590

Asp Tyr Val Lys Lys Val Asn Lys Ala Thr Glu Ala Ala Met Phe Leu
            595                 600                 605

Gly Trp Val Glu Gln Leu Val Tyr Asp Phe Thr Asp Glu Thr Ser Glu
610                 615                 620

Val Ser Thr Thr Asp Lys Ile Ala Asp Ile Thr Ile Ile Ile Pro Tyr
625                 630                 635                 640

Ile Gly Pro Ala Leu Asn Ile Gly Asn Met Leu Tyr Lys Asp Asp Phe
                645                 650                 655

Val Gly Ala Leu Ile Phe Ser Gly Ala Val Ile Leu Leu Glu Phe Ile
                660                 665                 670

Pro Glu Ile Ala Ile Pro Val Leu Gly Thr Phe Ala Leu Val Ser Tyr
            675                 680                 685

Ile Ala Asn Lys Val Leu Thr Val Gln Thr Ile Asp Asn Ala Leu Ser
            690                 695                 700

Lys Arg Asn Glu Lys Trp Asp Glu Val Tyr Lys Tyr Ile Val Thr Asn
705                 710                 715                 720

Trp Leu Ala Lys Val Asn Thr Gln Ile Asp Leu Ile Arg Lys Lys Met
                725                 730                 735
```

-continued

```
Lys Glu Ala Leu Glu Asn Gln Ala Glu Ala Thr Lys Ala Ile Ile Asn
            740                 745                 750
Tyr Gln Tyr Asn Gln Tyr Thr Glu Glu Lys Asn Asn Ile Asn Phe
            755                 760                 765
Asn Ile Asp Asp Leu Ser Ser Lys Leu Asn Glu Ser Ile Asn Lys Ala
            770                 775                 780
Met Ile Asn Ile Asn Lys Phe Leu Asn Gln Cys Ser Val Ser Tyr Leu
785                 790                 795                 800
Met Asn Ser Met Ile Pro Tyr Gly Val Lys Arg Leu Glu Asp Phe Asp
                805                 810                 815
Ala Ser Leu Lys Asp Ala Leu Leu Lys Tyr Ile Tyr Asp Asn Arg Gly
            820                 825                 830
Thr Leu Ile Gly Gln Val Asp Arg Leu Lys Asp Lys Val Asn Asn Thr
            835                 840                 845
Leu Ser Thr Asp Ile Pro Phe Gln Leu Ser Lys Tyr Val Asp Asn Gln
850                 855                 860
Arg Leu Leu Ser Thr Phe Thr Glu Tyr Ile Lys Asn Ile Ile Asn Thr
865                 870                 875                 880
Ser Ile Leu Asn Leu Arg Tyr Glu Ser Asn His Leu Ile Asp Leu Ser
                885                 890                 895
Arg Tyr Ala Ser Lys Ile Asn Ile Gly Ser Lys Val Asn Phe Asp Pro
            900                 905                 910
Ile Asp Lys Asn Gln Ile Gln Leu Phe Asn Leu Glu Ser Ser Lys Ile
            915                 920                 925
Glu Val Ile Leu Lys Asn Ala Ile Val Tyr Asn Ser Met Tyr Glu Asn
930                 935                 940
Phe Ser Thr Ser Phe Trp Ile Arg Ile Pro Lys Tyr Phe Asn Ser Ile
945                 950                 955                 960
Ser Leu Asn Asn Glu Tyr Thr Ile Ile Asn Cys Met Glu Asn Asn Ser
                965                 970                 975
Gly Trp Lys Val Ser Leu Asn Tyr Gly Glu Ile Ile Trp Thr Leu Gln
            980                 985                 990
Asp Thr Gln Glu Ile Lys Gln Arg Val Val Phe Lys Tyr Ser Gln Met
            995                 1000                1005
Ile Asn Ile Ser Asp Tyr Ile Asn Arg Trp Ile Phe Val Thr Ile
        1010                1015                1020
Thr Asn Asn Arg Leu Asn Asn Ser Lys Ile Tyr Ile Asn Gly Arg
        1025                1030                1035
Leu Ile Asp Gln Lys Pro Ile Ser Asn Leu Gly Asn Ile His Ala
        1040                1045                1050
Ser Asn Asn Ile Met Phe Lys Leu Asp Gly Cys Arg Asp Thr His
        1055                1060                1065
Arg Tyr Ile Trp Ile Lys Tyr Phe Asn Leu Phe Asp Lys Glu Leu
        1070                1075                1080
Asn Glu Lys Glu Ile Lys Asp Leu Tyr Asp Asn Gln Ser Asn Ser
        1085                1090                1095
Gly Ile Leu Lys Asp Phe Trp Gly Asp Tyr Leu Gln Tyr Asp Lys
        1100                1105                1110
Pro Tyr Tyr Met Leu Asn Leu Tyr Asp Pro Asn Lys Tyr Val Asp
        1115                1120                1125
Val Asn Asn Val Gly Ile Arg Gly Tyr Met Tyr Leu Lys Gly Pro
        1130                1135                1140
Arg Gly Ser Val Met Thr Thr Asn Ile Tyr Leu Asn Ser Ser Leu
```

```
            1145                1150                1155

Tyr Arg Gly Thr Lys Phe Ile Ile Lys Lys Tyr Ala Ser Gly Asn
        1160                1165                1170

Lys Asp Asn Ile Val Arg Asn Asn Asp Arg Val Tyr Ile Asn Val
    1175                1180                1185

Val Val Lys Asn Lys Glu Tyr Arg Leu Ala Thr Asn Ala Ser Gln
    1190                1195                1200

Ala Gly Val Glu Lys Ile Leu Ser Ala Leu Glu Ile Pro Asp Val
    1205                1210                1215

Gly Asn Leu Ser Gln Val Val Met Lys Ser Lys Asn Asp Gln
    1220                1225                1230

Gly Ile Thr Asn Lys Cys Lys Met Asn Leu Gln Asp Asn Asn Gly
    1235                1240                1245

Asn Asp Ile Gly Phe Ile Gly Phe His Gln Phe Asn Asn Ile Ala
    1250                1255                1260

Lys Leu Val Ala Ser Asn Trp Tyr Asn Arg Gln Ile Glu Arg Ser
    1265                1270                1275

Ser Arg Thr Leu Gly Cys Ser Trp Glu Phe Ile Pro Val Asp Asp
    1280                1285                1290

Gly Trp Gly Glu Arg Pro Leu
    1295                1300

<210> SEQ ID NO 19
<211> LENGTH: 1300
<212> TYPE: PRT
<213> ORGANISM: Artificial
<220> FEATURE:
<223> OTHER INFORMATION: Clostridium botulinum serotype A neurotoxin,
      chimera 5

<400> SEQUENCE: 19

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Glu Leu Asp Asp Arg Ala Asp Ala Leu Gln Met Leu Asp Glu Gln Gly
                85                  90                  95

Glu Gln Leu Glu Arg Glu Met Asp Glu Asn Leu Glu Gln Val Ser Gly
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190
```

```
Thr Phe Gly Phe Glu Glu Ser Leu Glu Val Asp Thr Asn Pro Leu Leu
            195                 200                 205
Gly Ala Gly Lys Phe Ala Thr Asp Pro Ala Val Thr Leu Ala His Ala
210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly His Asp Ala Lys
            260                 265                 270
Phe Ile Asp Glu Leu Asp Asp Arg Ala Asp Ala Leu Gln Met Leu Asp
            275                 280                 285
Glu Gln Gly Glu Gln Leu Glu Arg Leu Asn Lys Ala Lys Ser Ile Val
            290                 295                 300
Gly Thr Thr Ala Ser Glu Met Asp Glu Asn Leu Glu Gln Val Ser Gly
305                 310                 315                 320
Arg Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
            355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser His Thr Gln Ser Leu Asp Gln Gly Tyr Asn Asp
            435                 440                 445
Asp Asp Asp Lys Ala Leu Asn Asp Leu Cys Ile Lys Val Asn Asn Trp
450                 455                 460
Asp Leu Phe Phe Ser Pro Ser Glu Asp Asn Phe Thr Asn Asp Leu Asn
465                 470                 475                 480
Lys Gly Glu Glu Ile Thr Ser Asp Thr Asn Ile Glu Ala Ala Glu Glu
                485                 490                 495
Asn Ile Ser Leu Asp Leu Ile Gln Gln Tyr Tyr Leu Thr Phe Asn Phe
            500                 505                 510
Asp Asn Glu Pro Glu Asn Ile Ser Ile Glu Asn Leu Ser Ser Asp Ile
            515                 520                 525
Ile Gly Gln Leu Glu Leu Met Pro Asn Ile Glu Arg Phe Pro Asn Gly
            530                 535                 540
Lys Lys Tyr Glu Leu Asp Lys Tyr Thr Met Phe His Tyr Leu Arg Ala
545                 550                 555                 560
Gln Glu Phe Glu His Gly Lys Ser Arg Ile Ala Leu Thr Asn Ser Val
                565                 570                 575
Asn Glu Ala Leu Leu Asn Pro Ser Arg Val Tyr Thr Phe Phe Ser Ser
            580                 585                 590
Asp Tyr Val Lys Lys Val Asn Lys Ala Thr Glu Ala Ala Met Phe Leu
            595                 600                 605
Gly Trp Val Glu Gln Leu Val Tyr Asp Phe Thr Asp Glu Thr Ser Glu
```

```
                610              615              620
Val Ser Thr Thr Asp Lys Ile Ala Asp Ile Thr Ile Ile Ile Pro Tyr
625                  630              635                  640

Ile Gly Pro Ala Leu Asn Ile Gly Asn Met Leu Tyr Lys Asp Asp Phe
                645              650              655

Val Gly Ala Leu Ile Phe Ser Gly Ala Val Ile Leu Leu Glu Phe Ile
            660              665              670

Pro Glu Ile Ala Ile Pro Val Leu Gly Thr Phe Ala Leu Val Ser Tyr
        675              680              685

Ile Ala Asn Lys Val Leu Thr Val Gln Thr Ile Asp Asn Ala Leu Ser
    690              695              700

Lys Arg Asn Glu Lys Trp Asp Glu Val Tyr Lys Tyr Ile Val Thr Asn
705              710              715              720

Trp Leu Ala Lys Val Asn Thr Gln Ile Asp Leu Ile Arg Lys Lys Met
            725              730              735

Lys Glu Ala Leu Glu Asn Gln Ala Glu Ala Thr Lys Ala Ile Ile Asn
            740              745              750

Tyr Gln Tyr Asn Gln Tyr Thr Glu Glu Lys Asn Asn Ile Asn Phe
        755              760              765

Asn Ile Asp Asp Leu Ser Ser Lys Leu Asn Glu Ser Ile Asn Lys Ala
770              775              780

Met Ile Asn Ile Asn Lys Phe Leu Asn Gln Cys Ser Val Ser Tyr Leu
785              790              795              800

Met Asn Ser Met Ile Pro Tyr Gly Val Lys Arg Leu Glu Asp Phe Asp
            805              810              815

Ala Ser Leu Lys Asp Ala Leu Leu Lys Tyr Ile Tyr Asp Asn Arg Gly
            820              825              830

Thr Leu Ile Gly Gln Val Asp Arg Leu Lys Asp Lys Val Asn Asn Thr
        835              840              845

Leu Ser Thr Asp Ile Pro Phe Gln Leu Ser Lys Tyr Val Asp Asn Gln
850              855              860

Arg Leu Leu Ser Thr Phe Thr Glu Tyr Ile Lys Asn Ile Ile Asn Thr
865              870              875              880

Ser Ile Leu Asn Leu Arg Tyr Glu Ser Asn His Leu Ile Asp Leu Ser
            885              890              895

Arg Tyr Ala Ser Lys Ile Asn Ile Gly Ser Lys Val Asn Phe Asp Pro
            900              905              910

Ile Asp Lys Asn Gln Ile Gln Leu Phe Asn Leu Glu Ser Ser Lys Ile
        915              920              925

Glu Val Ile Leu Lys Asn Ala Ile Val Tyr Asn Ser Met Tyr Glu Asn
930              935              940

Phe Ser Thr Ser Phe Trp Ile Arg Ile Pro Lys Tyr Phe Asn Ser Ile
945              950              955              960

Ser Leu Asn Asn Glu Tyr Thr Ile Ile Asn Cys Met Glu Asn Asn Ser
            965              970              975

Gly Trp Lys Val Ser Leu Asn Tyr Gly Glu Ile Ile Trp Thr Leu Gln
            980              985              990

Asp Thr Gln Glu Ile Lys Gln Arg Val Val Phe Lys Tyr Ser Gln Met
        995              1000             1005

Ile Asn Ile Ser Asp Tyr Ile Asn Arg Trp Ile Phe Val Thr Ile
    1010             1015             1020

Thr Asn Asn Arg Leu Asn Asn Ser Lys Ile Tyr Ile Asn Gly Arg
    1025             1030             1035
```

```
Leu Ile Asp Gln Lys Pro Ile Ser Asn Leu Gly Asn Ile His Ala
    1040                1045                1050

Ser Asn Asn Ile Met Phe Lys Leu Asp Gly Cys Arg Asp Thr His
    1055                1060                1065

Arg Tyr Ile Trp Ile Lys Tyr Phe Asn Leu Phe Asp Lys Glu Leu
    1070                1075                1080

Asn Glu Lys Glu Ile Lys Asp Leu Tyr Asp Asn Gln Ser Asn Ser
    1085                1090                1095

Gly Ile Leu Lys Asp Phe Trp Gly Asp Tyr Leu Gln Tyr Asp Lys
    1100                1105                1110

Pro Tyr Tyr Met Leu Asn Leu Tyr Asp Pro Asn Lys Tyr Val Asp
    1115                1120                1125

Val Asn Asn Val Gly Ile Arg Gly Tyr Met Tyr Leu Lys Gly Pro
    1130                1135                1140

Arg Gly Ser Val Met Thr Thr Asn Ile Tyr Leu Asn Ser Ser Leu
    1145                1150                1155

Tyr Arg Gly Thr Lys Phe Ile Ile Lys Lys Tyr Ala Ser Gly Asn
    1160                1165                1170

Lys Asp Asn Ile Val Arg Asn Asn Asp Arg Val Tyr Ile Asn Val
    1175                1180                1185

Val Val Lys Asn Lys Glu Tyr Arg Leu Ala Thr Asn Ala Ser Gln
    1190                1195                1200

Ala Gly Val Glu Lys Ile Leu Ser Ala Leu Glu Ile Pro Asp Val
    1205                1210                1215

Gly Asn Leu Ser Gln Val Val Val Met Lys Ser Lys Asn Asp Gln
    1220                1225                1230

Gly Ile Thr Asn Lys Cys Lys Met Asn Leu Gln Asp Asn Asn Gly
    1235                1240                1245

Asn Asp Ile Gly Phe Ile Gly Phe His Gln Phe Asn Asn Ile Ala
    1250                1255                1260

Lys Leu Val Ala Ser Asn Trp Tyr Asn Arg Gln Ile Glu Arg Ser
    1265                1270                1275

Ser Arg Thr Leu Gly Cys Ser Trp Glu Phe Ile Pro Val Asp Asp
    1280                1285                1290

Gly Trp Gly Glu Arg Pro Leu
    1295                1300

<210> SEQ ID NO 20
<211> LENGTH: 1301
<212> TYPE: PRT
<213> ORGANISM: Artificial
<220> FEATURE:
<223> OTHER INFORMATION: Clostridium botulinum serotype A neurotoxin,
      chimera 6

<400> SEQUENCE: 20

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
```

-continued

```
                65                  70                  75                  80
Asp Asn Glu Lys Asp Asn Tyr Leu Lys Gly Val Thr Lys Leu Phe Glu
                    85                  90                  95

Arg Ile Tyr Ser Thr Asp Leu Gly Arg Met Leu Leu Thr Ser Ile Val
                100                 105                 110

Arg Gly Ile Pro Phe Trp Gly Ser Thr Ile Asp Thr Glu Leu Lys
            115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                    165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Ala
        210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                    245                 250                 255

Glu Val Ser Phe Glu Glu Leu Arg Thr Phe Gly Gly His Asp Ala Lys
                260                 265                 270

Phe Ile Asp Glu Leu Asp Asp Arg Ala Asp Ala Leu Gln Met Leu Asp
            275                 280                 285

Glu Gln Gly Glu Gln Leu Glu Arg Leu Asn Lys Ala Lys Ser Ile Val
        290                 295                 300

Gly Thr Thr Ala Ser Glu Met Asp Glu Asn Leu Glu Gln Val Ser Gly
305                 310                 315                 320

Arg Leu Leu Ser Glu Asp Thr Ser Gly Lys Phe Ser Val Asp Phe Met
                    325                 330                 335

Asp Glu Phe Phe Glu Gln Val Glu Glu Leu Thr Glu Ile Tyr Thr Glu
                340                 345                 350

Asp Asn Phe Val Lys Phe Phe Lys Val Leu Asn Arg Lys Thr Tyr Leu
            355                 360                 365

Asn Phe Asp Lys Ala Val Phe Lys Ile Asn Ile Val Pro Lys Val Asn
        370                 375                 380

Tyr Thr Ile Tyr Asp Gly Phe Asn Leu Arg Asn Thr Asn Leu Ala Ala
385                 390                 395                 400

Asn Phe Asn Gly Gln Asn Thr Glu Ile Asn Asn Met Asn Phe Thr Lys
                    405                 410                 415

Leu Lys Asn Phe Thr Gly Leu Phe Glu Phe Tyr Lys Leu Leu Cys Val
                420                 425                 430

Arg Gly Ile Ile Thr Ser His Thr Gln Ser Leu Asp Gln Gly Tyr Asn
            435                 440                 445

Asp Asp Asp Asp Lys Ala Leu Asn Asp Leu Cys Ile Lys Val Asn Asn
        450                 455                 460

Trp Asp Leu Phe Phe Ser Pro Ser Glu Asp Asn Phe Thr Asn Asp Leu
465                 470                 475                 480

Asn Lys Gly Glu Glu Ile Thr Ser Asp Thr Asn Ile Glu Ala Ala Glu
                    485                 490                 495
```

-continued

```
Glu Asn Ile Ser Leu Asp Leu Ile Gln Gln Tyr Tyr Leu Thr Phe Asn
            500                 505                 510

Phe Asp Asn Glu Pro Glu Asn Ile Ser Ile Glu Asn Leu Ser Ser Asp
        515                 520                 525

Ile Ile Gly Gln Leu Glu Leu Met Pro Asn Ile Glu Arg Phe Pro Asn
    530                 535                 540

Gly Lys Lys Tyr Glu Leu Asp Lys Tyr Thr Met Phe His Tyr Leu Arg
545                 550                 555                 560

Ala Gln Glu Phe Glu His Gly Lys Ser Arg Ile Ala Leu Thr Asn Ser
                565                 570                 575

Val Asn Glu Ala Leu Leu Asn Pro Ser Arg Val Tyr Thr Phe Phe Ser
            580                 585                 590

Ser Asp Tyr Val Lys Lys Val Asn Lys Ala Thr Glu Ala Ala Met Phe
        595                 600                 605

Leu Gly Trp Val Glu Gln Leu Val Tyr Asp Phe Thr Asp Glu Thr Ser
    610                 615                 620

Glu Val Ser Thr Thr Asp Lys Ile Ala Asp Ile Thr Ile Ile Ile Pro
625                 630                 635                 640

Tyr Ile Gly Pro Ala Leu Asn Ile Gly Asn Met Leu Tyr Lys Asp Asp
                645                 650                 655

Phe Val Gly Ala Leu Ile Phe Ser Gly Ala Val Ile Leu Leu Glu Phe
            660                 665                 670

Ile Pro Glu Ile Ala Ile Pro Val Leu Gly Thr Phe Ala Leu Val Ser
        675                 680                 685

Tyr Ile Ala Asn Lys Val Leu Thr Val Gln Thr Ile Asp Asn Ala Leu
    690                 695                 700

Ser Lys Arg Asn Glu Lys Trp Asp Glu Val Tyr Lys Tyr Ile Val Thr
705                 710                 715                 720

Asn Trp Leu Ala Lys Val Asn Thr Gln Ile Asp Leu Ile Arg Lys Lys
                725                 730                 735

Met Lys Glu Ala Leu Glu Asn Gln Ala Glu Ala Thr Lys Ala Ile Ile
            740                 745                 750

Asn Tyr Gln Tyr Asn Gln Tyr Thr Glu Glu Lys Asn Asn Ile Asn
        755                 760                 765

Phe Asn Ile Asp Asp Leu Ser Ser Lys Leu Asn Glu Ser Ile Asn Lys
    770                 775                 780

Ala Met Ile Asn Ile Asn Lys Phe Leu Asn Gln Cys Ser Val Ser Tyr
785                 790                 795                 800

Leu Met Asn Ser Met Ile Pro Tyr Gly Val Lys Arg Leu Glu Asp Phe
                805                 810                 815

Asp Ala Ser Leu Lys Asp Ala Leu Leu Lys Tyr Ile Tyr Asp Asn Arg
            820                 825                 830

Gly Thr Leu Ile Gly Gln Val Asp Arg Leu Lys Asp Lys Val Asn Asn
        835                 840                 845

Thr Leu Ser Thr Asp Ile Pro Phe Gln Leu Ser Lys Tyr Val Asp Asn
    850                 855                 860

Gln Arg Leu Leu Ser Thr Phe Thr Glu Tyr Ile Lys Asn Ile Ile Asn
865                 870                 875                 880

Thr Ser Ile Leu Asn Leu Arg Tyr Glu Ser Asn His Leu Ile Asp Leu
                885                 890                 895

Ser Arg Tyr Ala Ser Lys Ile Asn Ile Gly Ser Lys Val Asn Phe Asp
            900                 905                 910
```

Pro Ile Asp Lys Asn Gln Ile Gln Leu Phe Asn Leu Glu Ser Ser Lys
    915                 920                 925

Ile Glu Val Ile Leu Lys Asn Ala Ile Val Tyr Asn Ser Met Tyr Glu
930                 935                 940

Asn Phe Ser Thr Ser Phe Trp Ile Arg Ile Pro Lys Tyr Phe Asn Ser
945                 950                 955                 960

Ile Ser Leu Asn Asn Glu Tyr Thr Ile Ile Asn Cys Met Glu Asn Asn
            965                 970                 975

Ser Gly Trp Lys Val Ser Leu Asn Tyr Gly Glu Ile Ile Trp Thr Leu
            980                 985                 990

Gln Asp Thr Gln Glu Ile Lys Gln Arg Val Val Phe Lys Tyr Ser Gln
            995                1000                1005

Met Ile Asn Ile Ser Asp Tyr Ile Asn Arg Trp Ile Phe Val Thr
    1010                1015                1020

Ile Thr Asn Asn Arg Leu Asn Asn Ser Lys Ile Tyr Ile Asn Gly
    1025                1030                1035

Arg Leu Ile Asp Gln Lys Pro Ile Ser Asn Leu Gly Asn Ile His
    1040                1045                1050

Ala Ser Asn Asn Ile Met Phe Lys Leu Asp Gly Cys Arg Asp Thr
    1055                1060                1065

His Arg Tyr Ile Trp Ile Lys Tyr Phe Asn Leu Phe Asp Lys Glu
    1070                1075                1080

Leu Asn Glu Lys Glu Ile Lys Asp Leu Tyr Asp Asn Gln Ser Asn
    1085                1090                1095

Ser Gly Ile Leu Lys Asp Phe Trp Gly Asp Tyr Leu Gln Tyr Asp
    1100                1105                1110

Lys Pro Tyr Tyr Met Leu Asn Leu Tyr Asp Pro Asn Lys Tyr Val
    1115                1120                1125

Asp Val Asn Asn Val Gly Ile Arg Gly Tyr Met Tyr Leu Lys Gly
    1130                1135                1140

Pro Arg Gly Ser Val Met Thr Thr Asn Ile Tyr Leu Asn Ser Ser
    1145                1150                1155

Leu Tyr Arg Gly Thr Lys Phe Ile Ile Lys Lys Tyr Ala Ser Gly
    1160                1165                1170

Asn Lys Asp Asn Ile Val Arg Asn Asn Asp Arg Val Tyr Ile Asn
    1175                1180                1185

Val Val Val Lys Asn Lys Glu Tyr Arg Leu Ala Thr Asn Ala Ser
    1190                1195                1200

Gln Ala Gly Val Glu Lys Ile Leu Ser Ala Leu Glu Ile Pro Asp
    1205                1210                1215

Val Gly Asn Leu Ser Gln Val Val Val Met Lys Ser Lys Asn Asp
    1220                1225                1230

Gln Gly Ile Thr Asn Lys Cys Lys Met Asn Leu Gln Asp Asn Asn
    1235                1240                1245

Gly Asn Asp Ile Gly Phe Ile Gly Phe His Gln Phe Asn Asn Ile
    1250                1255                1260

Ala Lys Leu Val Ala Ser Asn Trp Tyr Asn Arg Gln Ile Glu Arg
    1265                1270                1275

Ser Ser Arg Thr Leu Gly Cys Ser Trp Glu Phe Ile Pro Val Asp
    1280                1285                1290

Asp Gly Trp Gly Glu Arg Pro Leu
    1295                1300

```
<210> SEQ ID NO 21
<211> LENGTH: 1301
<212> TYPE: PRT
<213> ORGANISM: Artificial
<220> FEATURE:
<223> OTHER INFORMATION: Clostridium botulinum serotype A neurotoxin,
      chimera 7

<400> SEQUENCE: 21
```

| | | | | | | | | | | | | | | |
|---|---|---|---|---|---|---|---|---|---|---|---|---|---|---|
| Met | Pro | Phe | Val | Asn | Lys | Gln | Phe | Asn | Tyr | Lys | Asp | Pro | Val | Asn | Gly |
| 1 | | | | 5 | | | | | 10 | | | | | 15 | |
| Val | Asp | Ile | Ala | Tyr | Ile | Lys | Ile | Pro | Asn | Ala | Gly | Gln | Met | Gln | Pro |
| | | | 20 | | | | | 25 | | | | | 30 | | |
| Val | Lys | Ala | Phe | Lys | Ile | His | Asn | Lys | Ile | Trp | Val | Ile | Pro | Glu | Arg |
| | | 35 | | | | | 40 | | | | | 45 | | | |
| Asp | Thr | Phe | Thr | Asn | Pro | Glu | Glu | Gly | Asp | Leu | Asn | Pro | Pro | Pro | Glu |
| | 50 | | | | | 55 | | | | | 60 | | | | |
| Ala | Lys | Gln | Val | Pro | Val | Ser | Tyr | Tyr | Asp | Ser | Thr | Tyr | Leu | Ser | Thr |
| 65 | | | | | 70 | | | | | 75 | | | | | 80 |
| Asp | Asn | Glu | Lys | Asp | Asn | Tyr | Leu | Lys | Gly | Val | Thr | Lys | Leu | Phe | Glu |
| | | | | 85 | | | | | 90 | | | | | 95 | |
| Arg | Ile | Tyr | Ser | Thr | Asp | Leu | Gly | Arg | Met | Leu | Leu | Thr | Ser | Ile | Val |
| | | | 100 | | | | | 105 | | | | | 110 | | |
| Arg | Gly | Ile | Pro | Phe | Trp | Gly | Gly | Ser | Thr | Ile | Asp | Thr | Glu | Leu | Lys |
| | | 115 | | | | | 120 | | | | | 125 | | | |
| Val | Ile | Asp | Thr | Asn | Cys | Ile | Asn | Val | Ile | Gln | Pro | Asp | Gly | Ser | Tyr |
| 130 | | | | | 135 | | | | | 140 | | | | | |
| Arg | Ser | Glu | Glu | Leu | Asn | Leu | Val | Ile | Ile | Gly | Pro | Ser | Ala | Asp | Ile |
| 145 | | | | | 150 | | | | | 155 | | | | | 160 |
| Ile | Gln | Phe | Glu | Cys | Lys | Ser | Phe | Gly | His | Glu | Val | Leu | Asn | Leu | Thr |
| | | | | 165 | | | | | 170 | | | | | 175 | |
| Arg | Asn | Gly | Tyr | Gly | Ser | Thr | Gln | Tyr | Ile | Arg | Phe | Ser | Pro | Asp | Phe |
| | | | 180 | | | | | 185 | | | | | 190 | | |
| Thr | Phe | Gly | Phe | Glu | Glu | Ser | Leu | Glu | Val | Asp | Thr | Asn | Pro | Leu | Leu |
| | | 195 | | | | | 200 | | | | | 205 | | | |
| Gly | Ala | Gly | Lys | Phe | Ala | Thr | Asp | Pro | Ala | Val | Thr | Leu | Ala | His | Ala |
| | 210 | | | | | 215 | | | | | 220 | | | | |
| Leu | Ile | His | Ala | Gly | His | Arg | Leu | Tyr | Gly | Ile | Ala | Ile | Asn | Pro | Asn |
| 225 | | | | | 230 | | | | | 235 | | | | | 240 |
| Arg | Val | Phe | Lys | Val | Asn | Thr | Asn | Ala | Tyr | Tyr | Glu | Met | Ser | Gly | Leu |
| | | | | 245 | | | | | 250 | | | | | 255 | |
| Glu | Val | Ser | Phe | Glu | Glu | Leu | Arg | Thr | Phe | Gly | Gly | His | Asp | Ala | Lys |
| | | | 260 | | | | | 265 | | | | | 270 | | |
| Phe | Ile | Asp | Glu | Leu | Asp | Asp | Arg | Ala | Asp | Ala | Leu | Gln | Met | Leu | Asp |
| | | 275 | | | | | 280 | | | | | 285 | | | |
| Glu | Gln | Gly | Glu | Gln | Leu | Glu | Arg | Leu | Asn | Lys | Ala | Lys | Ser | Ile | Val |
| | 290 | | | | | 295 | | | | | 300 | | | | |
| Gly | Thr | Thr | Ala | Ser | Glu | Met | Asp | Glu | Asn | Leu | Glu | Gln | Val | Ser | Gly |
| 305 | | | | | 310 | | | | | 315 | | | | | 320 |
| Arg | Leu | Leu | Ser | Glu | Asp | Thr | Ser | Gly | Lys | Phe | Ser | Val | Asp | Phe | Met |
| | | | | 325 | | | | | 330 | | | | | 335 | |
| Asp | Glu | Phe | Phe | Glu | Gln | Val | Glu | Glu | Leu | Thr | Glu | Ile | Tyr | Thr | Glu |
| | | | 340 | | | | | 345 | | | | | 350 | | |
| Leu | Glu | Asp | Met | Leu | Glu | Ser | Gly | Asn | Leu | Asn | Arg | Lys | Thr | Tyr | Leu |
| | | 355 | | | | | 360 | | | | | 365 | | | |

-continued

Asn Phe Asp Lys Ala Val Phe Lys Ile Asn Ile Val Pro Lys Val Asn
    370                 375                 380

Tyr Thr Ile Tyr Asp Gly Phe Asn Leu Arg Asn Thr Asn Leu Ala Ala
385                 390                 395                 400

Asn Phe Asn Gly Gln Asn Thr Glu Ile Asn Asn Met Asn Phe Thr Lys
                405                 410                 415

Leu Lys Asn Phe Thr Gly Leu Phe Glu Phe Tyr Lys Leu Leu Cys Val
                420                 425                 430

Arg Gly Ile Ile Thr Ser His Thr Gln Ser Leu Asp Gln Gly Tyr Asn
            435                 440                 445

Asp Asp Asp Asp Lys Ala Leu Asn Asp Leu Cys Ile Lys Val Asn Asn
450                 455                 460

Trp Asp Leu Phe Phe Ser Pro Ser Glu Asp Asn Phe Thr Asn Asp Leu
465                 470                 475                 480

Asn Lys Gly Glu Glu Ile Thr Ser Asp Thr Asn Ile Glu Ala Ala Glu
                485                 490                 495

Glu Asn Ile Ser Leu Asp Leu Ile Gln Gln Tyr Tyr Leu Thr Phe Asn
                500                 505                 510

Phe Asp Asn Glu Pro Glu Asn Ile Ser Ile Glu Asn Leu Ser Ser Asp
                515                 520                 525

Ile Ile Gly Gln Leu Glu Leu Met Pro Asn Ile Glu Arg Phe Pro Asn
530                 535                 540

Gly Lys Lys Tyr Glu Leu Asp Lys Tyr Thr Met Phe His Tyr Leu Arg
545                 550                 555                 560

Ala Gln Glu Phe Glu His Gly Lys Ser Arg Ile Ala Leu Thr Asn Ser
                565                 570                 575

Val Asn Glu Ala Leu Leu Asn Pro Ser Arg Val Tyr Thr Phe Phe Ser
                580                 585                 590

Ser Asp Tyr Val Lys Lys Val Asn Lys Ala Thr Glu Ala Ala Met Phe
            595                 600                 605

Leu Gly Trp Val Glu Gln Leu Val Tyr Asp Phe Thr Asp Glu Thr Ser
            610                 615                 620

Glu Val Ser Thr Thr Asp Lys Ile Ala Asp Ile Thr Ile Ile Pro
625                 630                 635                 640

Tyr Ile Gly Pro Ala Leu Asn Ile Gly Asn Met Leu Tyr Lys Asp Asp
                645                 650                 655

Phe Val Gly Ala Leu Ile Phe Ser Gly Ala Val Ile Leu Leu Glu Phe
                660                 665                 670

Ile Pro Glu Ile Ala Ile Pro Val Leu Gly Thr Phe Ala Leu Val Ser
            675                 680                 685

Tyr Ile Ala Asn Lys Val Leu Thr Val Gln Thr Ile Asp Asn Ala Leu
            690                 695                 700

Ser Lys Arg Asn Glu Lys Trp Asp Glu Val Tyr Lys Tyr Ile Val Thr
705                 710                 715                 720

Asn Trp Leu Ala Lys Val Asn Thr Gln Ile Asp Leu Ile Arg Lys Lys
                725                 730                 735

Met Lys Glu Ala Leu Glu Asn Gln Ala Glu Ala Thr Lys Ala Ile Ile
                740                 745                 750

Asn Tyr Gln Tyr Asn Gln Tyr Thr Glu Glu Glu Lys Asn Asn Ile Asn
                755                 760                 765

Phe Asn Ile Asp Asp Leu Ser Ser Lys Leu Asn Glu Ser Ile Asn Lys
770                 775                 780

Ala Met Ile Asn Ile Asn Lys Phe Leu Asn Gln Cys Ser Val Ser Tyr

```
            785              790              795              800
Leu Met Asn Ser Met Ile Pro Tyr Gly Val Lys Arg Leu Glu Asp Phe
                805              810              815

Asp Ala Ser Leu Lys Asp Ala Leu Leu Lys Tyr Ile Tyr Asp Asn Arg
                820              825              830

Gly Thr Leu Ile Gly Gln Val Asp Arg Leu Lys Asp Lys Val Asn Asn
                835              840              845

Thr Leu Ser Thr Asp Ile Pro Phe Gln Leu Ser Lys Tyr Val Asp Asn
850              855              860

Gln Arg Leu Leu Ser Thr Phe Thr Glu Tyr Ile Lys Asn Ile Ile Asn
865              870              875              880

Thr Ser Ile Leu Asn Leu Arg Tyr Glu Ser Asn His Leu Ile Asp Leu
                885              890              895

Ser Arg Tyr Ala Ser Lys Ile Asn Ile Gly Ser Lys Val Asn Phe Asp
                900              905              910

Pro Ile Asp Lys Asn Gln Ile Gln Leu Phe Asn Leu Glu Ser Ser Lys
                915              920              925

Ile Glu Val Ile Leu Lys Asn Ala Ile Val Tyr Asn Ser Met Tyr Glu
    930              935              940

Asn Phe Ser Thr Ser Phe Trp Ile Arg Ile Pro Lys Tyr Phe Asn Ser
945              950              955              960

Ile Ser Leu Asn Asn Glu Tyr Thr Ile Ile Asn Cys Met Glu Asn Asn
                965              970              975

Ser Gly Trp Lys Val Ser Leu Asn Tyr Gly Glu Ile Ile Trp Thr Leu
                980              985              990

Gln Asp Thr Gln Glu Ile Lys Gln Arg Val Val Phe Lys Tyr Ser Gln
                995              1000             1005

Met Ile Asn Ile Ser Asp Tyr Ile Asn Arg Trp Ile Phe Val Thr
    1010             1015             1020

Ile Thr Asn Asn Arg Leu Asn Asn Ser Lys Ile Tyr Ile Asn Gly
    1025             1030             1035

Arg Leu Ile Asp Gln Lys Pro Ile Ser Asn Leu Gly Asn Ile His
    1040             1045             1050

Ala Ser Asn Asn Ile Met Phe Lys Leu Asp Gly Cys Arg Asp Thr
    1055             1060             1065

His Arg Tyr Ile Trp Ile Lys Tyr Phe Asn Leu Phe Asp Lys Glu
    1070             1075             1080

Leu Asn Glu Lys Glu Ile Lys Asp Leu Tyr Asp Asn Gln Ser Asn
    1085             1090             1095

Ser Gly Ile Leu Lys Asp Phe Trp Gly Asp Tyr Leu Gln Tyr Asp
    1100             1105             1110

Lys Pro Tyr Tyr Met Leu Asn Leu Tyr Asp Pro Asn Lys Tyr Val
    1115             1120             1125

Asp Val Asn Asn Val Gly Ile Arg Gly Tyr Met Tyr Leu Lys Gly
    1130             1135             1140

Pro Arg Gly Ser Val Met Thr Thr Asn Ile Tyr Leu Asn Ser Ser
    1145             1150             1155

Leu Tyr Arg Gly Thr Lys Phe Ile Ile Lys Lys Tyr Ala Ser Gly
    1160             1165             1170

Asn Lys Asp Asn Ile Val Arg Asn Asn Asp Arg Val Tyr Ile Asn
    1175             1180             1185

Val Val Val Lys Asn Lys Glu Tyr Arg Leu Ala Thr Asn Ala Ser
    1190             1195             1200
```

```
Gln Ala Gly Val Glu Lys Ile Leu Ser Ala Leu Glu Ile Pro Asp
    1205                1210                1215

Val Gly Asn Leu Ser Gln Val Val Met Lys Ser Lys Asn Asp
    1220                1225                1230

Gln Gly Ile Thr Asn Lys Cys Lys Met Asn Leu Gln Asp Asn Asn
    1235                1240                1245

Gly Asn Asp Ile Gly Phe Ile Gly Phe His Gln Phe Asn Asn Ile
    1250                1255                1260

Ala Lys Leu Val Ala Ser Asn Trp Tyr Asn Arg Gln Ile Glu Arg
    1265                1270                1275

Ser Ser Arg Thr Leu Gly Cys Ser Trp Glu Phe Ile Pro Val Asp
    1280                1285                1290

Asp Gly Trp Gly Glu Arg Pro Leu
    1295                1300
```

<210> SEQ ID NO 22
<211> LENGTH: 1301
<212> TYPE: PRT
<213> ORGANISM: Artificial
<220> FEATURE:
<223> OTHER INFORMATION: Clostridium botulinum serotype A neurotoxin, chimera 8

<400> SEQUENCE: 22

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Glu Leu Asp Asp Arg Ala Asp Ala Leu Gln Met Leu Asp Glu Gln Gly
                85                  90                  95

Glu Gln Leu Glu Arg Glu Met Asp Glu Asn Leu Glu Gln Val Ser Gly
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Ala
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
```

-continued

```
                245                 250                 255
Glu Val Ser Phe Glu Glu Leu Arg Thr Phe Gly Gly His Asp Ala Lys
            260                 265                 270
Phe Ile Asp Glu Leu Asp Asp Arg Ala Asp Ala Leu Gln Met Leu Asp
            275                 280                 285
Glu Gln Gly Glu Gln Leu Glu Arg Leu Asn Lys Ala Lys Ser Ile Val
290                 295                 300
Gly Thr Thr Ala Ser Glu Met Asp Glu Asn Leu Glu Gln Val Ser Gly
305                 310                 315                 320
Arg Leu Leu Ser Glu Asp Thr Ser Gly Lys Phe Ser Val Asp Phe Met
            325                 330                 335
Asp Glu Phe Phe Glu Gln Val Glu Glu Leu Thr Glu Ile Tyr Thr Glu
            340                 345                 350
Asp Asn Phe Val Lys Phe Phe Lys Val Leu Asn Arg Lys Thr Tyr Leu
            355                 360                 365
Asn Phe Asp Lys Ala Val Phe Lys Ile Asn Ile Val Pro Lys Val Asn
370                 375                 380
Tyr Thr Ile Tyr Asp Gly Phe Asn Leu Arg Asn Thr Asn Leu Ala Ala
385                 390                 395                 400
Asn Phe Asn Gly Gln Asn Thr Glu Ile Asn Asn Met Asn Phe Thr Lys
            405                 410                 415
Leu Lys Asn Phe Thr Gly Leu Phe Glu Phe Tyr Lys Leu Leu Cys Val
            420                 425                 430
Arg Gly Ile Ile Thr Ser His Thr Gln Ser Leu Asp Gln Gly Tyr Asn
            435                 440                 445
Asp Asp Asp Asp Lys Ala Leu Asn Asp Leu Cys Ile Lys Val Asn Asn
            450                 455                 460
Trp Asp Leu Phe Phe Ser Pro Ser Glu Asp Asn Phe Thr Asn Asp Leu
465                 470                 475                 480
Asn Lys Gly Glu Glu Ile Thr Ser Asp Thr Asn Ile Glu Ala Ala Glu
            485                 490                 495
Glu Asn Ile Ser Leu Asp Leu Ile Gln Gln Tyr Tyr Leu Thr Phe Asn
            500                 505                 510
Phe Asp Asn Glu Pro Glu Asn Ile Ser Ile Glu Asn Leu Ser Ser Asp
            515                 520                 525
Ile Ile Gly Gln Leu Glu Leu Met Pro Asn Ile Glu Arg Phe Pro Asn
530                 535                 540
Gly Lys Lys Tyr Glu Leu Asp Lys Tyr Thr Met Phe His Tyr Leu Arg
545                 550                 555                 560
Ala Gln Glu Phe Glu His Gly Lys Ser Arg Ile Ala Leu Thr Asn Ser
            565                 570                 575
Val Asn Glu Ala Leu Leu Asn Pro Ser Arg Val Tyr Thr Phe Phe Ser
            580                 585                 590
Ser Asp Tyr Val Lys Lys Val Asn Lys Ala Thr Glu Ala Ala Met Phe
            595                 600                 605
Leu Gly Trp Val Glu Gln Leu Val Tyr Asp Phe Thr Asp Glu Thr Ser
            610                 615                 620
Glu Val Ser Thr Thr Asp Lys Ile Ala Asp Ile Thr Ile Ile Pro
625                 630                 635                 640
Tyr Ile Gly Pro Ala Leu Asn Ile Gly Asn Met Leu Tyr Lys Asp Asp
            645                 650                 655
Phe Val Gly Ala Leu Ile Phe Ser Gly Ala Val Ile Leu Leu Glu Phe
            660                 665                 670
```

```
Ile Pro Glu Ile Ala Ile Pro Val Leu Gly Thr Phe Ala Leu Val Ser
        675                 680                 685

Tyr Ile Ala Asn Lys Val Leu Thr Val Gln Thr Ile Asp Asn Ala Leu
690                 695                 700

Ser Lys Arg Asn Glu Lys Trp Asp Glu Val Tyr Lys Tyr Ile Val Thr
705                 710                 715                 720

Asn Trp Leu Ala Lys Val Asn Thr Gln Ile Asp Leu Ile Arg Lys Lys
                725                 730                 735

Met Lys Glu Ala Leu Glu Asn Gln Ala Glu Ala Thr Lys Ala Ile Ile
                740                 745                 750

Asn Tyr Gln Tyr Asn Gln Tyr Thr Glu Glu Lys Asn Asn Ile Asn
                755                 760                 765

Phe Asn Ile Asp Asp Leu Ser Ser Lys Leu Asn Glu Ser Ile Asn Lys
770                 775                 780

Ala Met Ile Asn Ile Asn Lys Phe Leu Asn Gln Cys Ser Val Ser Tyr
785                 790                 795                 800

Leu Met Asn Ser Met Ile Pro Tyr Gly Val Lys Arg Leu Glu Asp Phe
                805                 810                 815

Asp Ala Ser Leu Lys Asp Ala Leu Leu Lys Tyr Ile Tyr Asp Asn Arg
                820                 825                 830

Gly Thr Leu Ile Gly Gln Val Asp Arg Leu Lys Asp Lys Val Asn Asn
                835                 840                 845

Thr Leu Ser Thr Asp Ile Pro Phe Gln Leu Ser Lys Tyr Val Asp Asn
850                 855                 860

Gln Arg Leu Leu Ser Thr Phe Thr Glu Tyr Ile Lys Asn Ile Ile Asn
865                 870                 875                 880

Thr Ser Ile Leu Asn Leu Arg Tyr Glu Ser Asn His Leu Ile Asp Leu
                885                 890                 895

Ser Arg Tyr Ala Ser Lys Ile Asn Ile Gly Ser Lys Val Asn Phe Asp
                900                 905                 910

Pro Ile Asp Lys Asn Gln Ile Gln Leu Phe Asn Leu Glu Ser Ser Lys
                915                 920                 925

Ile Glu Val Ile Leu Lys Asn Ala Ile Val Tyr Asn Ser Met Tyr Glu
                930                 935                 940

Asn Phe Ser Thr Ser Phe Trp Ile Arg Ile Pro Lys Tyr Phe Asn Ser
945                 950                 955                 960

Ile Ser Leu Asn Asn Glu Tyr Thr Ile Ile Asn Cys Met Glu Asn Asn
                965                 970                 975

Ser Gly Trp Lys Val Ser Leu Asn Tyr Gly Glu Ile Ile Trp Thr Leu
                980                 985                 990

Gln Asp Thr Gln Glu Ile Lys Gln Arg Val Val Phe Lys Tyr Ser Gln
                995                 1000                1005

Met Ile Asn Ile Ser Asp Tyr Ile Asn Arg Trp Ile Phe Val Thr
        1010                1015                1020

Ile Thr Asn Asn Arg Leu Asn Asn Ser Lys Ile Tyr Ile Asn Gly
        1025                1030                1035

Arg Leu Ile Asp Gln Lys Pro Ile Ser Asn Leu Gly Asn Ile His
        1040                1045                1050

Ala Ser Asn Asn Ile Met Phe Lys Leu Asp Gly Cys Arg Asp Thr
        1055                1060                1065

His Arg Tyr Ile Trp Ile Lys Tyr Phe Asn Leu Phe Asp Lys Glu
        1070                1075                1080
```

-continued

```
Leu Asn Glu Lys Glu Ile Lys Asp Leu Tyr Asp Asn Gln Ser Asn
    1085                1090                1095

Ser Gly Ile Leu Lys Asp Phe Trp Gly Asp Tyr Leu Gln Tyr Asp
    1100                1105                1110

Lys Pro Tyr Tyr Met Leu Asn Leu Tyr Asp Pro Asn Lys Tyr Val
    1115                1120                1125

Asp Val Asn Asn Val Gly Ile Arg Gly Tyr Met Tyr Leu Lys Gly
    1130                1135                1140

Pro Arg Gly Ser Val Met Thr Thr Asn Ile Tyr Leu Asn Ser Ser
    1145                1150                1155

Leu Tyr Arg Gly Thr Lys Phe Ile Ile Lys Lys Tyr Ala Ser Gly
    1160                1165                1170

Asn Lys Asp Asn Ile Val Arg Asn Asn Asp Arg Val Tyr Ile Asn
    1175                1180                1185

Val Val Val Lys Asn Lys Glu Tyr Arg Leu Ala Thr Asn Ala Ser
    1190                1195                1200

Gln Ala Gly Val Glu Lys Ile Leu Ser Ala Leu Glu Ile Pro Asp
    1205                1210                1215

Val Gly Asn Leu Ser Gln Val Val Val Met Lys Ser Lys Asn Asp
    1220                1225                1230

Gln Gly Ile Thr Asn Lys Cys Lys Met Asn Leu Gln Asp Asn Asn
    1235                1240                1245

Gly Asn Asp Ile Gly Phe Ile Gly Phe His Gln Phe Asn Asn Ile
    1250                1255                1260

Ala Lys Leu Val Ala Ser Asn Trp Tyr Asn Arg Gln Ile Glu Arg
    1265                1270                1275

Ser Ser Arg Thr Leu Gly Cys Ser Trp Glu Phe Ile Pro Val Asp
    1280                1285                1290

Asp Gly Trp Gly Glu Arg Pro Leu
    1295                1300

<210> SEQ ID NO 23
<211> LENGTH: 1301
<212> TYPE: PRT
<213> ORGANISM: Artificial
<220> FEATURE:
<223> OTHER INFORMATION: Clostridium botulinum serotype A neurotoxin,
      chimera 9

<400> SEQUENCE: 23

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Glu Leu Asp Asp Arg Ala Asp Ala Leu Gln Met Leu Asp Glu Gln Gly
                85                  90                  95

Glu Gln Leu Glu Arg Glu Met Asp Glu Asn Leu Glu Gln Val Ser Gly
            100                 105                 110

Arg Gly Ile Pro Phe Trp Gly Gly Ser Thr Ile Asp Thr Glu Leu Lys
        115                 120                 125
```

```
Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
                195                 200                 205

Gly Ala Gly Lys Phe Ala Thr Asp Pro Ala Val Thr Leu Ala His Ala
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Glu Leu Asp Asp Arg Ala Asp Ala Leu Gln Met Leu Asp
                275                 280                 285

Glu Gln Gly Glu Gln Leu Glu Arg Leu Asn Lys Ala Lys Ser Ile Val
290                 295                 300

Gly Thr Thr Ala Ser Glu Met Asp Glu Asn Leu Glu Gln Val Ser Gly
305                 310                 315                 320

Arg Leu Leu Ser Glu Asp Thr Ser Gly Lys Phe Ser Val Asp Phe Met
                325                 330                 335

Asp Glu Phe Phe Glu Gln Val Glu Glu Leu Thr Glu Ile Tyr Thr Glu
                340                 345                 350

Leu Glu Asp Met Leu Glu Ser Gly Asn Leu Asn Arg Lys Thr Tyr Leu
                355                 360                 365

Asn Phe Asp Lys Ala Val Phe Lys Ile Asn Ile Val Pro Lys Val Asn
370                 375                 380

Tyr Thr Ile Tyr Asp Gly Phe Asn Leu Arg Asn Thr Asn Leu Ala Ala
385                 390                 395                 400

Asn Phe Asn Gly Gln Asn Thr Glu Ile Asn Asn Met Asn Phe Thr Lys
                405                 410                 415

Leu Lys Asn Phe Thr Gly Leu Phe Glu Phe Tyr Lys Leu Leu Cys Val
                420                 425                 430

Arg Gly Ile Ile Thr Ser His Thr Gln Ser Leu Asp Gln Gly Tyr Asn
                435                 440                 445

Asp Asp Asp Asp Lys Ala Leu Asn Asp Leu Cys Ile Lys Val Asn Asn
450                 455                 460

Trp Asp Leu Phe Phe Ser Pro Ser Glu Asp Asn Phe Thr Asn Asp Leu
465                 470                 475                 480

Asn Lys Gly Glu Glu Ile Thr Ser Asp Thr Asn Ile Glu Ala Ala Glu
                485                 490                 495

Glu Asn Ile Ser Leu Asp Leu Ile Gln Gln Tyr Tyr Leu Thr Phe Asn
                500                 505                 510

Phe Asp Asn Glu Pro Glu Asn Ile Ser Ile Glu Asn Leu Ser Ser Asp
                515                 520                 525

Ile Ile Gly Gln Leu Glu Leu Met Pro Asn Ile Glu Arg Phe Pro Asn
530                 535                 540
```

```
Gly Lys Lys Tyr Glu Leu Asp Lys Tyr Thr Met Phe His Tyr Leu Arg
545                 550                 555                 560

Ala Gln Glu Phe Glu His Gly Lys Ser Arg Ile Ala Leu Thr Asn Ser
            565                 570                 575

Val Asn Glu Ala Leu Leu Asn Pro Ser Arg Val Tyr Thr Phe Phe Ser
        580                 585                 590

Ser Asp Tyr Val Lys Lys Val Asn Lys Ala Thr Glu Ala Ala Met Phe
            595                 600                 605

Leu Gly Trp Val Glu Gln Leu Val Tyr Asp Phe Thr Asp Glu Thr Ser
        610                 615                 620

Glu Val Ser Thr Thr Asp Lys Ile Ala Asp Ile Thr Ile Ile Pro
625                 630                 635                 640

Tyr Ile Gly Pro Ala Leu Asn Ile Gly Asn Met Leu Tyr Lys Asp Asp
                645                 650                 655

Phe Val Gly Ala Leu Ile Phe Ser Gly Ala Val Ile Leu Leu Glu Phe
            660                 665                 670

Ile Pro Glu Ile Ala Ile Pro Val Leu Gly Thr Phe Ala Leu Val Ser
        675                 680                 685

Tyr Ile Ala Asn Lys Val Leu Thr Val Gln Thr Ile Asp Asn Ala Leu
            690                 695                 700

Ser Lys Arg Asn Glu Lys Trp Asp Glu Val Tyr Lys Tyr Ile Val Thr
705                 710                 715                 720

Asn Trp Leu Ala Lys Val Asn Thr Gln Ile Asp Leu Ile Arg Lys Lys
                725                 730                 735

Met Lys Glu Ala Leu Glu Asn Gln Ala Glu Ala Thr Lys Ala Ile Ile
            740                 745                 750

Asn Tyr Gln Tyr Asn Gln Tyr Thr Glu Glu Lys Asn Asn Ile Asn
            755                 760                 765

Phe Asn Ile Asp Asp Leu Ser Ser Lys Leu Asn Glu Ser Ile Asn Lys
770                 775                 780

Ala Met Ile Asn Ile Asn Lys Phe Leu Asn Gln Cys Ser Val Ser Tyr
785                 790                 795                 800

Leu Met Asn Ser Met Ile Pro Tyr Gly Val Lys Arg Leu Glu Asp Phe
            805                 810                 815

Asp Ala Ser Leu Lys Asp Ala Leu Leu Lys Tyr Ile Tyr Asp Asn Arg
        820                 825                 830

Gly Thr Leu Ile Gly Gln Val Asp Arg Leu Lys Asp Lys Val Asn Asn
            835                 840                 845

Thr Leu Ser Thr Asp Ile Pro Phe Gln Leu Ser Lys Tyr Val Asp Asn
850                 855                 860

Gln Arg Leu Leu Ser Thr Phe Thr Glu Tyr Ile Lys Asn Ile Ile Asn
865                 870                 875                 880

Thr Ser Ile Leu Asn Leu Arg Tyr Glu Ser Asn His Leu Ile Asp Leu
            885                 890                 895

Ser Arg Tyr Ala Ser Lys Ile Asn Ile Gly Ser Lys Val Asn Phe Asp
        900                 905                 910

Pro Ile Asp Lys Asn Gln Ile Gln Leu Phe Asn Leu Glu Ser Ser Lys
            915                 920                 925

Ile Glu Val Ile Leu Lys Asn Ala Ile Val Tyr Asn Ser Met Tyr Glu
        930                 935                 940

Asn Phe Ser Thr Ser Phe Trp Ile Arg Ile Pro Lys Tyr Phe Asn Ser
945                 950                 955                 960

Ile Ser Leu Asn Asn Glu Tyr Thr Ile Ile Asn Cys Met Glu Asn Asn
```

```
                965                 970                 975
Ser Gly Trp Lys Val Ser Leu Asn Tyr Gly Glu Ile Ile Trp Thr Leu
                    980                 985                 990

Gln Asp Thr Gln Glu Ile Lys Gln Arg Val Val Phe Lys Tyr Ser Gln
            995                 1000                1005

Met Ile Asn Ile Ser Asp Tyr Ile Asn Arg Trp Ile Phe Val Thr
        1010                1015                1020

Ile Thr Asn Asn Arg Leu Asn Asn Ser Lys Ile Tyr Ile Asn Gly
        1025                1030                1035

Arg Leu Ile Asp Gln Lys Pro Ile Ser Asn Leu Gly Asn Ile His
        1040                1045                1050

Ala Ser Asn Asn Ile Met Phe Lys Leu Asp Gly Cys Arg Asp Thr
        1055                1060                1065

His Arg Tyr Ile Trp Ile Lys Tyr Phe Asn Leu Phe Asp Lys Glu
        1070                1075                1080

Leu Asn Glu Lys Glu Ile Lys Asp Leu Tyr Asp Asn Gln Ser Asn
        1085                1090                1095

Ser Gly Ile Leu Lys Asp Phe Trp Gly Asp Tyr Leu Gln Tyr Asp
        1100                1105                1110

Lys Pro Tyr Tyr Met Leu Asn Leu Tyr Asp Pro Asn Lys Tyr Val
        1115                1120                1125

Asp Val Asn Asn Val Gly Ile Arg Gly Tyr Met Tyr Leu Lys Gly
        1130                1135                1140

Pro Arg Gly Ser Val Met Thr Thr Asn Ile Tyr Leu Asn Ser Ser
        1145                1150                1155

Leu Tyr Arg Gly Thr Lys Phe Ile Ile Lys Lys Tyr Ala Ser Gly
        1160                1165                1170

Asn Lys Asp Asn Ile Val Arg Asn Asn Asp Arg Val Tyr Ile Asn
        1175                1180                1185

Val Val Val Lys Asn Lys Glu Tyr Arg Leu Ala Thr Asn Ala Ser
        1190                1195                1200

Gln Ala Gly Val Glu Lys Ile Leu Ser Ala Leu Glu Ile Pro Asp
        1205                1210                1215

Val Gly Asn Leu Ser Gln Val Val Val Met Lys Ser Lys Asn Asp
        1220                1225                1230

Gln Gly Ile Thr Asn Lys Cys Lys Met Asn Leu Gln Asp Asn Asn
        1235                1240                1245

Gly Asn Asp Ile Gly Phe Ile Gly Phe His Gln Phe Asn Asn Ile
        1250                1255                1260

Ala Lys Leu Val Ala Ser Asn Trp Tyr Asn Arg Gln Ile Glu Arg
        1265                1270                1275

Ser Ser Arg Thr Leu Gly Cys Ser Trp Glu Phe Ile Pro Val Asp
        1280                1285                1290

Asp Gly Trp Gly Glu Arg Pro Leu
        1295                1300
```

<210> SEQ ID NO 24
<211> LENGTH: 5
<212> TYPE: PRT
<213> ORGANISM: Artificial
<220> FEATURE:
<223> OTHER INFORMATION: Enterokinase cleavage site

<400> SEQUENCE: 24

Asp Asp Asp Asp Lys

```
<210> SEQ ID NO 25
<211> LENGTH: 8
<212> TYPE: PRT
<213> ORGANISM: Artificial
<220> FEATURE:
<223> OTHER INFORMATION: Metalloprotease motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 25

His Glu Xaa Xaa His Xaa Xaa His
1               5

<210> SEQ ID NO 26
<211> LENGTH: 38
<212> TYPE: DNA
<213> ORGANISM: Artificial
<220> FEATURE:
<223> OTHER INFORMATION: annealed phosphorylated linker CBA01

<400> SEQUENCE: 26
ctagcatgcc atttgttaat aaacaattta attataag                          38

<210> SEQ ID NO 27
<211> LENGTH: 38
<212> TYPE: DNA
<213> ORGANISM: Artificial
<220> FEATURE:
<223> OTHER INFORMATION: annealed phosphorylated linker CBA02

<400> SEQUENCE: 27
gatccttata attaaattgt ttattaacaa atggcatg                          38

<210> SEQ ID NO 28
<211> LENGTH: 51
<212> TYPE: DNA
<213> ORGANISM: Artificial
<220> FEATURE:
<223> OTHER INFORMATION: oligonucleotide CBA03

<400> SEQUENCE: 28
tatctgcagg gatcctgtaa atggtgttga tattgcttat ataaaaattc c           51

<210> SEQ ID NO 29
<211> LENGTH: 46
<212> TYPE: DNA
<213> ORGANISM: Artificial
<220> FEATURE:
<223> OTHER INFORMATION: oligonucleotide CBA04

<400> SEQUENCE: 29
tatgaattca ccggtccgcg ggatctgtag caaatttgcc tgcacc                 46

<210> SEQ ID NO 30
<211> LENGTH: 55
<212> TYPE: DNA
<213> ORGANISM: Artificial
<220> FEATURE:
<223> OTHER INFORMATION: oligonucleotide CBA05
```

```
<400> SEQUENCE: 30
tataccgcgg taacattagc acatgaactt atacatgctg acatagatt atatg        55

<210> SEQ ID NO 31
<211> LENGTH: 73
<212> TYPE: DNA
<213> ORGANISM: Artificial
<220> FEATURE:
<223> OTHER INFORMATION: oligonucleotide CBA06

<400> SEQUENCE: 31
catagaattc aaacaatcca gtaaaatttt ttagtttagt aaaattcata ttattaattt  60
ctgtattttg acc                                                    73

<210> SEQ ID NO 32
<211> LENGTH: 52
<212> TYPE: DNA
<213> ORGANISM: Artificial
<220> FEATURE:
<223> OTHER INFORMATION: annealed phosphorylated linker CBA08

<400> SEQUENCE: 32
aattctataa gttgctatgt gtaagaggga taatactagt cacactcaat ct         52

<210> SEQ ID NO 33
<211> LENGTH: 53
<212> TYPE: DNA
<213> ORGANISM: Artificial
<220> FEATURE:
<223> OTHER INFORMATION: annealed phosphorylated linker CBA09

<400> SEQUENCE: 33
ctagagattg agtgtgacta gttattatcc ctcttacaca tagcaactta tag        53

<210> SEQ ID NO 34
<211> LENGTH: 45
<212> TYPE: DNA
<213> ORGANISM: Artificial
<220> FEATURE:
<223> OTHER INFORMATION: annealed phosphorylated linker CBA10

<400> SEQUENCE: 34
cgcgttagcc ataaatctgg ttataagcgc gcgaggtgtt aagtg                 45

<210> SEQ ID NO 35
<211> LENGTH: 45
<212> TYPE: DNA
<213> ORGANISM: Artificial
<220> FEATURE:
<223> OTHER INFORMATION: annealed phosphorylated liner CBA11

<400> SEQUENCE: 35
ctagcactta cacctcgcg cgcttataac cagatttatg gctaa                  45

<210> SEQ ID NO 36
<211> LENGTH: 89
<212> TYPE: DNA
<213> ORGANISM: Artificial
<220> FEATURE:
<223> OTHER INFORMATION: oligonucleotide CBA12

<400> SEQUENCE: 36
aatctgcagc cacagctgtg gggtacctta attggtcaag tagatagatt aaaagataaa 60
gttaataata cacttagtac agatatacc                                   89
```

<210> SEQ ID NO 37
<211> LENGTH: 80
<212> TYPE: DNA
<213> ORGANISM: Artificial
<220> FEATURE:
<223> OTHER INFORMATION: oligonucleotide CBA13

<400> SEQUENCE: 37
attagggccc ttaattaagc ggccgcctcg agctattaca gtggcctttc tccccatcca    60
tcatctacag gaataaattc                                                80

<210> SEQ ID NO 38
<211> LENGTH: 80
<212> TYPE: DNA
<213> ORGANISM: Artificial
<220> FEATURE:
<223> OTHER INFORMATION: oligonucleotide CBA14

<400> SEQUENCE: 38
atactgcagt ctagaccaag gatacaatga cgatgatgat aaggcattaa atgatttatg    60
tatcaaagtt aataattggg                                                80

<210> SEQ ID NO 39
<211> LENGTH: 56
<212> TYPE: DNA
<213> ORGANISM: Artificial
<220> FEATURE:
<223> OTHER INFORMATION: oligonucleotide CBA15

<400> SEQUENCE: 39
gcctaaaaac atagccgctt cggtcgcttt attaactttc tttacatagt ctgaag        56

<210> SEQ ID NO 40
<211> LENGTH: 50
<212> TYPE: DNA
<213> ORGANISM: Artificial
<220> FEATURE:
<223> OTHER INFORMATION: oligonucleotide CBA16

<400> SEQUENCE: 40
taataaagcg accgaagcgg ctatgttttt aggctgggta gaacaattag                50

<210> SEQ ID NO 41
<211> LENGTH: 63
<212> TYPE: DNA
<213> ORGANISM: Artificial
<220> FEATURE:
<223> OTHER INFORMATION: oligonucleotide CBA17

<400> SEQUENCE: 41
tatagggccc cctaggggta cctctattat catatatata ctttaataat gcatctttaa    60
gac                                                                  63

<210> SEQ ID NO 42
<211> LENGTH: 44
<212> TYPE: DNA
<213> ORGANISM: Artificial
<220> FEATURE:
<223> OTHER INFORMATION: oligonucleotide CBA22

<400> SEQUENCE: 42
taagcgcgca gaattctcta gaatgcccat gttaagcgct attg                      44

<210> SEQ ID NO 43
<211> LENGTH: 37
<212> TYPE: DNA
<213> ORGANISM: Artificial
<220> FEATURE:
<223> OTHER INFORMATION: oligonucleotide CBA23

<400> SEQUENCE: 43
taagctagcg tgatggtggt gatgatggac catggcc                              37

<210> SEQ ID NO 44
<211> LENGTH: 10
<212> TYPE: PRT
<213> ORGANISM: Artificial
<220> FEATURE:
<223> OTHER INFORMATION: construct coding sequence

<400> SEQUENCE: 44

Met His His His His His His Gly Ala Ser
1               5                   10

<210> SEQ ID NO 45
<211> LENGTH: 34
<212> TYPE: PRT
<213> ORGANISM: Artificial
<220> FEATURE:
<223> OTHER INFORMATION: gp64 signal peptide and hexahistadine affinity
      tag

<400> SEQUENCE: 45

Met Pro Met Leu Ser Ala Ile Val Leu Tyr Val Leu Leu Ala Ala Ala
1               5                   10                  15

Ala His Ser Ala Phe Ala Ala Met Val His His His His His His Ser
                20                  25                  30

Ala Ser

<210> SEQ ID NO 46
<211> LENGTH: 38
<212> TYPE: DNA
<213> ORGANISM: Artificial
<220> FEATURE:
<223> OTHER INFORMATION: phosphorylated oligonucleotide CBA18

<400> SEQUENCE: 46
cccgcggtga cattagcaca tgcacttata catgctgg                             38

<210> SEQ ID NO 47
<211> LENGTH: 38
<212> TYPE: DNA
<213> ORGANISM: Artificial
<220> FEATURE:
<223> OTHER INFORMATION: phosphorylated oligonucleotide CBA19

<400> SEQUENCE: 47
catgtgctaa tgtcaccgcg ggatctgtag caaatttg                             38

<210> SEQ ID NO 48
<211> LENGTH: 40
<212> TYPE: DNA
<213> ORGANISM: Artificial
<220> FEATURE:
<223> OTHER INFORMATION: oligonucleotide CBA20

<400> SEQUENCE: 48
attaaggatc ctgtgagcaa gggcgaggag ctgttcaccg                           40

<210> SEQ ID NO 49
<211> LENGTH: 51
<212> TYPE: DNA
<213> ORGANISM: Artificial
<220> FEATURE:
<223> OTHER INFORMATION: oligonucleotide CBA21

<400> SEQUENCE: 49
tatgaattca aacaatccag taaaattttt cttgtacagc tcgtccatgc c            51

<210> SEQ ID NO 50
<211> LENGTH: 44
<212> TYPE: DNA
<213> ORGANISM: Artificial
<220> FEATURE:
<223> OTHER INFORMATION: oligonucleotide CBA22

<400> SEQUENCE: 50
taagcgcgca gaattctcta gaatgcccat gttaagcgct attg                   44

<210> SEQ ID NO 51
<211> LENGTH: 37
<212> TYPE: DNA
<213> ORGANISM: Artificial
<220> FEATURE:
<223> OTHER INFORMATION: oligonucleotide CBA23

<400> SEQUENCE: 51
taagctagcg tgatggtggt gatgatggac catggcc                           37

<210> SEQ ID NO 52
<211> LENGTH: 93
<212> TYPE: DNA
<213> ORGANISM: Artificial
<220> FEATURE:
<223> OTHER INFORMATION: phosphorylated oligonucleotide CBCH1

<400> SEQUENCE: 52
gagttgttcg ccttgctcat ccaacatctg caacgcgtca gctcggtcat ccaactctgt   60
acttaaatat gttgaatcat aatatgaaac tgg                               93

<210> SEQ ID NO 53
<211> LENGTH: 79
<212> TYPE: DNA
<213> ORGANISM: Artificial
<220> FEATURE:
<223> OTHER INFORMATION: phosphorylated oligonucleotide CBCH2

<400> SEQUENCE: 53
gagcgcgaaa tggatgaaaa cctagagcag gtgagcggcc gaggaatacc attttggggt   60
ggaagtacaa tagatacag                                               79

<210> SEQ ID NO 54
<211> LENGTH: 51
<212> TYPE: DNA
<213> ORGANISM: Artificial
<220> FEATURE:
<223> OTHER INFORMATION: phosphorylated oligonucleotide CBCH3

<400> SEQUENCE: 54
cgcgtctgcc ctatcgtcta gttcatctat aaactttgca tcatgtcccc c            51

<210> SEQ ID NO 55

```
<211> LENGTH: 74
<212> TYPE: DNA
<213> ORGANISM: Artificial
<220> FEATURE:
<223> OTHER INFORMATION: phosphorylated oligonucleotide CBCH4

<400> SEQUENCE: 55
ttacaaatgc tagacgaaca gggagagcag ctcgagaggc ttaataaagc taaatcaata    60
gtaggtacta ctgc                                                     74

<210> SEQ ID NO 56
<211> LENGTH: 60
<212> TYPE: DNA
<213> ORGANISM: Artificial
<220> FEATURE:
<223> OTHER INFORMATION: phosphorylated oligonucleotide CBCH5

<400> SEQUENCE: 56
gcttacttgt tccaaattct cgtccatctc tgaagcagta gtacctacta ttgatttagc    60

<210> SEQ ID NO 57
<211> LENGTH: 29
<212> TYPE: DNA
<213> ORGANISM: Artificial
<220> FEATURE:
<223> OTHER INFORMATION: phosphorylated oligonucleotide CBCH6

<400> SEQUENCE: 57
ggccgtctcc tatctgaaga tacatctgg                                     29

<210> SEQ ID NO 58
<211> LENGTH: 32
<212> TYPE: DNA
<213> ORGANISM: Artificial
<220> FEATURE:
<223> OTHER INFORMATION: phosphorylated oligonucleotide CBCH7

<400> SEQUENCE: 58
aattcatcca tgaaatctac cgaaaatttt cc                                 32

<210> SEQ ID NO 59
<211> LENGTH: 41
<212> TYPE: DNA
<213> ORGANISM: Artificial
<220> FEATURE:
<223> OTHER INFORMATION: phosphorylated oligonucleotide CBCH8

<400> SEQUENCE: 59
ctttgaacag gtggaggaat taacagagat ttacacagag g                       41

<210> SEQ ID NO 60
<211> LENGTH: 30
<212> TYPE: DNA
<213> ORGANISM: Artificial
<220> FEATURE:
<223> OTHER INFORMATION: phosphorylted oligonucleotide CBCH9

<400> SEQUENCE: 60
tcgagctctg tgtaaatctc tgttaattcc                                    30

<210> SEQ ID NO 61
<211> LENGTH: 50
<212> TYPE: DNA
<213> ORGANISM: Artificial
<220> FEATURE:
<223> OTHER INFORMATION: phosphorylated oligonucleotide CBCH10
```

<400> SEQUENCE: 61
ggacatgctg gagagtggga atcttaacag aaaaacatat ttgaattttg          50

<210> SEQ ID NO 62
<211> LENGTH: 70
<212> TYPE: DNA
<213> ORGANISM: Artificial
<220> FEATURE:
<223> OTHER INFORMATION: oligonucleotide EGFPs

<400> SEQUENCE: 62
tattacgcgt gcgcgctatg aattctataa gttgctaatg gtgagcaagg gcgaggagct   60
gttcaccggg                                                          70

<210> SEQ ID NO 63
<211> LENGTH: 49
<212> TYPE: DNA
<213> ORGANISM: Artificial
<220> FEATURE:
<223> OTHER INFORMATION: oligonucleotide EGFPa

<400> SEQUENCE: 63
attagggccc ctattacttg tacagctcgt ccatgccgag agtgatccc          49

<210> SEQ ID NO 64
<211> LENGTH: 6
<212> TYPE: PRT
<213> ORGANISM: Artificial
<220> FEATURE:
<223> OTHER INFORMATION: cytosolic protein motif
<220> FEATURE:
<221> NAME/KEY: misc_feature
<222> LOCATION: (4)..(5)
<223> OTHER INFORMATION: Xaa can be any naturally occurring amino acid

<400> SEQUENCE: 64

Asp Ser Gly Xaa Xaa Ser
1               5

<210> SEQ ID NO 65
<211> LENGTH: 3888
<212> TYPE: DNA
<213> ORGANISM: Clostridium botulinum (serotype A) wt fragment
<220> FEATURE:
<221> NAME/KEY: misc_feature
<222> LOCATION: (4)..(30)
<223> OTHER INFORMATION: n is nucleotide encoding SEQ ID NO: 1
<220> FEATURE:
<221> NAME/KEY: misc_feature
<222> LOCATION: (40)..(648)
<223> OTHER INFORMATION: n is nucleotide encoding SEQ ID NO: 1
<220> FEATURE:
<221> NAME/KEY: misc_feature
<222> LOCATION: (658)..(1269)
<223> OTHER INFORMATION: n is nucleotide encoding SEQ ID NO: 1
<220> FEATURE:
<221> NAME/KEY: misc_feature
<222> LOCATION: (1348)..(1359)
<223> OTHER INFORMATION: n is nucleotide encoding SEQ ID NO: 1
<220> FEATURE:
<221> NAME/KEY: misc_feature
<222> LOCATION: (1363)..(1785)
<223> OTHER INFORMATION: n is nucleotide encoding SEQ ID NO: 1
<220> FEATURE:
<221> NAME/KEY: misc_feature
<222> LOCATION: (1807)..(2484)
<223> OTHER INFORMATION: n is nucleotide encoding SEQ ID NO: 1
<220> FEATURE:
<221> NAME/KEY: misc_feature
<222> LOCATION: (2491)..(3873)
<223> OTHER INFORMATION: n is nucleotide encoding SEQ ID NO: 1

<400> SEQUENCE: 65

```
atgnnnnnnn nnnnnnnnnn nnnnnnnnnn aaagatcctn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnncc agcagtannn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnng aattttataa gttgctatgt gtaagaggga taataacttc taaaactaaa    1320
tcattagata aaggatacaa taaggcannn nnnnnnnnnt gtnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnaaagc tacggaggca    1800
gctatgnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
nnnnnnnnnn nnnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnnnnnnn nnnnnnnnnn    2160
nnnnnnnnnn nnnnnnnnnn nnnnnnnnnn nnnnnnnnnn nnnnnnnnnn nnnnnnnnnn    2220
```

-continued

```
nnnnnnnnnn nnnnnnnnnn nnnnnnnnnn nnnnnnnnnn nnnnnnnnnn nnnnnnnnnn    2280
nnnnnnnnnn nnnnnnnnnn nnnnnnnnnn nnnnnnnnnn nnnnnnnnnn nnnnnnnnnn    2340
nnnnnnnnnn nnnnnnnnnn nnnnnnnnnn nnnnnnnnnn nnnnnnnnnn nnnnnnnnnn    2400
nnnnnnnnnn nnnnnnnnnn nnnnnnnnnn nnnnnnnnnn nnnnnnnnnn nnnnnnnnnn    2460
nnnnnnnnnn nnnnnnnnnn nnnnggaact nnnnnnnnnn nnnnnnnnnn nnnnnnnnnn    2520
nnnnnnnnnn nnnnnnnnnn nnnnnnnnnn nnnnnnnnnn nnnnnnnnnn nnnnnnnnnn    2580
nnnnnnnnnn nnnnnnnnnn nnnnnnnnnn nnnnnnnnnn nnnnnnnnnn nnnnnnnnnn    2640
nnnnnnnnnn nnnnnnnnnn nnnnnnnnnn nnnnnnnnnn nnnnnnnnnn nnnnnnnnnn    2700
nnnnnnnnnn nnnnnnnnnn nnnnnnnnnn nnnnnnnnnn nnnnnnnnnn nnnnnnnnnn    2760
nnnnnnnnnn nnnnnnnnnn nnnnnnnnnn nnnnnnnnnn nnnnnnnnnn nnnnnnnnnn    2820
nnnnnnnnnn nnnnnnnnnn nnnnnnnnnn nnnnnnnnnn nnnnnnnnnn nnnnnnnnnn    2880
nnnnnnnnnn nnnnnnnnnn nnnnnnnnnn nnnnnnnnnn nnnnnnnnnn nnnnnnnnnn    2940
nnnnnnnnnn nnnnnnnnnn nnnnnnnnnn nnnnnnnnnn nnnnnnnnnn nnnnnnnnnn    3000
nnnnnnnnnn nnnnnnnnnn nnnnnnnnnn nnnnnnnnnn nnnnnnnnnn nnnnnnnnnn    3060
nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnn nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn nnnnnnnnnn nnnnnnnnnn nnnnnnnnnn nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
nnnnnnnnnn nnnnnnnnnn nnnnnnnnnn nnnnnnnnnn nnnnnnnnnn nnnnnnnnnn    3840
nnnnnnnnnn nnnnnnnnnn nnnnnnnnnn nnnggagaaa ggccactg                 3888

<210> SEQ ID NO 66
<211> LENGTH: 3985
<212> TYPE: DNA
<213> ORGANISM: Clostridium botulinum (serotype A) td fragment
<220> FEATURE:
<221> NAME/KEY: misc_feature
<222> LOCATION: (55)..(81)
<223> OTHER INFORMATION: n is nucleotide encoding SEQ ID NO: 8
<220> FEATURE:
<221> NAME/KEY: misc_feature
<222> LOCATION: (91)..(699)
<223> OTHER INFORMATION: n is nucleotide encoding SEQ ID NO: 8
<220> FEATURE:
<221> NAME/KEY: misc_feature
<222> LOCATION: (709)..(1320)
<223> OTHER INFORMATION: n is nucleotide encoding SEQ ID NO: 8
<220> FEATURE:
<221> NAME/KEY: misc_feature
<222> LOCATION: (1411)..(1422)
<223> OTHER INFORMATION: n is nucleotide encoding SEQ ID NO: 8
<220> FEATURE:
<221> NAME/KEY: misc_feature
```

```
<222> LOCATION: (1426)..(1848)
<223> OTHER INFORMATION: n is nucleotide encoding SEQ ID NO: 8
<220> FEATURE:
<221> NAME/KEY: misc_feature
<222> LOCATION: (1870)..(2547)
<223> OTHER INFORMATION: n is nucleotide encoding SEQ ID NO: 8
<220> FEATURE:
<221> NAME/KEY: misc_feature
<222> LOCATION: (2554)..(3936)
<223> OTHER INFORMATION: n is nucleotide encoding SEQ ID NO: 8

<400> SEQUENCE: 66
acgcgttagc cataaatctg gttataagcg cgcgaggtgt taagtgctag catgnnnnnn      60
nnnnnnnnnn nnnnnnnnnn naacgatcct nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnc ccgcggtann nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
gaattctata agttgctatg tgtaagaggg ataataacta gtcacactca atctctagac    1380
caaggataca atgacgatga tgataaggca nnnnnnnnnn nntgtnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnaa agcgaccgaa    1860
gcggctatgn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
```

```
nnnnnnnnnn nnnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnnnnnnn nnnnnnnnnn    2160
nnnnnnnnnn nnnnnnnnnn nnnnnnnnnn nnnnnnnnnn nnnnnnnnnn nnnnnnnnnn    2220
nnnnnnnnnn nnnnnnnnnn nnnnnnnnnn nnnnnnnnnn nnnnnnnnnn nnnnnnnnnn    2280
nnnnnnnnnn nnnnnnnnnn nnnnnnnnnn nnnnnnnnnn nnnnnnnnnn nnnnnnnnnn    2340
nnnnnnnnnn nnnnnnnnnn nnnnnnnnnn nnnnnnnnnn nnnnnnnnnn nnnnnnnnnn    2400
nnnnnnnnnn nnnnnnnnnn nnnnnnnnnn nnnnnnnnnn nnnnnnnnnn nnnnnnnnnn    2460
nnnnnnnnnn nnnnnnnnnn nnnnnnnnnn nnnnnnnnnn nnnnnnnnnn nnnnnnnnnn    2520
nnnnnnnnnn nnnnnnnnnn nnnnnnnggt accnnnnnnn nnnnnnnnnn nnnnnnnnnn    2580
nnnnnnnnnn nnnnnnnnnn nnnnnnnnnn nnnnnnnnnn nnnnnnnnnn nnnnnnnnnn    2640
nnnnnnnnnn nnnnnnnnnn nnnnnnnnnn nnnnnnnnnn nnnnnnnnnn nnnnnnnnnn    2700
nnnnnnnnnn nnnnnnnnnn nnnnnnnnnn nnnnnnnnnn nnnnnnnnnn nnnnnnnnnn    2760
nnnnnnnnnn nnnnnnnnnn nnnnnnnnnn nnnnnnnnnn nnnnnnnnnn nnnnnnnnnn    2820
nnnnnnnnnn nnnnnnnnnn nnnnnnnnnn nnnnnnnnnn nnnnnnnnnn nnnnnnnnnn    2880
nnnnnnnnnn nnnnnnnnnn nnnnnnnnnn nnnnnnnnnn nnnnnnnnnn nnnnnnnnnn    2940
nnnnnnnnnn nnnnnnnnnn nnnnnnnnnn nnnnnnnnnn nnnnnnnnnn nnnnnnnnnn    3000
nnnnnnnnnn nnnnnnnnnn nnnnnnnnnn nnnnnnnnnn nnnnnnnnnn nnnnnnnnnn    3060
nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnn nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn nnnnnnnnnn nnnnnnnnnn nnnnnnnnnn nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
nnnnnnnnnn nnnnnnnnnn nnnnnnnnnn nnnnnnnnnn nnnnnnnnnn nnnnnnnnnn    3840
nnnnnnnnnn nnnnnnnnnn nnnnnnnnnn nnnnnnnnnn nnnnnnnnnn nnnnnnnnnn    3900
nnnnnnnnnn nnnnnnnnnn nnnnnnnnnn nnnnnnggag aaaggccact gtaatagctc    3960
gaggcggccg cttaattaag ggccc                                          3985
```